United States Patent
Beck et al.

(10) Patent No.: US 11,242,319 B2
(45) Date of Patent: Feb. 8, 2022

(54) IMMUNOREGULATORY AGENTS

(71) Applicant: FLEXUS BIOSCIENCES, INC., Princeton, NJ (US)

(72) Inventors: Hilary Plake Beck, Emerald Hills, CA (US); Juan Carlos Jaen, Burlingame, CA (US); Maksim Osipov, Belmont, CA (US); Jay Patrick Powers, Pacifica, CA (US); Maureen Kay Reilly, Belmont, CA (US); Hunter Paul Shunatona, San Francisco, CA (US); James Ross Walker, Menlo Park, CA (US); Mikhail Zibinsky, Lodi, CA (US); James Aaron Balog, Lambertville, NJ (US); David K. Williams, Delran, NJ (US); Weiwei Guo, Lawrenceville, NJ (US)

(73) Assignee: Flexus Biosciences, Inc., Princeton, NJ (US)

( * ) Notice: Subject to any disclaimer, the term of this patent is extended or adjusted under 35 U.S.C. 154(b) by 15 days.

(21) Appl. No.: 15/524,113

(22) PCT Filed: Nov. 5, 2015

(86) PCT No.: PCT/US2015/059271
§ 371 (c)(1),
(2) Date: May 3, 2017

(87) PCT Pub. No.: WO2016/073738
PCT Pub. Date: May 12, 2016

(65) Prior Publication Data
US 2019/0092729 A1    Mar. 28, 2019

Related U.S. Application Data

(60) Provisional application No. 62/075,663, filed on Nov. 5, 2014.

(51) Int. Cl.
*C07D 213/75* (2006.01)
*A61K 45/06* (2006.01)
(Continued)

(52) U.S. Cl.
CPC .......... *C07D 213/75* (2013.01); *A61K 31/167* (2013.01); *A61K 31/195* (2013.01);
(Continued)

(58) Field of Classification Search
None
See application file for complete search history.

(56) References Cited

U.S. PATENT DOCUMENTS 5,382,584 A   1/1995   Balasubramanian
5,455,273 A   10/1995  Maier et al.
(Continued)

FOREIGN PATENT DOCUMENTS

CN   102108078 A   6/2011
EP     0596298 B1   1/2002
(Continued)

OTHER PUBLICATIONS

Database Caplus Chemical Abstracts Service, Columbus, Ohio, US; Database Accession No. 1911:16627, Abstract of Thole et al., Proceedings of the Chemical Society, London (1911), 27, 42 (Year: 1911).*

(Continued)

*Primary Examiner* — Karl J Puttlitz
(74) *Attorney, Agent, or Firm* — BakerHostetler

(57) ABSTRACT

Compounds that modulate the oxidoreductase enzyme indoleamine 2,3-dioxygenase, and compositions containing the compounds, are described herein. The use of such compounds and compositions for the treatment and/or prevention of a diverse array of diseases, disorders and conditions, including cancer- and immune-related disorders, that (Continued)

are mediated by indoleamine 2,3-dioxygenase is also provided.

23 Claims, 28 Drawing Sheets

(51) Int. Cl.
| | |
|---|---|
| A61K 31/167 | (2006.01) |
| C07C 255/60 | (2006.01) |
| C07C 317/40 | (2006.01) |
| C07D 239/42 | (2006.01) |
| C07C 233/15 | (2006.01) |
| C07D 295/155 | (2006.01) |
| C07C 233/29 | (2006.01) |
| C07C 237/22 | (2006.01) |
| C07C 233/66 | (2006.01) |
| C07D 213/56 | (2006.01) |
| C07C 321/28 | (2006.01) |
| C07D 295/15 | (2006.01) |
| C07C 235/26 | (2006.01) |
| A61K 31/195 | (2006.01) |
| C07C 255/57 | (2006.01) |
| C07C 235/38 | (2006.01) |
| C07D 207/27 | (2006.01) |
| C07D 231/12 | (2006.01) |
| C07C 317/44 | (2006.01) |
| C07C 237/20 | (2006.01) |
| C07D 309/06 | (2006.01) |
| C07D 309/04 | (2006.01) |
| C07C 235/36 | (2006.01) |
| C07D 317/46 | (2006.01) |
| C07D 277/30 | (2006.01) |
| A61K 31/426 | (2006.01) |
| A61K 39/39 | (2006.01) |
| A61P 35/00 | (2006.01) |
| A61P 37/06 | (2006.01) |
| A61K 31/277 | (2006.01) |
| A61K 31/343 | (2006.01) |
| A61K 31/44 | (2006.01) |
| A61K 31/505 | (2006.01) |
| A61K 31/5375 | (2006.01) |
| C07C 233/11 | (2006.01) |
| C07C 233/28 | (2006.01) |
| C07C 323/41 | (2006.01) |
| C07D 317/66 | (2006.01) |
| A61K 39/00 | (2006.01) |

(52) U.S. Cl.
CPC .......... *A61K 31/277* (2013.01); *A61K 31/343* (2013.01); *A61K 31/426* (2013.01); *A61K 31/44* (2013.01); *A61K 31/505* (2013.01); *A61K 31/5375* (2013.01); *A61K 39/39* (2013.01); *A61K 45/06* (2013.01); *A61P 35/00* (2018.01); *A61P 37/06* (2018.01); *C07C 233/11* (2013.01); *C07C 233/15* (2013.01); *C07C 233/28* (2013.01); *C07C 233/29* (2013.01); *C07C 233/66* (2013.01); *C07C 235/26* (2013.01); *C07C 235/36* (2013.01); *C07C 235/38* (2013.01); *C07C 237/20* (2013.01); *C07C 237/22* (2013.01); *C07C 255/57* (2013.01); *C07C 255/60* (2013.01); *C07C 317/40* (2013.01); *C07C 317/44* (2013.01); *C07C 321/28* (2013.01); *C07C 323/41* (2013.01); *C07D 207/27* (2013.01); *C07D 213/56* (2013.01); *C07D 231/12* (2013.01); *C07D 239/42* (2013.01); *C07D 277/30* (2013.01); *C07D 295/15* (2013.01); *C07D 295/155* (2013.01); *C07D 309/04* (2013.01); *C07D 309/06* (2013.01); *C07D 317/46* (2013.01); *C07D 317/66* (2013.01); *A61K 2039/55511* (2013.01); *C07C 2601/02* (2017.05); *C07C 2601/08* (2017.05); *C07C 2601/14* (2017.05); *Y02A 50/30* (2018.01)

(56) References Cited

U.S. PATENT DOCUMENTS

| | | | |
|---|---|---|---|
| 5,723,464 | A | 3/1998 | Brightwell et al. |
| 6,100,279 | A | 8/2000 | Vaccaro et al. |
| 6,127,357 | A | 10/2000 | Cliffe et al. |
| 6,509,340 | B1 | 1/2003 | Van Amsterdam et al. |
| 6,514,977 | B1 | 2/2003 | Anantanarayan et al. |
| 6,525,059 | B1 | 2/2003 | Anantanarayan et al. |
| 6,632,836 | B1 | 10/2003 | Baker et al. |
| 6,660,744 | B1 | 12/2003 | Hirst et al. |
| 6,979,686 | B1 | 12/2005 | Naraian et al. |
| 7,645,771 | B2 | 1/2010 | Kazmierski et al. |
| 8,088,803 | B2 | 1/2012 | Combs et al. |
| 9,643,972 | B2 | 5/2017 | Beck et al. |
| 10,106,546 | B2 | 10/2018 | Beck et al. |
| 2002/0016463 | A1 | 2/2002 | Zablocki et al. |
| 2003/0013721 | A1 | 1/2003 | Meghani et al. |
| 2003/0190298 | A1 | 10/2003 | Bradley et al. |
| 2004/0029887 | A1 | 2/2004 | Bhatia et al. |
| 2004/0157886 | A1 | 8/2004 | Domany et al. |
| 2004/0234623 | A1 | 11/2004 | Munn et al. |
| 2005/0096376 | A1 | 5/2005 | Sundermann et al. |
| 2006/0258719 | A1 | 11/2006 | Combs et al. |
| 2006/0281772 | A1 | 12/2006 | Baindur et al. |
| 2007/0129347 | A1* | 6/2007 | Hinze .................. C07C 237/20 514/210.17 |
| 2007/0197584 | A1 | 8/2007 | Schwink et al. |
| 2008/0039453 | A1 | 2/2008 | Putman et al. |
| 2008/0146569 | A1 | 6/2008 | Blake et al. |
| 2008/0312206 | A1 | 12/2008 | Brian et al. |
| 2009/0027523 | A1 | 1/2009 | Chang |
| 2009/0247507 | A1 | 10/2009 | Bavetsias et al. |
| 2009/0264405 | A1 | 10/2009 | Ali et al. |
| 2009/0264650 | A1 | 10/2009 | Cho et al. |
| 2009/0275523 | A1 | 11/2009 | Schudok et al. |
| 2009/0286833 | A1 | 11/2009 | Oberboersch et al. |
| 2009/0298834 | A1 | 12/2009 | Pajouhesh et al. |
| 2010/0008866 | A1 | 1/2010 | Blum et al. |
| 2010/0233166 | A1 | 9/2010 | Prendergast et al. |
| 2011/0218183 | A1 | 9/2011 | Chen et al. |
| 2011/0237583 | A1 | 9/2011 | Schiemann et al. |
| 2011/0306644 | A1 | 12/2011 | Hoekstra et al. |
| 2012/0046278 | A1 | 2/2012 | Herdewijn et al. |
| 2012/0088763 | A1 | 4/2012 | Finch et al. |
| 2013/0197095 | A1 | 8/2013 | Nolte et al. |
| 2013/0217706 | A1 | 8/2013 | Tran et al. |
| 2014/0212444 | A1 | 7/2014 | Holoshitz et al. |
| 2016/0137652 | A1 | 5/2016 | Beck et al. |
| 2016/0137653 | A1 | 5/2016 | Beck et al. |

FOREIGN PATENT DOCUMENTS

| | | |
|---|---|---|
| EP | 1781656 B1 | 12/2007 |
| EP | 1918281 | 5/2008 |
| JP | 2000-508670 A | 7/2000 |
| JP | 2002-513018 A | 5/2002 |
| JP | 2002-533333 A | 10/2002 |
| JP | 2003-509428 A | 3/2003 |
| JP | 2003-518126 A | 6/2003 |
| JP | 2005-170743 A | 6/2005 |
| JP | 2006-157472 A | 6/2006 |
| JP | 2007-501828 A | 2/2007 |
| JP | 2009-501135 A | 1/2009 |
| JP | 2009-516649 A | 4/2009 |
| JP | 2009-520791 A | 5/2009 |
| JP | 2010-500989 A | 1/2010 |

(56) References Cited

FOREIGN PATENT DOCUMENTS

| | | |
|---|---|---|
| JP | 2012-510481 A | 5/2012 |
| JP | 2012-517992 A | 8/2012 |
| JP | 2012-520269 A | 9/2012 |
| WO | 95/33743 A1 | 12/1995 |
| WO | 97/40038 A1 | 10/1997 |
| WO | 99/29310 A2 | 6/1999 |
| WO | 99/55697 A1 | 11/1999 |
| WO | 00/56727 A1 | 9/2000 |
| WO | 2001/019829 A2 | 3/2001 |
| WO | 01/46199 A1 | 6/2001 |
| WO | 2001/046200 A1 | 6/2001 |
| WO | 01/92204 A1 | 12/2001 |
| WO | 2003/048109 A1 | 6/2003 |
| WO | 2004/089415 A2 | 10/2004 |
| WO | 2004/094409 A1 | 11/2004 |
| WO | 2005/025498 | 3/2005 |
| WO | 2005/025554 | 3/2005 |
| WO | 2005/080317 A2 | 9/2005 |
| WO | 2006/018279 A2 | 2/2006 |
| WO | 2006/029879 A2 | 3/2006 |
| WO | 2006/105021 A2 | 10/2006 |
| WO | 2006/135721 A1 | 12/2006 |
| WO | 2007/005874 A2 | 1/2007 |
| WO | 2007/063839 | 6/2007 |
| WO | 2007/070173 A2 | 6/2007 |
| WO | 2007/072017 A2 | 6/2007 |
| WO | 2007/076055 A2 | 7/2007 |
| WO | 2007/095050 A2 | 8/2007 |
| WO | 2008/020270 A1 | 2/2008 |
| WO | 2008/132601 A1 | 11/2008 |
| WO | 2009/009116 A2 | 1/2009 |
| WO | 2009/044273 A2 | 4/2009 |
| WO | 2009/052320 A1 | 4/2009 |
| WO | 2010/012817 A2 | 2/2010 |
| WO | 2010/015655 A1 | 2/2010 |
| WO | 2010/019570 A2 | 2/2010 |
| WO | 2010/025308 A2 | 3/2010 |
| WO | 2010/063352 A1 | 6/2010 |
| WO | 2010/075376 A2 | 7/2010 |
| WO | 2010/077634 A1 | 7/2010 |
| WO | 2010/094956 A1 | 8/2010 |
| WO | 2010/103130 A2 | 9/2010 |
| WO | 2010/107768 A1 | 9/2010 |
| WO | 2011/028683 A1 | 3/2011 |
| WO | 2011/056652 | 5/2011 |
| WO | 2011/070024 A1 | 6/2011 |
| WO | 2011/107553 A1 | 9/2011 |
| WO | 2011/109400 A2 | 9/2011 |
| WO | 2011/131407 A1 | 10/2011 |
| WO | 2011/139636 A1 | 11/2011 |
| WO | 2011/140249 A2 | 11/2011 |
| WO | 2012/032433 A1 | 3/2012 |
| WO | 2012/145493 A1 | 10/2012 |
| WO | 2013/079174 A1 | 6/2013 |
| WO | 2013/079425 A1 | 6/2013 |
| WO | 2013/087699 A1 | 6/2013 |
| WO | 2013/119716 A1 | 8/2013 |
| WO | 2013/132044 A1 | 9/2013 |
| WO | 2013/169264 A1 | 11/2013 |
| WO | 2014/008218 A1 | 1/2014 |
| WO | 2014/036357 A1 | 3/2014 |
| WO | 2014/036412 A2 | 3/2014 |
| WO | 2014/079850 | 5/2014 |
| WO | 2014/086453 A1 | 6/2014 |
| WO | 2014/150677 A1 | 9/2014 |
| WO | 2014/160967 A2 | 10/2014 |
| WO | 2015/184099 A1 | 12/2015 |
| WO | 2015/188085 A1 | 12/2015 |
| WO | 2016/071283 A1 | 5/2016 |
| WO | 2016/073738 A2 | 5/2016 |
| WO | 2016/073770 A1 | 5/2016 |
| WO | 2016/073774 A2 | 5/2016 |
| WO | 2016102672 * | 6/2016 |

OTHER PUBLICATIONS

Database Caplus Chemical Abstracts Service, Columbus, Ohio, US; Database Accession No. 2005:1241225, Abstract of US 20070129347, Gruenenthal GmbH, Germany, Hinze et al., Jun. 17, 2007 (Year: 2007).*

Database Caplus Chemical Abstracts Service, Columbus, Ohio, US; Database Accession No. 2015:1976475, Abstract of WO 2015188085, Flexus Biosciences, Inc., USA, Jaen et al., Dec. 10, 2015 (Year: 2015).*

Database Caplus Chemical Abstracts Service, Columbus, Ohio, US; Database Accession No. 1942:42838, Abstract of Erdtman et al., Svensk Papperstidning (1942), 45, 315-23 (Year: 1942).*

Database Caplus Chemical Abstracts Service, Columbus, Ohio, US; Database Accession No. 1938:50470, Abstract of Ahmed et al., Journal of the Indian Chemical Society (1938), 15, 152-9 (Year: 1938).*

Database Caplus Chemical Abstracts Service, Columbus, Ohio, US; Database Accession No. 1938:50470, Abstract of WO 2003048109, Novo Nordisk A/S, Den., Kodra et al. (Year: 2003).*

Database Caplus Chemical Abstracts Service, Columbus, Ohio, US; Database Accession No. 1992:73028, Abstract of Amhed et al., Journal of the Indian Chemical Society (1938) (Year: 1938).*

Kurz et al., Tetrahedron 61 (2005) 7247-7251 (Year: 2005).*

Database Caplus Chemical Abstracts Service, Columbus, Ohio, US; Database Accession No. 2005:544136, Abstract of Kurz et al., Tetrahedron 61 (2005) 7247-7251 (Year: 2005).*

Sippl et al., Journal of Computer-Aided Molecular Design (2001), 15(5), 395-410 (Year: 2001).*

Vanneman et al., Combining immunotherapy and targeted therapies in cancer treatment. Nature reviews cancer. Apr. 2012;12(4):237-251.

Li, Int Immunopharmacology, 47, 70-77, 2017. (Year: 2017).

Ibrahim, Seminars in Oncology, 42(3), 474-483, 2015. (Year: 2015).

Wang, et al., Indoleamine-2,3-dioxygenase, an immunosuppressive enzyme that inhibits natural killer cell function, as a useful target for ovarian cancer therapy, International Journal of Oncology, 40,2012, 929-934.

Spranger et al., Mechanism of tumor rejection with doublets of CTLA-4, PD-1/PD-L1, or IDO blockade involves restored IL-2 production and proliferation of CD8+ T cells directly within the tumor microenvironment, Journal for Immunotherapy of Cancer, 2014, 14 pages.

Smith, et al., IDO is a Nodal Pathogenic Driver of Lung Cancer and Metastasis Development; Cancer Discovery—American Association for Cancer Research, Aug. 2012, 722-735.

Smith, et al., Epacadostat Plus Pembrolizumab in Patients with Advanced Urothelial Carcinoma: Preliminary Phase ½ Results of ECHO-202/KEYNOTE-037, Abstract #4503, presented at the ASCO Annual Meeting 2017, Chicago, IL, Jun. 2-6, 2017, 16 pages.

Liu et al, Selective inhibition of IDO1 effectively regulates mediators of antitumor immunity, Blood, vol. 115, No. 17, Apr. 2010, 3520-3530.

Lara, et al., Epacadostat Plus Pembrolizumab in Patients with Advanced RCC: Preliminary Phase ½ Results from ECHO-202/KEYNOTE-037 Poster, 4515, presented at the 53rd Annual Meeting of the American Society of Clinical Oncology, Chicago, IL, Jun. 2-6, 2017.

Koblish, et al., Hydroxyamidine Inhibitors of Indoleamine-2,3-dioxygenase Potently Suppress Systemic Tryptophan Catabolism and the Growth of IDO-Expressing Tumors, Molecular Cancer Therapeutics, 9(2) Feb. 2010,489-498.

Hamid, et al., Epacadostat Plus Pembrolizumab in Patients with Advanced Melanoma: Phase 1 and 3 Efficacy and Safety Results from ECHO-202/KEYNOTE-037, Presentation #12140, Presented at the ESMO Annual Meeting 2017, Madrid, Spain, Sep. 9, 2017, 21 pages.

Hamid, Epacadostat Plus Pembrolizumab in Patients with SCCHN: Preliminary Phase ½ Results from ECHO-202/KEYNOTE-037, Abstract #6010, presented at the ASCO Annual Meeting 2017, Chicago, IL, Jun. 2-6, 2017, 19 pages.

(56) References Cited

OTHER PUBLICATIONS

Gangadhar et al, Efficacy and Safety of Epacadostat Plus Pembrolizumab Treatment of NSCLC: Preliminary Phase ½ Results of ECHO-202/KEYNOTE-037 Poster, 9014, presented at the 53rd Annual Meeting of the American Society of Clinical Oncology, Chicago, IL, Jun. 2-6, 2017.
ACS (American Chemical Society), (c) 2005. STN Database. RN 866251-45-8.
Reddy et al, Design, Synthesis, and Structure-Activity Relationship Exploration of 1-Substituted 4-Aroyl-3-hydroxy-5-phenyl-1H-pyrrol-2(5H)-one Analogues as Inhibitors of the Annexin A2-S100A10 Protein interaction, Journal of Medicinal Chemistry, vol. 54, No. 7, Apr. 14, 2011, pp. 2080-2094.
Patel et al, Discovery of 3-Methyl- N-(1-oxy-31,4',5',61-tetrahydro-21H-[2,41-bipyridine]-11-ylmethyl)benzamide (ABT-670), an Orally Bioavailable Dopamine D 4 Agonist for the Treatment of Erectile Dysfunction, Journal of Medicinal Chemistry, vol. 49, No. 25, Dec. 1, 2006, pp. 7450-7465.
Moreland et al, A-412997 is a selective dopamine D 4 receptor Agonist in rats, Pharmacology Biochemistry and Behavior, Elsevier, US, vol. 82, No. 1, Sep. 1, 2005, pp. 140-147.
Humber, Agents Affecting Lipid Metabolism. XVI. The Synthesis of Analogs 1-3,6 of trans-l,4-Bis(2-chlorobenzylaminomethyl)cyclohexane 1, Journal of Medicinal Chemistry, vol. 8, No. 3, May 1, 1965, pp. 401-404.
Gibney, Preliminary results from a phase ½ study of INCB024360 combined with ipilimumab (ipi) in patients (pts) with melanoma. | 2014 ASCO Annual Meeting | Abstracts | Meeting Library, May 1, 2004, XP055348796, Retrieved from the Internet: URL:http://meetinglibrary.asco.org/content/127143-144 [retrieved on Feb. 22, 2017].
Yamamoto, et al., Additional reaction of arylboronic acid to aldehydes and Alpha,Beta-unsaturated carbonyl compounds catalyzed by conventional palladium complexes in the presence of chloroform, J Organomet, Chem., 69(9) 4:1325-1332, Apr. 2009.
Vilums, Design and synthesis of novel small molecule CCR2 antagonists: Evaluation of 4- aminopiperidine derivatives, Bioorganic Medical Chemistry Letters, 24(23):5377, Dec. 2014.
Stucchi, et al., Multicomponent Synthesis and Biological Evaluation of a Piperazine-Based Dopamine Receptor Ligand Library, ACS medicinal chemistry letters 6(8), Jun. 2015, 882-887.
Stocks et al., Evidence for a Common Non-Heme Chelatable-Iron-Dependent Activation Mechanism for Semisynthetic and Synthetic Endoperoxide Antimalarial Drugs, Angew. Chem. Int. Ed., Aug. 2007, 46(33), 6278-6283.
Serafini, P. et al., Myeloid suppressor cells in cancer: recruitment, phenotype, properties, and mechanisms of immune suppression. Seminars in Cancer Biology, 16(1):53-65 Feb. 2, 2006.
Sawaya et al., Risk of cervical cancer associated with extending the interval between cervical-cancer screenings, New England Journal of Medicine, 349(16): 1501-1509, Oct. 2003.
Sarkar, et al., Induction of indoleamine 2, 3-dioxygenase by interferon-yin human islets, Diabetes, 56(1):72-79, Jan. 2007.
Robinson et al, Kinetic Resolution Strategies using non-enzymatic Catalysts, Tetrahedron, Jun. 2003, 14(1), 1407-1446.
Ramirez-Montagut et al., Immunity to melanoma: unraveling the relation of tumor immunity and autoimmunity, Oncogene, 22(20):3180-3187, May 2003.
Qureshi et al., Indoleamine 2, 3-dioxygenase: potential in cancer immunotherapy, Science Vision, 2013, vol. 19(1,2), pp. 33-40.
Pubchem SID=162741420, May 22, 2013, pp. 1-5 [online], [retrieved on Dec. 21, 2015], retrieved from the Internet <URL: https://pubchem.ncbi.nlm.nih.gov/substance/162741420>; p. 3 (accessed Jul. 11, 2016).
Pubchem CID 57911539, Aug. 19, 2012, pp. 1-11 [online], [retrieved on Dec. 17, 2015], Retrieved from the Internet <URL:https://pubchem.ncbi.nlm.nih.gov/compound/57911539#section=Top.>; p. 3.
Platten, M. et al., Tryptophan catabolism in cancer: beyond IDO and tryptophan depletion, Cancer Research, 72 (21):5435-5440, Nov. 2012.
Pardall, The blockade of immune checkpoints in cancer immunotherapy, Nature Reviews Cancer, 12(4):252-264, Apr. 2012.
National Center for Biotechnology Information, Pubchem Compound Database; CID=24231423, https://pubchem.ncbi.nlm.nih.gov/compound/24231423 (accessed Jun. 23, 2016) 9 pages.
Munsen et al., Ligand a versatile computerized approach for characterization of ligand- binding systems, Analytical Biochemistry, 107(1), 220-239, Sep. 1980.
Ishiyama, et al., Palladium (0)-catalyzed cross-coupling reaction of alkoxydiboron with halorenes: a direct procedure for arylboronic esters., J. Org. Chem., 60, 7508-7510, Nov. 1995.
Littlejohn, et al., Expression and Purification of Recombinant Human Indoleamine 2,3- Dioxygenase, Protein Expression and Purification, 19(1):22-29, Jun. 2000.
Li, W. et al., Current drug research on PEGylation with small molecular agents, Progress in Polymer Science, 38:421-444, Apr. 2013.
Li, G. et al., Discovery of novel orally active ureido NPY Y5 receptor antagonists, Bioorganic & Medical Chemistry Letters, 18(3):1146-1150, Feb. 2008.
Kotha et al, Recent applications of Suzuki-Miyaura cross-coupling reaction in organic synthesis, Tetrahedron, Nov. 2002, 58:9633-9695.
Kohrt, et al., Anti-KIR antibody enhancement of anti-lymphoma activity of natural killer cells as monotherapy and in combinatin with anti-CD20 antibodies, Blood 123.5, Jan. 2014, 678-686.
Kinzel et al., A new palladium precatalyst allows for the fast Suzuki-Miyaura coupling reactions of unstable polyfluorophenyl and 2-heteroaryl boronic acids, Jouranl of the American Chemical Society, Sep. 2010, 132(40), 14073-14075.
Kawamura et al., Iron-catalysed cross-coupling of halohydrins with aryl aluminum reagents: a protecting-group-free strategy attaining remarkable rate enhancement and diastereoinduction, Chemical Communications, 48 (75):9376-9378, Aug. 2012.
International Search Report dated May 17, 2016 issued in PCT/US15/59316, 2 pages.
International Search Report dated May 13, 2016 issued in PCT/US15/59271, 3 pages.
International Search Report dated Mar. 17, 2016 issued in PCT/US15/59311, 3 pages.
International Search Report dated Dec. 10, 2015 issued in PCT/US15/34449, 1 page.
https://pubchem.ncbi.nlm.gov/compound/70339979#section=top; Pub Chern Open Chemistry Database; Compound Summary for CID 70339979; Dec. 20, 2015: 3 pages.
Fox, et al., Discovery of 6-phenylpyrimido [4,5-b][1,4] oxazines as potent and selective acyl CoA: diacylglycerol acytransferase 1 (DGAT1) inhibitors with in vivo efficacy in rodents, Journal of Medical Chemistry, 57(8):3464-3483, Apr. 2014.
Evans, et al., Asymmetric alkylation reactions of chiral imide enolates. A practical approach to the enantioselective synthesis of alpha-substituted carboxylic acid derivatives, Journal of the American Chemical Society, 104(6), pp. 1737-1739, Mar. 1982.
Evans et al., Contrasteric carboximide hydrolysis with lithium hydroperoxide, Tetrahedron Letters, Dec. 1987, 28 (49), 6141-6144.
El-Faham, et al., Peptide coupling reagents, more than a letter soup, Chemical Reviews, 111.11, 6557-6602, Aug. 2011.
Corsello, et al. Endorine Side effects induced by immune checkpoint inhibitors, 98(4), Apr. 2013, 1361-1375.
Chiang et al., An Fc Domain Protein-Small Molecule Conjugate as an Enhanced Immunomodular, Journal of the American Chemical Society, 136(9):3370-3373, Feb. 2014.
Brandacher, G. et al., Prognostic value of indolemaine 2,3-dioxygenase expression in colorectal cancer: effect on tumor-infiltrasting T cells, Clin. Cancer Res., 12(4):1144-1151 Feb. 2006.
Berge, S. M. et al., Pharmaceutical Salts, J. Pharm. Sci., 66:1-19, Jan. 1977.
Barlind et al., Design and optimization of pyrazinecarboxamide-based inhibitors of diacylglycerol acyltransferase 1 (DGAT1) leading to a clinical candidate dimethylpyrazinecarboxamide

(56) References Cited

OTHER PUBLICATIONS phenylcyclohexylacetic acid (AZD7687), Journal of medicinal chemistry, Nov. 2012, 55(23), 10610-10629.
Ball, H.J. et al., Characterization of an indoleamine 2, 3-dioxygenase-like protein found in humans and mice, Gene, 396(1):203-213 Jul. 2007.
Database PubChem [Online], Feb. 29, 2008, Database accession No. CID24231423.
Patani et al., "Bioisosterism: A Rational Approach in Drug Design", Chem. Rev., 1996, 96, 3147-3176.
Registry[online], Apr. 4, 2014, [retrieved on Jul. 25, 2019], Retrieved from: STN, CAS accession No. 1584048-57-6, 2 pages.
Registry[online], Mar. 18, 2014, [retrieved on Jul. 25, 2019], Retrieved from: STN, CAS accession No. 1570034-84-2, 2 pages.
Registry[online], Mar. 24, 2014, [retrieved on Jul. 25, 2019], Retrieved from: STN, CAS accession No. 1572377-00-4, 2 pages.
Registry[online], Mar. 26, 2014, [retrieved on Jul. 25, 2019], Retrieved from: STN, CAS accession No. 1573869-23-4, 2 pages.
Registry[online], Mar. 30, 2014, [retrieved on Jul. 25, 2019], Retrieved from: STN, CAS accession No. 1576175-97-7, 2 pages.
Registry[online], Mar. 31, 2014, [retrieved on Jul. 25, 2019], Retrieved from: STN, CAS accession No. 1576367-12-8, 2 pages.
Registry[online], May 19, 2014, [retrieved on Jul. 25, 2019], Retrieved from: STN, CAS accession No. 1606467-00-8, 2 pages.
Registry[online], May 19, 2014, [retrieved on Jul. 25, 2019], Retrieved from: STN, CAS accession No. 1606662-14-9, 2 pages.
Registry[online], Sep. 26, 2014, [retrieved on Jul. 25, 2019], Retrieved from: STN, CAS accession No. 1626606-12-9, 2 pages.
Registry[online], Sep. 26, 2014, [retrieved on Jul. 25, 2019], Retrieved from: STN, CAS accession No. 1626620-57-2, 2 pages.
Zhao et al., "Discovery of Tyrosine Kinase Inhibitors by Docking into an Inactive Kinase Conformation Generated by Molecular Dynamics", Chemmedchem, 2012, 7, 1983-1990.

\* cited by examiner

| | Potency | | Potency |
|---|---|---|---|
|  | A |  | A |
|  | B |  | B |
|  | A |  | A |
|  | A |  | A |
|  | A | | |

IMMUNOREGULATORY AGENTS

CROSS-REFERENCES TO RELATED APPLICATIONS

This application is a National Stage Application filed under 35 U.S.C. 371 of International Application No. PCT/US2015/059271 filed Nov. 5, 2015, which claims priority to U.S. Provisional Application Ser. No. 62/075,663, filed Nov. 5, 2014 the entire content of which is incorporated herein by reference.

BACKGROUND OF THE INVENTION

Indolcamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini, P. et al., *Semin. Cancer Biol.*, 16(1):53-65 (February 2006) and Ball, H. J. et al., *Gene*, 396(1):203-213 (Jul. 1, 2007).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4): 1144-1151) (Feb. 15, 2006).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in WO 2004/094409.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

BRIEF SUMMARY OF THE INVENTION

The present invention relates to compounds that modulate the oxidoreductase enzyme indoleamine 2,3-dioxygenase (IDO), and compositions (e.g., pharmaceutical compositions) comprising the compounds. Such compounds, including methods of their synthesis, and compositions are described in detail below.

The present invention also relates to the use of such compounds and compositions for the treatment and/or prevention of a diverse array of diseases, disorders and conditions mediated, in whole or in part, by IDO. Such diseases, disorders and conditions are described in detail elsewhere herein. Unless otherwise indicated, when uses of the compounds of the present invention are described herein, it is to be understood that such compounds may be in the form of a composition (e.g., a pharmaceutical composition).

As discussed hereafter, although the compounds of the present invention are believed to effect their activity by inhibition of IDO, a precise understanding of the compounds' underlying mechanism of action is not required to practice the invention. It is envisaged that the compounds may alternatively effect their activity through inhibition of tryptophan-2,3-dioxygenase (TDO) activity. It is also envisaged that the compounds may effect their activity through inhibition of both IDO and TDO function. Although the compounds of the invention are generally referred to herein as IDO inhibitors, it is to be understood that the term "IDO inhibitors" encompasses compounds that act individually through inhibition of TDO or IDO, and/or compounds that act through inhibition of both IDO and TDO.

In one aspect, the present invention provides compounds represented by formula (I):

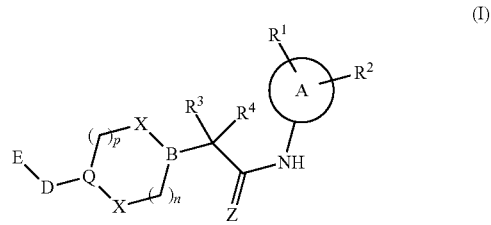

or a pharmaceutically acceptable salt, hydrate or solvate thereof, wherein the subscript n is 1 or 0; the subscript p is 1 or 0. In formula (I), the ring designated as A is phenyl, 5- or 6-membered heteroaryl, or $C_{5-7}$ cycloalkyl; Z is O; B is N, $C(OR^{5a})$, or $C(R^{3a})$; each X is independently $NR^{5a}$, O, $CHR^5$, C(O), or $CH(OR^{5a})$; Q is N, C(CN), or $CR^6$; and D is a bond, O, $C(R^5)_2$, $NR^{5a}$, or $N(R')_2$. The letter E may be absent or is hydrogen, optionally substituted $C_1$-$C_6$ alkyl, optionally substituted phenyl, optionally substituted $C_3$-$C_6$ cycloalkyl, optionally substituted 3- to 6-membered cycloheteroalkyl, or optionally substituted monocyclic heteroaryl. Each of $R^1$ and $R^2$ are independently hydrogen, halogen, optionally substituted $C_1$-$C_4$ haloalkyl, optionally substituted $C_3$-$C_6$ cycloalkyl, optionally substituted 3- to 6-membered cycloheteroalkyl, optionally substituted phenyl, optionally substituted heteroaryl, optionally substituted $C_1$-$C_4$ alkyl, optionally substituted $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl. Each of $R^3$, $R^{3a}$ and $R^4$ are independently hydrogen, optionally substituted $C_1$-$C_6$ alkyl, optionally substituted $C_1$-$C_6$ haloalkyl, fluorine, OH, CN, $CO_2H$, $C(O)NH_2$, $N(R^5)_2$, optionally substituted —O—$C_1$-$C_6$ alkyl, —$(CR^5R^5)_m$OH, —$(CR^5R^5)_m CO_2H$, —$(CR^5R^5)_m C(O)NH_2$, —$(CR^5R^5)_m$—$C(O)NHR^5$, $(CR^5R^5)_m N(R^5)_2$, —NH$(CR^5R^5)_m CO_2H$ or —NH$(CR^5R^5)$—$C(O)NH_2$. Each $R^5$ is independently H, F, OH, or optionally substituted $C_1$-$C_6$ alkyl; each $R^{5a}$ is independently H, or optionally substituted $C_1$-$C_6$ alkyl; and each $R^6$ is H, OH, F, optionally substituted $C_1$-$C_6$ alkyl, optionally substituted —O—$C_1$-$C_6$ alkyl, or —$N(R^{5a})_2$. In the above groups, the subscript m, will in each instance, be 1, 2, or 3.

In yet another aspect, the present invention provides compositions in which compounds of formula (I), are combined with one or more pharmaceutically acceptable excipients.

In some embodiments, the present invention contemplates methods for treating or preventing cancer in a subject (e.g., a human) comprising administering to the subject a therapeutically effective amount of at least one IDO inhibitor described herein. The present invention includes methods of treating or preventing a cancer in a subject by administering to the subject an IDO inhibitor in an amount effective to reverse or stop the progression of IDO-mediated immunosuppression. In some embodiments, the IDO-mediated immunosuppression is mediated by an antigen-presenting cell (APC).

Examples of the cancers that may be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, or Kaposi's sarcoma. Cancers that are candidates for treatment with the compounds and compositions of the present invention are discussed further hereafter.

The present invention contemplates methods of treating a subject receiving a bone marrow transplant or peripheral blood stem cell transplant by administering a therapeutically effective amount of an IDO inhibitor sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present invention contemplates methods for treating or preventing an infective disorder (e.g., a viral infection) in a subject (e.g., a human) comprising administering to the subject a therapeutically effective amount of at least one IDO inhibitor (e.g., a novel inhibitor of the instant invention). In some embodiments, the infective disorder is a viral infection (e.g., a chronic viral infection), a bacterial infection, or a parasitic infection. In certain embodiments, the viral infection is human immunodeficiency virus or cytomegalovirus. In other embodiments, the bacterial infection is a *Mycobacterium* infection (e.g., *Mycobacterium leprae* or *Mycobacterium tuberculosis*). In still other embodiments, the parasitic infection is *Leishmania donovani, Leishmania tropica, Leishmania major, Leishmania aethiopica, Leishmania mexicana, Plasmodium falciparum, Plasmodium vivax, Plasmodium ovale,* or *Plasmodium malariae*. In further embodiments, the infective disorder is a fungal infection.

In still other embodiments, the present invention contemplates methods for treating or preventing an immune-related disease, disorder or condition in a subject (e.g., a human), comprising administering to the subject a therapeutically effective amount of at least one IDO inhibitor (e.g., preferably a novel inhibitor of the instant invention). Examples of immune-related diseases, disorders and conditions are described hereafter.

Other diseases, disorders and conditions that may be treated or prevented, in whole or in part, by modulation of IDO activity are candidate indications for the IDO inhibitor compounds that are described herein.

The present invention further contemplates the use of the IDO inhibitors described herein in combination with one or more additional agents. The one or more additional agents may have some IDO modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the IDO inhibitor(s) and the one additional agent(s) may be in the form of a single composition or multiple compositions, and the treatment modalities may be administered concurrently, sequentially, or through some other regimen. By way of example, the present invention contemplates a treatment regimen wherein a radiation phase is followed by a chemotherapeutic phase. The combination therapy may have an additive or synergistic effect. Other benefits of combination therapy are described hereafter.

In some embodiments, the present invention further comprises the use of the IDO inhibitors described herein in combination with bone marrow transplantation, peripheral blood stem cell transplantation, or other types of transplantation therapy.

In particular embodiments, the present invention contemplates the use of the inhibitors of IDO function described herein in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors. Immune checkpoint inhibitors, and combination therapy therewith, are discussed in detail elsewhere herein.

In other embodiments, the present invention provides methods for treating cancer in a subject, comprising administering to the subject a therapeutically effective amount of at least one IDO inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of the IDO inhibitors in combination with other agents known in the art (e.g., arsenic trioxide) and other chemotherapeutic agents developed in the future.

In some embodiments drawn to methods of treating cancer, the administration of a therapeutically effective amount of an IDO inhibitor in combination with at least one chemotherapeutic agent results in a cancer survival rate greater than the cancer survival rate observed by administering either alone. In further embodiments drawn to methods of treating cancer, the administration of a therapeutically effective amount of an IDO inhibitor in combination with at least one chemotherapeutic agent results in a reduction of tumor size or a slowing of tumor growth greater than reduction of the tumor size or tumor growth observed by administration of one agent alone.

In further embodiments, the present invention contemplates methods for treating or preventing cancer in a subject, comprising administering to the subject a therapeutically effective amount of at least one IDO inhibitor and at least one signal transduction inhibitor (STI). In a particular embodiment, the at least one STI is selected from the group consisting of bcr/abl kinase inhibitors, epidermal growth factor (EGF) receptor inhibitors, her-2/ncu receptor inhibitors, and farnesyl transferase inhibitors (FTIs). Other candidate STI agents are set forth elsewhere herein.

The present invention also contemplates methods of augmenting the rejection of tumor cells in a subject comprising administering an IDO inhibitor in conjunction with at least one chemotherapeutic agent and/or radiation therapy, wherein the resulting rejection of tumor cells is greater than that obtained by administering either the IDO inhibitor, the chemotherapeutic agent or the radiation therapy alone.

In further embodiments, the present invention provides methods for treating cancer in a subject, comprising administering to the subject a therapeutically effective amount of at least one IDO inhibitor and at least one immunomodulator other than an IDO inhibitor. In particular embodiments, the at least one immunomodulator is selected from the group consisting of CD40L, B7, B7RP1, ant-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-α/-β, M-CSF, IL-3, GM-CSF, IL-13, and anti-IL-10. Other candidate immunomodulator agents are set forth elsewhere herein.

The present invention contemplates embodiments comprising methods for treating or preventing an infective disorder (e.g., a viral infection) in a subject (e.g., a human) comprising administering to the subject a therapeutically effective amount of at least one IDO inhibitor and a therapeutically effective amount of an anti-infective agent(s).

In some embodiments of the present invention, the additional therapeutic agent is a cytokine, including, for example, granulocyte-macrophage colony stimulating factor (GM-CSF) or flt3-ligand. The present invention also contemplates methods for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackie virus, and human immunodeficiency virus (HIV). The use of the IDO inhibitors described herein to treat (either alone or as a component of combination therapy) infection is discussed further hereafter.

In additional embodiments, treatment of an infective disorder is effected through the co-administration of a vaccine in combination with administration of a therapeutically effective amount of an IDO inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-CSF). In particular embodiments, the vaccine includes one or more immunogenic peptides and/or dendritic cells.

In some embodiments, the present invention contemplates methods of using the IDO inhibitors disclosed herein in combination with one or more antimicrobial agents.

In certain embodiments drawn to treatment of an infection by administering an IDO inhibitor and at least one additional therapeutic agent, a symptom of infection observed after administering both the IDO inhibitor and the additional therapeutic agent is improved over the same symptom of infection observed after administering either alone.

In some embodiments, the symptom of infection observed may be reduction in viral load, increase in $CD4^+$ T cell count, decrease in opportunistic infections, increased survival time, eradication of chronic infection, or a combination thereof.

DETAILED DESCRIPTION OF THE INVENTION

Figure 1A:
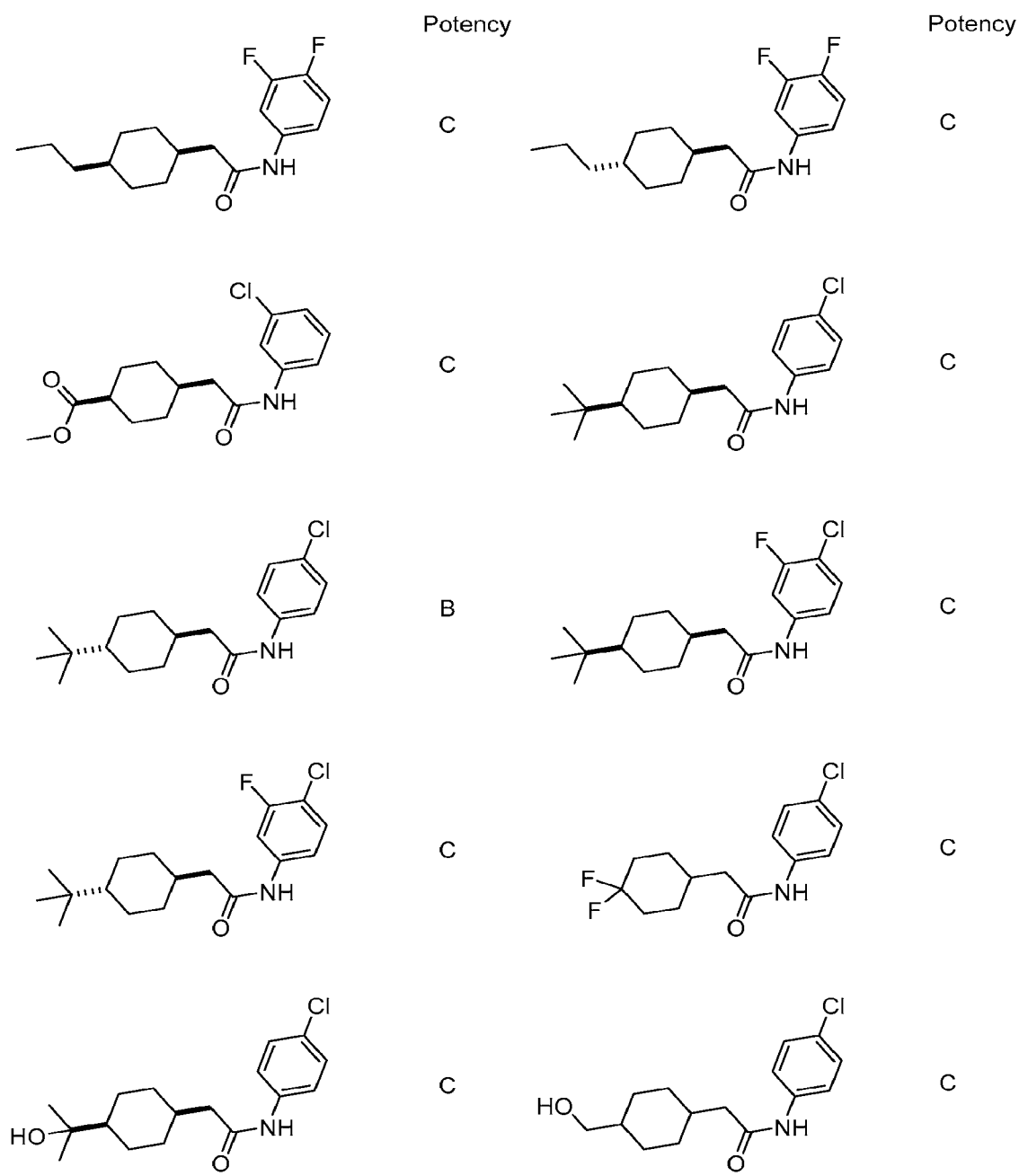
FIGS. 1A-1BB provide structures and biological activity for compounds described herein. The activity for compounds described herein is provided in FIG. 1A-1BB, wherein potency levels are provided as follows: (IDO potency: $IC_{50}$: A<0.1 µM; B<1 µM; C<10 µM).

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology such as "solely", "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

Immune dysregulation is intimately associated with tumor evasion of the host immune system, resulting in tumor growth and progression. Traditional treatment approaches comprising chemotherapy and radiotherapy are generally difficult for the patient to tolerate and become less effective as tumors evolve to survive such treatments. By utilizing the patient's own immune system to identify and eliminate tumor cells, immunotherapy has the benefit of reduced toxicity. As upregulation of the immunoregulatory enzyme indoleamine 2,3-dioxygenase comprises one mechanism manipulated by tumors to promote growth, agents (e.g., small molecule compounds) that inhibit enzyme activity present a promising avenue for prophylaxis and/or treatment.

In addition, a large body of experimental data indicates a role for IDO inhibition in immunosuppression, tumor resistance and/or rejection, chronic infections, HIV-infection, and autoimmune diseases or disorders. Inhibition of IDO may also be an important treatment strategy for patients with neurological or neuropsychiatric diseases or disorders such as depression. The compounds, compositions and methods herein address the need for new classes of IDO modulators.

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycyclic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A cycloheteroalkyl group can be attached to the remainder of the molecule through a ring carbon or a heteroatom.

As used herein, a wavy line, "〰", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation:

—C(O)NH— or —NHC(O)—, and similarly, "—O—CH$_2$CH$_2$—" is meant to include both —O—CH$_2$CH$_2$— and —CH$_2$CH$_2$—O—. The terms "alkoxy", "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "halo" or "halogen", by themselves or as part of another substituent, mean, unless otherwise stated, a fluorine, chlorine, bromine, or iodine atom.

Additionally, terms such as "haloalkyl", are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl", "aryl" and "heteroaryl"), in some embodiments, will be optionally substituted. Selected substituents for each type of radical are provided below.

Optional substituents for the alkyl radicals (including those groups often referred to as alkylene, alkenyl, alkynyl and cycloalkyl) can be a variety of groups selected from: halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted C$_{1-8}$ alkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M. et al., "Pharmaceutical Salts", *J. Pharm. Sci.*, 66:1-19 (1977)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. "Substantially free of" another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as, for example, tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of IDO, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", "treatment" and the like refer to a course of action (such as administering an inhibitor of IDO or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an IDO inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of and IDO inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

As used herein, the terms "IDO inhibitor", "IDO blocker" and terms similar thereto refer to agents capable of inhibiting the activity of IDO, thereby reversing IDO-mediated immunosuppression. An IDO inhibitor may be a competitive, noncompetitive, or irreversible IDO inhibitor. "A competitive IDO inhibitor" is a compound that reversibly inhibits IDO enzyme activity at the catalytic site; "a noncompetitive IDO Inhibitor" is a compound that reversibly inhibits IDO enzyme activity at a non-catalytic site; and "an irreversible IDO inhibitor" is a compound that irreversibly eliminates IDO enzyme activity by forming a covalent bond (or other stable means of inhibiting enzyme function) with the enzyme. A number of IDO inhibitors are commercially available (e.g., 5-Br-4-Cl-indoxyl 1,3-diacetate and 1-methyl-DL-tryptophan (1 MT); both available from Sigma-Aldrich, St. Louis, Mo.) and may be used as, for example, "tool" or "reference" compounds.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex".

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of IDO, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen et al., *Analyt. Biochem.*, 107:220-239 (1980)).

The term "response", for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide", "peptide", and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Indoleamine 2,3-Dioxygenase

As previously alluded to, IDO is an immune regulatory enzyme that is normally expressed in tumor cells and in activated immune cells. IDO is one of several immune response checkpoints that are involved in tumor immune escape; thus, IDO inhibitors disrupt mechanisms by which tumors evade the body's normal immune system.

IDO down-regulates the immune response mediated through oxidation of tryptophan. This results in inhibition of T-cell activation and induction of T-cell apoptosis, creating an environment in which tumor-specific cytotoxic T lymphocytes are rendered functionally inactive or are no longer able to attack a subject's cancer cells. Therefore, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO modulators.

The expression of IDO is modulated by a complex array of signals, thus implicating a number of different mechanisms of actions. For example, IDO may be induced by inhibition of DNA methyl transferases or histone deacetylases. The NF-κB signaling pathway has also been implicated in IDO function. Inhibiting NF-κB activity blocks IDO expression and produces robust anti-tumor responses that are both T cell- and IDO-dependent; alternatively, NF-κB activation (which may be effected by various factors such as interferon-γR1/-γR2 signaling and toll-like-receptor activation) induces IDO gene expression.

Other mechanisms are involved with modulation of IDO function. By way of example, inhibitors of reactive oxidative species (ROS) may effect stabilization of IDO; IDO levels may be modulated by inhibition or activation of pathways that are both downstream and upstream of IDO; and activation of interferon-γ can activate an autocrine induction of 1DO.

Studies indicate that the IDO pathway is active in many cancers, both within tumor cells as a direct defense against T cell attack, and also within antigen-presenting cells (APCs) in tumor-draining lymph nodes resulting in peripheral tolerance to tumor-associated antigens (TAAs). Cancers may use the IDO pathway to facilitate survival, growth, invasion, and metastasis of malignant cells expressing TAAs that might otherwise be recognized and attacked by the immune system.

As alluded to herein, tryptophan catabolism in tumor tissue by the rate-limiting enzyme IDO provides an opportunity for the use of IDO inhibitors as a therapeutic alternative to, or an additive with, conventional chemotherapy. However, certain cancers are capable of catabolizing tryptophan but are largely IDO-negative. Recent studies indicate that the alternative enzymatic pathway of tryptophan catabolism involving tryptophan-2,3-dioxygenase (TDO) is also relevant in cancer. TDO, which is considered responsible for regulating systemic tryptophan levels in the liver, is constitutively expressed in some cancers and is also capable of suppressing antitumor immune responses (See, e.g., Platten, M. et al., *Cancer Res.*, 72(21):5435-5440 (Nov. 1, 2012)).

IDO is expressed in a wide variety of human tumors and tumor cell lines as well as in host APCs, which correlates with a worse clinical prognosis. Therefore, inhibition of IDO may improve survival in cancer patients with IDO-mediated immunosuppression. In comparison, TDO is expressed in a wide variety of human tumors and tumor cell lines, and expression of TDO is evident in advanced human glioblastomas. The identification of tumors expressing high levels of IDO or TDO may allow more selective inhibition of the tryptophan-regulated immunosuppressive pathways. Alternatively, compounds inhibiting both IDO and TDO could provide the greatest coverage to prevent tumor escape by compensatory expression of the other tryptophan-degrading enzyme. Therefore, the use of dual IDO/TDO inhibitors or combinations of IDO- and TDO-specific inhibitors may prove to be a superior treatment alternative in immunotherapy of cancer to block immunosuppression mediated by tryptophan metabolism.

Although a precise understanding of the underlying mechanism of action by which the compounds of the present invention effect their activity is not required to practice the invention, the compounds (or a subset thereof) are believed to inhibit IDO function. Alternatively, the compounds (or a subset thereof) may inhibit TDO function. The compounds (or a subset thereof) may also have inhibitory activity on both IDO and TDO function. Although the compounds of the invention are generally referred to herein as IDO inhibitors, it is to be understood that the term "IDO inhibitors" encompasses compounds that act individually through inhibition of TDO or IDO, and/or compounds that act through inhibition of both IDO and TDO.

Identification of IDO Inhibitors Possessing Desirable Characteristics

The present invention is drawn, in part, to the identification of inhibitors of IDO with at least one property or characteristic that is of therapeutic relevance. Candidate inhibitors may be identified by using, for example, an art-accepted assay or model, examples of which are described herein.

After identification, candidate inhibitors can be further evaluated by using techniques that provide data regarding characteristics of the inhibitors (e.g., pharmacokinetic parameters, means of determining solubility or stability). Comparisons of the candidate inhibitors to a reference standard (which may the "best-of-class" of current inhibitors) are indicative of the potential viability of such candidates.

COMPOUNDS OF THE INVENTION

As noted above, the present invention provides compounds represented by formula (I):

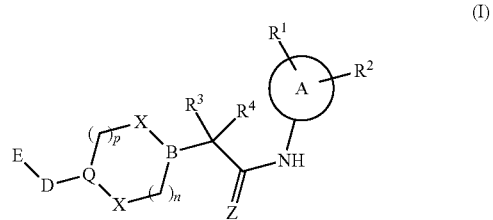

or a pharmaceutically acceptable salt, hydrate or solvate thereof, wherein, the subscript n is 1 or 0; the subscript p is 1 or 0. In formula (I), the ring designated as A is phenyl, 5- or 6-membered heteroaryl, or $C_{5-7}$ cycloalkyl; Z is O; B is N, $C(OR^{5a})$, or $C(R^{3a})$; each X is independently $NR^{5a}$, O, $CHR^5$, $C(O)$, or $CH(OR^{5a})$; Q is N, C(CN) or $CR^6$; and D is a bond, O, $C(R^5)_2$, $NR^{5a}$, or $N(R^{5a})_2$. The letter E may be absent or is hydrogen, optionally substituted $C_1$-$C_6$ alkyl, optionally substituted phenyl, optionally substituted $C_3$-$C_6$ cycloalkyl, optionally substituted 3- to 6-membered cycloheteroalkyl, or optionally substituted monocyclic heteroaryl. Each of $R^1$ and $R^2$ are independently hydrogen, halogen, optionally substituted $C_1$-$C_4$ haloalkyl, optionally substituted $C_3$-$C_6$ cycloalkyl, optionally substituted 3- to 6-membered cycloheteroalkyl, optionally substituted phenyl, optionally substituted heteroaryl, optionally substituted $C_1$-$C_4$ alkyl, optionally substituted $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl. Each of $R^3$, $R^{3a}$ and $R^4$ are independently hydrogen, optionally substituted $C_1$-$C_6$ alkyl, optionally substituted $C_1$-$C_6$ haloalkyl, fluorine, OH, CN, $CO_2H$, C(O)$NH_2$, $N(R^5)_2$, optionally substituted —O—$C_1$-$C_6$ alkyl, —$(CR^5R^5)_m$OH, —$(CR^5R^5)_m$ $CO_2H$, —$(CR^5R^5)_m$C(O)$NH_2$, —$(CR^5R^5)_m$C(O)NHR$^5$, —$(CR^5R^5)_m$N(R$^5$)$_2$, —NH$(CR^5R^5)_m$CO$_2$H or —NH$(CR^5R^5)_m$—C(O)NH$_2$. Each $R^5$ is independently H, F, OH, or optionally substituted $C_1$-$C_6$ alkyl; each $R^{5a}$ is independently H, or optionally substituted $C_1$-$C_6$ alkyl; and each $R^6$ is H, OH, F, optionally substituted $C_1$-$C_6$ alkyl, optionally substituted —O—$C_1$-$C_6$ alkyl, or —N(R$^{5a}$)$_2$. In the above groups, the subscript m, will in each instance, be 1, 2, or 3.

In one group of embodiments, compounds of formula (I) are provided wherein Q is C(CN) or $CR^6$; and E is hydrogen, optionally substituted $C_1$-$C_6$ alkyl, optionally substituted phenyl, optionally substituted $C_3$-$C_6$ cycloalkyl, optionally substituted 3- to 6-membered cycloheteroalkyl, or optionally substituted monocyclic heteroaryl.

In another group of embodiments, compounds are provided having the formula:

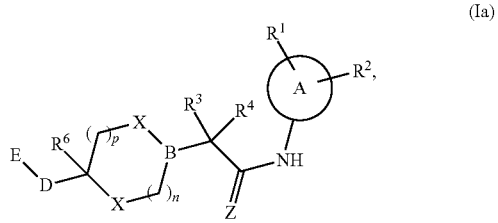

wherein the letters A, B, D, E, X and Z; the symbols $R^1$, $R^2$, $R^3$, $R^4$ and $R^6$; and the subscripts n and p, all have the meaning provided with reference to formula (I).

In still another group of embodiments, compounds are provided having the formula:

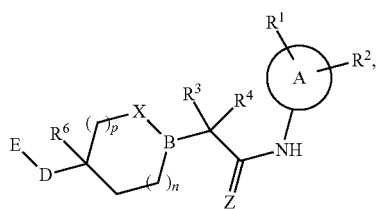
(Ib)

wherein the letters A, B, D, E, X and Z; the symbols $R^1$, $R^2$, $R^3$, $R^4$ and $R^6$; and the subscripts n and p, all have the meaning provided with reference to formula (I).

In yet another group of embodiments, compounds are provided having the formula:

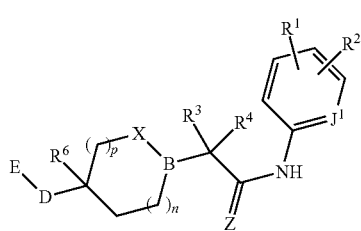
(Ic)

wherein $J^1$ is CH, N or optionally $C(R^2)$ when $R^2$ is attached to the ring vertex identified as $J^1$, and the remaining letters, symbols and subscripts have the meanings provided for formula (I). In some selected embodiments of formula (Ic), compounds are provided having the formula (Ic1), (Ic2), (Ic3), (Ic4), (Ic5), (Ic6), or (Ic7):

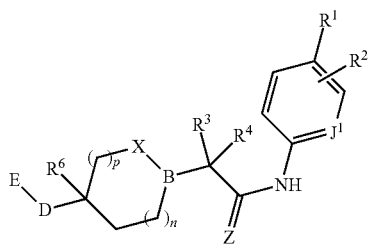
(Ic1)

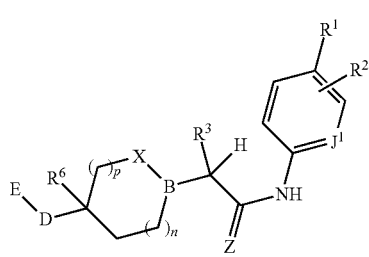
(Ic2)

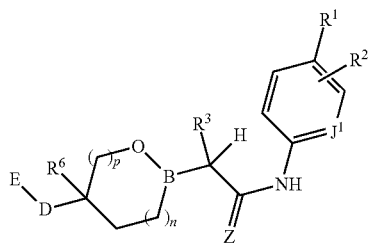
(Ic3)

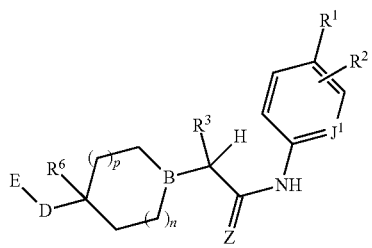
(Ic4)

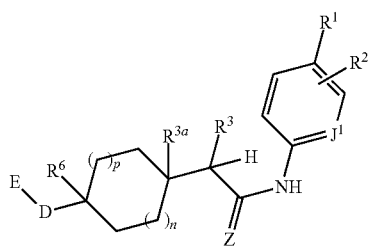
(Ic5)

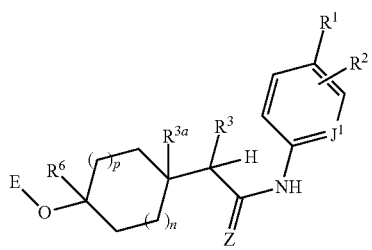
(Ic6)

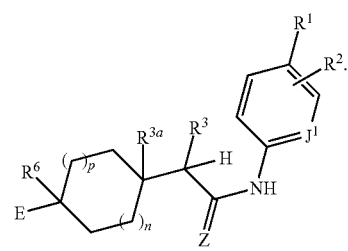
(Ic7)

In other selected embodiments of formula (Ic), compounds are provided having the formula:

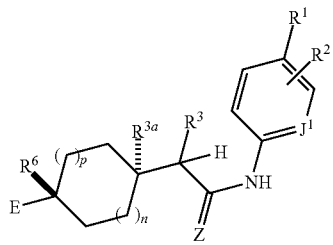
(Ic8)

which is substantially free of other isomers at the carbon atoms to which each of $R^{3a}$ and $R^6$ are attached.

In other selected embodiments of formula (Ic), compounds are provided having the formula:

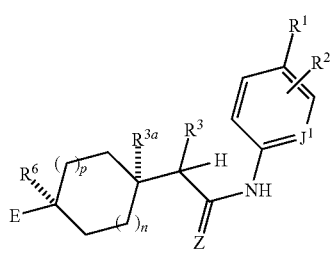
(Ic9)

which is substantially free of other isomers at the carbon atoms to which each of $R^{3a}$ and $R^6$ are attached.

In other selected embodiments of formula (Ic), compounds are provided having the formula (Id):

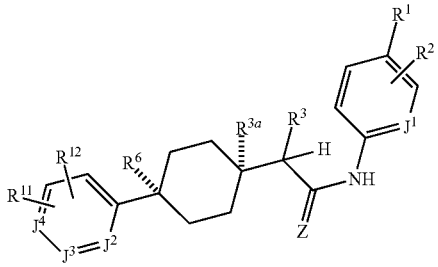
(Id)

wherein $J^2$ is N or CH, or optionally is $C(R^{11})$, when $R^{11}$ is attached to the ring vertex identified as $J^2$; $J^3$ is N or CH, or optionally is $C(R^{11})$, when $R^{11}$ is attached to the ring vertex identified as $J^3$; $J^4$ is N or CH, or optionally is $C(R^{12})$, when $R^{12}$ is attached to the ring vertex identified as $J^4$; and wherein $R^{11}$ and $R^{12}$ are independently hydrogen, halogen, optionally substituted $C_1$-$C_4$ haloalkyl, optionally substituted $C_3$-$C_6$ cycloalkyl, optionally substituted 3- to 6-membered cycloheteroalkyl, optionally substituted phenyl, optionally substituted heteroaryl, optionally substituted $C_1$-$C_4$ alkyl, optionally substituted $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl. The compounds of formula (Id) are substantially free of other isomers at the carbon atoms to which each of $R^{3a}$ and $R^6$ are attached.

In some selected embodiments of formula (Id), compounds are provided having the formula (Id1), (Id2), (Id3), (Id4), (Id5) and (Id6):

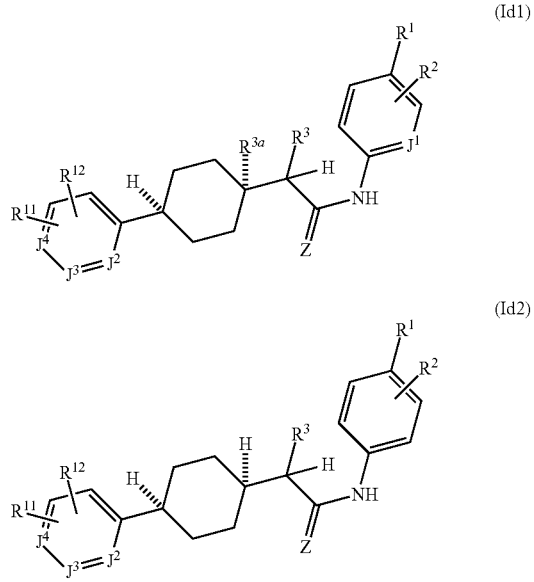
(Id1)

(Id2)

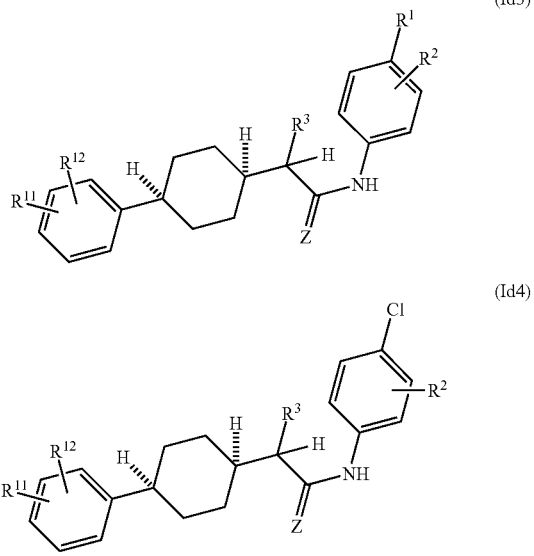
(Id3)

(Id4)

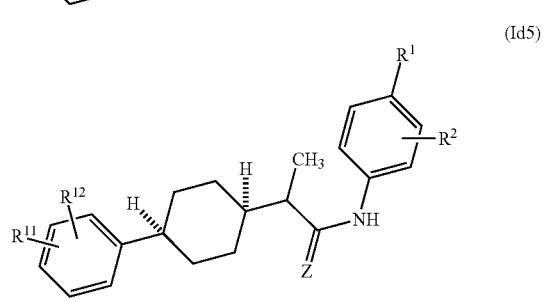
(Id5)

-continued

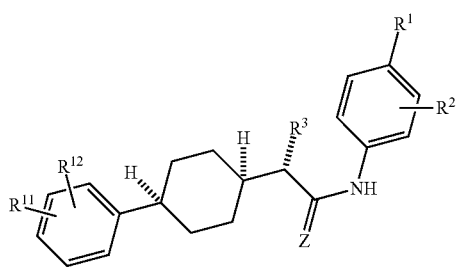

(Id6)

each of which is substantially free of other isomers at the stereocenters of the cyclohexane ring; and wherein Z, $R^1$, $R^2$, $R^3$, and $R^{3a}$, all have the meanings provided with reference to formula (I); and each of $J^1$, $J^2$, $J^3$, $J^4$, $R^{11}$ and $R^{12}$ have the meanings provided with reference to formula (Ic) and (Id).

In some selected embodiments, compounds of formulae (Ie) are provided:

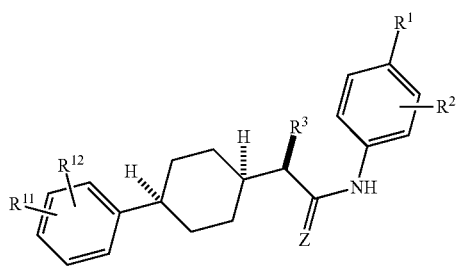

(Ie)

which is substantially free of other isomers at each of the three stereocenters shown, and wherein each of the letters and symbols have the meanings provided with reference to formula (I) and (Id).

In other selected embodiments, compounds of formulae (If) are provided:

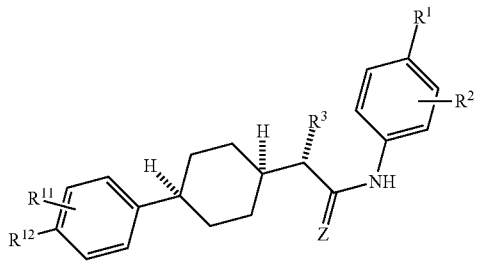

(If)

wherein $R^1$ is Cl, F, optionally substituted phenyl, or CN; and which is substantially free of other isomers at each of the three stereocenters shown; and wherein the remaining letters and symbols have the meanings provided with reference to formulae (I) and (Id).

In other selected embodiments, compounds of formulae (Ig) are provided:

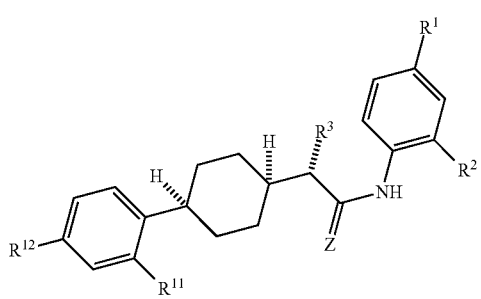

(Ig)

wherein $R^{11}$ is H or F; and $R^{12}$ is H or —O—$C_1$-$C_3$ alkyl; and wherein the remaining letters and symbols have the meanings provided with reference to formulae (I) and (Id); and which is substantially free of other isomers at each of the three stereocenters shown.

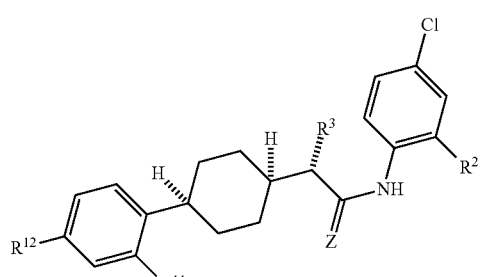

In some selected embodiments, compounds of formula (Ig) are provided having the subformulae (Ig1), (Ig2), (Ig3) or (Ig4), each of which is substantially free of other isomers at each of the stereocenters shown:

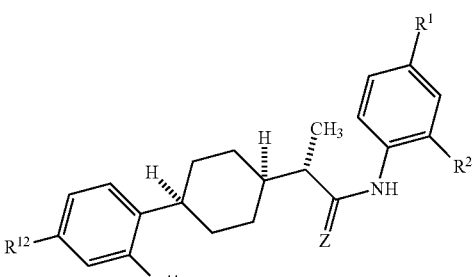

(Ig1)

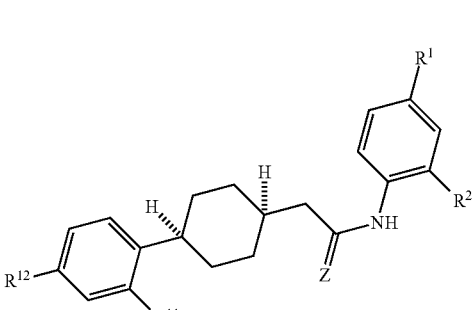

(Ig2)

-continued

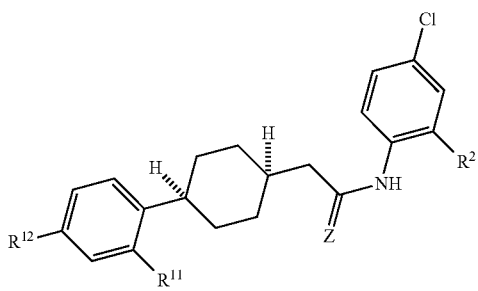

(Ig3)

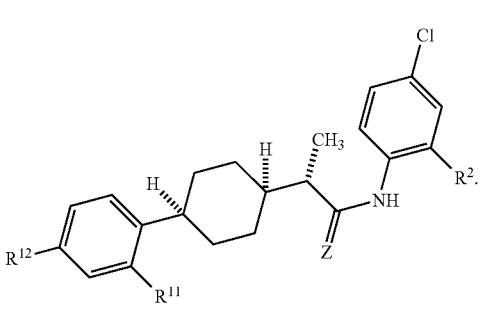

(Ig4)

In still other selected embodiments, compounds of formula (Ih) are provided

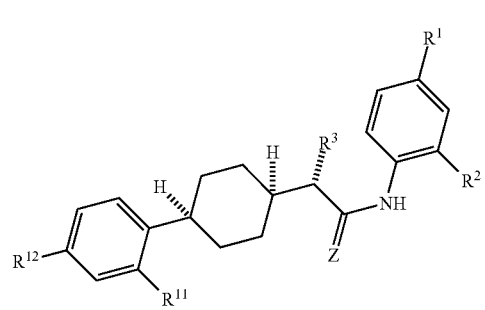

(Ih)

wherein $R^{11}$ is H or F; and $R^{12}$ is $CO_2H$, $C(O)NH_2$, $—(CR^5R^5)_mCO_2H$ or $—(CR^5R^5)_mC(O)NH_2$; and the remaining letters and symbols have the meanings provided with reference to formula (I), and wherein the compound is substantially free of other isomers at each of the three stereocenters shown.

Figure 1B:
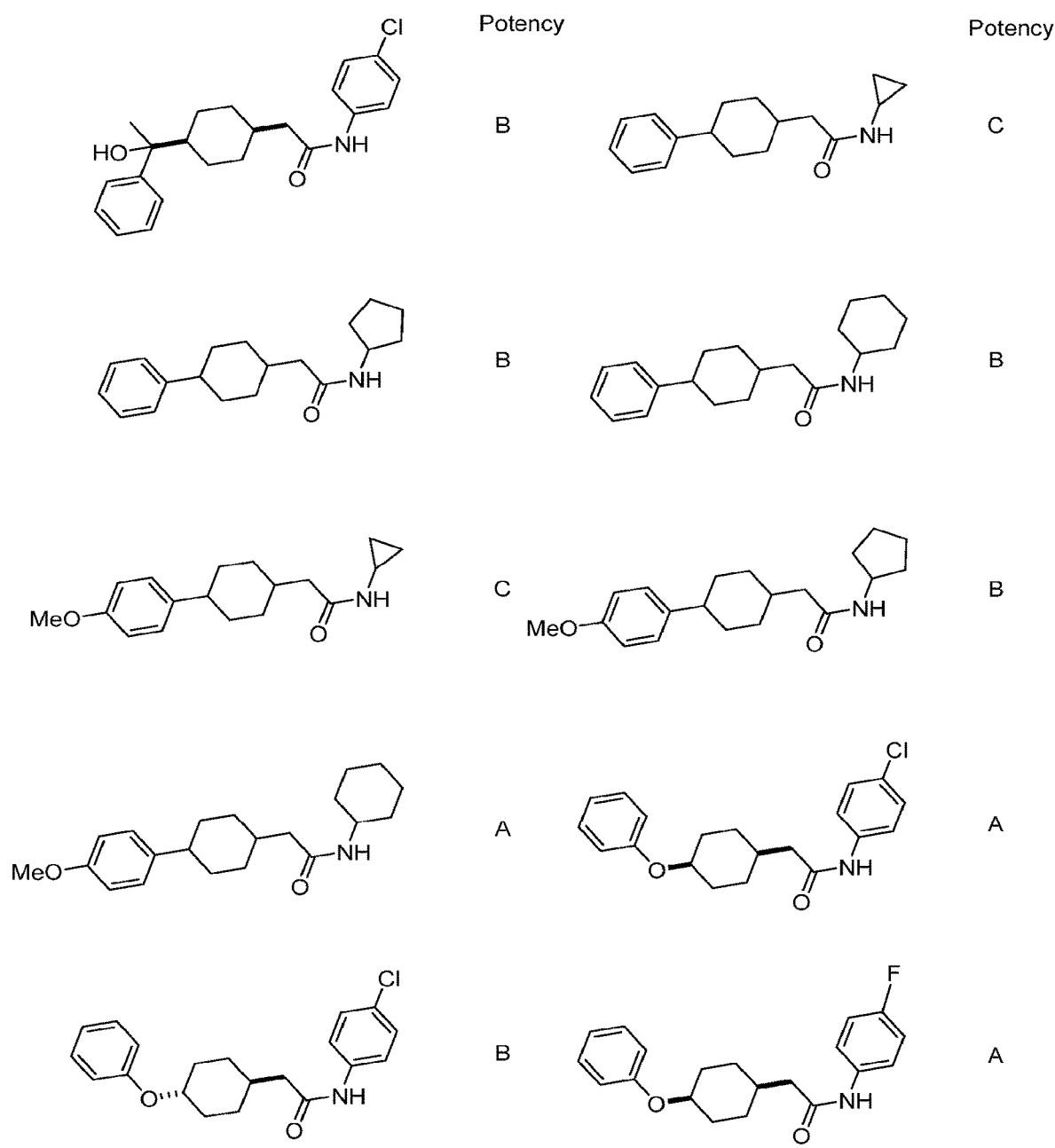
Figure 1C:
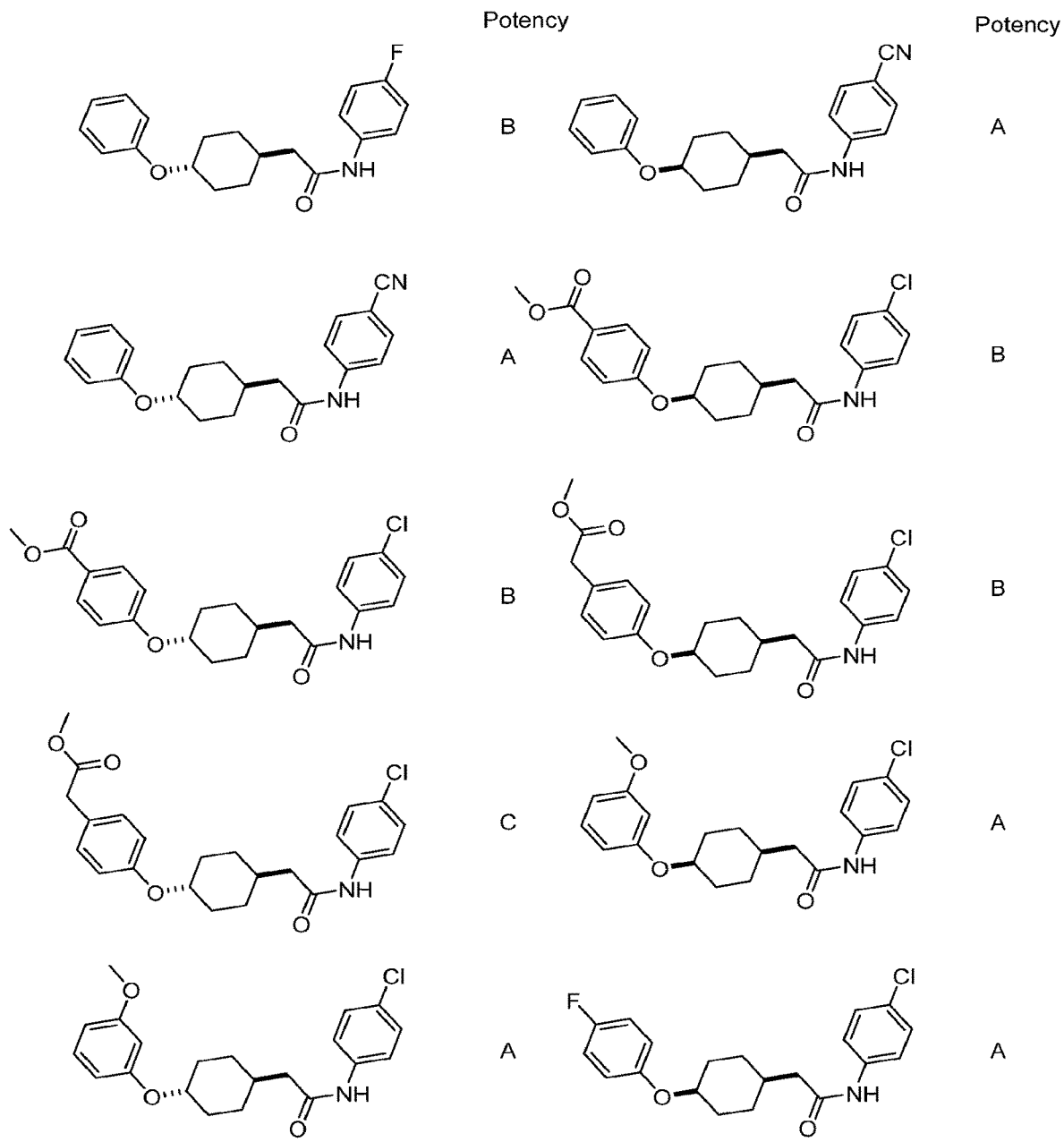
Figure 1D:
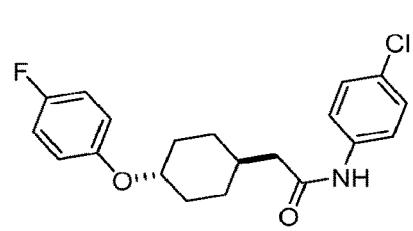
Figure 1D:
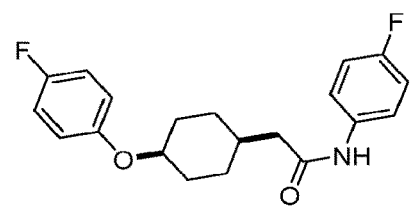
Figure 1D:
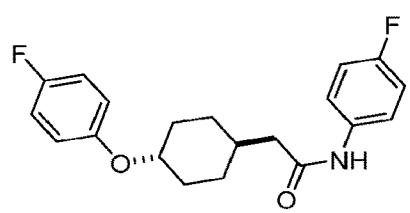
Figure 1D:
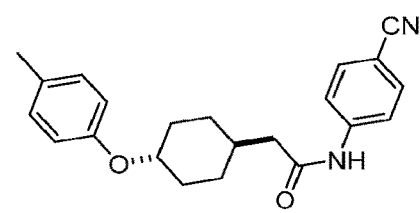
Figure 1D:
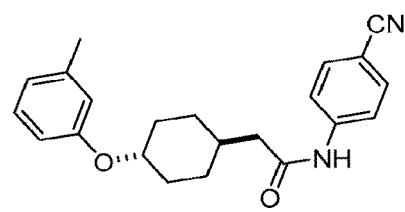
Figure 1D:
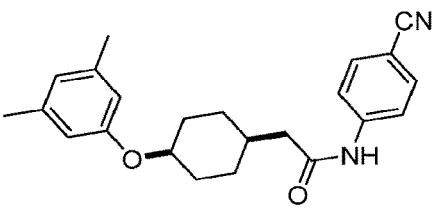
Figure 1D:
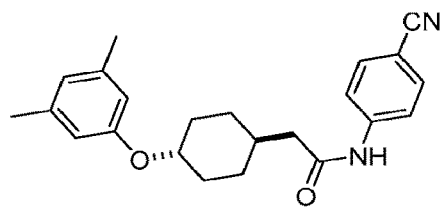
Figure 1D:
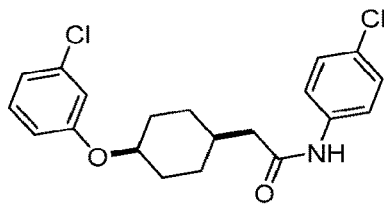
Figure 1D:
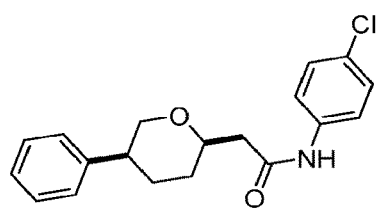
Figure 1E:
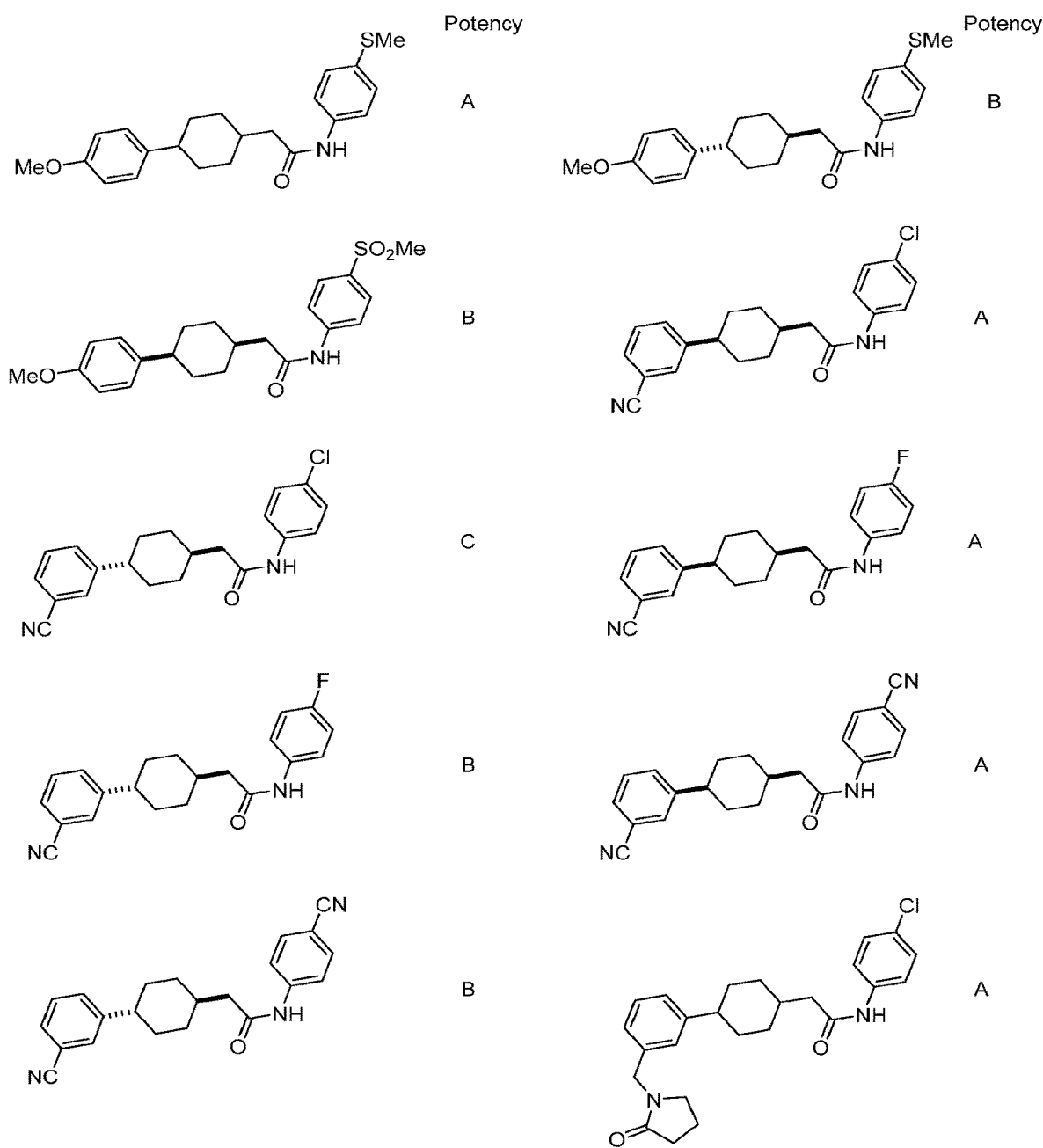
Figure 1F:
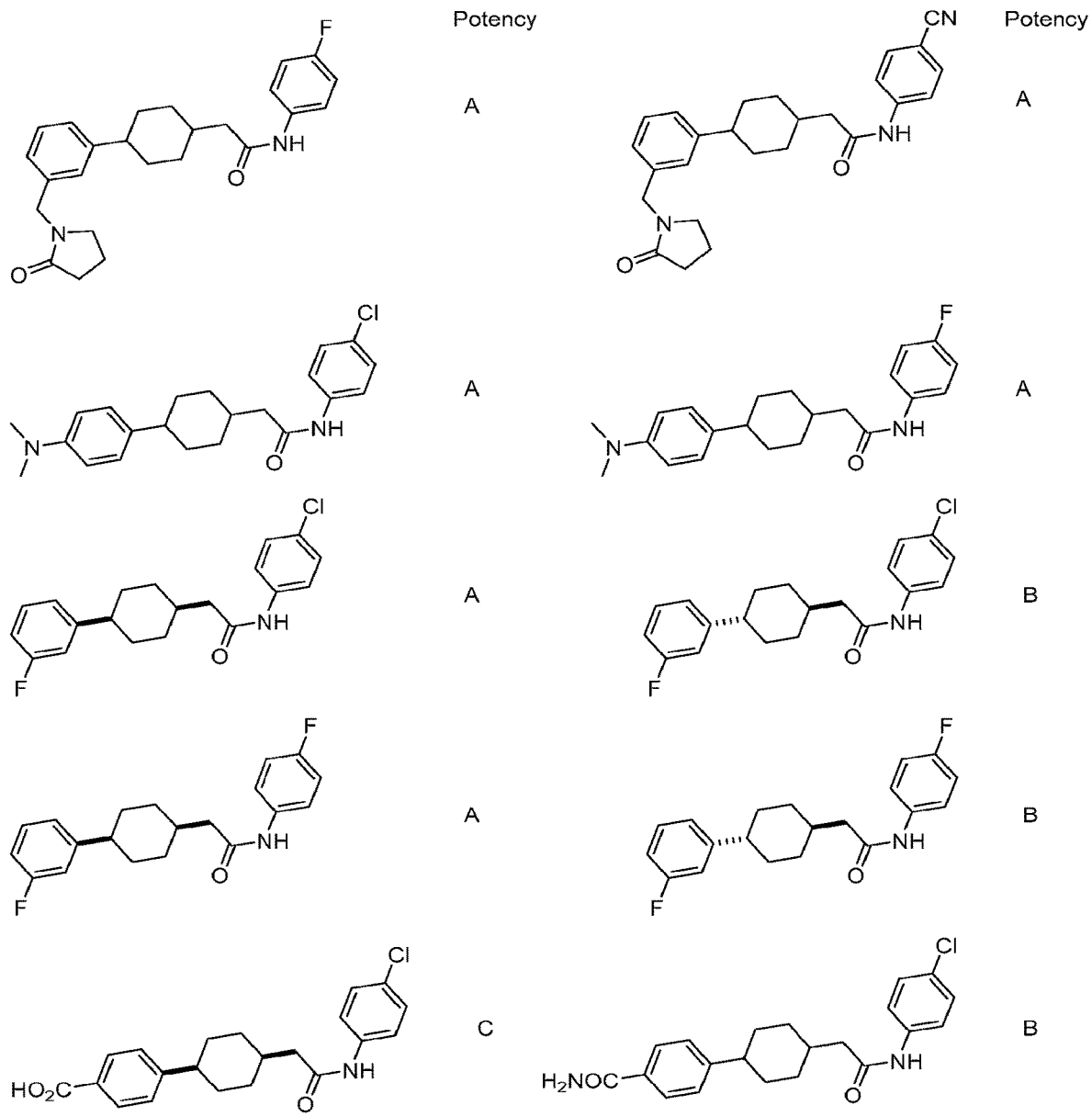
Figure 1G:
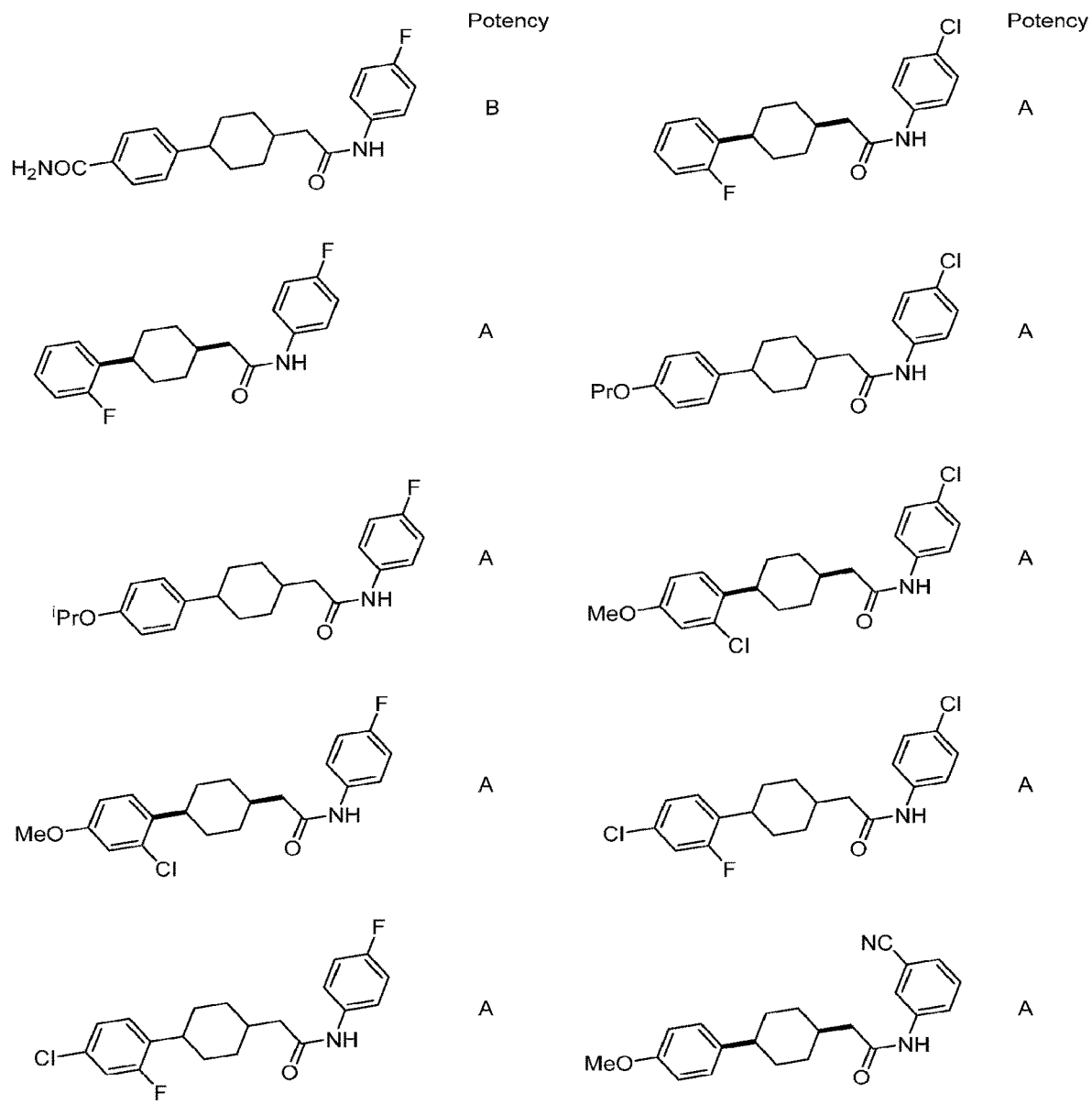
Figure 1H:
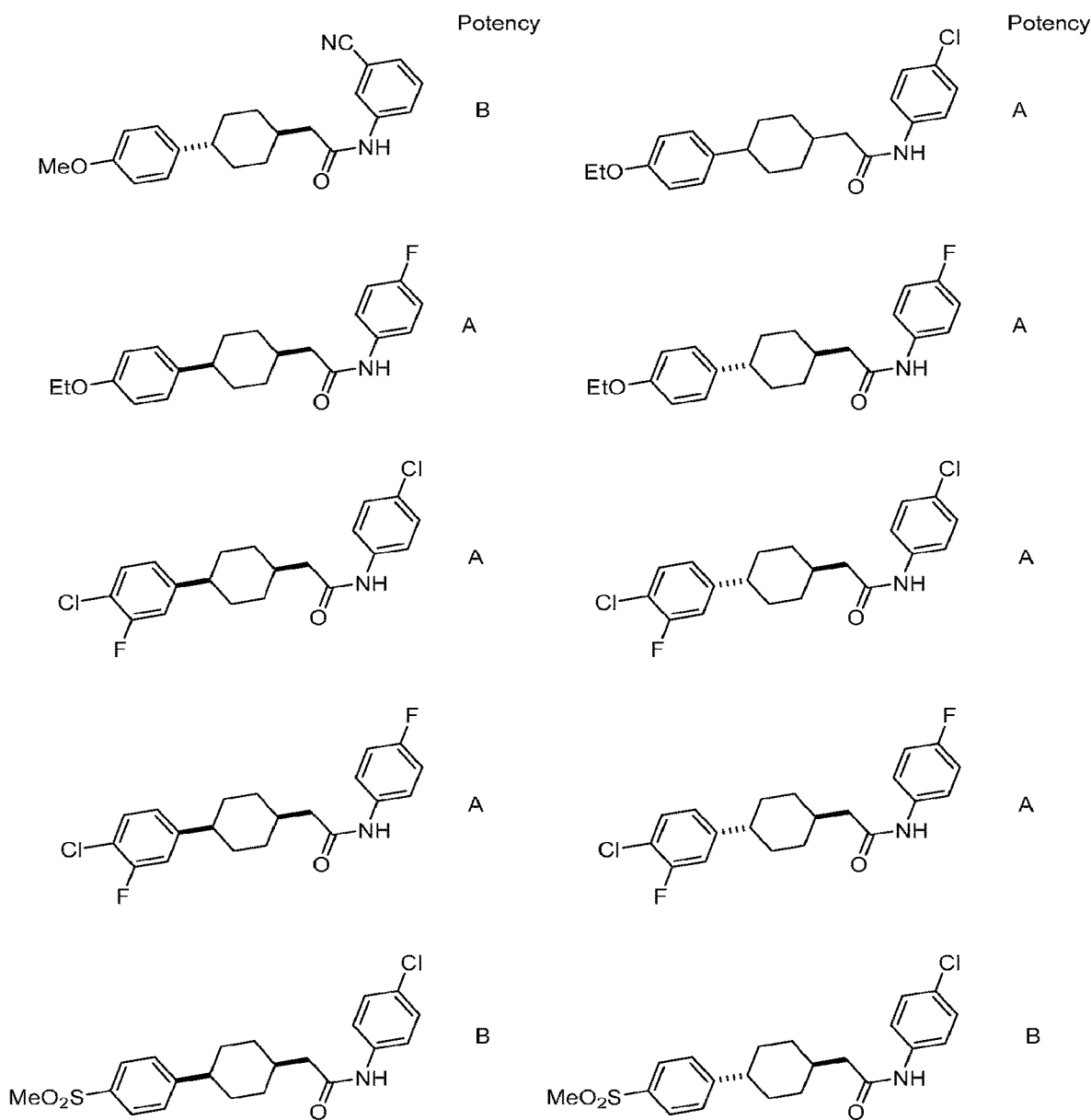
Figure 1I:
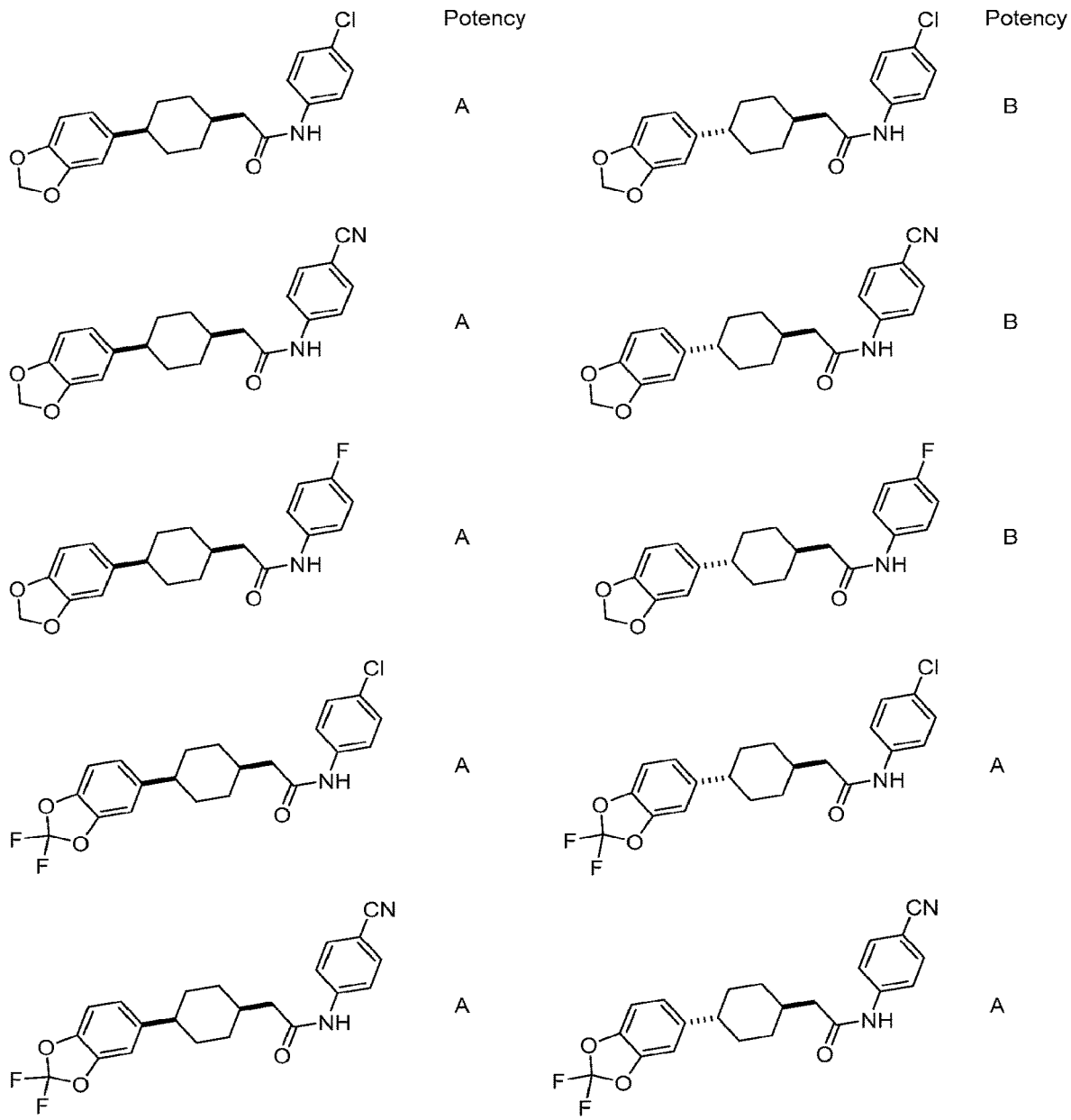
Figure 1J:
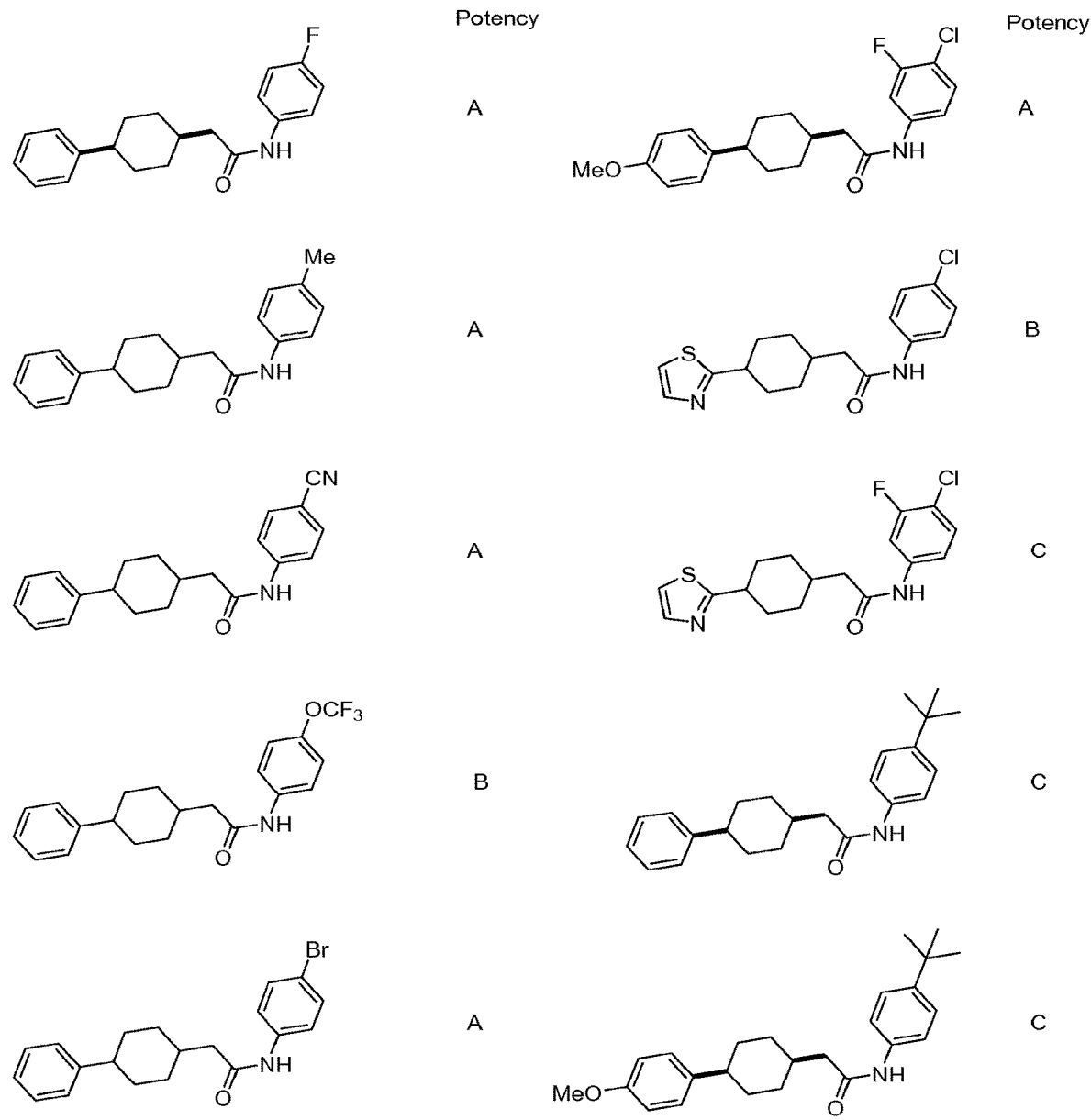
Figure 1K:
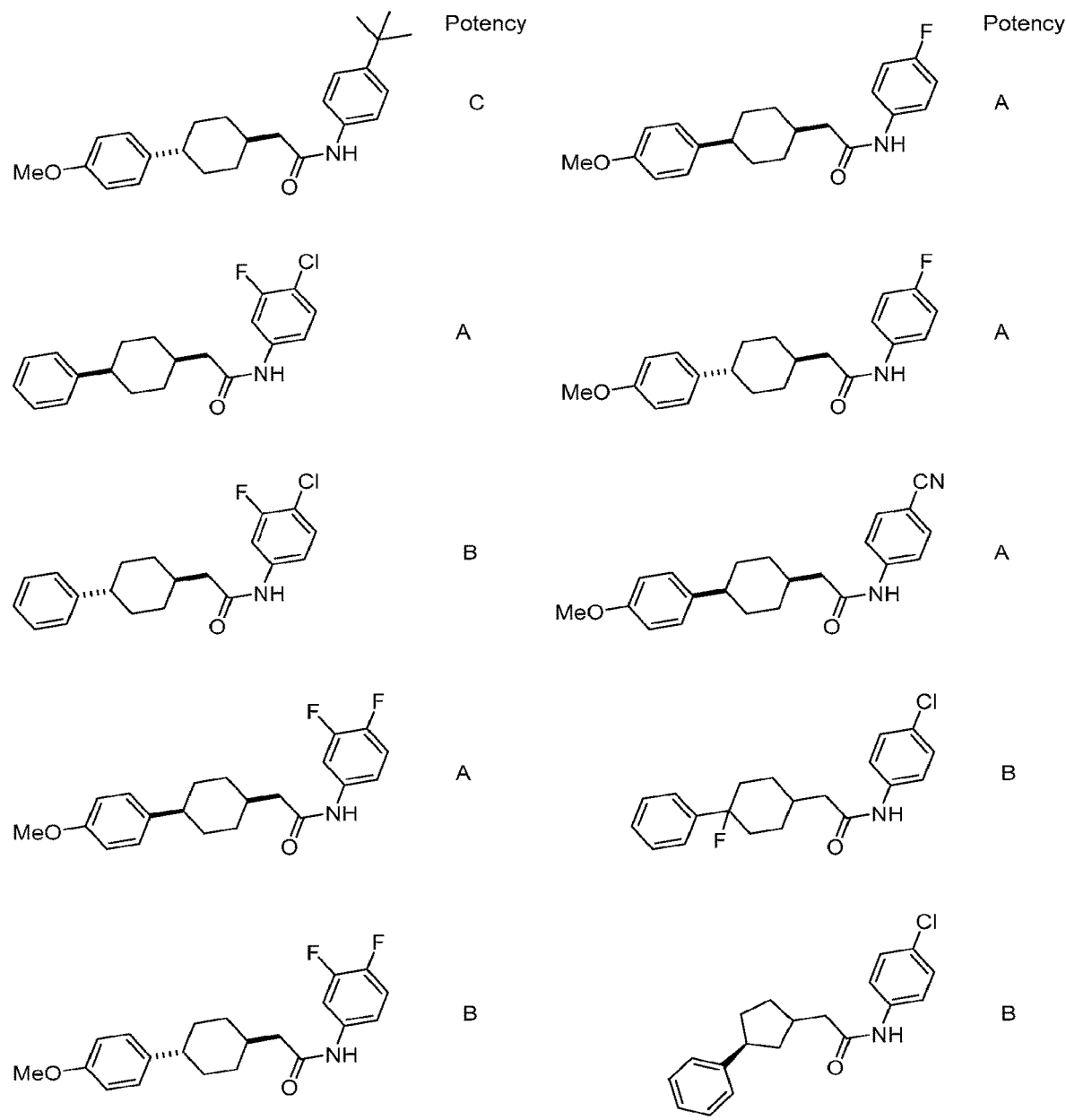
Figure 1L:
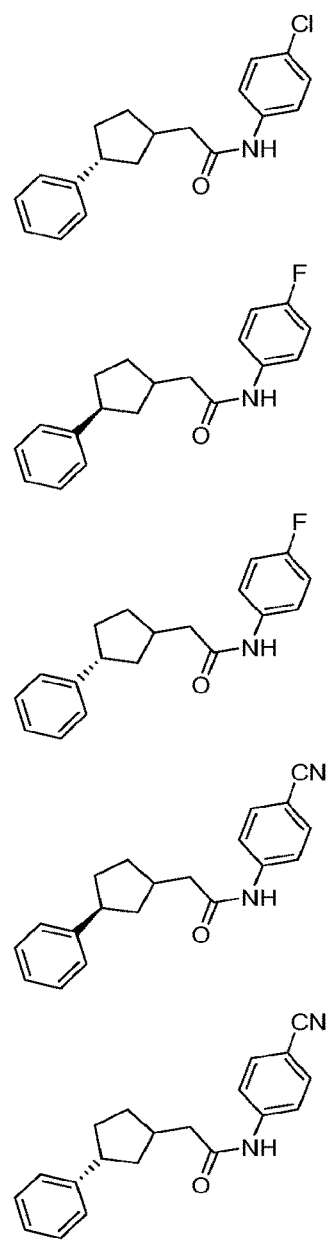
Figure 1L:
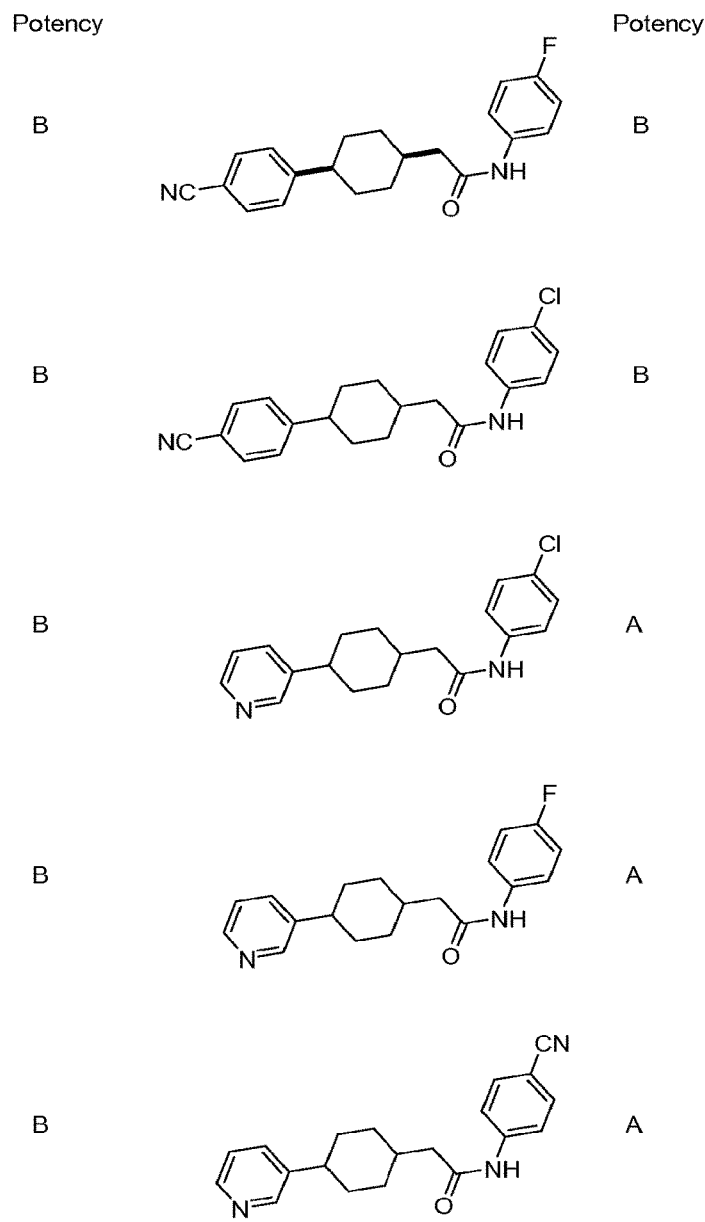
Figure 1M:
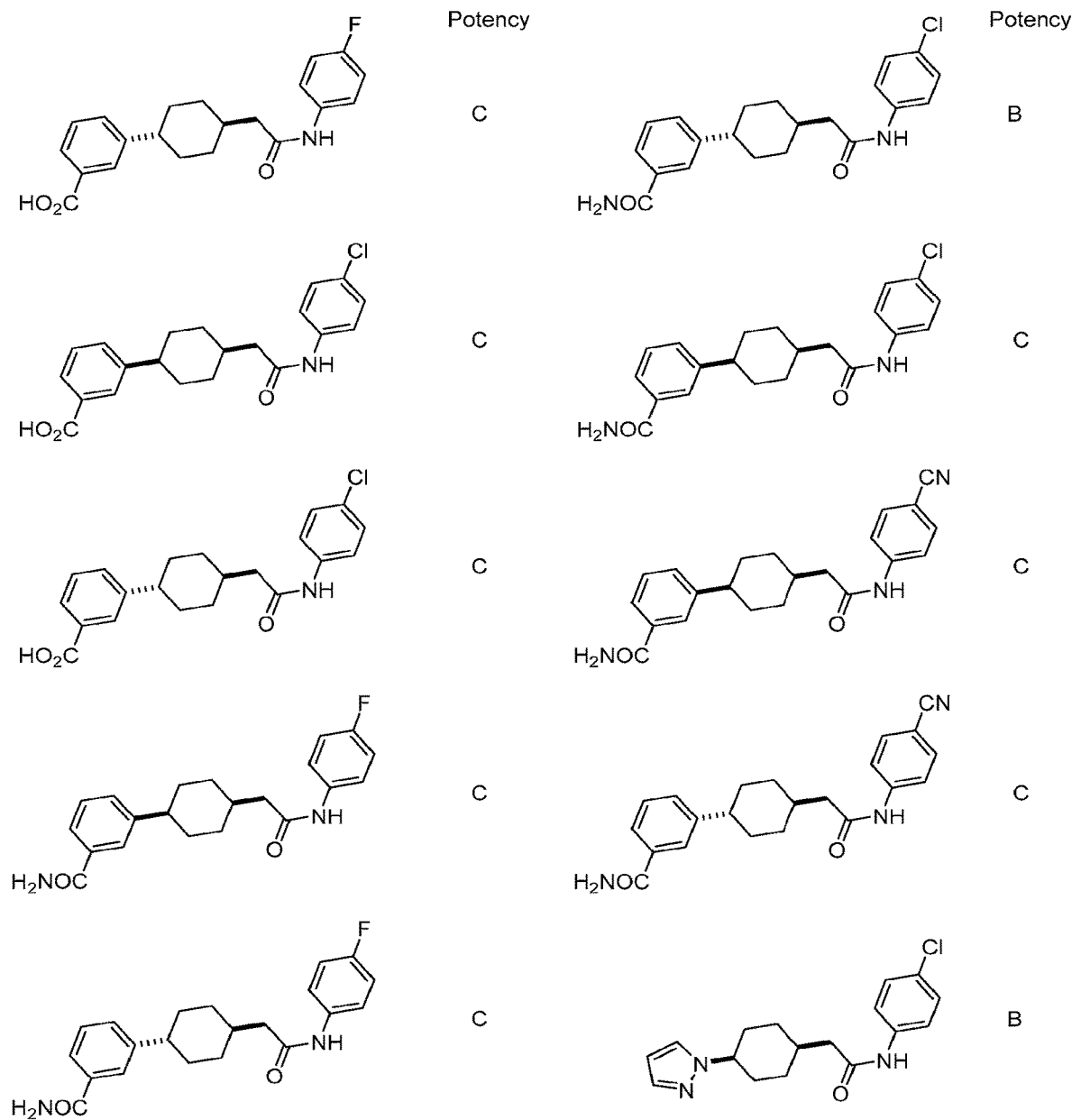
Figure 1N:
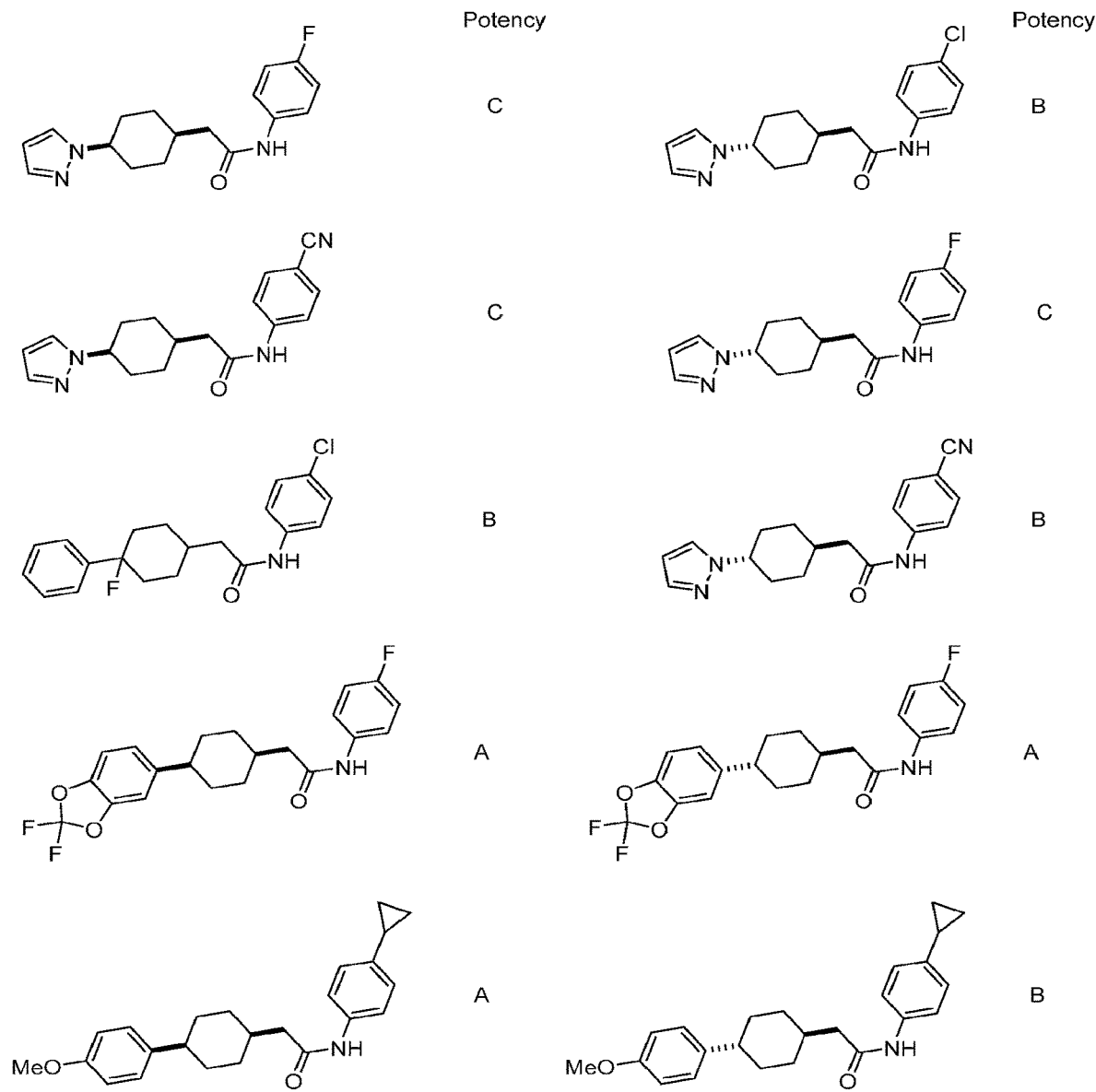
Figure 1O:
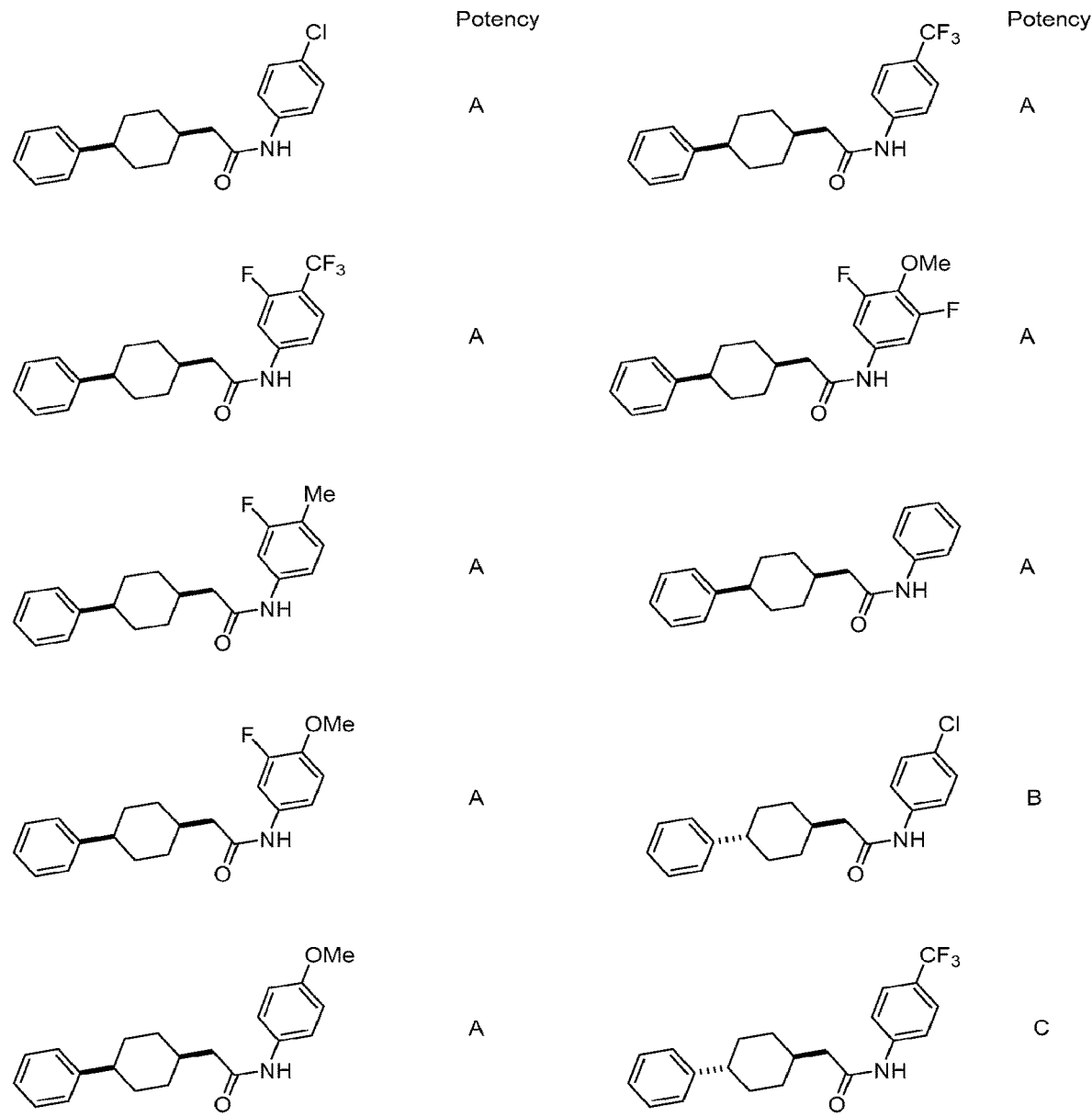
Figure 1P:
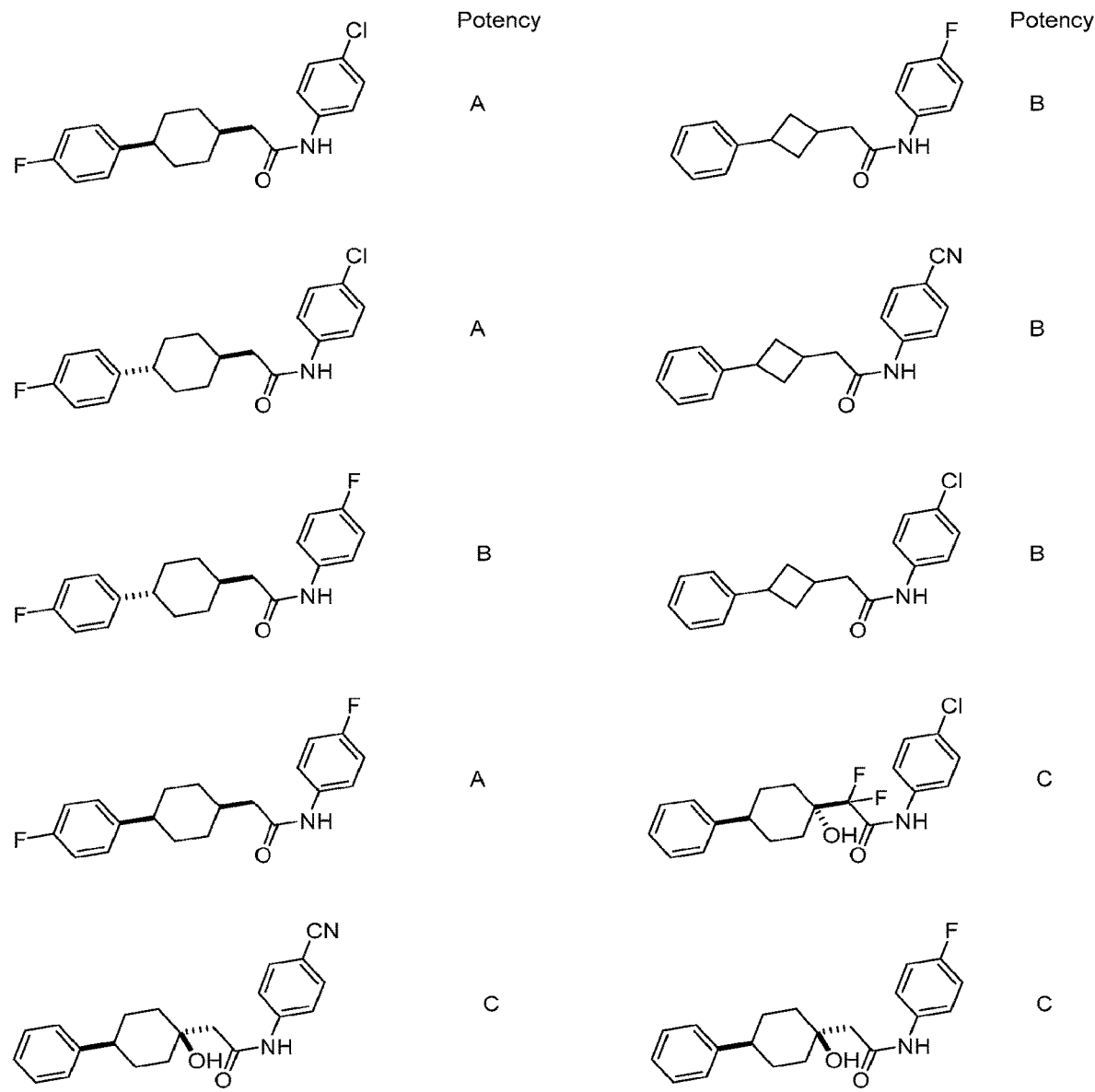
Figure 1Q:
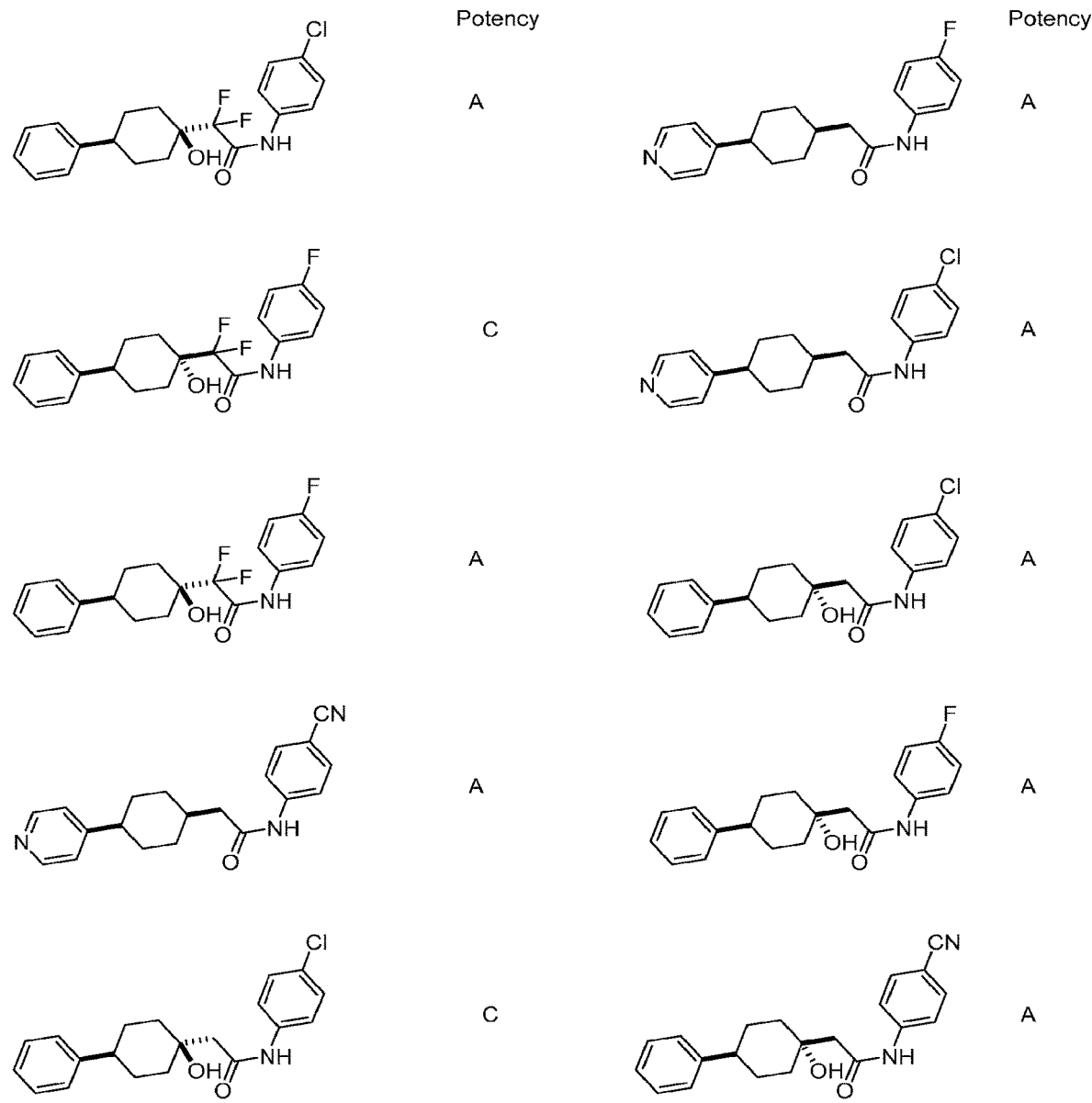
Figure 1R:
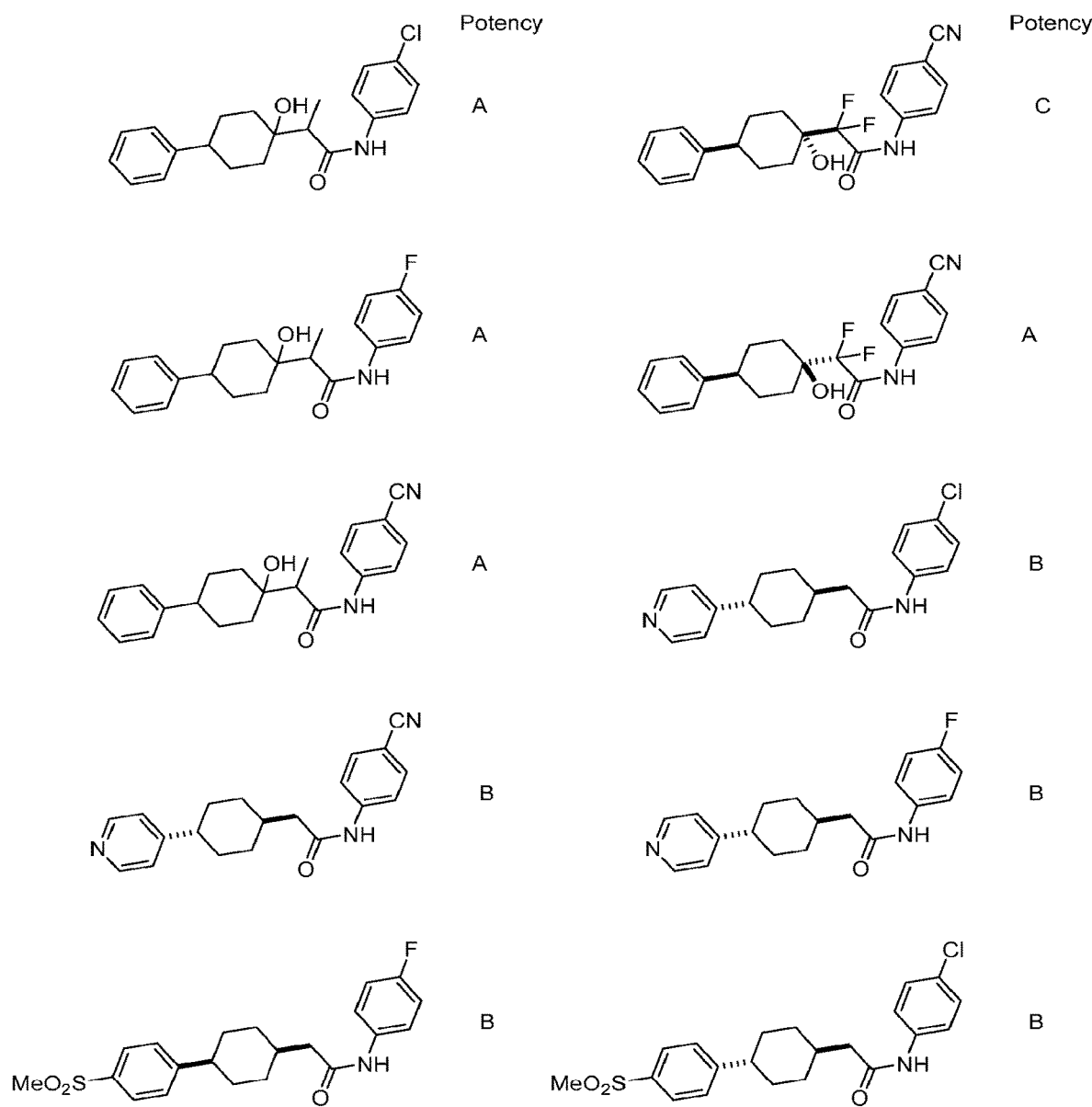
Figure 1S:
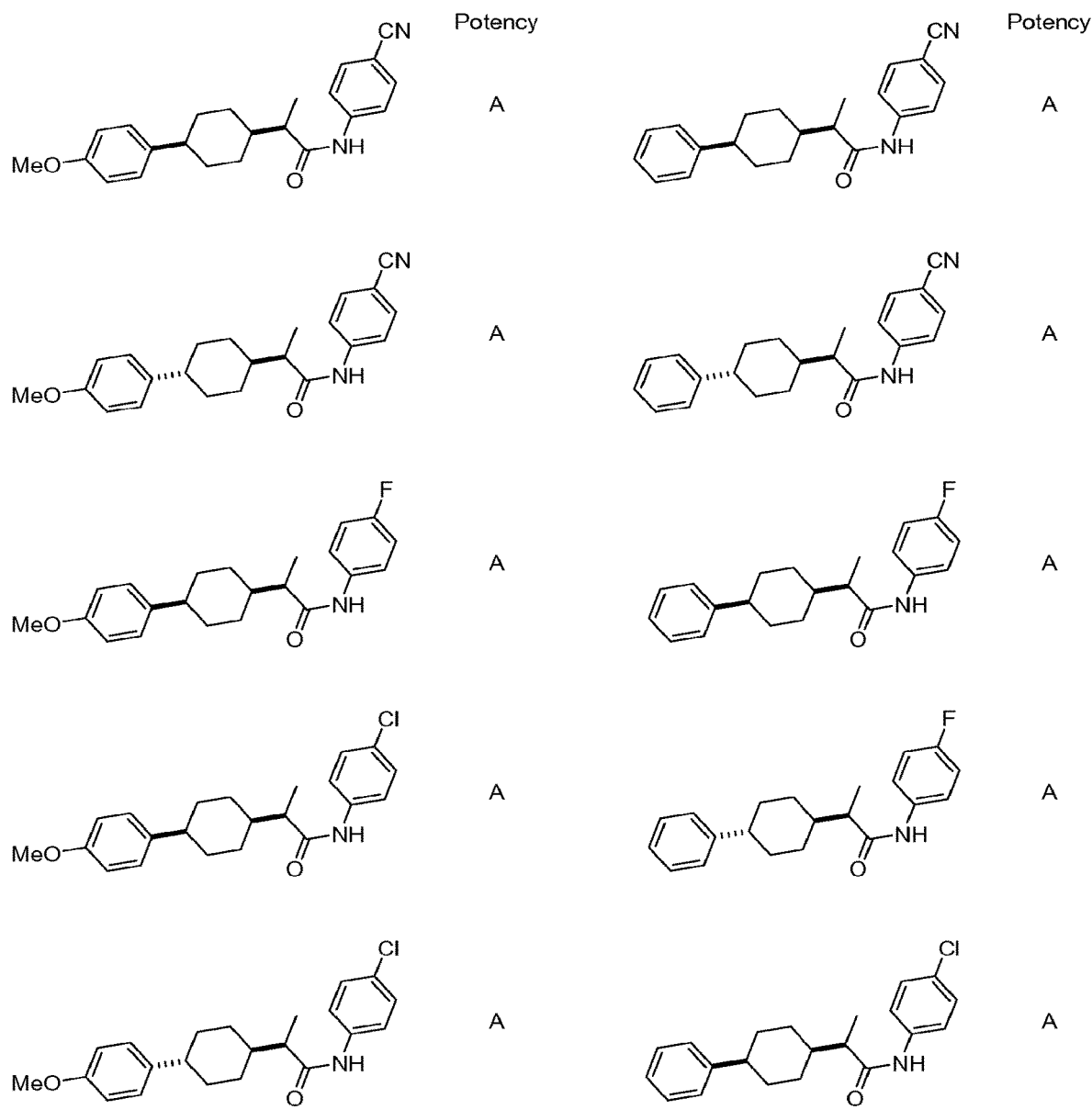
Figure 1T:
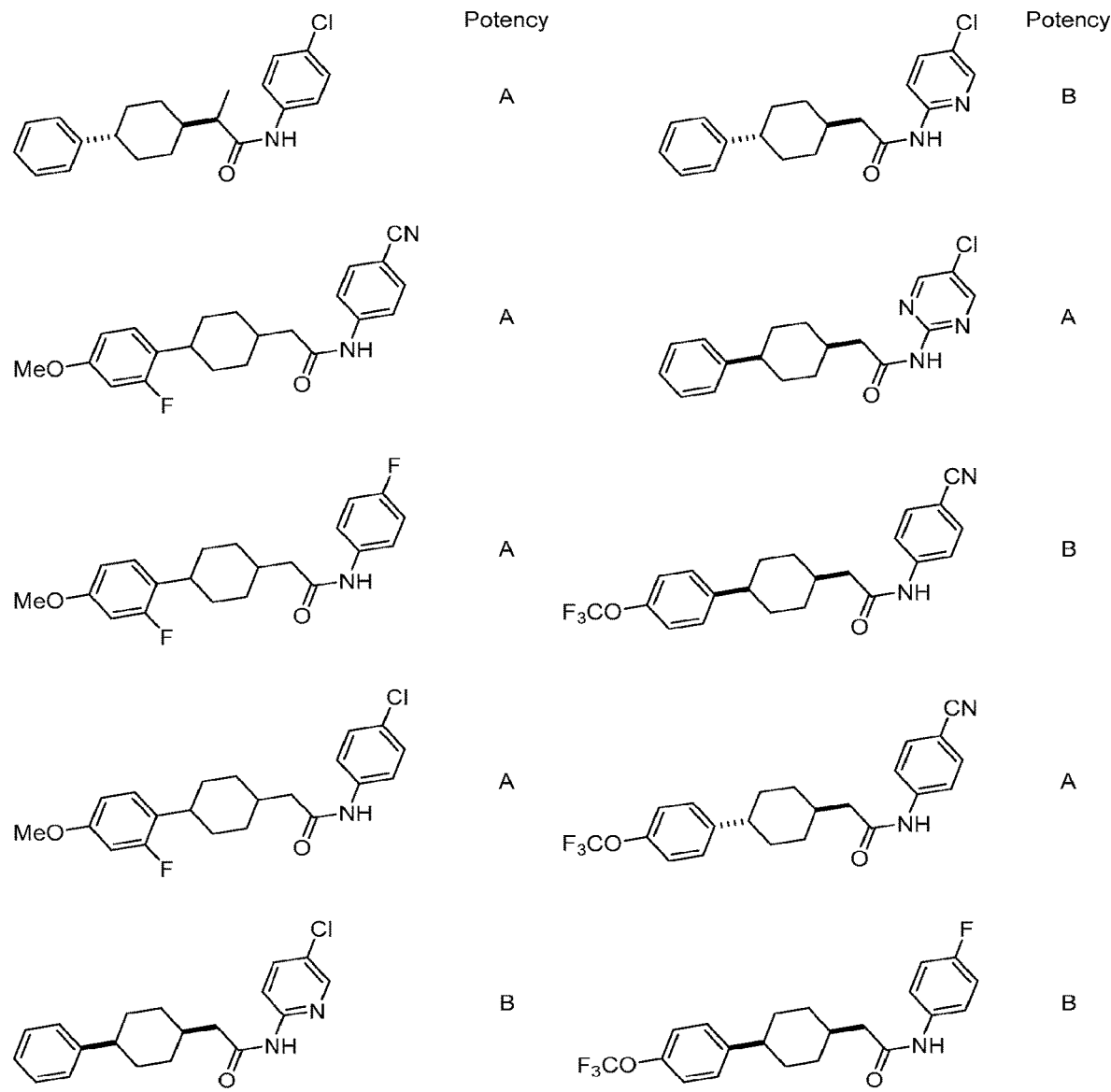
Figure 1U:
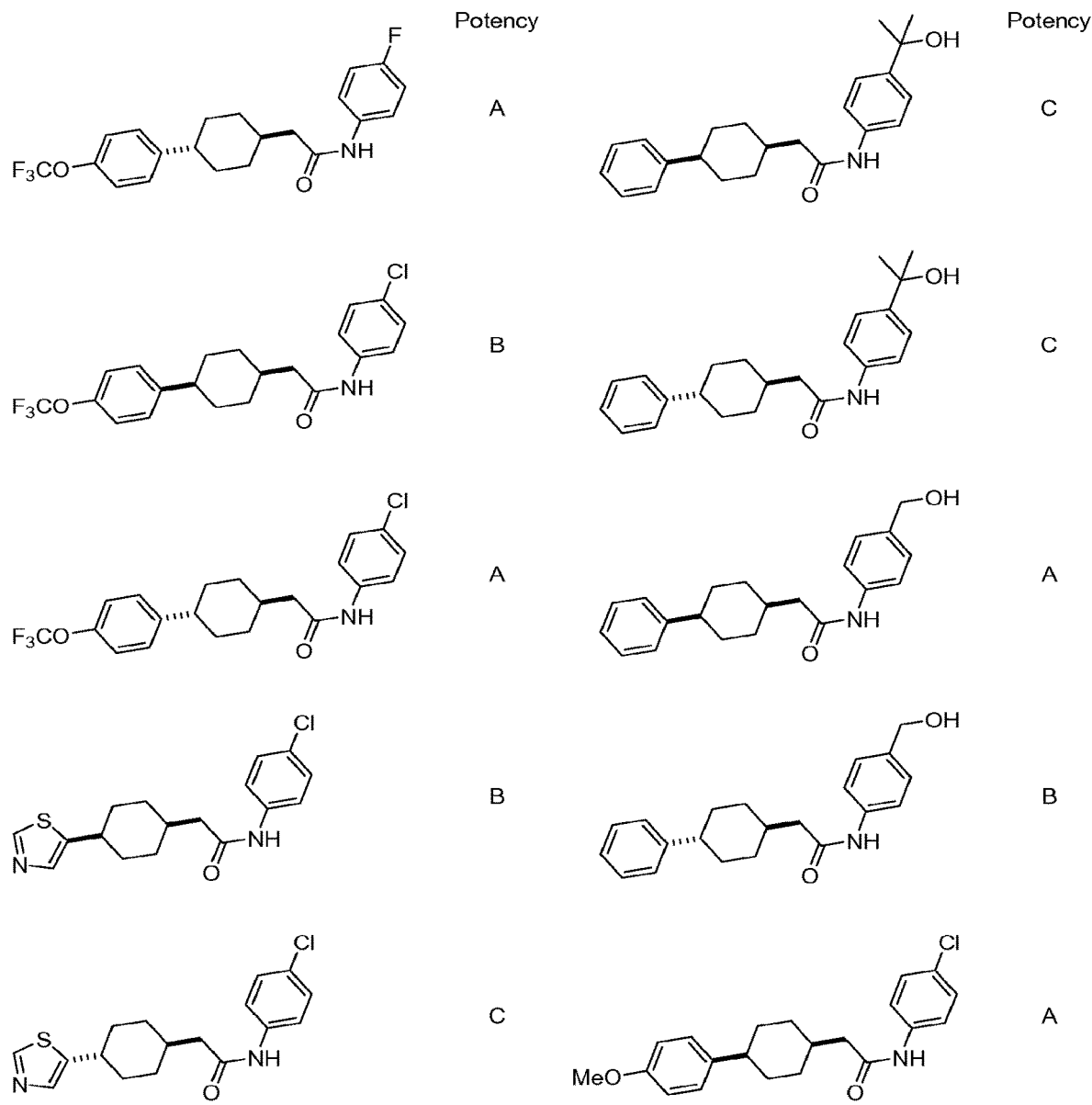
Figure 1V:
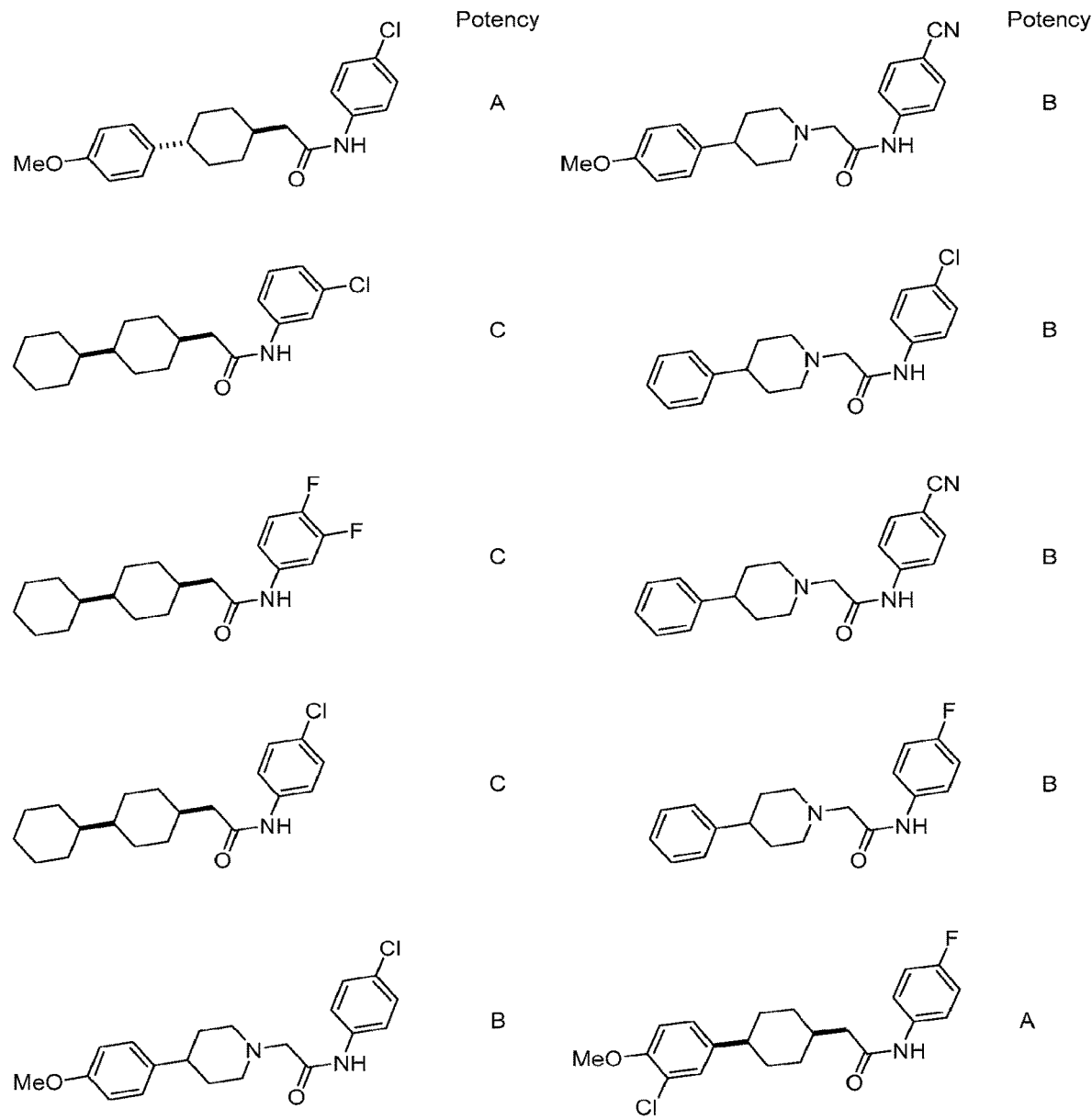
Figure 1W:
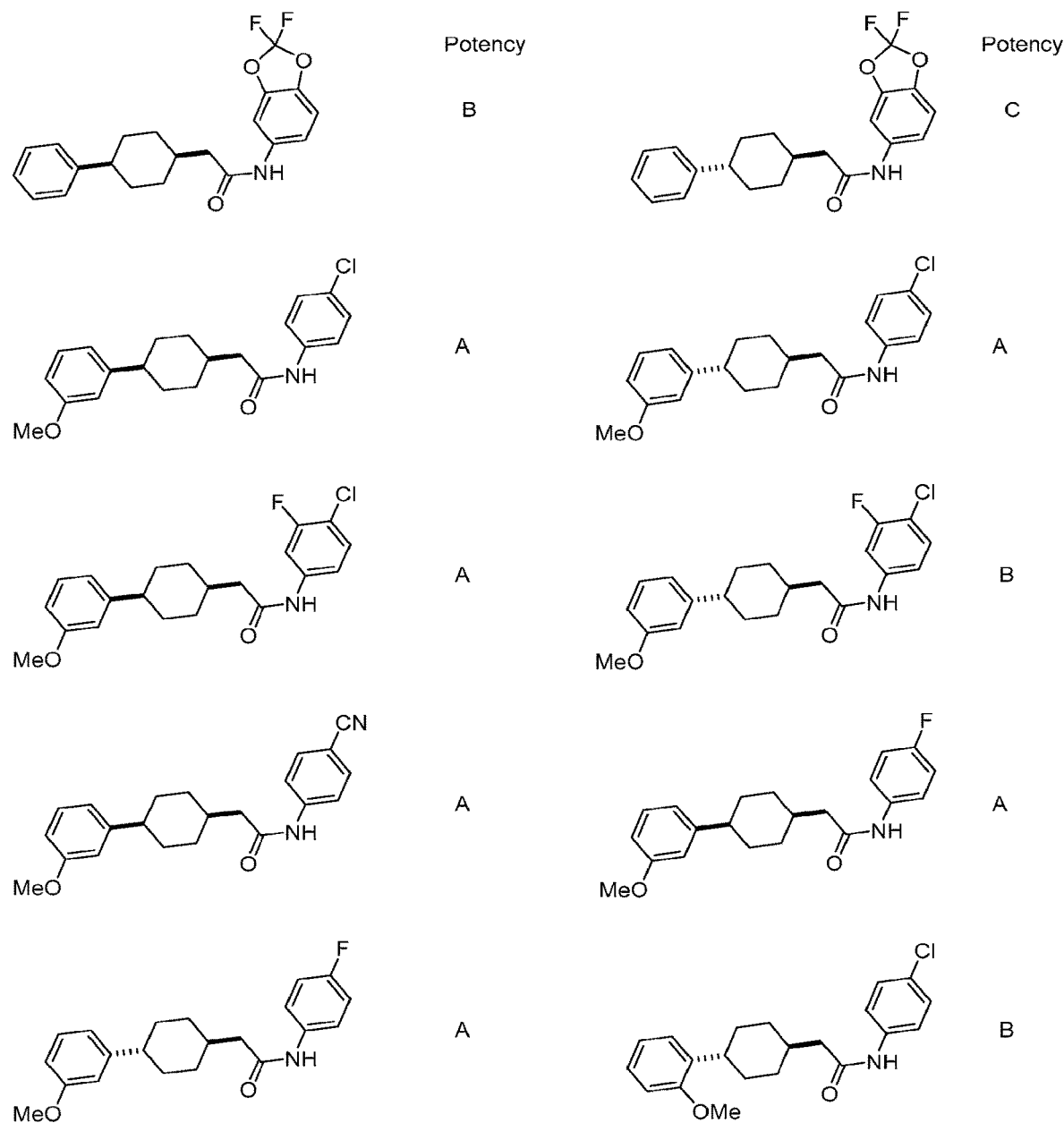
Figure 1X:
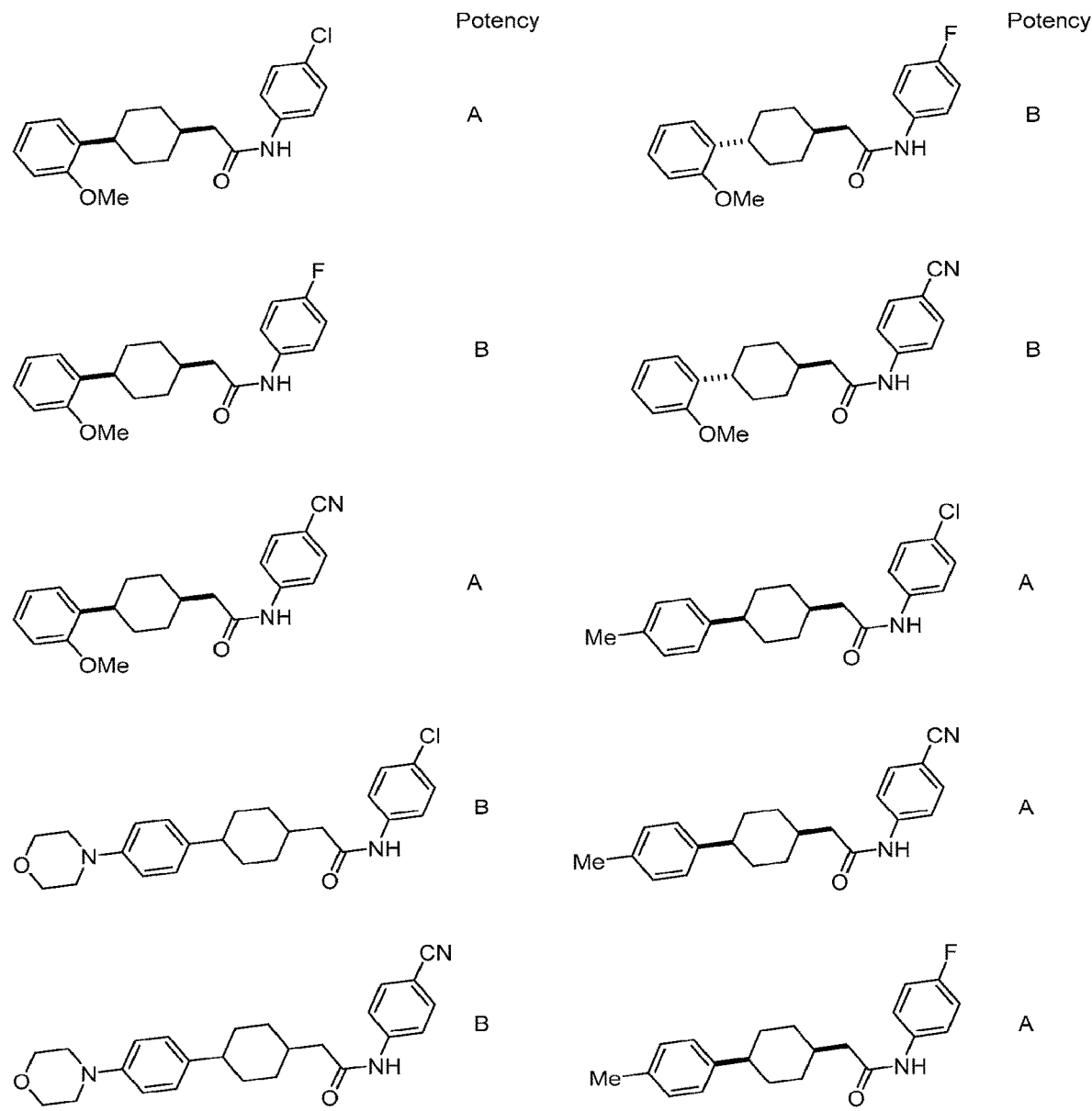
Figure 1Y:
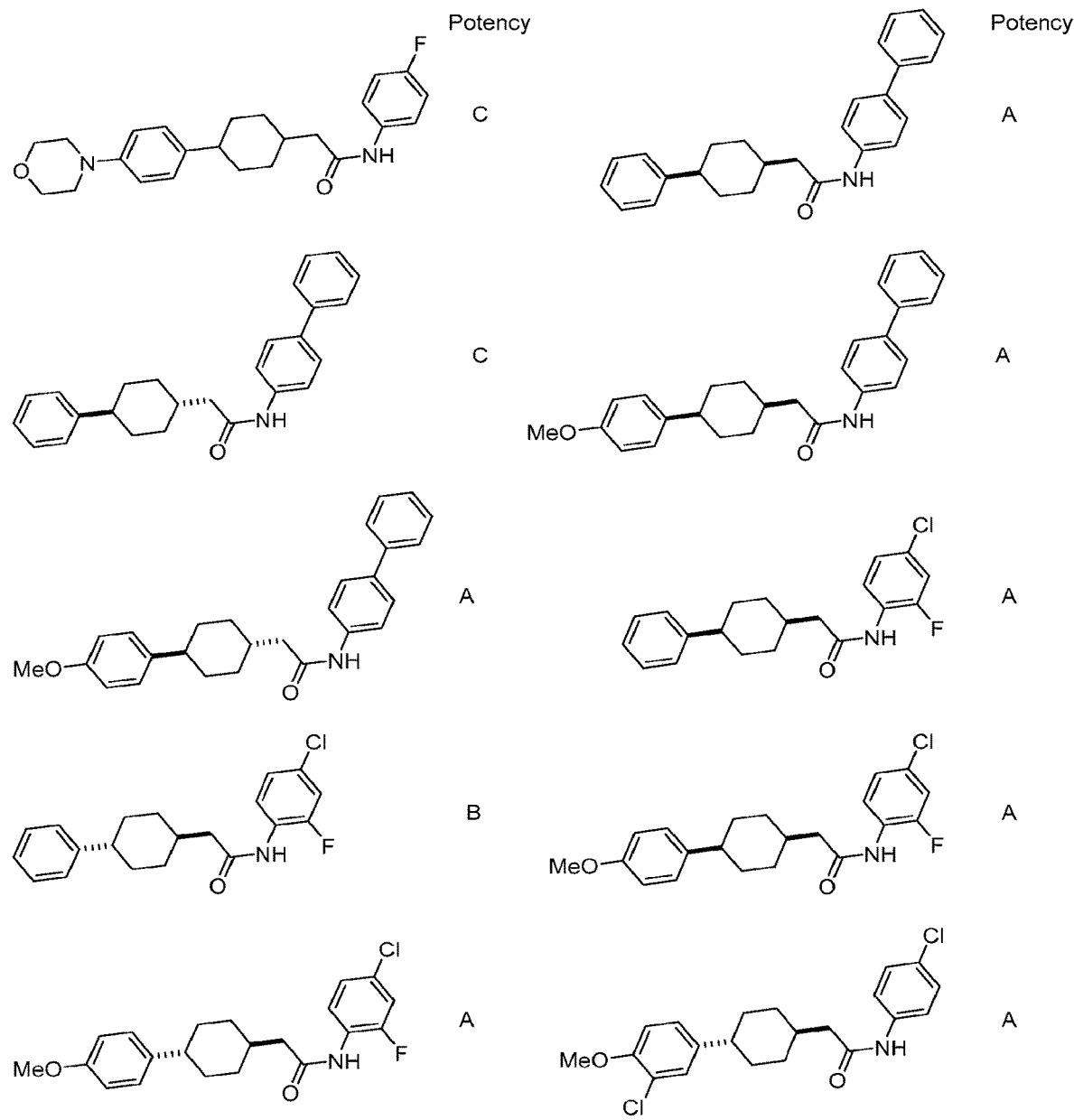
Figure 1Z:
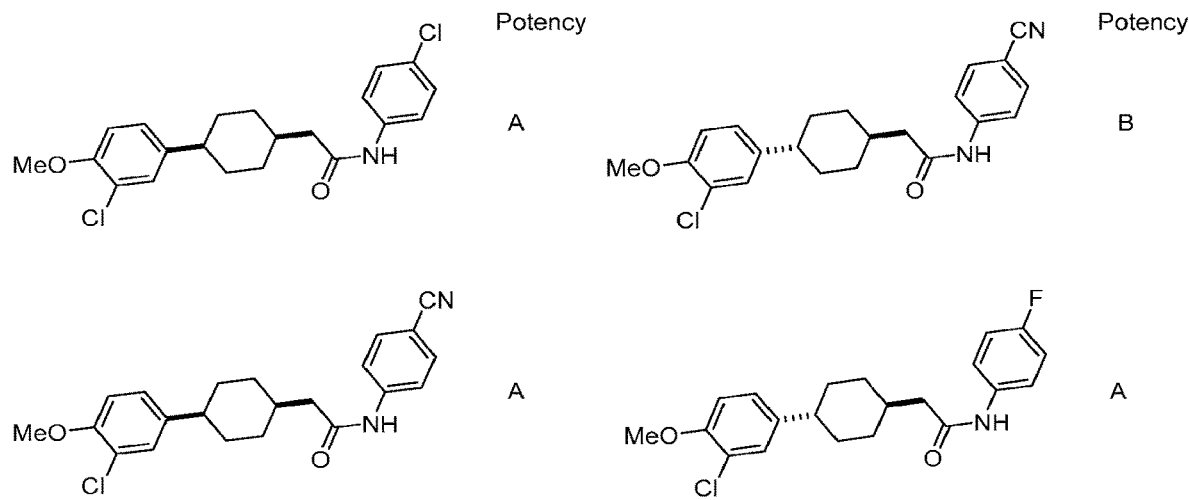
Figure 1A:
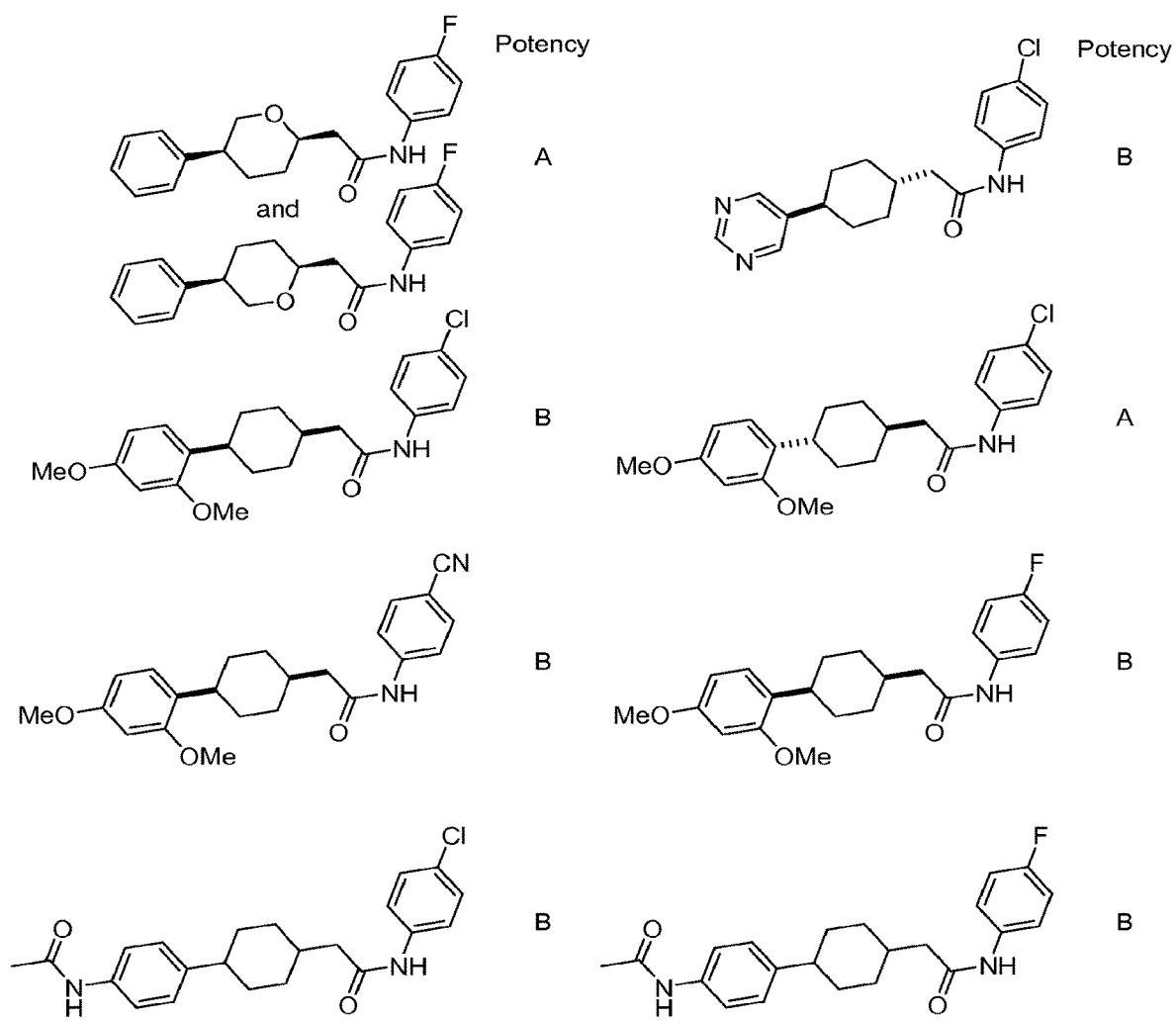
Figure 1B:
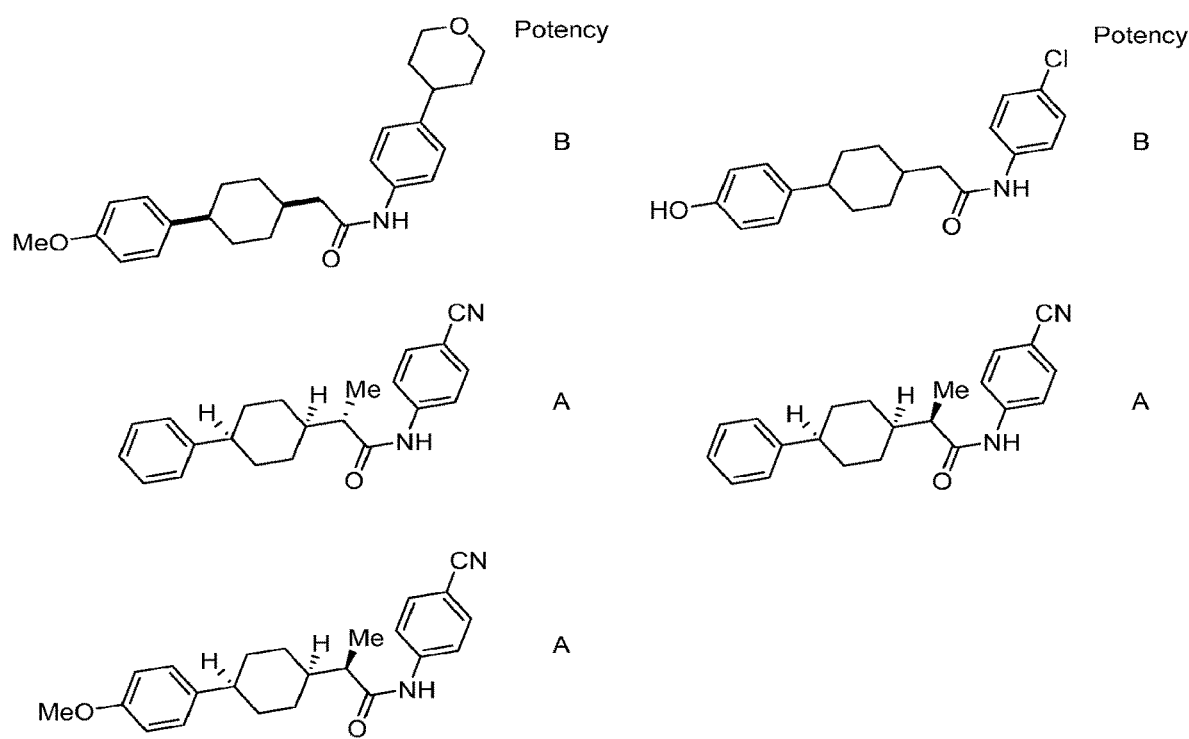

In one group of selected embodiments, any one compound of FIG. 1 is provided.

In another group of selected embodiments, any one compound of FIG. 1 is provided having an activity level identified as "A" or "B".

In another group of selected embodiments, any one compound of FIG. 1 is provided having an activity level identified as "A".

Methods of Synthesis

The compounds described herein can be prepared by a variety of methods, utilizing synthetic transformations provided in the Examples and other general synthetic methods known to one of skill in the art.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (*J. Am. Chem. Soc.*, 136(9):3370-3373 (2014)) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., *Prog. Polym. Sci.*, 38:421-444 (2013)).

Therapeutic and Prophylactic Uses

The present invention contemplates the use of the IDO inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-Related Disorders.

In accordance with the present invention, an IDO inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut et al., *Oncogene*, 22:3180-3187 (2003); and Sawaya et al., *New Engl. J. Med.*, 349:1501-1509 (2003)). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In some embodiments, the present invention provides methods for treating a proliferative condition, cancer, tumor, or precancerous condition with an IDO inhibitor and at least one additional therapeutic or diagnostic agent, examples of which are set forth elsewhere herein.

Immune- and Inflammatory-Related Disorders.

As used herein, terms such as "immune disease", "immune condition", "immune disorder", "inflammatory disease", "inflammatory condition", "inflammatory disorder" and the like are meant to broadly encompass any immune- or inflammatory-related condition (e.g., pathological inflammation and autoimmune diseases). Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

A non-limiting list of immune- and inflammatory-related diseases, disorders and conditions which may be treated or prevented with the compounds and compositions of the present invention include, arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Among other immune-related disorders, it is contemplated that inhibition of IDO function may also play a role in immunologic tolerance and prevention of fetal rejection in utero.

In some embodiments, an IDO inhibitor described herein can be combined with an immunosuppressive agent to reduce the number of immune effector cells.

Some of the aforementioned diseases, disorders and conditions for which an IDO inhibitor may be particularly efficacious (due to, for example, limitations of current therapies) are described in more detail hereafter.

Rheumatoid Arthritis (RA), which is generally characterized by chronic inflammation in the membrane lining (the synovium) of the joints, affects approximately 1% of the U.S. population (~2.1 million people). Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL® (etanercept), REMICADE® (infliximab), HUMIRA® (adalimumab) and KINERET® (anakinra). Though some of these agents relieve symptoms, inhibit progression of structural damage, and improve physical function in particular patient populations, there is still a need for alternative agents with improved efficacy, complementary mechanisms of action, and fewer/less severe adverse effects.

Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL® (etanercept), REMICADE® (infliximab) and HUMIRA® (adalimumab)), and T-cell inhibitors such as AMEVIVE® (alefacept) and RAPTIVA® (efalizumab). Though several of these agents are effective to some extent in certain patient populations, none have been shown to effectively treat all patients.

Subjects suffering from multiple sclerosis (MS), a seriously debilitating autoimmune disease comprising multiple areas of inflammation and scarring of the myelin in the brain and spinal cord, may be particularly helped by the IDO inhibitors described herein, as current treatments only alleviate symptoms or delay the progression of disability.

Similarly, the IDO inhibitors may be particularly advantageous for subjects afflicted with neurodegenerative disorders, such as Alzheimer's disease (AD), a brain disorder that seriously impairs patients' thought, memory, and language processes; and Parkinson's disease (PD), a progressive disorder of the CNS characterized by, for example, abnormal movement, rigidity and tremor. These disorders are progressive and debilitating, and no curative agents are available.

Viral-Related Disorders.

The present invention contemplates the use of the IDO inhibitors in the treatment and/or prevention of any viral disease, disorder or condition for which treatment with an IDO inhibitor may be beneficial. In particular embodiments, the viral disorder is a chronic viral disorder. Examples of viral diseases, disorders and conditions that are contemplated include, but are not limited to, hepatitis B virus (HBV), hepatitis C virus (HCV), human papilloma virus (HPV), HIV, AIDS (including its manifestations such as cachexia, dementia, and diarrhea), herpes simplex virus (HSV), Epstein-Barr virus (EBV), varicella zoster virus, coxsackie virus, and cytomegalovirus (CMV).

Bacterial- and Parasitic-Related Disorders.

Embodiments of the present invention contemplate the administration of the IDO inhibitors described herein to a subject for the treatment of a bacterial infection, for example, a *Mycobacterium* infection (e.g., *Mycobacterium leprae* or *Mycobacterium tuberculosis*) or an infection caused by *Listeria monocytogenes* or *Toxoplasma gondii*. Other embodiments contemplate the treatment of a parasitic infection including, but not limited to, *Leishmania donovani, Leishmania tropica, Leishmania major, Leishmania aethiopica, Leishmania mexicana, Plasmodium falciparum, Plasmodium vivax, Plasmodium ovale*, or *Plasmodium malariae*. Frequently, anti-parasitic therapy is administered prophylactically (e.g., before a subject travels to an area with a high frequency of parasitic infection).

Pharmaceutical Compositions

The IDO inhibitors of the present invention may be in the form of compositions suitable for administration to a subject. In general, such compositions are "pharmaceutical compositions" comprising an IDO inhibitor(s) and one or more pharmaceutically acceptable or physiologically acceptable diluents, carriers or excipients. In certain embodiments, the IDO inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of IDO function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example, peanut oil, liquid paraffin, or olive oil.

Aqueous suspensions contain the active materials in admixture with excipients suitable for the manufacture thereof. Such excipients can be suspending agents, for example, sodium carboxymethylcellulose, methylcellulose, hydroxy-propylmethylcellulose, sodium alginate, polyvinylpyrrolidone, gum tragacanth and gum acacia; dispersing or wetting agents, for example, a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example, olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The pharmaceutical compositions typically comprise a therapeutically effective amount of an IDO inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-hydroxyethyl)piperazine-N'-(2-ethanesulfonic acid) (HEPES), 2-(N-morpholino) ethanesulfonic acid (MES), 2-(N-morpholino)ethanesulfonic acid sodium salt (MES), 3-(N-morpholino)propanesulfonic acid (MOPS), and N-tris[hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EPIPEN®)), whereas a multi-use container (e.g., a multi-use vial) is provided in other embodiments. Any drug delivery apparatus may be used to deliver and IDO inhibitor, including implants (e.g., implantable pumps) and catheter systems, slow injection pumps and devices, all of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, CREMOPHOR® EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the IDO inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The IDO inhibitors contemplated by the present invention may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present invention contemplates the administration of IDO inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), sublingual and inhalation. Depot injections, which are generally administered subcutaneously or intramuscularly, may also be utilized to release the IDO inhibitors disclosed herein over a defined period of time.

Particular embodiments of the present invention contemplate oral administration.

Combination Therapy

The present invention contemplates the use of IDO inhibitors in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the IDO inhibitors are administered or applied sequentially, e.g., where one agent is administered prior to one or more other agents. In other embodiments, the IDO inhibitors are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The IDO inhibitors of the present invention may be used in combination with at least one other (active) agent in any manner appropriate under the circumstances. In one embodiment, treatment with the at least one active agent and at least one IDO inhibitor of the present invention is maintained over a period of time. In another embodiment, treatment with the at least one active agent is reduced or discontinued (e.g., when the subject is stable), while treatment with an IDO inhibitor of the present invention is maintained at a constant dosing regimen. In a further embodiment, treatment with the at least one active agent is reduced or discontinued (e.g., when the subject is stable), while treatment with an IDO inhibitor of the present invention is reduced (e.g., lower dose, less frequent dosing or shorter treatment regimen). In yet another embodiment, treatment with the at least one active agent is reduced or discontinued (e.g., when the subject is stable), and treatment with the IDO inhibitor of the present invention is increased (e.g., higher dose, more frequent dosing or longer treatment regimen). In yet another embodiment, treatment with the at least one active agent is maintained and treatment with the IDO inhibitor of the present invention is reduced or discontinued (e.g., lower dose, less frequent dosing or shorter treatment regimen). In yet another embodiment, treatment with the at least one active agent and treatment with the IDO inhibitor of the present invention are reduced or discontinued (e.g., lower dose, less frequent dosing or shorter treatment regimen).

Oncology-Related Disorders.

The present invention provides methods for treating and/or preventing a proliferative condition, cancer, tumor, or precancerous disease, disorder or condition with an IDO inhibitor and at least one additional therapeutic or diagnostic agent.

In certain embodiments, the present invention provides methods for tumor suppression of tumor growth comprising administration of an IDO inhibitor described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC®); (ii) epidermal growth factor (EGF) receptor inhibitors, including kinase inhibitors and antibodies; (iii) her-2/neu receptor inhibitors (e.g., HERCEPTIN®); (iv) inhibitors of Akt family kinases or the Akt pathway (e.g., rapamycin); (v) cell cycle kinase inhibitors (e.g., flavopiridol); and (vi) phosphatidyl inositol kinase inhibitors.

Agents involved in in immunomodulation can also be used in combination with the IDO inhibitors described herein for the suppression of tumor growth in cancer patients. Suitable immunomodulators that may be used in the present invention include CD40L, B7, and B7RP1; activating monoclonal antibodies (mAbs) to stimulatory receptors, such as, ant-CD40, anti-CD38, anti-ICOS, and 4-IBB ligand; dendritic cell antigen loading (in vitro or in vivo); dendritic cell cancer vaccine; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); and immune-stimulatory oligonucleotides.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and docetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; NOVANTRONE®; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including, for example, tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with an IDO inhibitor include a cytokine or cytokine antagonist, such as IL-12, INFα, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., as a soluble protein or as a nucleic acid encoding the protein) are also provided herein.

Cardiovascular Diseases.

The present invention provides methods for treating and/or preventing certain cardiovascular- and/or metabolic-related diseases, disorders and conditions, as well as disorders associated therewith, with an IDO inhibitor and at least one additional therapeutic or diagnostic agent.

Examples of therapeutic agents useful in combination therapy for the treatment of hypercholesterolemia (and atherosclerosis as well) include statins (e.g., CRESTOR®, LESCOL®, LIPITOR®, MEVACOR®, PRAVACHOL®, and ZOCOR®), which inhibit the enzymatic synthesis of cholesterol; bile acid resins (e.g., COLESTID®, LoCholest, PREVALITE®, QUESTRAN®, and WELCHOL®), which sequester cholesterol and prevent its absorption; ezetimibe (ZETIA®), which blocks cholesterol absorption; fabric acid (e.g., TRICOR®), which reduces triglycerides and may modestly increase HDL; niacin (e.g., NIACOR®), which modestly lowers LDL cholesterol and triglycerides; and/or a combination of the aforementioned (e.g., VYTORIN® (ezetimibe with simvastatin). Alternative cholesterol treatments that may be candidates for use in combination with the IDO inhibitors described herein include various supplements and herbs (e.g., garlic, policosanol, and guggul). The present invention encompasses pharmaceutically acceptable salts, acids or derivatives of any of the above.

Immune- and Inflammatory-Related Disorders.

The present invention provides methods for treating and/or preventing immune- and/or inflammatory-related diseases, disorders and conditions, as well as disorders associated therewith, with an IDO inhibitor and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, buloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-1β, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE®, anti-TNF antibody fragments (e.g., CDP870), and soluble p55 or p75 TNF receptors, derivatives thereof, p75TNFRIgG (ENBREL®) or p55TNFR1gG (Lenercept), soluble IL-13 receptor (sIL-13), and also TNFα-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the IDO inhibitors described herein include interferon-β1a (AVONEX®); interferon-β1b (BETASERON®); COPAXONE®; hyperbaric oxygen; intravenous immunoglobulin; clabribine; and antibodies to, or antagonists of, other human cytokines or growth factors (e.g., antibodies to CD40 ligand and CD80).

Immune Checkpoint Inhibitors.

The present invention contemplates the use of the inhibitors of IDO function described herein in combination with immune checkpoint inhibitors, a relatively new class of therapeutic (and potential therapeutic) agents.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms. In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor-ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, *Nature Rev. Cancer,* 12:252-264 (April 2012)].

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, Nature Rev. Cancer, 12:252-264 (April 2012)].

The present invention contemplates the use of the inhibitors of IDO function described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY®; Bristol-Myers Squibb) became the first immune checkpoint inhibitor to receive regulatory approval in the US. Fusion proteins comprising CTLA4 and an antibody (CTLA4-Ig; abatacept (ORENCIA®; Bristol-Myers Squibb)) have been used for the treatment of rheumatoid arthritis, and other fusion proteins have been shown to be effective in renal transplantation patients that are sensitized to Epstein Barr Virus. PD1 antibodies are under development (e.g., nivolumab (Bristol-Myers Squibb) and lambrolizumab (Merck)), and anti-PDL1 antibodies are also being evaluated (e.g., MPDL3280A (Roche)). Nivolumab has shown promise in patients with melanoma, lung and kidney cancer.

The present invention encompasses pharmaceutically acceptable salts, acids or derivatives of any of the above.

Viral Diseases.

The present invention provides methods for treating and/or preventing viral diseases, disorders and conditions, as well as disorders associated therewith, with an IDO inhibitor and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddI, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an IDO inhibitor include, but are not limited to, the following: abacavir, adefovir, amantadine, amprenavir, ampligen, arbidol, atazanavir, ATRIPLA®, boceprevirertet, cidofovir, COMBIVIR®, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, TRIZIVIR®, tromantadine, TRUVADA®, valaciclovir, valganciclovir, vicriviroc, vidarabine, viramidine, and zalcitabine.

The present invention encompasses pharmaceutically acceptable salts, acids or derivatives of any of the above.

Parasitic Disorders.

The present invention contemplates the use of the inhibitors of IDO function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

The present invention encompasses pharmaceutically acceptable salts, acids or derivatives of any of the above.

Bacterial Infections.

Embodiments of the present invention contemplate the use of the IDO inhibitors described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

The present invention encompasses pharmaceutically acceptable salts, acids or derivatives of the agents (and members of the classes of agents) set forth above.

Dosing

The IDO inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the IDO inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired IDO inhibitor is contained in a "unit dosage form". The phrase "unit dosage form" refers to physically discrete units, each unit containing a predetermined amount of the IDO inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising an IDO inhibitor, and pharmaceutical compositions thereof. The kits are generally in the form of a physical structure housing various components, as described below, and may be utilized, for example, in practicing the methods described above.

A kit can include one or more of the IDO inhibitors disclosed herein (provided in, e.g., a sterile container), which may be in the form of a pharmaceutical composition suitable for administration to a subject. The IDO inhibitors can be provided in a form that is ready for use (e.g., a tablet or capsule) or in a form requiring, for example, reconstitution or dilution (e.g., a powder) prior to administration. When the IDO inhibitors are in a form that needs to be reconstituted or diluted by a user, the kit may also include diluents (e.g., sterile water), buffers, pharmaceutically acceptable excipients, and the like, packaged with or separately from the IDO inhibitors. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbccco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press, Cold Spring Harbor, N.Y. (2001); and Ausubel et al., *Current Protocols in Molecular Biology*, Vols. 1-4, John Wiley and Sons, Inc. New York, N.Y. (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan et al., *Current Protocols in Protein Science*, Vols. 1-2, John Wiley and Sons, Inc., NY (2000)).

Software packages and databases for determining, e.g., antigenic fragments, leader sequences, protein folding, functional domains, glycosylation sites, and sequence alignments, are available (see, e.g., GCG® Wisconsin Package (Accelrys, Inc., San Diego, Calif.); and DECYPHER® (TimeLogic Corp., Crystal Bay, Nev.).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, Mo.) unless specified otherwise. Groups of 1,000 human islets can be cultured for 24 h in 1 mL medium with cytokines, recovered by centrifugation for 5 min at 800×g and sonicated in 150 µL PBS containing a protease inhibitor cocktail (Set 2; Calbiochem, EMD Biosciences, San Diego, Calif.). The sonicate can be centrifuged for 10 min at 10,000×g, and the supernatant can be assayed in triplicate by incubating a 40 µl sample with an equal volume of 100 mmol/L potassium phosphate buffer, pH 6.5, containing 40 mmol/L ascorbic acid (neutralized to pH 7.0), 100 µmol/L methylene blue, 200 µg/mL catalase, and 400 µmol/l L-Trp for 30 min at 37° C. The assay can be terminated by the addition of 16 µL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 µg/mL; 500-2,000 units/mL) and 1-α-methyl Trp (1-MT; 40 µmol/L) can be added to the incubation media as indicated. This assay can also form the basis of a cell-based assay, and may be quantified via LCMS/MS as an alternative to UV/Vis detection.

Western Blot Analyses.

Groups of 1,000-1,200 islets incubated for 24 h in Miami medium in the presence of cytokines can be harvested and sonicated in PBS as above, and 50 µg protein samples can be electrophoresed on 10% SDS-PAGE gels. COST cells ($0.6 \times 10^6$ cells/60 mm3 petri dish) transfected with human-IDO plasmid (3 µg) or empty vector cells can be used as positive and negative controls, respectively. Proteins can be transferred electrophoretically onto polyvinylidine fluoride membranes by semidry method and blocked for 1 h with 5% (w/v) nonfat dry milk in Tris-buffered saline and 0.1% Tween and then incubated overnight with anti-human mouse IDO antibody (1:500; Chemicon, Temecula, Calif.), phospho-$STAT_{1\alpha}$ p91, and $STAT_{1\alpha}$ p91 (1:500; Zymed, San Francisco, Calif.). Immunoreactive proteins can be visualized with ECL PLUS® Western blotting detection reagent (Amersham BioSciences, Buckinghamshire, U.K.) after incubation for 1 h with anti-mouse horseradish peroxidase-conjugated secondary antibody (Jackson Immunolabs, West Grove, Pa.).

Immunohistochemical Detection of IDO.

Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 µm sections that were stained with antibodies raised against pancreatic duodenal homeobox 1 (PDX1) and IDO. Antigen retrieval can be performed in a water bath for 30 min in a buffer containing 10 mmol/l Tris and 1 mmol/l EDTA (pH 9.0) at 97° C. The sections can be blocked for 1 h with 5% normal goat serum in PBS. The tissues can then be reacted with mouse monoclonal anti-human IDO antibody (1:20; Chemicon) and goat polyclonal anti-human PDX1 antibody (1:2,000; which may be requested from Dr. Chris Wright, School of Medicine, Vanderbilt, Tenn.) overnight at room temperature in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258 (Molecular Probes, Eugene, Oreg.). Images can be acquired by Intelligent Imaging System software from an Olympus 1X81 inverted motorized microscope equipped with Olympus DSU (spinning disk confocal) and Hamamatsu ORCA IIER monochromatic CCD camera.

Alternative means for evaluating the IDO inhibitors of the present invention are described in WO 2010/0233166 and are summarized hereafter.

Biochemical Assay.

cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K. et al., *Prot. Exp. Purif*, 19:22-29 (2000)). To screen for IDO inhibitory activity, compounds can be evaluated at a single concentration of, for example, 200 µM against 50 ng of IDO enzyme in 100 µL reaction volumes with tryptophan added at increasing concentrations at, for example, 0, 2, 20, and 200 µM. Kynurenine production can be measured at 1 hour.

Cell-Based Assay.

COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at $6\times10^4$ cells per well. The following day, the wells can be washed and new media (phenol red free) containing 20 µg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 µM. More extensive dose-escalation profiles can be collected for select compounds.

Pharmacodynamic and Pharmacokinetic Evaluation.

A pharmacodynamic assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in scrum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 µL sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective $IC_{50}$ for IDO inhibition in vivo can be roughly estimated. Compounds exhibiting efficacy can be evaluated to determine a maximum dose that achieves 100% IDO inhibition at the peak concentration.

METHODS OF PREPARATION

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group (s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

Referring to Scheme 1, treatment of the cyclohexanone II under standard Horner-Wadsworth Emmons conditions with the phosphonate III will afford the corresponding unsaturated ester. Catalytic hydrogenation with, for instance, Pd/C and hydrogen gas and subsequent ketal hydrolysis under acidic conditions gives the appended cycloalkanone of general structure IV. Treatment of compound IV with triflic anhydride and an organic base such as 2,6-lutidine will afford a vinyl triflate of general structure V. Coupling of V with arylboronic acids or esters E-B(OR)$_2$, preferably under the conditions of Suzuki (see Kotha, S. et al., *Tetrahedron*, 58:9633-9695 (2002)) affords cycloalkenes of general structure VI. Typically, this reaction is performed by heating the halide and the boronic acid or ester to from about 90 to about 98° C. with a base such as aqueous tribasic sodium or potassium phosphate or sodium or potassium carbonate in a solvent such as dioxane, DMF, THF, or NMP using a catalyst such as tetrakis(triphenylphosphine)palladium or Cl$_2$Pd (dppf). Many variations on this reaction involving the use of different temperatures, solvents, bases, anhydrous conditions, catalysts, boronate derivatives, and halide surrogates such as triflates are known to those skilled in the art of organic/medicinal chemistry. Mild conditions have been reported for the coupling of sensitive boronic acid derivatives. See Kinzel, T. et al., *J. Am. Chem. Soc.*, 132(40): 14073-14075 (2010). Saturation of the olefin in VII can be accomplished by treatment with Pd/C in an atmosphere of hydrogen to give a compound of general structure VII as a mixture of cis and trans isomers about the carbocycle. Further substitution of the ester can be accomplished by treatment with a strong base, such as LDA or LiHMDS, followed by addition of an electrophile R$^4$—X where X is Br or I, to afford compounds of general structure VIII after basic hydrolysis with a base such as LiOH. Coupling of the acid VIII with amines of general structure IX under standard conditions, well-known to one skilled in the art, will afford compounds of general structure I.

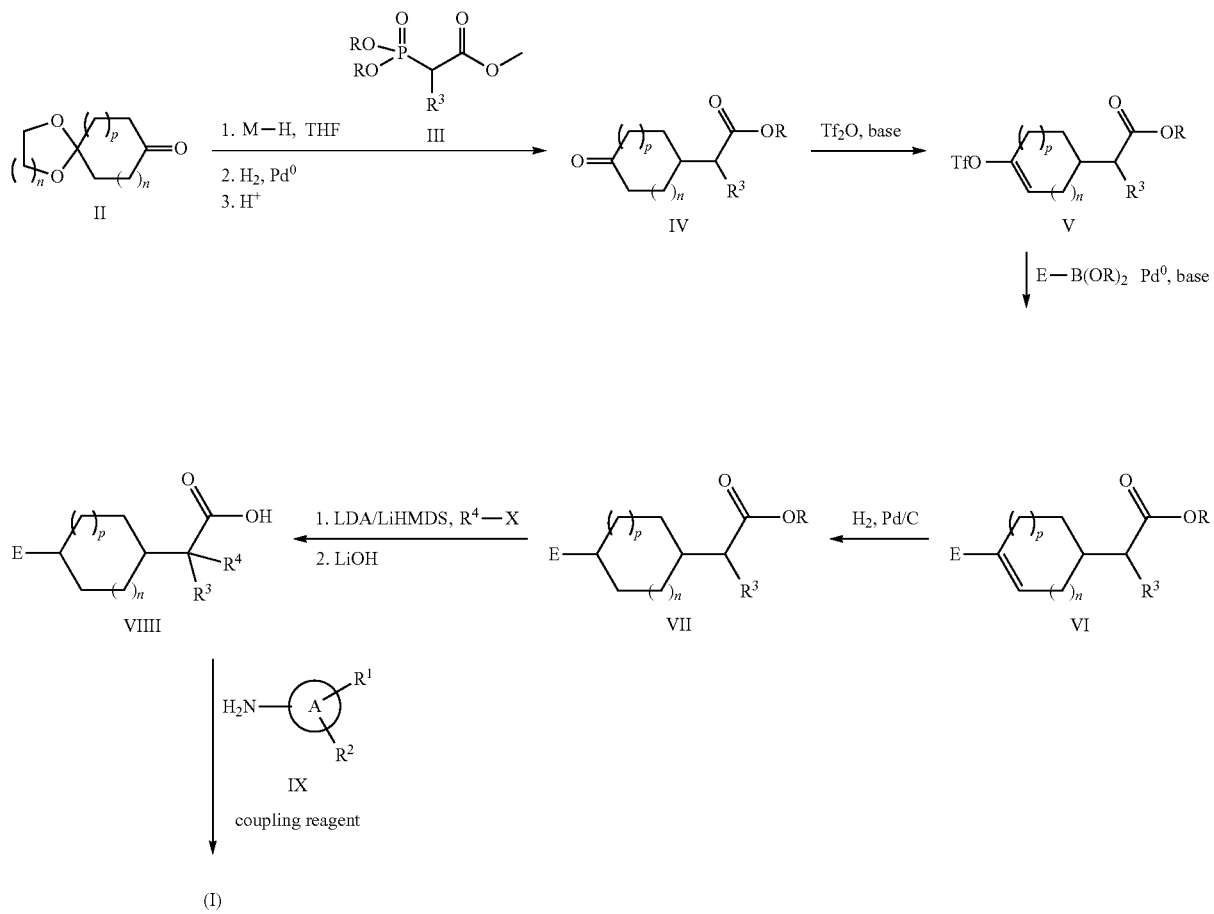

Scheme 1

As represented in Scheme 2, the olefin VT can be hydroborated by treatment with a borane, such as catechol borane, followed by standard oxidative workup with hydrogen peroxide to afford a hydroxylated compound of general structure X, most likely as a mixture of isomers. Compound X can then be converted to a compound of general structure I by methods depicted in Scheme 1.

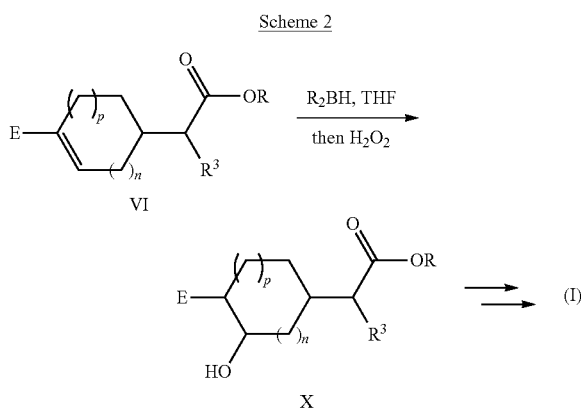

Scheme 2

In Scheme 3 N-alkylation of a protected piperdinone of general structure XI can be accomplished by treatment with a haloacetate of general structure III (X=Br, Cl), subsequent acidic hydrolysis of the ketal will give a keto ester of general structure XII. Vinyl triflate formation, as previously described, will give a compound of general structure XIII. Treatment of the vinyl triflate with a diborane, such as bis-pinnacolatoborane, in the presence of a source of Pd(0), such as $(PPh_3)_4Pd$, will give a vinyl bornic ester of general structure XIV. Suzuki coupling of aryl halides, E-X, where X=Br, I, Cl, OTf, under standard conditions described previously, will afford an unsaturated compound of general structure XV. Compounds of general structure XV can be converted to compounds of general structure I by methods previously described herein. In another embodiment, compounds of general structure XV can first be treated with a borane, such as catechol borane, followed by oxidative workup with hydrogen peroxide, to afford compounds of general structure XVI, which can be converted to compounds of general structure I by methods already described.

Scheme 3

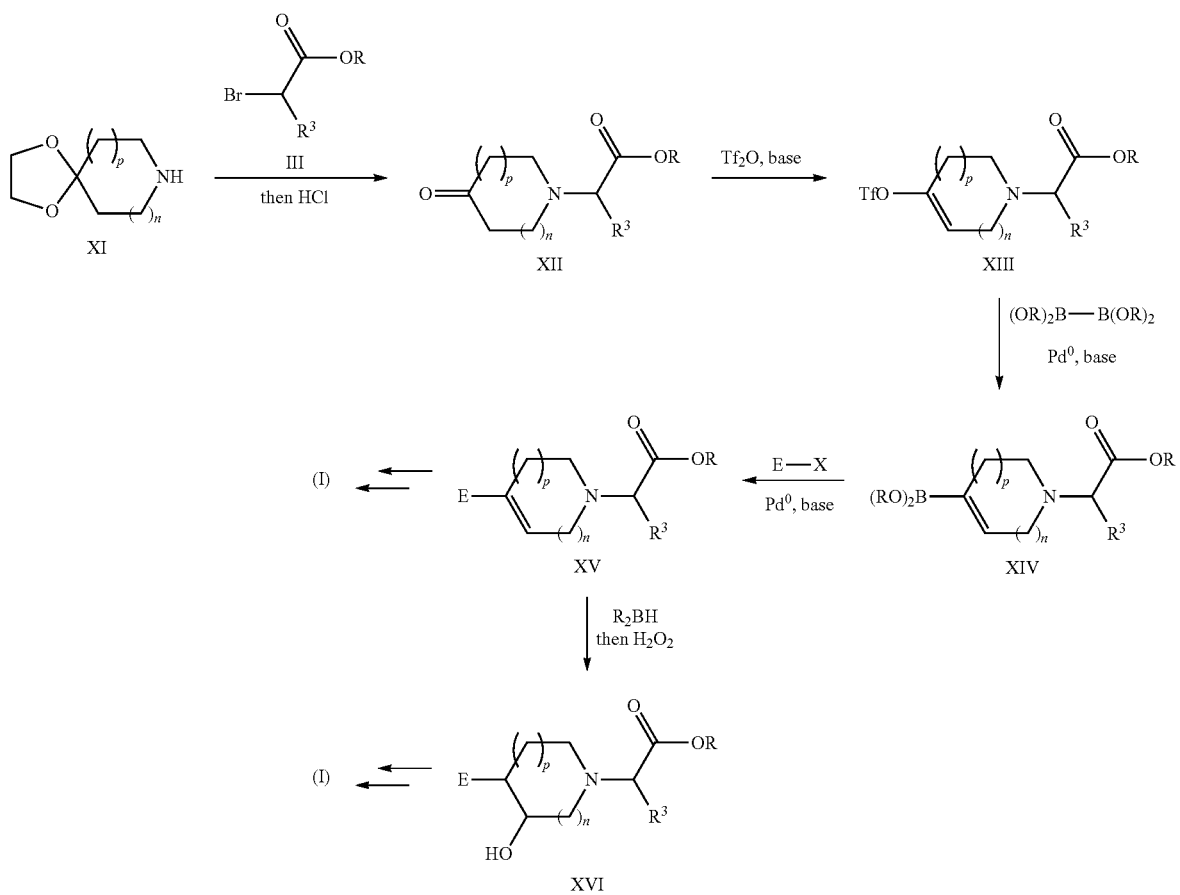

Scheme 4 depicts amide formation via an acyl chloride of general structure XVIII. Treatment of an acid of general structure XVII with chlorinating reagent, such as oxalyl chloride, will afford the desired acyl chloride of general structure XVIII. Compounds of general structure XVIII can be converted to a amides of general structure I by treatment with an amine of general structure IX and an organic base, such as diisopropylethylamine.

Scheme 4

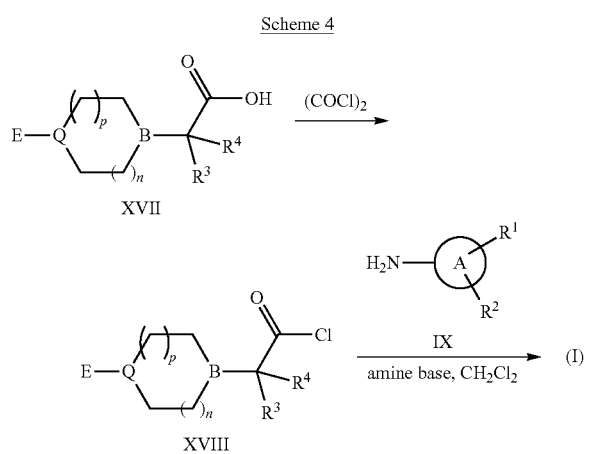

Scheme 5 illustrates a method for controlling the absolute stereochemistry of intermediate XXXIII and materials arising from it. Treatment of an acid of general structure XIX with an acid chloride such as pivaloyl chloride provides a mixed anhydride intermediate. In a separate vessel, an optically pure oxazolidinone of known stereochemistry and general structure XX is deprotonated by treatment with a strong base such as n-BuLi. These activated species are combined to form the acyloxazolidinone XXI which is deprotonated by bases such as NaHMDS. Alkylation of the resulting enolate proceeds with predictable control of stereochemistry at the newly-formed center to provide materials of general structure XXII. Removal of the chiral auxiliary to give optically-active carboxylic acids XXIII is accomplished by treatment with a solution of basic hydrogen peroxide. For a review of the history and scope scope of this reaction see: D. A. Evans, M. D. Ennis, D. J. Mathre. J. Am. Chem. Soc., 1982, 104 (6), pp 1737-1739. Acids of general structure XIII can be converted to compounds of the invention (1) by methods described herein.

Scheme 5

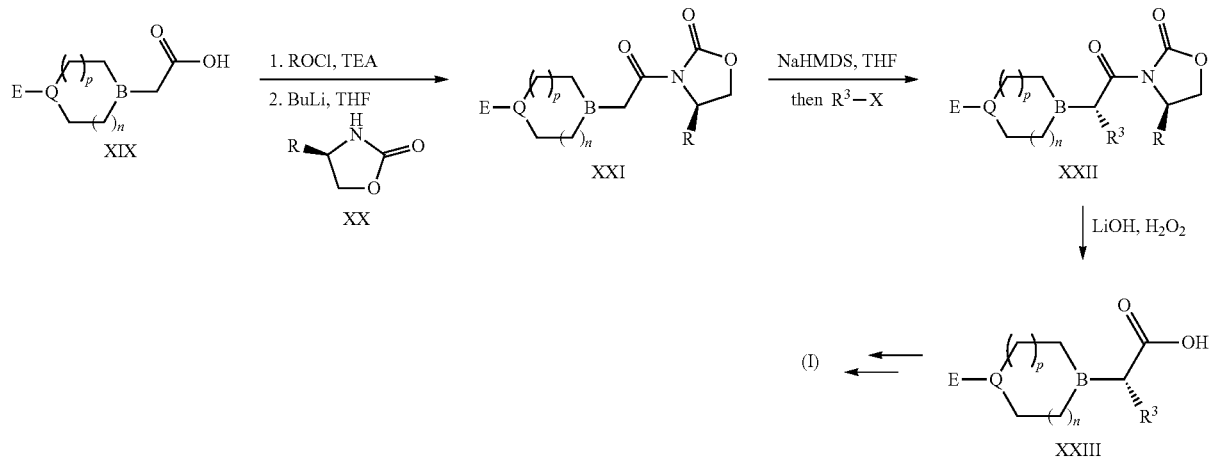

In Scheme 6, a ketone of general structure XXIV, which can be prepared by the methods described in Scheme 1, can be treated under strongly reducing conditions with a borohydride such as sodium borohydride, to give an alcohol of general structure XXV. The alcohol can be treated with a strong base in the presence of activated halo-substituted heteroaromatics to afford an ether of general structure XXVI. Alternatively, the alcohol XXV can be treated under standard Mitsunobu conditions of DIAD and triphenylphosphine to afford ethers of general structure XXVI, which can be converted to compounds of general structure I by methods already described herein.

Scheme 6

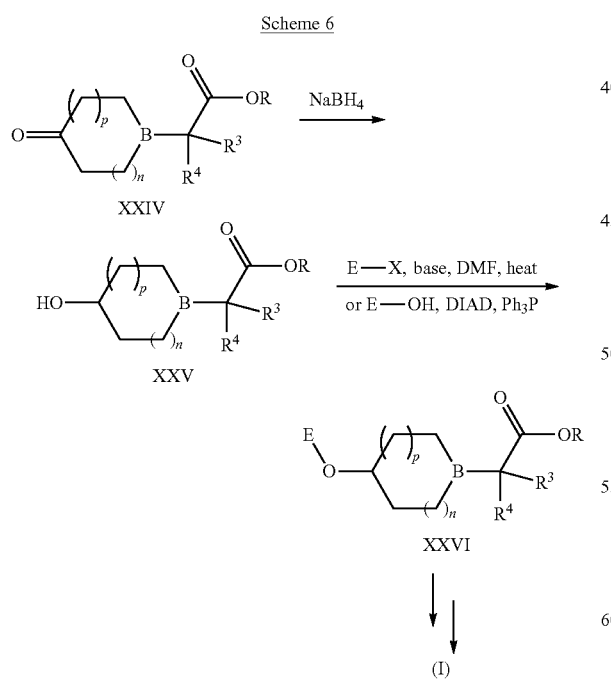

Scheme 7 demonstrates how a ketone of general structure XXIV can be converted to an amine of general structure XXVII via reductive amination. This can be accomplished first by sequential treatment with an amine followed by a reducing agent, such as sodium borohydride. The amine in XXVII can be appended by E-X where X=Cl, Br or I via thermal conditions, such as heat in a solvent such as DMF, or via palladium catalyzed coupling, such as a Buchwald coupling, to afford an amine of general structure XXVIII. The ester of general structure XXVIII can then be converted to a compound of general structure I via methods described herein.

Scheme 7

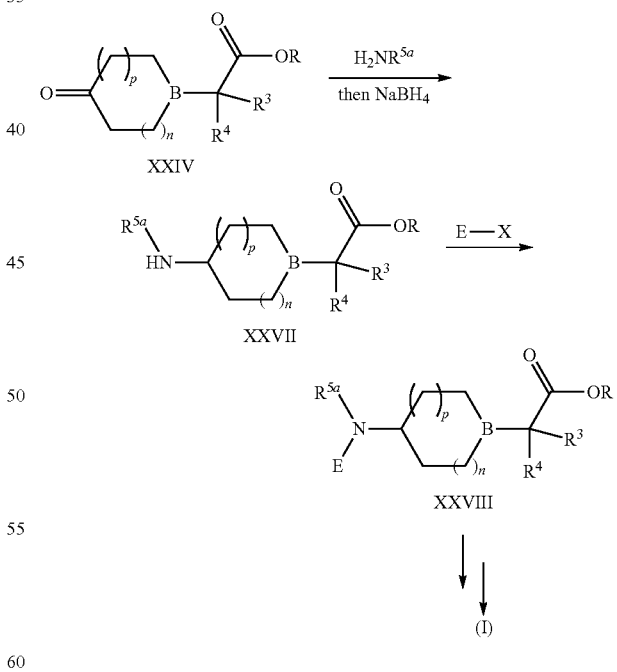

As shown in Scheme 8, a ketone of general structure XXIX can be treated with a haloacetate of general structure III in the presence of activated zinc metal to afford a tertiary alcohol of general structure XXX. The ester of general structure XXX can then be converted to a compound of general structure I via methods already described herein.

Scheme 8

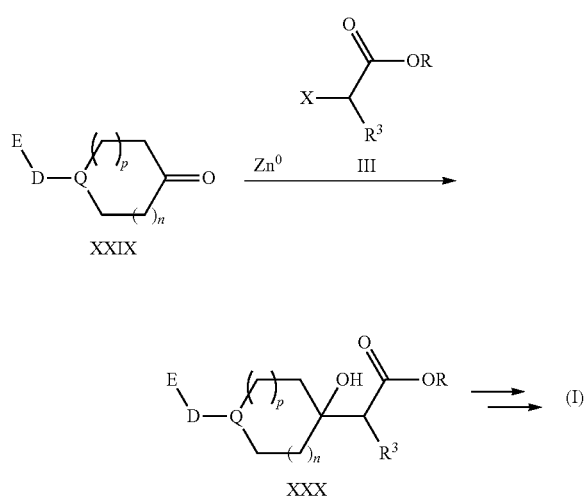

As shown in Scheme 9, a ketone of general structure XXIV can be treated with a metalated species E-M, where M=Li, Na or K, produced by treatment of an aryl halide with, for example an alkyl lithium, such as tert-butyllithium, to produce a tertiary alcohol of general structure XXXI. The ester of general structure XXXI can be converted to a compound of general structure I via methods already described herein.

Scheme 9

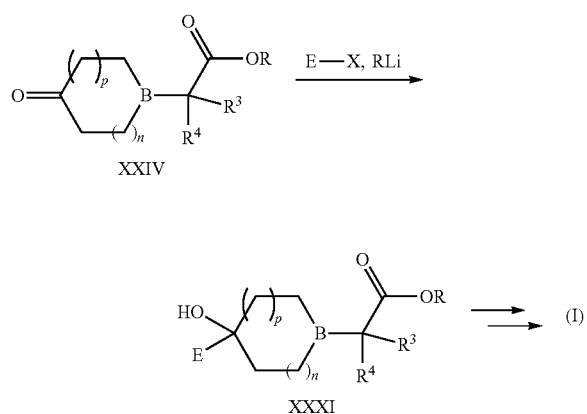

As shown in Scheme 10, a monoprotected diamine of general structure XXXII can be converted to a compound of general structure XXXIII by methods described in Scheme 3 followed by deprotection of the carbamate under acidic or reducing conditions. Treatment of an amine of general structure XXXIII with E-X, where X=Cl, Br, I, and a palldium catalyst, such as $Pd(Ph_3P)_4$, will afford a compound of general structure XXXIV. Alternatively, an amine of general structure XXXIII can be treated with a compound $ECH_2X$ under basic conditions sufficient for N-alkylation to afford a compound of general structure XXXIV. An ester of general structure XXXIV can then be converted to a compound of general structure I by methods already described herein.

Scheme 10

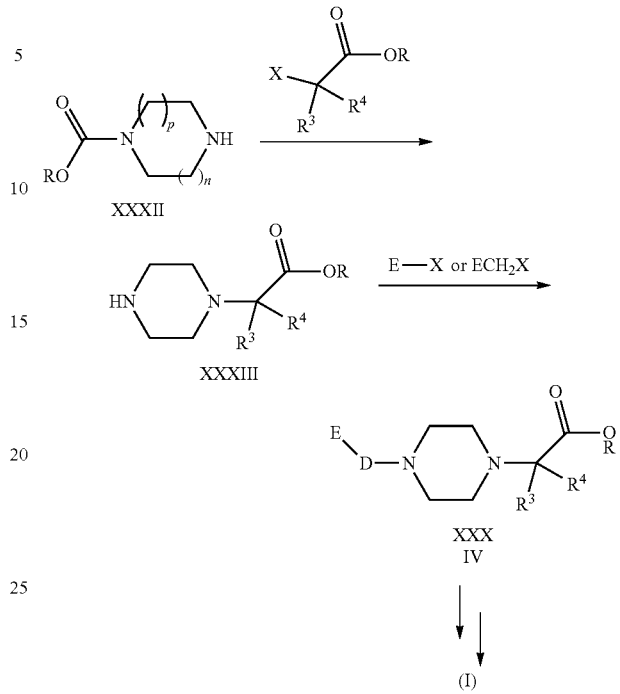

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS and Preparatory/Analytical HPLC Methods Employed in Characterization or Purification of Examples Analytical HPLC/MS was performed using the following methods:

Method A: Waters Acquity SDS using the following method: Linear Gradient of 2% to 98% Solvent B over 1.7 min; UV visualization at 220 nm; Column: BEH C18 2.1 mm×50 mm; 1.7 µm particle (Heated to Temp. 50° C.); Flow rate: 0.8 ml/min; Mobile Phase A: 100% water, 0.05% TFA; Mobile Phase B: 100% acetonitrile, 0.05% TFA.

Method B: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.00 mL/min; Detection: UV at 220 nm.

Method C: Berger Prep SFC MGII, Column: IC 25×3 cm ID, 5 µm Flow rate:85.0 mL/min, Mobile Phase:75/25 $CO_2$/MeOH, Detector Wavelength: 220 nm.

Method D: Berger analytical SFC, Column: Chiral IC 250×4.6 mm ID, 5 µm, Flow rate: 2.0 mL/min, Mobile Phase: 70/30 $CO_2$/MeOH.

Method E: Berger Prep SFC MGII, Column: IC 25×3 cm ID, 5 µm Flow rate:85.0 mL/min, Mobile Phase:82/18 CO$_2$/MeOH w/0.1% diethylamine, Detector Wavelength: 220 nm.

Method F: Aurora analytical SFC, Column: Chiral AS 250×4.6 mm ID, 5 µm, Flow rate: 2.0 mL/min, Mobile Phase: 80/20 CO$_2$/MeOH w/0.1% diethylamine.

Method G: Preparative Conditions: Berger SFC MGII; Stage-1: Column: Chiral OD-H 25×3 cm ID, 5-µm particles; Mobile Phase:82/18 CO$_2$/MeOH; Detector Wavelength: 220 nm; Flow: 85 mL/min. Stage-2: Chiral IF 25×3 cm ID, 5-µm particles; Mobile Phase:80/20 CO$_2$/MeOH; Detector Wavelength: 220 nm; Flow: 85 mL/min. Analytical Conditions: Aurora analytical SFC; Stage-1: Column: Chiral OD-H 250×4.6 mm ID, 5 µm; Mobile Phase:80/20 CO$_2$/MeOH; Flow: 2.0 mL/min; Stage-2: Column: Chiral IF 250×4.6 mm ID, 5 µm; Mobile Phase:80/20 CO$_2$/MeOH; Flow: 2.0 mL/min. Tr corresponds to the analytical condition.

Method H: Preparative Conditions: Berger SFC MGII; Stage-1: Column: Chiral OD-H 25×3 cm ID, 5-µm particles; Mobile Phase:80/20 CO$_2$/MeOH; Detector Wavelength: 220 nm; Flow: 85 mL/min. Stage-2: Chiral IF 25×3 cm ID, 5-µm particles; Mobile Phase:80/20 CO$_2$/MeOH; Detector Wavelength: 220 nm; Flow: 85 mL/min. Analytical Conditions: Aurora analytical SFC; Stage-1: Column: Chiral OD-H 250×4.6 mm ID, 5 µm; Mobile Phase:80/20 CO$_2$/MeOH; Flow: 2.0 mL/min; Stage-2: Column: Chiral IF 250×4.6 mm ID, 5 µm; Mobile Phase:80/20 CO$_2$/MeOH; Flow: 2.0 mL/min. Tr corresponds to the analytical condition.

Method I: Preparative Conditions: Berger SFC MGII; Column: WHELK-O® 1 KROMASIL® 25×3 cm ID, 5-µm particles; Mobile Phase:80/20 CO$_2$/MeOH; Detector Wavelength: 220 nm; Flow: 85 mL/min. Analytical Conditions: Aurora analytical SFC; Column: WHELK-O® 1 KROMASIL® 250×4.6 mm ID, 5 µm; Mobile Phase:80/20 CO$_2$/MeOH; Flow: 2.0 mL/min; Tr corresponds to the analytical condition.

Method J: Preparative Conditions: Berger SFC MGII; Column: Chiral OJ 25×3 cm ID, 5-µm; Mobile Phase:90/10 CO$_2$/MeOH; Detector Wavelength: 220 nm; Flow: 85 mL/min. Analytical Conditions: Aurora analytical SFC; Column: Chiral OJ 250×4.6 mm ID, 5 µm; Mobile Phase:90/10 CO$_2$/MeOH; Flow: 2.0 mL/min; Tr corresponds to the analytical condition.

Method K: Preparative Conditions: Waters SFC-100 MS; Column: PHENOMENEX® Lux Cellulose-2 25×3 cm ID, 5 µm; Mobile Phase:75/25 CO$_2$/MeOH; Detector Wavelength: 220 nm; Flow: 100 mL/min. Analytical Conditions: Aurora analytical SFC; Column: PHENOMENEX® Lux Cellulose-2 250×4.6 mm ID, 5 µm; Mobile Phase:75/25 CO$_2$/MeOH; Flow: 2.0 mL/min; Tr corresponds to the analytical condition.

Method L: Preparative Conditions: Berger SFC MGII; Column: Chiral AD 25×3 cm ID, 5-µm; Mobile Phase:80/20 CO$_2$/MeOH; Detector Wavelength: 220 nm; Flow: 85 mL/min. Analytical Conditions: Aurora analytical SFC; Column: Chiral AD 250×4.6 mm ID, 5 µm; Mobile Phase:80/20 CO$_2$/MeOH; Flow: 2.0 mL/min; Tr corresponds to the analytical condition.

Method M: Preparative Conditions: Berger SFC MGII; Column: Chiral AD 25×3 cm ID, 5-µm; Mobile Phase:87/13 CO$_2$/MeOH; Detector Wavelength: 220 nm; Flow: 85 mL/min. Analytical Conditions: Aurora analytical SFC; Column: Chiral AD 250×4.6 mm ID, 5 µm; Mobile Phase:85/15 CO$_2$/MeOH; Flow: 2.0 mL/min; Tr corresponds to the analytical condition.

Method N: Preparative Conditions: Berger SFC MGII; Column: Chiral IF 25×3 cm ID, 5-µm; Mobile Phase:75/25 CO$_2$/MeOH; Detector Wavelength: 220 nm; Flow: 85 mL/min. Analytical Conditions: Aurora analytical SFC; Column: Chiral IF 250×4.6 mm ID, 5 µm; Mobile Phase:70/30 CO$_2$/MeOH; Flow: 2.0 mL/min; Tr corresponds to the analytical condition.

Method O: Preparative Conditions: Waters SFC100-MS; Column: Chiral IC 25×3 cm ID, 5-µm coupled to WHELK-O® (R,R) KROMASIL® 25×3 cm ID 5-µm; Mobile Phase: 70/30 CO$_2$/MeOH; Detector Wavelength: 220 nm; Flow: 100 mL/min. Analytical Conditions: Aurora analytical SFC; Column: Chiral IC 250×4.6 mm ID, 5 µm coupled to WHELK-O® (R,R) KROMASIL® 25×3 cm ID 5-µm; Mobile Phase:70/30 CO$_2$/MeOH; Flow: 2.0 mL/min; Tr corresponds to the analytical condition.

Method P: Preparative Conditions: Waters SFC100-MS; Column: Chiral OJ-H 25×3 cm ID, 5-µm; Mobile Phase:70/30 CO$_2$/MeOH; Detector Wavelength: 220 nm; Flow: 100 mL/min. Analytical Conditions: Aurora analytical SFC; Column: Chiral OJ-H 250×4.6 mm ID, 5 µm; Mobile Phase: 70/30 CO$_2$/MeOH; Flow: 2.0 mL/min; Tr corresponds to the analytical condition.

Method Q: Preparative Conditions: Berger SFC MGII; Column: Chiral WHELK-O® 25×3 cm ID, 5-µm; Mobile Phase:80/20 CO$_2$/MeOH; Detector Wavelength: 220 nm; Flow: 85 mL/min. Analytical Conditions: Aurora analytical SFC; Column: Chiral WHELK-O® 250×4.6 mm ID, 5 µm; Mobile Phase:80/20 CO$_2$/MeOH; Flow: 2.0 mL/min; Tr corresponds to the analytical condition.

Method R: Waters Acquity SDS using the following method: Linear Gradient of 2% to 98% Solvent B over 1.6 min; UV visualization at 220 nm; Column: BEH C18 2.1 mm×50 mm; 1.7 µm particle (Heated to Temp. 50° C.); Flow rate: 1 ml/min; Mobile Phase A: 100% water, 0.05% TFA; Mobile Phase B: 100% acetonitrile, 0.05% TFA.

NMR Employed in Characterization of Examples $^1$H NMR spectra (unless otherwise noted) were obtained with JEOL® or Bruker FOURIER® transform spectrometers operating at 400 MHz or 500 MHz.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for CD$_3$SOCD$_2$H, 3.30 ppm for CD$_2$HOD, 1.94 for CHD$_2$CN, 7.26 ppm for CHCl$_3$, 5.32 ppm for CDHCl$_2$). Abbreviations used in the description of NMR peaks: "a"=apparent, "br. s."=broad singlet

EXAMPLES

General Procedures

General Procedure A: Preparation of Aryl Cyclohexenes via Suzuki Cross-Coupling Reaction

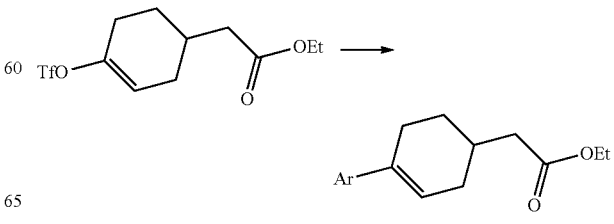

To ethyl 2-(4-(((trifluoromethyl)sulfonyl)oxy)cyclohex-3-en-1-yl)acetate (1.0 equiv), aryl boronic acid (1.2 equiv), K₃PO₄ (1.5 equiv), KBr (1.1 equiv) in 1,4-dioxane (0.25M) was added water (0.025M) followed by Pd(PPh₃)₄ (5-10 mol %). The resulting reaction mixture was heated to 80° C. for 16 h, upon which the crude reaction mixture was concentrated. The resulting solids were diluted with EtOAc and water and the layers were separated. The aqueous layer was extracted with EtOAc (3×). The combined organic extracts were dried over anhydrous MgSO₄, filtered, and concentrated under reduced pressure. The crude reaction mixture was purified employing silica gel chromatography (0% to 100% EtOAc in hexanes) to afford the desired product.

* ethyl 2-(4-(((trifluoromethyl)sulfonyl)oxy)cyclohex-3-en-1-yl)acetate is a known compound that can be prepared from commercially available 1,4-dioxaspiro[4.5]decan-8-one using the procedures outlined in 1) Stocks, P. A.; et. al, *Angew. Chem. Int. Et.* (2007) v. 46, pp. 6278-6283; 2) Barlind, J. G.; et. al, *J. Med. Chem.* (2012) v. 55, pp. 10610-10629.

General Procedure B: Hydrogenation

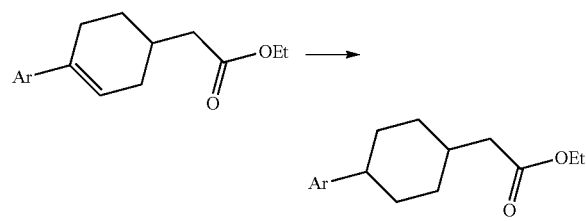

A solution of the unsaturated starting material in the indicated solvent (MeOH, EtOAc, EtOH etc). was purged with nitrogen and 20 wt. % of the indicated catalyst (dry activated Pd/C 10 wt. %, or Degussa Pd/C 10 wt. %, or 10 wt. % Pd(OH)₂/C) was added. The flask was closed with a rubber septum and hydrogen gas was bubbled through the heterogeneous mixture until complete disappearance of the starting material (determined by TLC, and/or LC-MS, and/or NMR). Upon completion, reaction mixture was purged with nitrogen, filtered through a pad of Celite®, and concentrated under reduced pressure. The crude reaction mixture was purified employing silica gel chromatography (0% to 100% EtOAc in hexanes) to afford the desired product.

General Procedure C: Horner-Wadsworth-Emmons Olefination

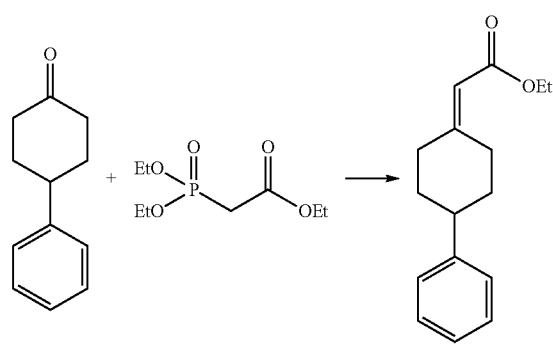 [SMILES: O=C1CCC(c2ccccc2)CC1 ; CCOC(=O)CP(=O)(OCC)OCC ; CCOC(=O)C=C1CCC(c2ccccc2)CC1]

To a suspension of either NaO^tBu or NaH (1.1 equiv) in THF (1.6 M) at 0° C. was added triethylphosphono acetate (1.1 equiv) over 1 h. The reaction mixture was stirred for 1 h at 0° C. and a solution of the appropriate ketone (1.0 equiv) in THF (1.5 M) was added dropwise. The reaction mixture was slowly warmed to rt and was stirred for 90 min before being poured into saturated aqueous NH₄Cl and EtOAc. The layers were separated, and aqueous layer was extracted with EtOAc (3×). The combined organics were washed sequentially with saturated NaHCO₃ and brine before drying over anhydrous Na₂SO₄, filtration, and concentration under reduced pressure. The crude material was purified via silica gel chromatography (10% EtOAc in hexanes) to afford the desired product.

General Procedure D: Reduction of α,β-Unsaturated Esters with Stryker's Reagent

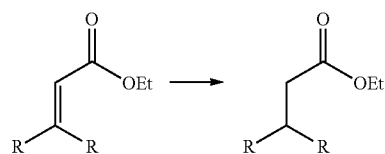

To a solution of α,β-unsaturated ester (1.0 equiv) in toluene (0.5 M) were added [PPh₃CuH]₆ (1 mol %) and ^tBuOH (1.1 equiv). The solution was bubbled with argon for 5 min before polymethylhydrosiloxane (125 μL for each mmol of α,β-unsaturated ester used) was added. The resulting reaction mixture was stirred under argon at rt for 14 h at which point saturated aqueous NaHCO₃ and diethyl ether were added. The heterogeneous mixture was stirred for 3 h, and the layers were separated. The aqueous layer was extracted with diethyl ether (2×). The combined organic extracts were dried over anhydrous Na₂SO₄, filtered, concentrated under reduced pressure and the resulting crude reaction mixture was purified employing silica gel chromatography (0% to 100% EtOAc in hexanes) to afford the desired product.

General Procedure E: Ester Hydrolysis

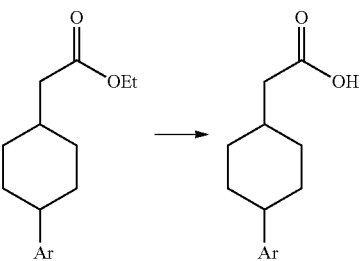

To a solution of ester (1.0 equiv.) in EtOH (1.0 M) was added an equal volume of aqueous LiOH solution (7.25 M). The reaction mixture was stirred vigorously, heated to 50° C. for 1 h and then diluted with 50 mL of water and further heated to 50° C. for 5 h. The reaction mixture was cooled with an ice bath and acidified (pH~1) by slow addition of 3 M HCl solution. EtOAc was added, the layers were separated, and the aqueous phase was extracted with EtOAc (3×). The combined organic extracts were dried over anhydrous Na₂SO₄, filtered and concentrated under reduced pressure to afford desired carboxylic acid which was used without further purification.

General Procedure F: Amide Bond Coupling

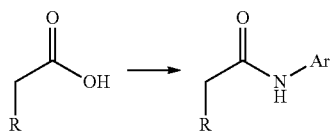

To a stirred solution of carboxylic acid (1.0 equiv) in DMF (0.3 M) were added aniline (1.5 equiv), $^{i}Pr_2NEt$ (2 equiv), and 1-[bis(dimethylamino)methylene]-1H-1,2,3-triazolo[4,5-b]pyridinium 3-oxid hexafluorophosphate (HATU) (1.2 equiv). The resulting reaction mixture was stirred at rt for 3 h at which point 3 M HCl and $CH_2Cl_2$ were added. The layers were separated and the aqueous layer was extracted with $CH_2Cl_2$ (2×). The combined organic extracts were dried over anhydrous $Na_2SO_4$, concentrated under reduced pressure and the resulting residue was purified by silica gel chromatography (0% to 100% EtOAc in hexanes) to afford the desired product.

General Procedure G: Aniline Addition to Esters

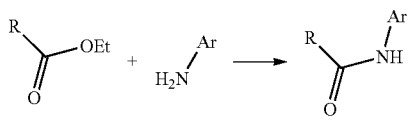

To a solution of the aniline (2.0 equiv) in THF (0.25 M) at 0° C. was added a solution of $^{i}PrMgCl$ (2.0 equiv, 2 M in THF). The resulting solution was warmed to rt, stirred for 5 min at which point the ester (1.0 equiv) was added dropwise. The resulting reaction mixture was stirred at rt for 8 h and was poured onto a saturated solution of $NH_4Cl$. EtOAc was added and the layers were separated. The aqueous layer was extracted with EtOAc (3×). The combined organic extracts were dried over anhydrous $MgSO_4$, filtered, and concentrated under reduced pressure. The crude reaction mixture was purified employing silica gel chromatography (0% to 100% EtOAc in hexanes) to afford the desired product.

General Procedure H: Preparation of Aryl Cyclohexenes via Suzuki Cross-Coupling Reaction

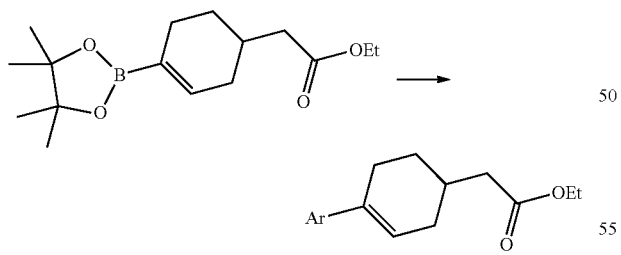

To ethyl 2-(4-(4,4,5,5-tetramethyl-1,3,2-dioxaborolan-2-yl)cyclohex-3-en-1-yl)acetate (1.0 equiv), aryl halide (1.0 equiv), $Na_2CO_3$ (3.0 equiv), and $Pd(PPh_3)_4$ (5-10 mol %), were added 1,4-dioxane/water (9:1, 0.2M). The resulting reaction mixture was degassed with nitrogen and heated to 85° C. for 24 h upon which the crude reaction mixture was concentrated. The resulting solids were diluted with EtOAc and water and the layers were separated. The aqueous layer was extracted with EtOAc (3×). The combined organic extracts were dried over anhydrous $MgSO_4$, filtered, and concentrated under reduced pressure. The crude reaction mixture was purified employing silica gel chromatography (0% to 100% EtOAc in hexanes) to afford the desired product.

* ethyl 2-(4-(4,4,5,5-tetramethyl-1,3,2-dioxaborolan-2-yl) cyclohex-3-en-1-yl)acetate is a known compound that can be prepared from commercially available 1,4-dioxaspiro [4.5]decan-8-one using the procedures outlined in Barlind, J. G.; et. al, *J. Med. Chem.* (2012) v. 55, pp. 10610-10629.

General Procedure I: Reformatsky Reaction

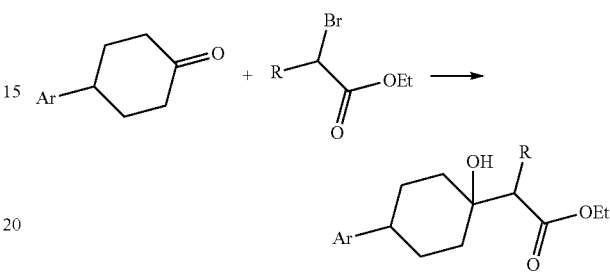

To a solution of 4-arylcyclohexanone (1.0 equiv) and zinc dust (1.2 equiv) in THF (1.0M) was added α-bromoester (1.1-1.5 equiv) in THF over 5 min. The resulting reaction mixture was heated to reflux for 3-12 h. The reaction mixture was cooled to rt and filtered through a pad of CELITE® and concentrated under reduced pressure. The crude reaction mixture was purified employing silica gel chromatography (0% to 100% EtOAc in hexanes) to afford the desired product.

General Procedure J: Chloroaniline Formation

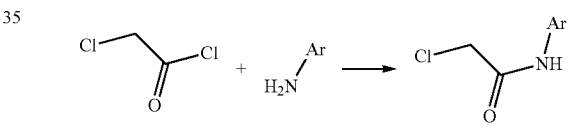

To a solution of aniline (1.0 equiv) in HOAc (2 M relative to aniline) was added chloroacetyl chloride (1.04 equiv) followed by a saturated solution of NaOAc (2 M relative to aniline) and water (relative to aniline). The resulting slurry was stirred at rt for 10 min and water was added. The suspension was filtered and the residue collected was washed with water and dried under vacuum to afford the desired product.

Example 1 cis-N-(5-Chloropyridin-2-yl)-2-((1,4)-4-phenylcyclohexyl)acetamide

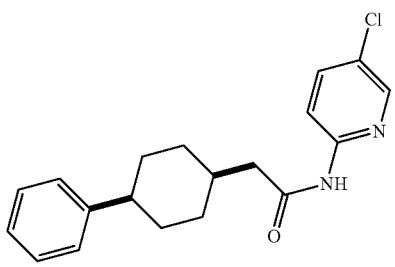

Preparation 1A: Ethyl 2-(4-phenylcyclohexylidene)acetate

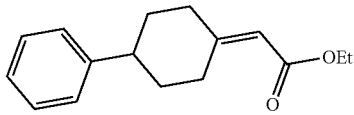 [SMILES: CCOC(=O)C=C1CCC(c2ccccc2)CC1]

Sodium tert-butoxide (6.1 g, 63.2 mmol) was suspended in THF (72 mL) and cooled to 0° C. Triethylphosphonoacetate (12.5 mL, 63.2 mmol) was added dropwise and the reaction was warmed to rt. After warming, the solution became colorless. The reaction was cooled to 0° C. and a THF (72 mL) solution of 4-phenylcyclohexanone (10 g, 57.5 mmol) was added dropwise over 30 min. After addition, the reaction was warmed to room temperature during which time the reaction became biphasic. Stirring was continued for 1 h then the solvent was removed under reduced pressure. The residue was dissolved in EtOAc (150 mL) and washed with 1 M HCl (100 mL). The organic layer was dried with anhydrous $Na_2SO_4$, concentrated under reduced pressure and purified by silica gel chromatography (0%-30% EtOAc in hexanes) which afforded Preparation 1A as a clear oil (13.3 g, 95%). $^1$H NMR (400 MHz, $CDCl_3$) δ 7.35-7.26 (m, 2H), 7.23-7.15 (m, 3H), 5.68 (s, 1H), 4.15 (d, J=7.5 Hz, 2H), 4.03-3.89 (m, 1H), 2.79 (tt, J=12.2, 3.4 Hz, 1H), 2.49-2.28 (m, 2H), 2.13-1.97 (m, 3H), 1.74-1.59 (m, 2H), 1.36-1.22 (m, 3H).

Preparation 1B: Ethyl 2-(4-phenylcyclohexyl)acetate

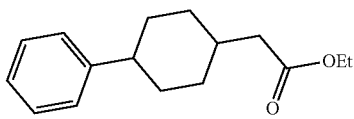 [SMILES: CCOC(=O)CC1CCC(c2ccccc2)CC1]

To a degassed solution of Preparation 1A (11.1 g, 45.5 mmol) in toluene (91 mL) was added tert-butanol (4.8 mL, 50 mmol), $[PPh_3CuH]_6$ (890 mg, 1 mol %), and polymethylhydrosiloxane (5.6 mL). The brown reaction mixture was stirred vigorously under an atmosphere of argon at rt for 15 h. After that time saturated aqueous $NaHCO_3$ (100 mL) and diethyl ether (100 mL) were added and the biphasic mixture was stirred vigorously for 3 h. The layers were separated and the aqueous layer extracted with diethyl ether (100 mL). The combined organic extracts were dried with anhydrous $Na_2SO_4$, concentrated under reduced pressure and purified by silica gel chromatography (0%-30% EtOAc in hexanes) to afford Preparation 1B as a clear oil (10.1 g, 90%). $^1$H NMR (400 MHz, $CDCl_3$, 1:1 mixture of diastereomers) δ 7.38-7.09 (m, 10H), 4.19-4.09 (m, 4H), 2.65-2.52 (m, 1H), 2.52-2.40 (m, 3H), 2.37-2.27 (m, 1H), 2.23 (d, J=6.7 Hz, 2H), 1.96-1.81 (m, 5H), 1.77-1.59 (m, 8H), 1.57-1.43 (m, 2H), 1.28-1.22 (m, 6H), 1.22-1.06 (m, 2H).

Example 1: cis-N-(5-Chloropyridin-2-yl)-2-((1,4)-4-phenylcyclohexyl)acetamide Prepared with General Procedure G employing Preparation 1B (246 mg, 1.0 mmol), 5-chloropyridin-2-amine (257 mg, 2.0 mmol), $^i$PrMgCl (1.0 mL, 2.0 mmol) in THF (5.0 mL). Purified using silica gel chromatography (5% to 15% EtOAc in hexanes) to afford the desired product as a white solid. $^1$H NMR (400 MHz; $CDCl_3$): δ 8.24-8.21 (m, 2H), 7.93 (s, 1H), 7.67 (ddd, J=8.9, 2.6, 0.3 Hz, 1H), 7.34-7.29 (m, 2H), 7.26-7.18 (m, 3H), 2.67-2.60 (m, 1H), 2.50 (d, J=7.1 Hz, 2H), 2.45-2.38 (m, 1H), 1.80-1.66 (m, 8H). m/z 329.2 $(M+H)^+$.

Example 4 trans-N-(5-Chloropyridin-2-yl)-2-((1,4)-4-phenylcyclohexyl)acetamide

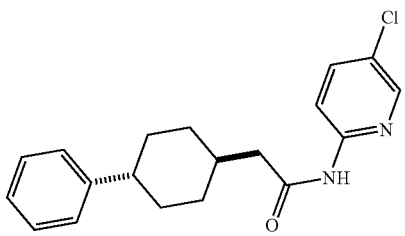

Further elution from the column in the previous example afforded the desired product as a white solid and the second eluting isomer. $^1$H NMR (400 MHz; $CDCl_3$): δ 8.25-8.22 (m, 2H), 7.91 (s, 1H), 7.67 (ddd, J=8.9, 2.6, 0.5 Hz, 1H), 7.31-7.27 (m, 2H), 7.22-7.16 (m, 3H), 2.49 (tt, J=12.2, 3.3 Hz, 1H), 2.32 (d, J=6.7 Hz, 2H), 2.01-1.90 (m, 5H), 1.54 (qd, J=12.8, 3.0 Hz, 2H), 1.28-1.16 (m, 2H). m/z 329.2 $(M+H)^+$.

Example 5 cis-N-(5-Chloropyrimidin-2-yl)-2-((1,4)-4-phenylcyclohexyl)acetamide

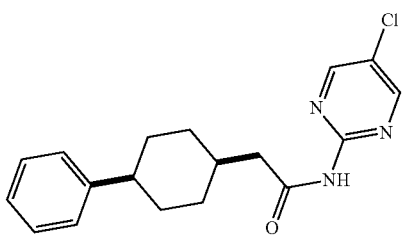

Prepared with General Procedure G employing ethyl 2-(4-phenylcyclohexyl) acetate (Preparation 1B, 246 mg, 1.0 mmol), 5-chloropyrimidin-2-amine (259 mg, 2.0 mmol), $^i$PrMgCl (1.0 mL, 2.0 mmol) in THF (5.0 mL). Purified using silica gel chromatography (25% to 75% EtOAc in hexanes) to afford the desired product as a white solid. $^1$H NMR (400 MHz; $CDCl_3$): δ 8.77 (s, 1H), 8.58 (s, 2H), 7.33-7.29 (m, 2H), 7.26-7.24 (m, 2H), 7.22-7.17 (m, 1H), 2.83 (d, J=7.5 Hz, 2H), 2.65-2.59 (m, 1H), 2.48-2.42 (m, 1H). m/z 338.2 $(M+H)^+$.

Example 6 cis-N-(4-(2-Hydroxypropan-2-yl)phenyl)-2-((1,4)-4-phenylcyclohexyl)acetamide

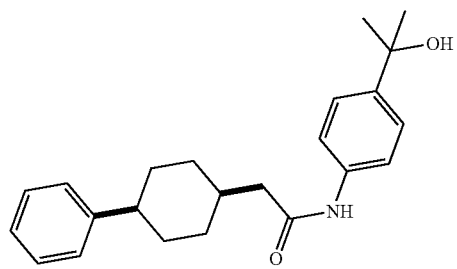

Preparation 6A: 2-(4-Aminophenyl)propan-2-ol

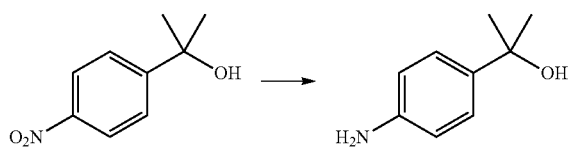

2-(4-Nitrophenyl)propan-2-ol (136 mg, 0.75 mmol) and Pd/C (14 mg, 10 wt. % Pd) were stirred in MeOH (2 mL) under an atmosphere of $H_2$ for 6 h. The resulting reaction mixture was filtered through CELITE® and concentrated under reduced pressure. The resulting residue was purified using silica gel chromatography (0% to 40% EtOAc in δ 7.28 (dt, J=8.9, 2.4 Hz, 2H), 6.68-6.64 (m, 2H), 3.64 (s, 1H), 1.55 (d, J=3.8 Hz, 6H).

Example 6 cis-N-(4-(2-Hydroxypropan-2-yl)phenyl)-2-((1,4)-4-phenylcyclohexyl)acetamide

Prepared with General Procedures E employing Preparation 1B and F employing 2-(4-phenylcyclohexyl)acetic acid (24 mg, 0.11 mmol), Preparation 6A (15 mg, 0.1 mmol), HATU (64 mg, 0.11 mmol), and $^iPr_2NEt$ (65 mg, 0.5 mmol) in DMF (500 µL). Purified using silica gel chromatography (40% EtOAc in hexanes) to afford the desired product as a white solid. $^1H$ NMR (400 MHz; CDCl$_3$): δ 7.49-7.46 (m, 2H), 7.43-7.41 (m, 2H), 7.33-7.28 (m, 3H), 7.24-7.17 (m, 2H), 2.65-2.60 (m, 1H), 2.46-2.39 (m, 3H), 1.77-1.67 (m, 8H), 1.56 (s, 6H). m/z 334.3 (M–H$_2$O).

Example 8 trans-N-(4-(2-Hydroxypropan-2-yl)phenyl)-2-((1,4)-4-phenylcyclohexyl)acetamide

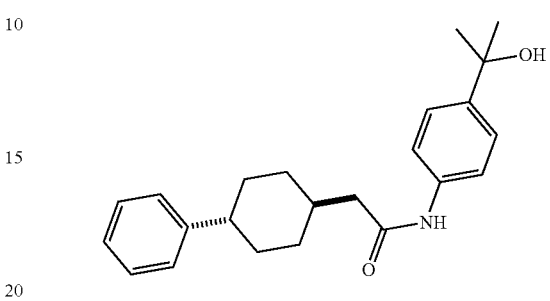

Further elution from the column in the previous example afforded the desired product as a white solid and the second eluting isomer. $^1H$ NMR (400 MHz; CDCl$_3$): δ 7.52-7.48 (m, 2H), 7.45-7.43 (m, 2H), 7.31-7.26 (m, 2H), 7.21-7.16 (m, 3H), 2.52-2.43 (m, 1H), 2.28 (d, J=6.7 Hz, 2H), 2.00-1.89 (m, 5H), 1.55-1.48 (m, 2H), 1.26-1.16 (m, 2H), 1.57 (s, 6H). m/z 334.3 (M–H$_2$O).

Example 9 cis-N-(4-(Hydroxymethyl)phenyl)-2-((1,4)-4-phenylcyclohexyl)acetamide

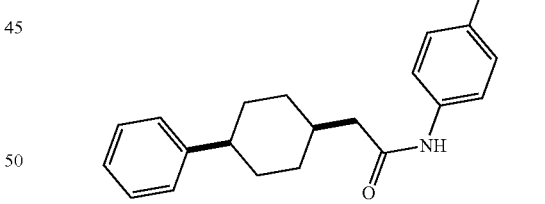

Prepared with General Procedures E employing Preparation 1B and F employing 2-(4-phenylcyclohexyl)acetic acid (44 mg, 0.2 mmol), 4-(4-aminophenyl)methanol (37 mg, 0.3 mmol), HATU (174 mg, 0.3 mmol), and $^iPr_2NEt$ (129 mg, 1.0 mmol) in DMF (1.0 mL). Purified using silica gel chromatography (30% to 60% EtOAc in hexanes) to afford the desired product as a white solid. $^1H$ NMR (400 MHz; CDCl$_3$): δ 7.52-7.49 (m, 2H), 7.32-7.28 (m, 5H), 7.24-7.17 (m, 2H), 4.64 (s, 2H), 2.66-2.60 (m, 1H), 2.47-2.36 (m, 3H), 1.84-1.57 (m, 8H). m/z 324.3 (M+H)$^1$.

Example 10 trans-N-(4-(Hydroxymethyl)phenyl)-2-((1,4)-4-phenylcyclohexyl)acetamide

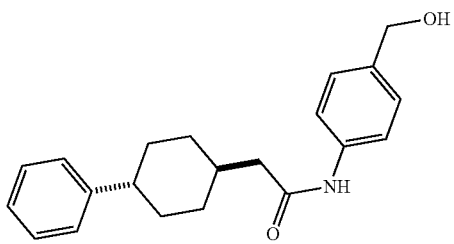

Further elution from the column in the previous example afforded the desired product as a white solid and the second eluting isomer. ¹H NMR (400 MHz; CDCl₃): δ 7.53-7.51 (m, 2H), 7.33-7.30 (m, 3H), 7.29-7.26 (m, 2H), 7.21-7.18 (m, 3H), 4.65 (s, 2H), 2.52-2.42 (m, 1H), 2.28 (d, J=6.6 Hz, 2H), 1.99-1.90 (m, 5H), 1.76-1.68 (m, 2H), 1.59-1.48 (m, 2H), 1.26-1.15 (m, 2H). m/z 324.2 (M+H)⁺.

Example 11 cis-N-(4-Chlorophenyl)-2-(4-phenylcyclohexyl)acetamide

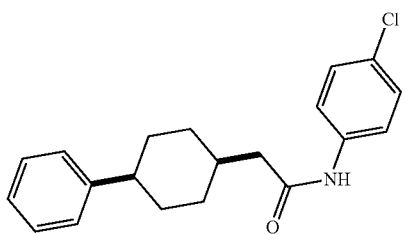

Prepared using General Procedure E employing Preparation 1B and F. General procedure F employed 200 mg 2-(4-phenylcyclohexyl)acetic acid (mixture of diastereomers), and 140 mg 4-chloroaniline. Purified using silica gel chromatography (0% to 30% EtOAc in hexanes) to afford the desired cis-diastereomer as the first eluting isomer. ¹H NMR of cis-isomer (400 MHz; CDCl₃): δ 7.45-7.50 (m, 2H), 7.18-7.34 (m, 7H), 7.14 (bs, 1H), 2.60-2.68 (m, 1H), 2.36-2.47 (m, 3H), 2.03-2.14 (m, 1H), 1.64-1.82 (m, 7H) ppm. m/z 328.1 (M+H)⁺.

Example 12 trans-N-(4-Chlorophenyl)-2-(4-phenylcyclohexyl)acetamide

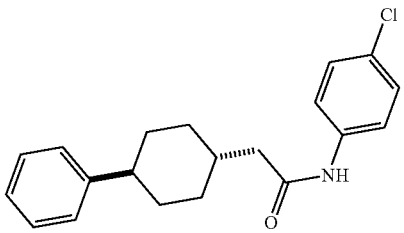

Further elution from the column afforded the desired trans-diastereomer as the second eluting isomer. ¹H NMR of trans-isomer (400 MHz; DMSO-d₆): δ 10.04 (s, 1H), 7.60-7.66 (m, 2H), 7.31-7.36 (m, 2H), 7.20-7.30 (m, 4H), 7.13-7.18 (m, 1H), 2.46 (tt, J=12.2 Hz, J=3.1 Hz, 1H), 2.23 (d, J=6.6 Hz, 2H), 1.75-1.90 (m, 5H), 1.40-1.53 (m, 2H), 1.08-1.23 (m, 2H) ppm. m/z 328.1 (M+H)⁺.

Example 13 cis-N-Phenyl-2-(4-phenylcyclohexyl)acetamide

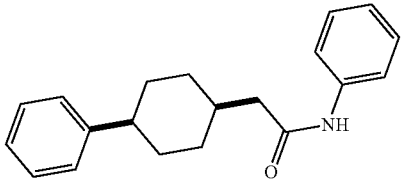

Prepared using General Procedures C, D, E, and F. General Procedure F employed 200 mg 2-(4-phenylcyclohexyl)acetic acid (mixture of diastereomers), and 103 mg aniline. Purified using silica gel chromatography (0% to 30% EtOAc in hexanes) to afford the desired cis-diastereomer as the first eluting isomer. ¹H NMR of cis-isomer (400 MHz; DMSO-d₆): δ 9.9 (bs, 1H), 7.55-7.60 (m, 2H), 7.21-7.30 (m, 6H), 7.14-7.18 (m, 1H), 6.97-7.02 (m, 1H), 2.48-2.58 (m, 1H), 2.43 (d, J=7.7 Hz, 2H), 2.30 m (m, 1H), 1.53-1.65 (m, 8H) ppm. m/z 294.2 (M+H)⁺.

Example 14 cis-N-(4-Methoxyphenyl)-2-(4-phenylcyclohexyl)acetamide

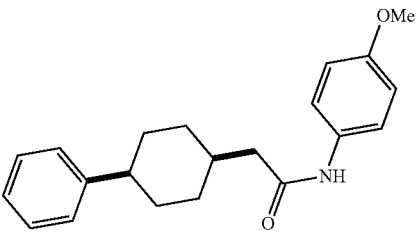

Prepared using General Procedures C, D, E, and F. General Procedure F employed 100 mg 2-(4-phenylcyclohexyl)acetic acid (mixture of diastereomers), and 68 mg 4-methoxyaniline. Purified using silica gel chromatography (0% to 30% EtOAc in hexanes) to afford the desired cis-diastereomer as the first eluting isomer. ¹H NMR of cis-isomer (400 MHz; CDCl₃): δ 7.39-7.44 (m, 2H), 7.17-7.34 (m, 5H), 7.08 (bs, 1H), 6.83-6.88 (m, 2H), 3.79 (s, 3H), 2.60-2.80 (m, 1H), 2.36-2.46 (m, 3H), 1.66-1.82 (m, 8H) ppm. m/z 324.2 (M+H)⁺.

Example 15 cis-N-(4-Methoxy-3-fluorophenyl)-2-(4-phenylcyclohexyl)acetamide

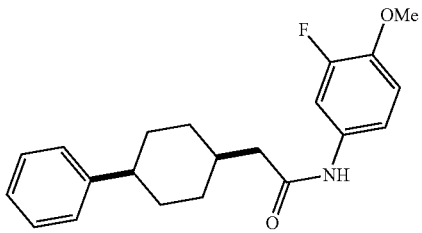

Prepared using General Procedures C, D, E, and F. General Procedure F employed 100 mg 2-(4-phenylcyclohexyl)acetic acid (mixture of diastereomers), and 78 mg 4-methoxy-3-fluoroaniline. Purified using silica gel chromatography (0% to 30% EtOAc in hexanes) to afford the desired cis-diastereomer as the first eluting isomer. ¹H NMR of cis-isomer (400 MHz; CDCl₃): δ 7.41-7.47 (m, 1H), 7.10-7.34 (m, 6H), 6.86-5.92 (m, 1H), 3.86 (s, 3H), 1.64-1.81 (8H) ppm. m/z 342.2 (M+H)⁺.

Example 16 cis-N-(4-Fluorophenyl)-2-(4-phenylcyclohexy)acetamide

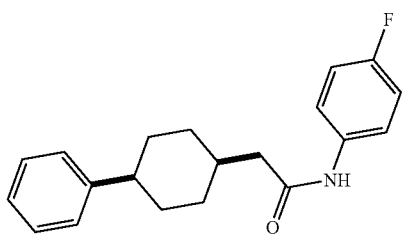

Prepared using General Procedure G using ethyl 2-(4-phenylcyclohexyl)acetate (Preparation 1B) and 4-fluoroaniline. Purified by silica gel chromatography (0%-50% EtOAc in hexanes) which afforded the desired product as a white crystalline solid. ¹H NMR (400 MHz; CDCl₃): δ 7.47 (dd, J=8.9, 4.7 Hz, 2H), 7.37-7.14 (m, 5H), 7.00 (t, J=8.6 Hz, 2H), 2.70-2.56 (m, 1H), 2.48-2.32 (m, 3H), 1.82-1.62 (m, 8H).

Example 17 cis-N-(4-Methylphenyl)-2-(4-phenylcyclohexyl) acetamide

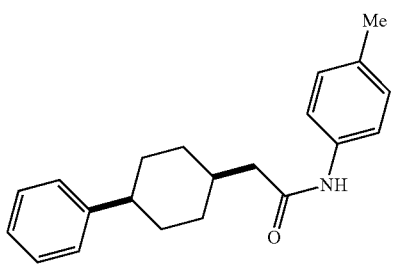

Prepared using General Procedure G using ethyl 2-(4-phenylcyclohexyl)acetate (Preparation 1B) and 4-methylaniline. Purified by silica gel chromatography (0%-50% EtOAc in hexanes) which afforded the desired product as a white crystalline solid. ¹H NMR (400 MHz; CDCl₃): δ 7.40 (d, J=8.4 Hz, 2H), 7.35-7.16 (m, 5H), 7.12 (d, J=8.1 Hz, 2H), 2.69-2.58 (m, 1H), 2.48-2.36 (m, 3H), 2.31 (s, 3H), 1.81-1.64 (m, 8H).

Example 18

N-(4-Cyanophenyl)-2-(4-phenylcyclohexyl)acetamide

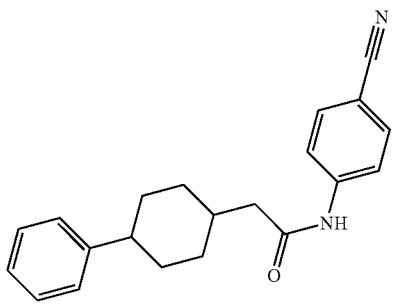 [SMILES: N#Cc1ccc(NC(=O)CC2CCC(c3ccccc3)CC2)cc1]

Prepared using General Procedure G using ethyl 2-(4-phenylcyclohexyl)acetate (Preparation 1B) and 4-cyanoaniline. Purified by silica gel chromatography (0%-60% EtOAc in hexanes) which afforded the desired product as a white crystalline solid (3:2 cis:trans). ¹H NMR (400 MHz; CDCl₃): δ 7.73-7.64 (m, 5H), 7.64-7.56 (m, 5H), 7.54 (s, 1.5H), 7.49 (s, 1H), 7.34-7.15 (m, 12.5H), 2.70-2.57 (m, 1.5H), 2.55-2.36 (m, 5.5H), 2.32 (d, J=6.7 Hz, 2H), 2.02-1.87 (m, 5H), 1.83-1.64 (m, 12H), 1.60-1.45 (m, 2H), 1.29-1.13 (m, 2H).

Example 19

N-(4-Trifluoromethoxyphenyl)-2-(4-phenylcyclohexyl)acetamide

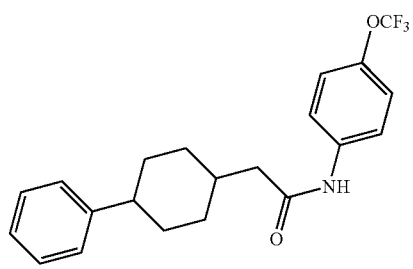 [SMILES: O=C(CC1CCC(c2ccccc2)CC1)Nc1ccc(OC(F)(F)F)cc1]

Prepared using General Procedure G using ethyl 2-(4-phenylcyclohexyl)acetate (Preparation 1B) and 4-trifluoromethoxyaniline. Purified by silica gel chromatography (0%-50% EtOAc in hexanes) which afforded the desired product as a white crystalline solid (4:1 cis:trans). $^1$H NMR (400 MHz; CDCl$_3$): δ 7.61-7.50 (m, 10H), 7.36-7.12 (m, 21H), 2.70-2.57 (m, 4H), 2.51-2.35 (m, 13H), 2.28 (d, J=6.6 Hz, 2H), 2.02-1.85 (m, 5H), 1.83-1.61 (m, 32H), 1.58-1.46 (m, 2H), 1.26-1.11 (m, 2H).

Example 20

N-(4-Bromophenyl)-2-(4-phenylcyclohexyl)acetamide

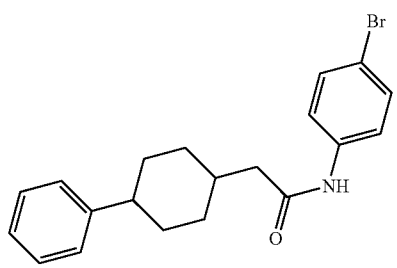 [SMILES: O=C(CC1CCC(c2ccccc2)CC1)Nc1ccc(Br)cc1]

Prepared using General Procedure G using ethyl 2-(4-phenylcyclohexyl)acetate and 4-bromoaniline. Purified by silica gel chromatography (0%-50% EtOAc in hexanes) which afforded the desired product as a white crystalline solid (1:1 cis:trans). $^1$H NMR (400 MHz; CDCl$_3$): δ 7.43 (d, J=3.1 Hz, 4H), 7.34-7.26 (m, 6H), 7.23-7.11 (m, 8H), 2.69-2.58 (m, 1H), 2.54-2.35 (m, 4H), 2.27 (d, J=6.6 Hz, 2H), 2.01-1.97 (m, 5H), 1.81-1.63 (m, 8H), 1.59-1.45 (m, 2H), 1.28-1.11 (m, 2H).

Example 21 cis-N-(4-Tertbutylphenyl)-2-(4-phenylcyclohexyl)acetamide

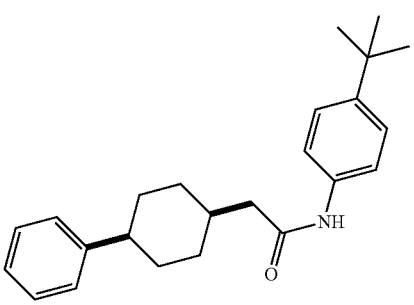

Prepared using General Procedures E employing (Preparation 1B and F using 2-(4-phenylcyclohexyl)acetic acid and 4-tertbutylaniline. Purified by silica gel chromatography (0%-50% EtOAc in hexanes) which afforded the desired product as a white crystalline solid. $^1$H NMR (400 MHz, CDCl$_3$) δ 7.49-7.41 (m, 2H), 7.39-7.17 (m, 7H), 2.64 (s, 1H), 2.51-2.36 (m, 3H), 1.83-1.64 (m, 8H), 1.29 (s, 9H).

Example 22 cis-N-(3-Fluoro-4-chlorophenyl)-2-(4-(4-methoxyphenyl)cyclohexyl)acetamide

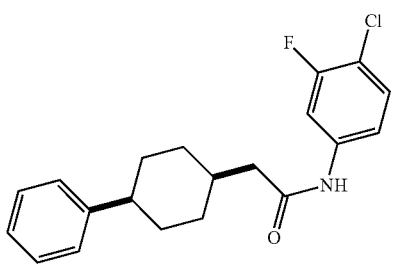

Prepared using General Procedure s E employing (Preparation 1B and F using 2-(4-phenylcyclohexyl)acetic acid and 3-fluoro-4-chloroaniline. Purified by silica gel chromatography (0%-40% EtOAc in hexanes) which afford the desired product as the first eluting isomer. $^1$H NMR (400 MHz, CDCl$_3$) δ 7.66 (d, J=10.8 Hz, 1H), 7.36-7.16 (m, 5H), 7.16-7.06 (m, 2H), 2.65 (s, 1H), 2.50-2.37 (m, 3H), 1.88-1.63 (m, 8H).

Example 23 trans-N-(3-Fluoro-4-chlorophenyl)-2-(4-(4-methoxyphenyl)cyclohexyl)acetamide

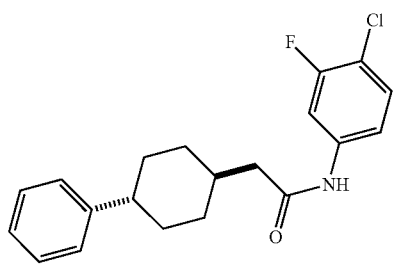

Further elution from the column in the previous example afforded the desired product as the second eluting isomer. $^1$H NMR (400 MHz, CDCl$_3$) δ 7.66 (d, J=11.2 Hz, 1H), 7.37-7.04 (m, 7H), 2.55-2.39 (m, 1H), 2.29 (d, J=6.7 Hz, 2H), 2.04-1.86 (m, 5H), 1.62-1.46 (m, 4H), 1.32-1.09 (m, 2H).

Example 24 cis-N-(2,2-Difluorobenzo[d][1,3]dioxol-5-yl)-2-4-phenylcyclohexyl)acetamide

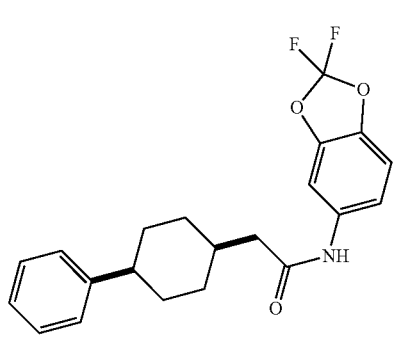

Prepared using General Procedures E employing Preparation 1B and F employing 2-(4-phenylcyclohexyl)acetic acid and 5-amino-2,2-difluoro-1,3-benzodioxole. Purified using silica gel chromatography (0% to 20% EtOAc in hexanes) to afford the first eluting isomer as the desired product as a white solid. $^1$H NMR (400 MHz; CDCl$_3$): δ 7.63 (s, 1H), 7.33-7.15 (m, 5H), 6.97-6.95 (m, 2H), 2.68-2.62 (m, 1H), 2.46-2.41 (m, 3H), 1.79-1.64 (m, 8H).

Example 25 trans-N-(2,2-Difluorobenzo[d][1,3]dioxol-5-yl)-2-4-phenylcyclohexyl)acetamide

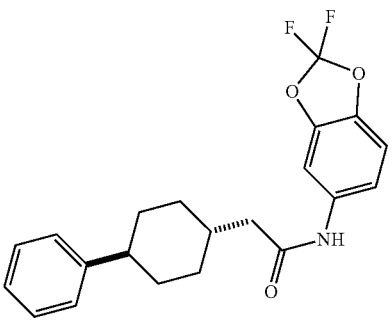

Further elution from the column in the previous example afforded the desired product as the second eluting isomer as a white solid. $^1$H NMR (400 MHz; CDCl$_3$): δ 7.64 (s, 1H), 7.31-7.15 (m, 5H), 6.99-6.96 (m, 2H), 2.48 (tt, J=11.8, 3.0 Hz, 1H), 2.27 (d, J=6.6 Hz, 2H), 1.97-1.91 (m, 5H), 1.58-1.49 (m, 2H), 1.27-1.19 (m, 2H).

Example 26 cis-N-([1,1-Biphenyl]-4-yl)-2-(4-phenylcyclohexyl)acetamide

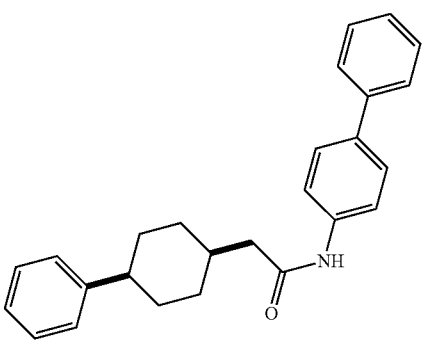

Prepared using General Procedure G employing ethyl 2-(4-phenylcyclohexyl) acetate (Preparation 1B) and 4-aminobiphenyl. Purified using silica gel chromatography (0% to 25% EtOAc in hexanes) to afford the first eluting isomer as the desired product and white solid. $^1$H NMR (400 MHz; CDCl$_3$): δ 7.62-7.52 (m, 6H), 7.43 (t, J=7.6 Hz, 2H), 7.30 (dd, J=15.6, 8.4 Hz, 6H), 7.20 (t, J=7.1 Hz, 1H), 2.68-2.62 (m, 1H), 2.52 (d, J=7.2 Hz, 2H), 2.47-2.38 (m, 1H), 1.81-1.65 (m, 4H), 1.35-1.19 (m, 4H).

Example 27 trans-N-([1,1'-Biphenyl]-4-yl)-2-(4-phenylcyclohexyl)acetamide

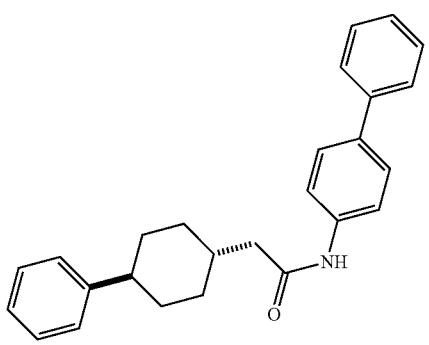

Further elution from the column in the previous example afforded the desired product as the second eluting isomer as a yellow solid. $^1$H NMR (400 MHz; CDCl$_3$): δ 7.64-7.49 (m, 6H), 7.47-7.26 (m, 7H), 7.19 (dd, J=13.3, 7.1 Hz, 2H), 6.80-6.72 (m, 4H), 2.53-2.45 (m, 1H), 2.31 (d, J=6.8 Hz, 2H), 2.02-1.86 (m, 3H), 1.54-1.52 (m, 2H), 1.28-1.24 (m, 4H).

Example 28 cis-N-(4-Chloro-2-fluorophenyl)-2-(4-phenylcyclohexyl)acetamide

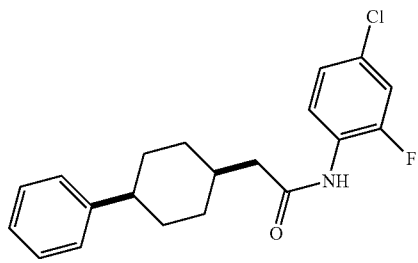

Prepared using General Procedure G employing ethyl 2-(4-phenylcyclohexyl) acetate (Preparation 1B) and 4-chloro-2-fluoroaniline. Purified using silica gel chromatography (0% to 25% EtOAc in hexanes) to afford the first eluting isomer as the desired product as a purple solid. $^1$H NMR (400 MHz; CDCl$_3$): δ 8.31 (t, J=8.6 Hz, 1H), 7.37-7.27 (m, 3H), 7.26-7.16 (m, 3H), 7.12 (d, J=9.0 Hz, 2H), 2.69-2.59 (m, 1H), 2.52 (d, J=7.5 Hz, 2H), 2.42-2.39 (m, 1H), 1.81-1.65 (m, 5H), 1.65-1.46 (m, 2H), 1.17-0.99 (m, 1H).

Example 29 trans-N-(4-Chloro-2-fluorophenyl)-2-(4-phenylcyclohexyl)acetamide

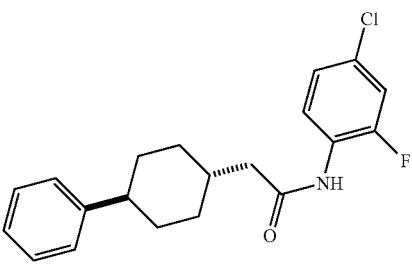

Further elution from the column in the previous example afforded the desired product as the second eluting isomer as a red solid. $^1$H NMR (400 MHz; CDCl$_3$): δ 8.33 (t, J=8.5 Hz, 1H), 7.35-7.24 (m, 3H), 7.23-7.03 (m, 5H), 2.49 (tt, J=12.1, 3.1 Hz, 1H), 2.33 (d, J=6.7 Hz, 2H), 1.95 (t, J=12.0 Hz, 5H), 1.62-1.45 (m, 2H), 1.25-1.17 (m, 2H).

Example 33

2-(-4-(4-Methoxyphenyl)cyclohexyl)-N-(4-(methylthio)phenyl)acetamide

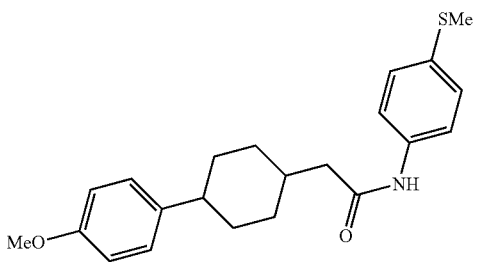 [SMILES: COc1ccc(C2CCC(CC(=O)Nc3ccc(SC)cc3)CC2)cc1]

Preparation 33A: Ethyl 2-(4-(4-hydroxyphenyl)cyclohexylidene)acetate

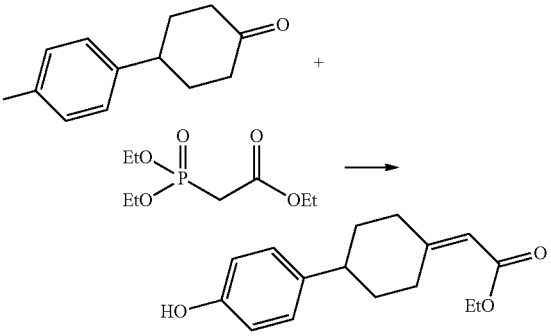

To an oven-dried flask (Flask #1) was added NaH (60% dispersion in oil, 11.8 g, 295 mmol) and 120 mL of THF and cooled to 0° C. Tritethylphosphonoacetate (46.9 mL, 236 mmol) was dissolved in 250 mL of THF and added dropwise to the NaH mixture over 1 hour. After the addition, the reaction is stirred for 1 hour at rt.

To a separate flask was added 37.47 grams (196.9 mmol) of 4-(4-hydroxyphenyl) cyclohexanone was dissolved in 250 mL THF with heating. After cooling this solution to rt, it was carefully added over 45 minutes to a another flask (Flask #2) which contained a 0° C. mixture of NaH (60% dispersion in oil, 8.67 g, 216 mmol) in 100 mL THF. After addition, the mixture was stirred at rt for 2 hours until the mixture became a clear solution. Once this solution was clear, Flask #1 was cooled back to 0° C. and the contents of Flask #2 were added via cannulation. After the addition, the reaction is warmed back to room temperature and stirred for 2 hours, or until the starting material was consumed by LCMS.

The reaction was quenched by careful addition of ice and water (1 L) and subsequently extracted with EtOAc (3×500 mL) and the combined organics were then washed with brine (1 L), dried over sodium sulfate, filtered, and concentrated to provide Preparation 33A in 97% yield as a white solid.

Preparation 33B: Ethyl 2-(4-(4-hydroxyphenyl)cyclohexyl)acetate

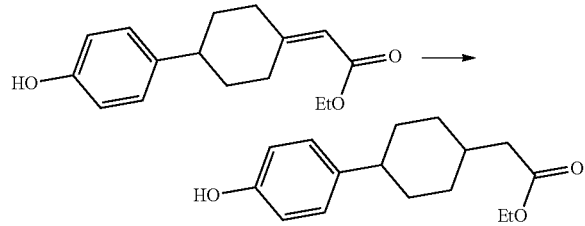

To a solution Preparation 33A (9.74 g, 35.8 mmol) in EtOAc was added Pd/C (0.974 g, 10 wt. %). The reaction solution was sparged with a balloon of $H_2$ gas and stirred under an atmosphere of hydrogen for 2 days. The reaction mixture was filtered through CELITE®, washing generously with EtOAc, and concentrated under reduced pressure to afford Preparation 33B as a white crystalline solid in quantitative yield as a mixture of diastereomers.

Preparation 33C: Ethyl 2-(4-(4-methoxyphenyl)cyclohexyl)acetate

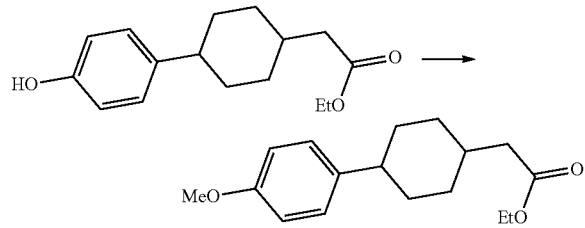

To a solution of Preparation 33B (34.1 g, 130 mmol) in DMF (300 mL) was added $Cs_2CO_3$ (65.0 g, 200 mmol) followed by iodomethane (21.3 g, 150 mmol). The resulting suspension was stirred at rt overnight. The reaction mixture was concentrated and partitioned between EtOAc (150 ml) and water (200 mL). The layers were separated and the aqueous layer was extracted with EtOAc (3×150 mL). The combined organic extracts were dried over anhydrous $MgSO_4$, filtered, and concentrated under reduced pressure. The crude reaction mixture was purified employing silica gel chromatography (0% to 30% EtOAc in hexanes) to afford Preparation 33C as a clear oil.

Example 33: 2-(-4-(4-Methoxyphenyl)cyclohexyl)-N-(4-(methylthio)phenyl)acetamide Prepared using General Procedure G employing Preparation 33C and 4-(methylthio)aniline. Purified using silica gel chromatography (50% $CH_2Cl_2$ in hexanes and then 25% EtOAc in hexanes) to afford the desired product as a mixture of isomers. m/z 370.2 (M+H)$^+$.

Example 34 trans-2-(4-(4-Methoxyphenyl)cyclohexyl)-N-(4-(methylthio)phenyl)acetamide

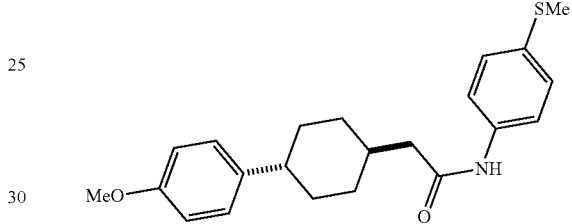

Further elution from the column in the previous example afforded the desired product as the second eluting isomer. $^1$H NMR (400 MHz, CDCl$_3$) δ 7.48 (d, J=8.6 Hz, 2H), 7.30-7.22 (m, 3H), 7.17-7.09 (m, 2H), 6.91-6.81 (m, 2H), 3.80 (d, =5.2 Hz, 3H), 2.50-2.35 (m, 4H), 2.28 (d, J=6.6 Hz, 2H), 2.10-1.80 (m, 5H), 1.50 (dt, J=23.0, 11.3 Hz, 2H), 1.34-1.09 (m, 2H). m/z 370.2 (M+H)$^+$.

Example 35 cis-2-(4-(4-Methoxyphenyl)cyclohexyl)-N-(4-(methylsulfonyl)phenyl)acetamide

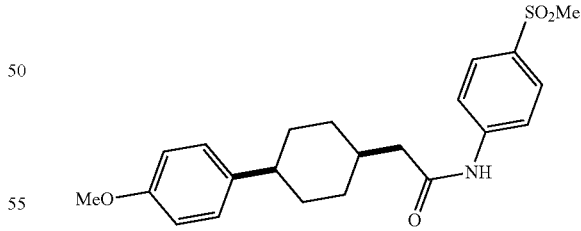

To a solution of 2-(-4-(4-methoxyphenyl)cyclohexyl)-N-(4-(methylthio)phenyl) acetamide (Example 33, 154 mg, 0.417 mmol) in $CH_2Cl_2$ (8 mL) at 0° C. was added m-chloroperoxybenzoic acid (192 mg, 0.834 mmol). The resulting mixture was warmed to rt and stirred for 30 min at rt. Then 2 M sodium thiosulfate was added and the mixture was stirred at rt for 30 min. The mixture was diluted with EtOAc and the layers were separated. The organic layer was dried over anhydrous $Na_2SO_4$, filtered, and concentrated under reduced pressure. The resulting mixture was purified employing silica gel chromatography (50% EtOAc in hexanes) to afford the desired product as the first eluting isomer. $^1$H NMR (400 MHz, CDCl$_3$) δ 7.93-7.86 (m, 2H), 7.79-7.72 (m, 2H), 7.55 (s, 1H), 7.22-7.15 (m, 2H), 6.91-6.84 (m, 2H), 3.81 (d, J=5.2 Hz, 3H), 3.05 (s, 3H), 2.66-2.57 (m, 1H), 2.52 (d, J=7.2 Hz, 2H), 2.43 (s, 1H) 1.94-1.45 (m, 8H). m/z 402.2 (M+H)$^+$.

Example 36 cis-N-(3-Cyanophenyl)-2-(4-(4-methoxyphenyl)cyclohexyl)acetamide

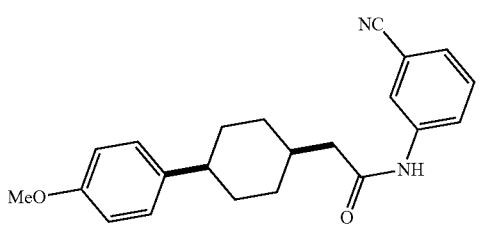

Prepared using General Procedure G employing ethyl 2-(4-(4-methoxyphenyl) cyclohexyl)acetate (Preparation 33C) and 3-aminobenzonitrile. Purified using silica gel chromatography (5-25% EtOAc in hexanes) to afford the desired product as the first eluting isomer. $^1$H NMR (400 MHz, CDCl$_3$) δ 7.94 (d, J=1.5 Hz, 2H), 7.84-7.76 (m, 1H), 7.38 (ddd, J=11.1, 7.7, 4.5 Hz, 2H), 7.20-7.13 (m, 2H), 6.88-6.80 (m, 2H), 3.82-3.77 (m, 3H), 2.85-2.50 (m, 2H), 2.50-2.25 (m, 2H), 1.90-1.48 (m, 8H). m/z 349.2 (M+H)$^+$.

Example 37 trans-N-(3-Cyanophenyl)-2-(4-(4-methoxyphenyl)cyclohexyl)acetamide

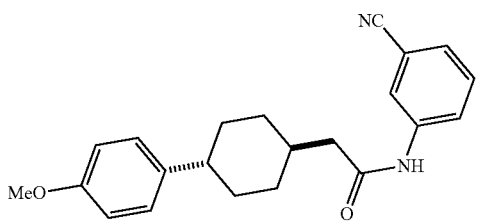

Further elution from the column in the previous example afforded the desired product as the second eluting isomer. $^1$H NMR (400 MHz, CDCl$_3$) δ 7.98 (s, 1H), 7.81-7.65 (m, 2H), 7.46-7.34 (m, 2H), 7.11 (t, =5.8 Hz, 2H), 6.84 (t, =5.8 Hz, 2H), 3.78 (d, J=0.9 Hz, 3H), 2.42 (dd, J=13.6, 10.6 Hz, 1H), 2.31 (d, J=6.7 Hz, 2H), 1.93 (dd, J=27.8, 12.7 Hz, 5H), 1.59-1.38 (m, 2H), 1.27-1.07 (m, 2H). m/z 349.2 (M+H)$^+$.

Example 38 cis-N-(4-Cyclopropylphenyl)-2-((1,4)-4-(4-methoxyphenyl)cyclohexyl)acetamide

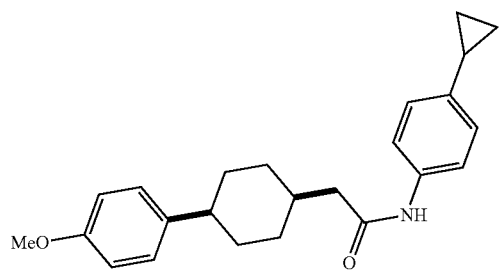

Preparation 38A: 4-Cyclopropylaniline

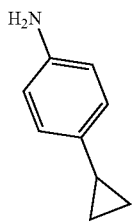

To a vial containing 4-cyclopropylphenylboronic acid (0.50 g, 3.1 mmol) was added ammonia (=30% in water, 15 mL), CuSO$_4$-5H$_2$O (76 mg, 0.31 mmol), and sodium hydroxide (250 mg, 6.2 mmol) in air. The reaction mixture turned bright blue, and the sticky solid in the mixture was distributed along the inside of the reaction flask by scraping. The mixture was stirred for 16 h, during which time all solid disappeared. The reaction solution was then extracted with EtOAc (30 mL), dried over anhydrous MgSO$_4$, filtered, and concentrated under reduced pressure to provide an orange oil. The crude residue was purified using silica gel chromatography (0% to 15% EtOAc in hexanes) to afford Preparation 38A as a clear, colorless film. $^1$H NMR (400 MHz; CDCl$_3$): δ 6.90 (d, J=8.6 Hz, 2H), 6.61 (d, J=8.6 Hz, 2H), 1.89-1.67 (m, 1H), 1.58 (br s, 2H), 0.84 (t, J=4.3 Hz, 2H), 0.62-0.56 (m, 2H); m/z 134.1 (M+H)$^+$.

Example 38: cis-N-(4-Cyclopropylphenyl)-2-((1,4)-4-(4-methoxyphenyl)cyclohexyl)acetamide Prepared using General Procedure G employing ethyl 2-(4-(4-methoxyphenyl) cyclohexyl)acetate (72 mg, 0.260 mmol) and Preparation 38A (51 mg, 0.38 mmol). Purified using silica gel chromatography (0% to 20% EtOAc in hexanes) to afford the first eluting isomer as the desired product. $^1$H NMR (400 MHz; CDCl$_3$): δ 7.39 (d, J=8.6 Hz, 2H), 7.22-7.11 (m, 3H), 7.02 (d, J=8.6 Hz, 2H), 6.85 (d, J=8.8 Hz, 2H), 3.79 (s, 3H), 2.63-2.54 (m, 1H), 2.46-2.33 (m, 3H), 1.92-1.81 (m, 1H), 1.78-1.64 (m, 8H), 1.02-0.82 (m, 2H), 0.70-0.62 (m, 2H).

Example 39 trans-N-(4-Cyclopropylphenyl)-2-((1,4)-4-(4-methoxyphenyl)cyclohexyl)acetamide

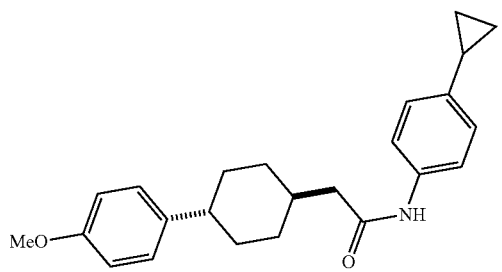

Further elution from the column in the previous example afforded the desired product as the second eluting isomer. $^1$H NMR (400 MHz; CDCl$_3$): δ 7.41 (d, J=8.4 Hz, 2H), 7.27-7.08 (m, 3H), 7.03 (d, J=8.4 Hz, 2H), 6.83 (d, J=8.4 Hz, 2H), 3.78 (s, 3H), 2.47-2.38 (m, 1H), 2.25 (d, J=6.6 Hz, 2H), 2.05-1.83 (m, 6H), 1.64-1.42 (m, 2H), 1.33-1.08 (m, 2H), 0.93 (q, J=6.3 Hz, 2H), 0.70-0.62 (m, 2H).

Example 40 cis-N-(3-Fluoro-4-chlorophenyl)-2-(4-(4-methoxyphenyl)cyclohexyl)acetamide

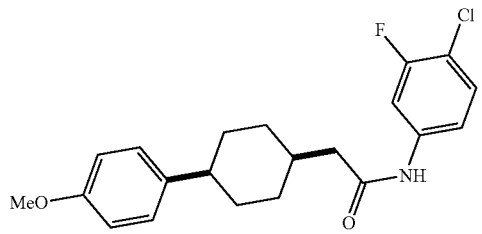

Prepared using General Procedures E employing Preparation 33C and F using 2-(4-(4-methoxyphenyl)cyclohexyl)acetic acid and 3-fluoro-4-chloroaniline. Purified by silica gel chromatography (0%-40% EtOAc in hexanes) which afforded the desired product as a white crystalline solid. $^1$H NMR (400 MHz, CDCl$_3$) δ 7.62 (dd, J=11.0, 2.2 Hz, 1H), 7.26 (dd, J=11.4, 5.3 Hz, 1H), 7.19-7.04 (m, 2H), 6.83 (d, J=5.8 Hz, 2H), 6.41 (ddd, J=11.2, 9.7, 2.6 Hz, 1H), 3.79 (s, 3H), 2.64-2.52 (m, 1H), 2.44 (d, J=7.7 Hz, 2H), 2.41-2.31 (m, 1H), 1.78-1.56 (m, 8H).

Example 41 cis-N-(4-Tertbutylphenyl)-2-(4-(4-methoxyphenyl)cyclohexyl)acetamide

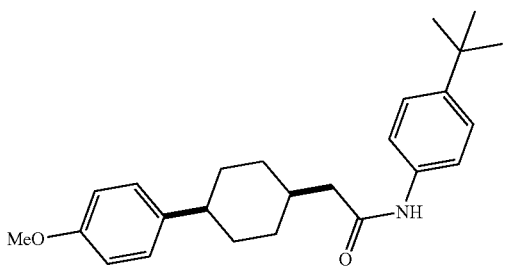

Prepared using General Procedures E employing Preparation 33C and F using 2-(4-(4-methoxyphenyl)cyclohexyl)acetic acid and 4-tertbutylaniline. Purified by silica gel chromatography (0%-40% EtOAc in hexanes) which afforded the desired product as the first eluting isomer. $^1$H NMR (400 MHz, CDCl$_3$) δ 7.44 (d, J=8.8 Hz, 2H), 7.37-7.30 (m, 2H), 7.17 (d, J=8.6 Hz, 2H), 6.84 (d, J=8.3 Hz, 2H), 2.65-2.53 (m, 1H), 2.48-2.35 (m, 3H), 1.81-1.61 (m, 8H), 1.28 (s, 9H).

Example 42 cis-N-(3,4-Difluorophenyl)-2-(4-(4-methoxyphenyl)cyclohexyl)acetamide

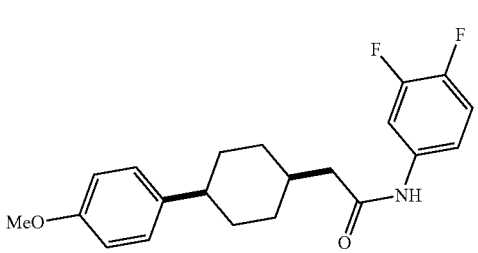

Prepared using General Procedures E employing Preparation 33C and F using 2-(4-(4-methoxyphenyl)cyclohexyl)acetic acid and 3,4-difluoroaniline. Purified by silica gel chromatography (0%-40% EtOAc in hexanes) which afforded the desired product as the first eluting isomer. $^1$H NMR (400 MHz, CDCl$_3$) δ 7.70-7.56 (m, 1H), 7.17 (d, J=8.6 Hz, 2H), 7.13-7.02 (m, 3H), 6.90-6.79 (m, 2H), 3.80 (s, 3H), 2.67-2.54 (m, 1H), 2.49-2.34 (m, 3H), 1.83-1.61 (m, 8H).

Example 43 trans-N-(3,4-Difluorophenyl)-2-(4-(4-methoxyphenyl)cyclohexyl)acetamide

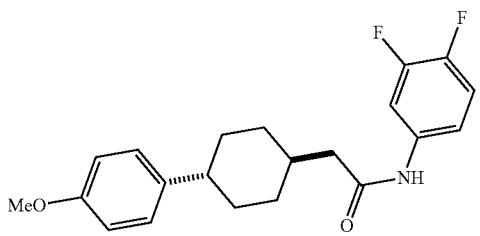

Further elution from the column in the previous example afforded the desired product as the second eluting isomer. $^1$H NMR (400 MHz, CDCl$_3$) δ 7.70-7.61 (m, 1H), 7.17-7.03 (m, 5H), 6.88-6.80 (m, 2H), 2.51-2.38 (m, 1H), 2.27 (d, J=6.6 Hz, 2H), 2.03-1.84 (m, 5H), 1.55-1.41 (m, 2H), 1.30-1.10 (m, 2H).

Example 44 cis-N-(4-Fluorophenyl)-2-(4-(4-methoxyphenyl)cyclohexyl)acetamide

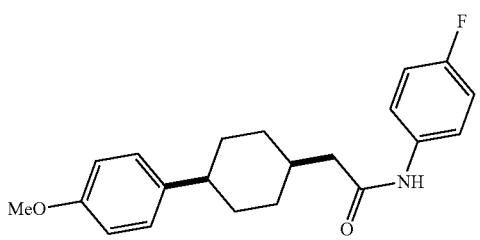

Prepared using General Procedures E employing Preparation 33C and F using 2-(4-(4-methoxyphenyl)cyclohexyl)acetic acid and 4-fluoroaniline. Purified by silica gel chromatography (0%-40% EtOAc in hexanes) which afforded the desired product as the first eluting isomer. $^1$H NMR (400 MHz, CDCl$_3$) δ 7.53-7.39 (m, 2H), 7.16 (d, J=8.6 Hz, 3H), 7.05-6.95 (m, 2H), 6.89-6.79 (m, 2H), 3.78 (s, 3H), 2.68-2.51 (m, 1H), 2.50-2.29 (m, 3H), 1.83-1.61 (m, 8H).

Example 45 trans-N-(4-Fluorophenyl)-2-(4-(4-methoxyphenyl)cyclohexyl)acetamide

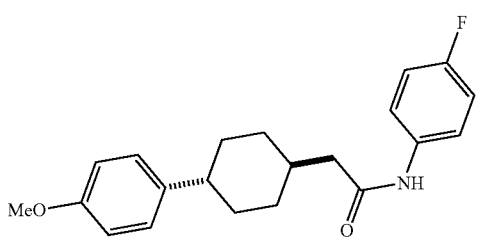

Further elution from the column in the previous example afforded the desired product as the second eluting isomer. $^1$H NMR (400 MHz, CDCl$_3$) δ 7.52-7.44 (m, 2H), 7.15-7.05 (m, 3H), 7.05-6.96 (m, 2H), 6.87-6.79 (m, 2H), 3.78 (s, 3H), 2.48-2.37 (m, 1H), 2.26 (d, J=6.6 Hz, 2H), 2.05-1.84 (m, 5H), 1.56-1.43 (m, 2H), 1.28-1.12 (m, 2H).

Example 46 cis-N-(4-Cyanophenyl)-2-(4-(4-methoxyphenyl)cyclohexyl)acetamide

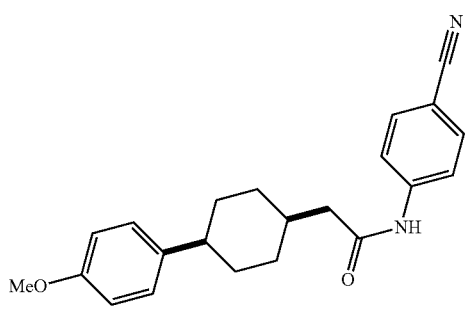

Prepared using a modified General Procedures E employing Preparation 33C and F using 2-(4-(4-methoxyphenyl)cyclohexyl)acetic acid and 4-cyanoaniline. Four equivalents of 4-cyanoaniline were used and the reaction was conducted at 60° C. for 15 h. Purified by silica gel chromatography (0%-60% EtOAc in hexanes) which afforded the desired product as a white crystalline product. $^1$H NMR (400 MHz, CDCl$_3$) δ 7.71-7.57 (m, 4H), 7.17 (d, J=8.3 Hz, 2H), 6.86 (d, J=8.7 Hz, 2H), 3.80 (s, 3H), 2.66-2.55 (m, 1H), 2.49 (d, J=8.0 Hz, 2H), 2.46-2.34 (m, 1H), 1.83-1.60 (m, 8H).

Example 47 cis-N-(4-Chlorophenyl)-2-((1,4)-4-(4-methoxyphenyl)cyclohexyl)acetamide

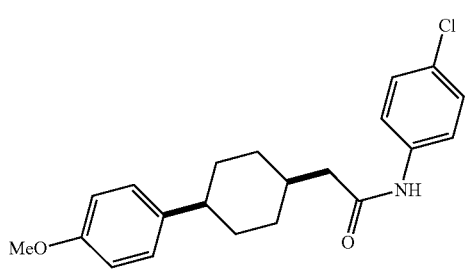

Prepared with General Procedures E employing Preparation 33C and F employing 2-(4-(4-methoxyphenyl) cyclohexyl)acetic acid (124 mg, 0.5 mmol), 4-chloroaniline (97 mg, 0.75 mmol), HATU (435 mg, 0.75 mmol), and $^i$Pr$_2$NEt (323 mg, 2.5 mmol) in DMF (1.0 mL). Purified using silica gel chromatography (0% to 25% EtOAc in hexanes) to afford the desired product as a white solid. $^1$H NMR (400 MHz; CDCl$_3$): δ 7.49-7.45 (m, 2H), 7.29-7.26 (m, 2H), 7.17-7.15 (m, 3H), 6.87-6.83 (m, 2H), 3.79 (s, 3H), 2.63-2.55 (m, 1H), 2.45-2.37 (m, 3H), 1.77-1.64 (m, 8H). m/z 358.2 (M+H)$^+$.

Example 48 trans-N-(4-Chlorophenyl)-2-((1,4)-4-(4-methoxyphenyl)cyclohexyl)acetamide

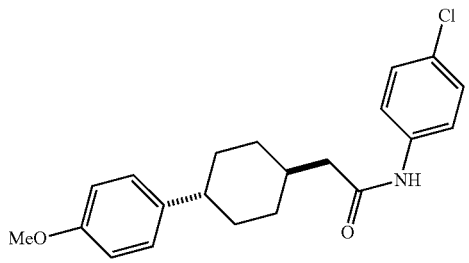

Further elution from the column in the previous example afforded the desired product as a white solid and the second eluting isomer. ¹H NMR (400 MHz; CDCl₃): δ 7.49-7.47 (m, 2H), 7.29-7.27 (m, 2H), 7.15 (s, 1H), 7.13-7.10 (m, 2H), 6.86-6.82 (m, 2H), 3.78 (s, 3H), 2.47-2.39 (m, 1H), 2.26 (dd, J=7.6, 3.8 Hz, 2H), 2.00-1.86 (m, 5H), 1.54-1.44 (m, 2H), 1.24-1.13 (m, 2H). m/z 358.2 (M+H)⁺.

Example 49 cis-N-([1,1'-Biphenyl]-4-yl)-2-(4-(4-methoxyphenyl)cyclohexyl)acetamide

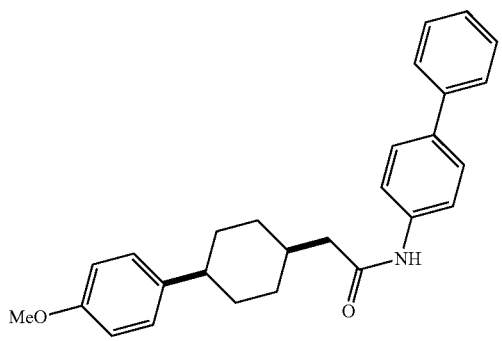

Prepared using General Procedures E employing Preparation 33C and F employing 2-(4-(4-methoxyphenyl) cyclohexyl)acetic acid and 4-aminobiphenyl. Purified using silica gel chromatography (0% to 25% EtOAc in hexanes) to afford the first eluting isomer as the desired product as a white solid. ¹H NMR (400 MHz; CDCl₃): δ 7.62-7.55 (m, 6H), 7.43 (t, J=7.7 Hz, 2H), 7.33 (t, J=7.2 Hz, 1H), 7.25-7.14 (m, 3H), 6.87 (d, =8.5 Hz, 2H), 3.81 (s, 3H), 2.73-2.52 (m, 1H), 2.52-2.40 (m, 3H), 1.89-1.64 (m, 8H).

Example 50 cis-N-(4-Chloro-2-fluorophenyl)-2-(4-(4-methoxyphenyl)cyclohexyl)acetamide

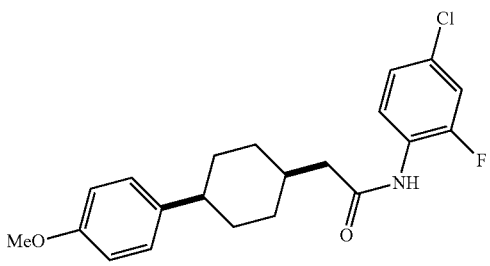

Prepared using General Procedures E employing Preparation 33C and F employing 2-(4-(4-methoxyphenyl) cyclohexyl)acetic acid and 4-chloro-2-fluoroaniline. Purified using silica gel chromatography (0% to 25% EtOAc in hexanes) to afford the first eluting isomer as the desired product as a white solid. ¹H NMR (400 MHz; CDCl₃): δ 8.32 (t, J=8.5 Hz, 1H), 7.28 (s, 1H), 7.15 (dd, J=21.1, 8.7 Hz, 4H), 6.89-6.81 (m, 2H), 3.80 (s, 3H), 2.67-2.55 (m, 1H), 2.50 (d, J=7.6 Hz, 2H), 2.44-2.35 (m, 1H), 1.83-1.61 (m, 8H).

Example 51 trans-N-(4-Chloro-2-fluorophenyl)-2-(4-(4-methoxyphenyl)cyclohexyl)acetamide

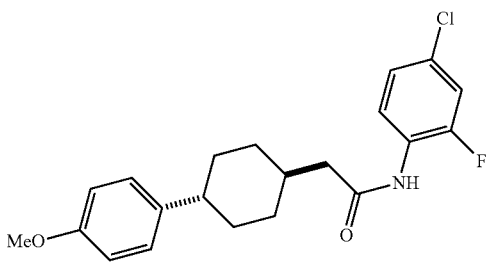

Further elution from the column in the previous example afforded the desired product as the second eluting isomer as a white solid. ¹H NMR (400 MHz; CDCl₃): δ 8.33 (t, J=8.5 Hz, 1H), 7.31 (s, 1H), 7.13 (d, J=8.8 Hz, 4H), 6.89-6.80 (m, 2H), 3.79 (s, 3H), 2.48-2.40 (m, 1H), 2.33 (d, J=6.6 Hz, 2H), 2.03-1.84 (m, 5H), 1.78-1.64 (m, 2H), 1.56-1.44 (m, 2H).

Example 52 cis-N-(4-Chlorophenyl)-2-(4-(4-cyanophenyl)cyclohexyl)acetamide

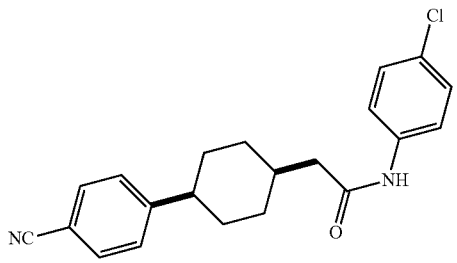

Prepared using General Procedures A, B and G. General Procedure A employed 4-cyanophenyl boronic acid and ethyl 2-(4-(((trifluoromethyl)sulfonyl)oxy)cyclohex-3-en-1-yl)acetate. The product was hydrogenated using General Procedure B with 10% Pd/C as catalyst and acetic acid as solvent. General Procedure G used ethyl 2-(4-(4-cyanophenyl) cyclohexyl)acetate and 4-chloroaniline. Purification by silica gel chromatography (0%-60% EtOAc in hexanes) afforded the desired product as the first eluting isomer. $^1$H NMR (400 MHz, CDCl$_3$) δ 7.59 (d, J=8.4 Hz, 2H), 7.47 (d, J=8.9 Hz, 2H), 7.35 (d, J=8.1 Hz, 2H), 7.32-7.27 (m, 2H), 7.11 (s, 1H), 2.79-2.65 (m, 1H), 2.49-2.38 (m, 3H), 1.85-1.59 (m, 8H).

Example 53 cis-N-(4-Fluorophenyl)-2-(4-(4-cyanophenyl)cyclohexyl)acetamide

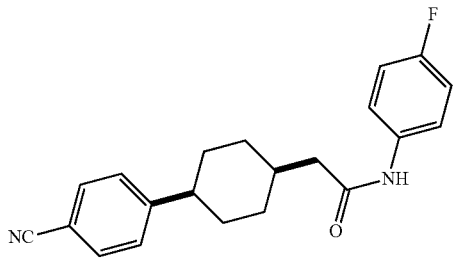

Prepared using General Procedures A, B and G. General Procedure A employed 4-cyanophenyl boronic acid and ethyl 2-(4-(((trifluoromethyl)sulfonyl)oxy)cyclohex-3-en-1-yl)acetate. The product was hydrogenated using General Procedure B with 10% Pd/C as catalyst and acetic acid as solvent. General Procedure G used ethyl 2-(4(4-cyanophenyl) cyclohexyl)acetate and 4-fluoroaniline. Purification by silica gel chromatography (0%-60% EtOAc in hexanes) afforded the desired product as the first eluting isomer. $^1$H NMR (400 MHz, CDCl$_3$) δ 7.60 (d, J=8.2 Hz, 2H), 7.47 (dd, J=9.1, 4.6 Hz, 2H), 7.35 (d, J=8.0 Hz, 2H), 7.09 (s, 1H), 7.06-6.96 (m, 2H), 2.81-2.61 (m, 1H), 2.48-2.38 (m, 3H), 1.86-1.62 (m, 8H).

Example 54 cis-N-(4-Chlorophenyl)-2-(4-(4-fluorophenyl)cyclohexyl)acetamide

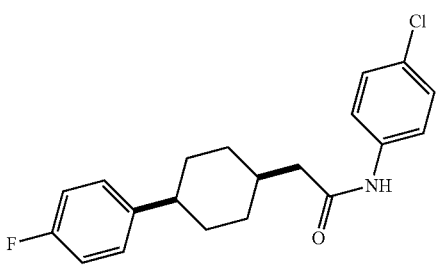

Prepared using General Procedure A, B, and G. General Procedure A employed 1 g (3.2 mmol) of ethyl 2-(4-(((trifluoromethyl)sulfonyl)oxy)cyclohex-3-en-1-yl)acetate, 493 mg (3.5 mmol) of 4-fluorophenylboronic acid, 185 mg (5 mol. %) of Pd(PPh$_3$)$_4$, 417 mg of KBr (3.5 mmol), and 687 mg (6.4 mmol) of sodium carbonate. General Procedure B employed activated 10 wt. % Pd/C and EtOAc as solvent. General Procedure G employed 120 mg 2-(4-phenylcyclohexyl)acetic acid ethyl ester (mixture of diastereomers), and 115 mg 4-chloroaniline. Purified using silica gel chromatography (0% to 30% EtOAc in hexanes) to afford the desired cis-diastereomer as the first eluting isomer. $^1$H NMR of cis-isomer (400 MHz; CDCl$_3$): δ 7.45-7.50 (m, 2H), 7.26-7.30 (m, 2H), 7.17-7.23 (m, 2H), 7.16 (bs, 1H), 6.95-7.02 (m, 2H), 2.58-2.67 (m, 1H), 2.37-2.46 (m, 3H), 1.62-1.80 (m, 8H) ppm. m/z 346.1 (M+H)$^+$.

Example 55 trans-N-(4-Chlorophenyl)-2-(4-(4-fluorophenyl)cyclohexyl)acetamide

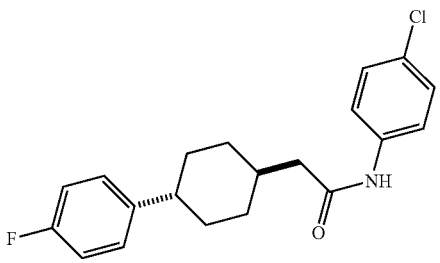

Further elution from the column afforded the desired trans-diastereomer as the second eluting isomer. $^1$H NMR of trans-isomer (400 MHz; CDCl$_3$): δ 7.46-7.51 (m, 2H), 7.26-7.31 (m, 2H), 7.12-7.19 (m, 3H), 6.94-6.99 (m, 1H), 2.46 (tt, J=12.6 Hz, J=3.5 Hz, 1H), 2.28 (d, J=6.6 Hz, 2H), 1.86-2.00 (m, 5H), 1.49 (dq, J=12.9 Hz, J=2.7 Hz, 2H), 1.19 (dq, J=12.7 Hz, J=2.5 Hz, 2H) ppm. m/z 346.1 (M+H)$^+$.

Example 56 cis-N-(4-Fluorophenyl)-2-(4-(4-fluorophenyl)cyclohexyl)acetamide

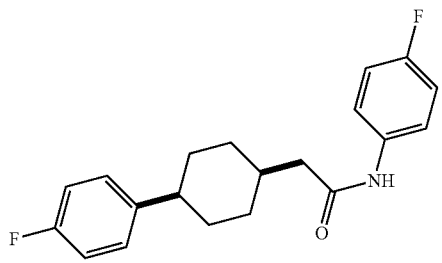

Prepared using General Procedure A, B, and G. General Procedure A employed 1 g (3.2 mmol) of ethyl 2-(4-(((trifluoromethyl)sulfonyl)oxy)cyclohex-3-en-1-yl)acetate, 493 mg (3.5 mmol) of 4-fluorophenylboronic acid, 185 mg (5 mol. %) of Pd(PPh$_3$)$_4$, 417 mg of KBr (3.5 mmol), and 687 mg (6.4 mmol) of sodium carbonate. General Procedure B employed activated 10 wt. % Pd/C and EtOAc as solvent. General Procedure G employed 120 mg 2-(4-phenylcyclohexyl)acetic acid ethyl ester (mixture of diastereomers), and 100 mg 4-fluoroaniline. Purified using silica gel chromatography (0% to 30% EtOAc in hexanes) to afford the desired cis-diastereomer as the first eluting isomer. $^1$H NMR of cis-isomer (400 MHz; CDCl$_3$): δ 7.44-7.50 (m, 2H), 7.14-7.23 (m, 3H), 6.95-7.05 (m, 4H), 2.58-2.66 (m, 1H), 2.37-2.45 (m, 3H), 1.63-1.80 (m, 8H) ppm. m/z 330.2 (M+H)$^+$.

Example 57 trans-N-(4-Fluorophenyl)-2-(4-(4-fluorophenyl)cyclohexyl)acetamide

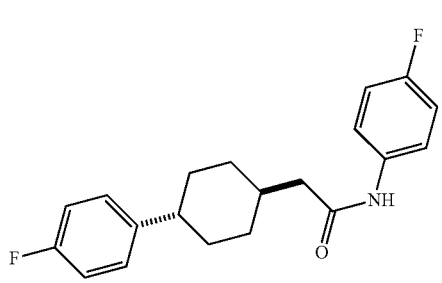

Further elution from the column afforded the desired trans-diastereomer as the second eluting isomer. $^1$H NMR of trans-isomer (400 MHz; CDCl$_3$): δ 7.45-7.56 (m, 2H), 7.10-7.18 (m, 3H), 6.93-7.05 (m, 4H), 2.47 (tt, J=12.7 Hz, J=3.5 Hz, 1H), 2.27 (d, 6.6 Hz, 2H), 1.86-2.10 (m, 5H), 1.49 (dq, J=13.1 Hz, J=3.0 Hz, 2H), 1.19 (dq, J=12.5, J=2.7 Hz, 2H) ppm. m/z 330.2 (M+H)$^+$.

Example 58 cis-N-(4-Chlorophenyl)-2-(4-(4-methylphenyl)cyclohexyl)acetamide

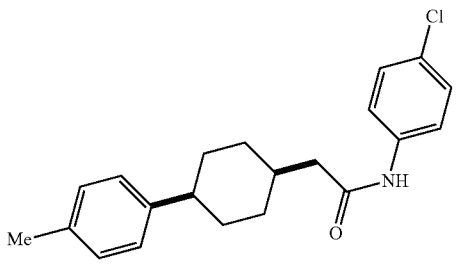

Prepared using General Procedures A, B and G employing ethyl 2-(4-(4-methylphenyl) cyclohexyl)acetate and 4-chloroaniline. Purified using silica gel chromatography (0% to 20% EtOAc in hexanes) to afford the first eluting isomer as the desired product as a white solid. $^1$H NMR (400 MHz; CDCl$_3$): δ 7.47 (d, J=8.8 Hz, 2H), 7.28-7.26 (m, 2H), 7.20-7.06 (m, 4H), 2.61-2.59 (m, 1H), 2.49-2.35 (m, 3H), 2.32 (s, 3H), 1.80-1.62 (m, 8H).

Example 59 cis-N-(4-Cyanophenyl)-2-(4-(4-methylphenyl)cyclohexyl)acetamide

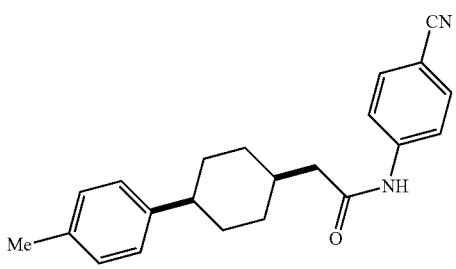

Prepared using General Procedures A, B and G employing ethyl 2-(4-(4-methylphenyl) cyclohexyl)acetate and 4-cyanoaniline. Purified using silica gel chromatography (0% to 20% EtOAc in hexanes) to afford the first eluting isomer as the desired product as a white solid. $^1$H NMR (400 MHz; CDCl$_3$): δ 7.74-7.63 (m, 2H), 7.63-7.50 (m, 2H), 7.47 (s, 1H), 7.16-7.05 (m, 4H), 2.72-2.54 (m, 1H), 2.49 (d, J=7.2 Hz, 2H), 2.42-2.37 (m, 1H), 2.32 (s, 3H), 1.75-1.61 (m, 8H).

Example 60 cis-N-(4-Fluorophenyl)-2-(4-(4-methylphenyl)cyclohexyl)acetamide

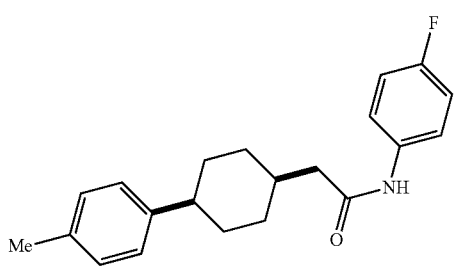

Prepared using General Procedures A, B and G employing ethyl 2-(4-(4-methylphenyl) cyclohexyl)acetate and 4-fluoroaniline. Purified using silica gel chromatography (0% to 20% EtOAc in hexanes) to afford the first eluting isomer as the desired product as a white solid. $^1$H NMR (400 MHz; CDCl$_3$): δ 7.52-7.41 (m, 2H), 7.22-7.05 (m, 5H), 7.05-6.94 (m, 2H), 2.66-2.54 (m, 1H), 2.48-2.35 (m, 3H), 2.33 (s, 3H), 1.81-1.62 (m, 8H).

Example 61

N-(4-Chlorophenyl)-2-(4-(4-morpholinophenyl)cyclohexyl)acetamide

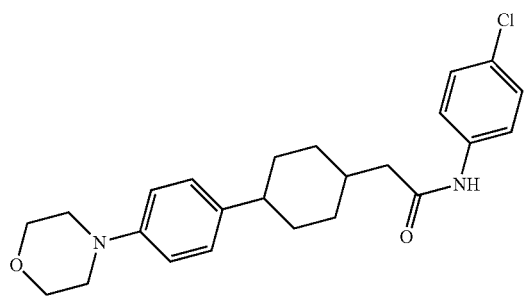 [SMILES: O=C(CC1CCC(c2ccc(N3CCOCC3)cc2)CC1)Nc1ccc(Cl)cc1]

Preparation 61A: Ethyl 2-(4-(4-(((trifluoromethyl)sulfonyl)oxy)phenyl)cyclohexyl)-acetate

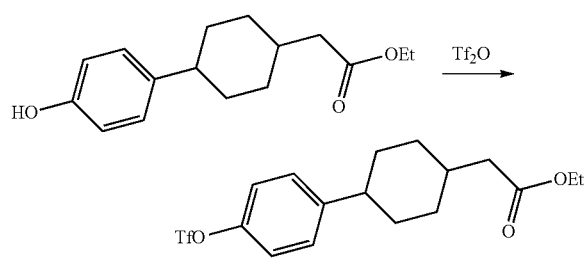

To a flame-dried round bottom flask was added ethyl 2-(4-(4-hydroxyphenyl) cyclohexyl)acetate (Preparation 33B, 1.5 g, 6.4 mmol) and methylene chloride (30 mL). This solution was cooled to 0° C. before the dropwise addition of triflic anhydride (1.22 mL, 7.25 mmol). The reaction was stirred for 20 min at 0° C. Next, triethylamine (2.1 mL, 15.1 mmol) was added dropwise over 30 min, at which point the reaction turned to a red-black color. The solution was stirred at 0° C. for 1.5 h before slowly warming to rt. The reaction was quenched by the cautious addition of water (20 mL) and subsequent extraction with methylene chloride (2×30 mL). The combined organic layers were washed once each with sat. sodium bicarbonate (50 mL) and brine (50 mL) before drying over sodium sulfate, filtration, and concentration under reduced pressure. The crude residue was purified by silica gel chromatography (10% to 25% EtOAc in hexanes) to afford Preparation 61A as a yellow-orange oil (1.5 g, 65%).

Preparation 61B: Ethyl 2-(4-(4-morpholinophenyl)cyclohexyl)acetate

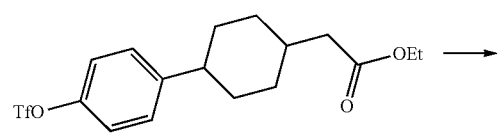

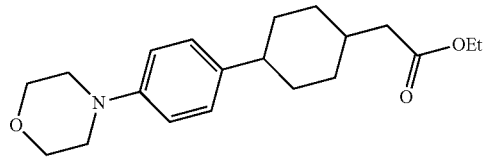

To a sealed tube were added Preparation 61A (380 mg, 1.0 mmol), morpholine (0.11 mL, 1.3 mmol), palladium acetate (22 mg, 0.1 mmol), X-phos (2-dicyclohexylphosphino-2',4',6'-triisopropylbiphenyl) (48 mg, 0.1 mmol), cesium carbonate (326 mg, 1.0 mmol), and toluene (5 mL). The mixture was then degassed for 15 min with bubbling nitrogen and then sealed and heated at 116° C. for 16 h. The mixture was then cooled to rt before being filtered through a pad of CELITE®, washing generously with methylene chloride, and concentrated under reduced pressure. The crude residue was purified by silica gel chromatography (20% to 100% EtOAc in hexanes) to afford Preparation 61B (63%).

Example 61: N-(4-Chlorophenyl)-2-(4-(4-morpholinophenyl)cyclohexyl)acetamide

Prepared using General Procedure G employing Preparation 61B and 4-chloroaniline. Purified using silica gel chromatography (0% to 20% EtOAc in hexanes) to afford the desired product as a white solid and mixture of diastereomers. $^1$H NMR (400 MHz; CDCl$_3$): δ 7.48 (dd, J=8.6, 4.0 Hz, 2H), 7.28-7.25 (m, 2H), 7.14 (dd, J=19.5, 8.4 Hz, 3H), 6.86 (dd, J=8.1, 5.8 Hz, 2H), 3.85 (dd, J=9.2, 4.3 Hz, 4H), 3.12 (dd, J=9.6, 4.9 Hz, 4H), 2.63-2.51 (m, 0.6H), 2.45-2.36 (m, 2.5H), 2.26 (d, J=6.5 Hz, 0.9H), 2.01-1.82 (m, 2.3H), 1.80-1.62 (m, 3.9H), 1.56-1.42 (m, 0.9H), 1.21-1.11 (m, 0.9H).

Example 64

N-(4-Chlorophenyl)-2-(4-(4-morpholinophenyl)cyclohexyl)acetamide

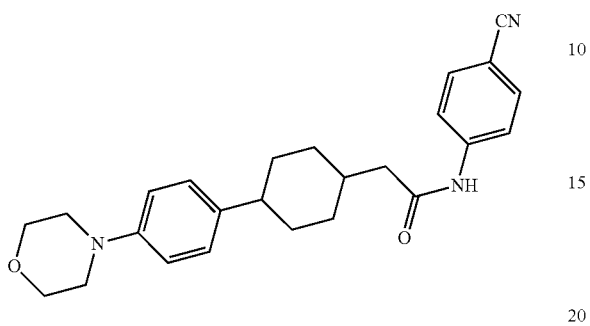

Prepared using General Procedure G employing ethyl 4-(4-morpholinophenyl) cyclohexylacetate (Preparation 61B) and 4-cyanoaniline. Purified using silica gel chromatography (0% to 20% EtOAc in hexanes) to afford the desired product as a mixture of diastereomers. $^1$H NMR (400 MHz; CDCl$_3$): δ 6 7.71-7.64 (m, 2H), 7.64-7.57 (m, 2H), 7.42 (d, J=7.0 Hz, 1H), 7.14 (dd, J=19.3, 8.7 Hz, 2H), 6.93-6.81 (m, 2H), 3.90-3.78 (m, 4H), 3.16-3.06 (m, 4H), 2.63-2.54 (m, 0.6H), 2.51-2.35 (m, 2.6H), 2.31 (d, J=6.7 Hz, 0.8H), 1.92 (t, J=13.9 Hz, 2H), 1.79-1.64 (m, 4.8H), 1.49 (qd, J=13.0, 3.0 Hz, 0.6H), 1.17 (dd, J=18.5, 7.2 Hz, 0.6H).

Example 65

N-(4-Fluorophenyl)-2-(4-(4-morpholinophenyl)cyclohexyl)acetamide

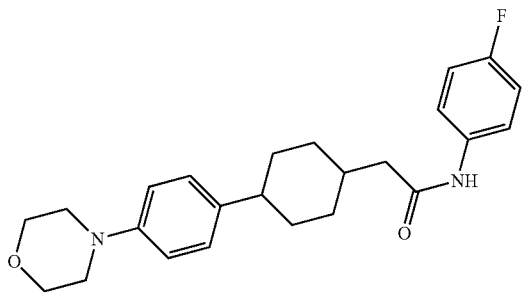

Prepared using General Procedure G employing ethyl 4-(4-morpholinophenyl) cyclohexylacetate (Preparation 61B) and 4-fluoroaniline. Purified using silica gel chromatography (0% to 20% EtOAc in hexanes) to afford the desired product as a mixture of diastereomers. $^1$H NMR (400 MHz; CDCl$_3$): δ 7.58-7.43 (m, 2H), 7.29 (s, 1H), 7.14 (dd, J=20.1, 8.6 Hz, 2H), 7.08-6.95 (m, 2H), 6.95-6.80 (m, 2H), 3.86 (dt, J=6.5, 3.5 Hz, 4H), 3.19-3.04 (m, 4H), 2.65-2.48 (m, 0.7H), 2.48-2.32 (m, 2.6H), 2.26 (d, J=6.6 Hz, 0.7H), 2.00-1.83 (m, 1.8H), 1.82-1.60 (m, 5H), 1.58-1.41 (m, 0.6H), 1.18 (dt, J=22.8, 11.5 Hz, 0.6H).

Example 67

2-(4-(4-(Dimethylamino)phenyl)cyclohexyl)-N-(4-chlorophenyl)acetamide

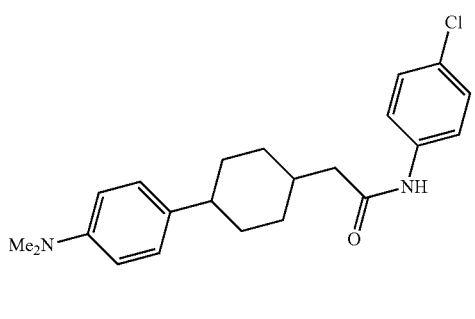 [SMILES: CN(C)c1ccc(C2CCC(CC(=O)Nc3ccc(Cl)cc3)CC2)cc1]

67A. Ethyl 2-(4-(4-(dimethylamino)phenyl)cyclohexyl)acetate

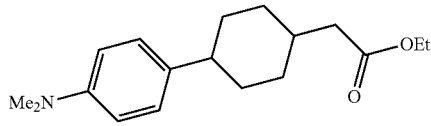

To a sealed tube was added ethyl 2-(4-(4-(((trifluoromethyl)sulfonyl)oxy)phenyl) cyclohexyl)acetate (1 g, 2.6 mmol), dimethylamine (5.26 mL, 10.4 mmol), palladium acetate (59 mg, 0.26 mmol), X-phos (125 mg, 0.26 mmol), cesium carbonate (860 mg, 2.6 mmol), and toluene (13 mL). The mixture was then degassed for 15 min with bubbling nitrogen and then sealed and heated at 116° C. for 16 h. The mixture was then cooled to rt before being filtered through a pad of CELITE®, washing generously with methylene chloride, and concentrated under reduced pressure. The crude residue was purified by silica gel chromatography (0-30% EtOAc in hexanes) to afford Preparation 67A.

Example 67: 2-(4-(4-(Dimethylamino)phenyl)cyclohexyl)-N-(4-chlorophenyl)acetamide Prepared using General Procedure G employing ethyl 2-(4-(4-(dimethylamino) phenyl)cyclohexyl)acetate (Preparation 67A) and 4-chloroaniline. Purified using silica gel chromatography (100% CH$_2$Cl$_2$ and then 0-50% EtOAc in hexanes) to afford the desired product as a mixture of isomers. m/z 371.3 (M+H)$^+$.

Example 68

2-(4-(4-(Dimethylamino)phenyl)cyclohexyl)-N-(4-fluorophenyl)acetamide

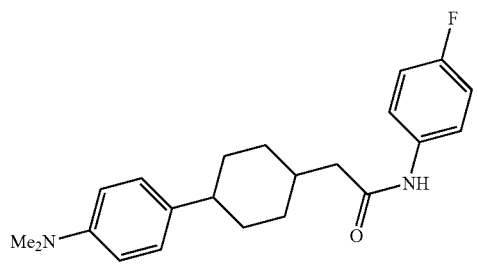 [SMILES: CN(C)c1ccc(C2CCC(CC(=O)Nc3ccc(F)cc3)CC2)cc1]

Prepared using General Procedure G employing ethyl 2-(4-(4-(dimethylamino) phenyl)cyclohexyl)acetate (Preparation 67A) and 4-fluoroaniline. Purified using silica gel chromatography (100% $CH_2Cl_2$ and then 0-50% EtOAc in hexanes) to afford the desired product as a mixture of isomers. m/z 355.3 $(M+H)^+$.

Example 69 cis-N-(4-Chlorophenyl)-2-(4-(4-isopropoxyphenyl)cyclohexyl)acetamide, or trans-N-(4-Chlorophenyl)-2-(4-(4-isopropoxyphenyl)cyclohexyl)acetamide (Relative Stereochemistry not Determined)

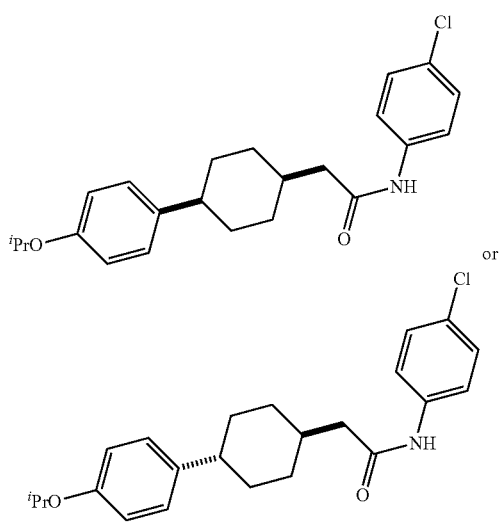

Prepared using General Procedures A, B and G. General Procedure A employed ethyl 2-(4-(((trifluoromethyl)sulfonyl)oxy)cyclohex-3-en-1-yl)acetate and (4-isopropoxyphenyl)boronic acid. The product was hydrogenated using General Procedure B with 10% Pd/C as catalyst and acetic acid as solvent. General Procedure G used ethyl 2-(4-(4-isopropoxyphenyl)cyclohexyl)acetate and 4-chloroaniline. Purified using silica gel chromatography (0-20% EtOAc in hexanes) to afford the desired product as the first eluting isomer. $^1$H NMR (400 MHz, $CDCl_3$) δ 7.48 (d, J=8.8 Hz, 2H), 7.32-7.24 (m, 2H), 7.24-7.10 (m, 3H), 6.88-6.79 (m, 2H), 4.52 (dt, J=12.1, 6.1 Hz, 1H), 2.59 (d, J=8.6 Hz, 1H), 2.46-2.19 (m, 3H), 1.89-1.54 (m, 8H), 1.34 (dd, J=6.1, 0.5 Hz, 6H). m/z 386.3 $(M+H)^+$.

Example 70 cis-N-(4-Chlorophenyl)-2-(4-(4-isopropoxyphenyl)cyclohexyl)acetamide, or trans-N-(4-Chlorophenyl)-2-(4-(4-isopropoxyphenyl)cyclohexyl)acetamide (Relative Stereochemistry not Determined)

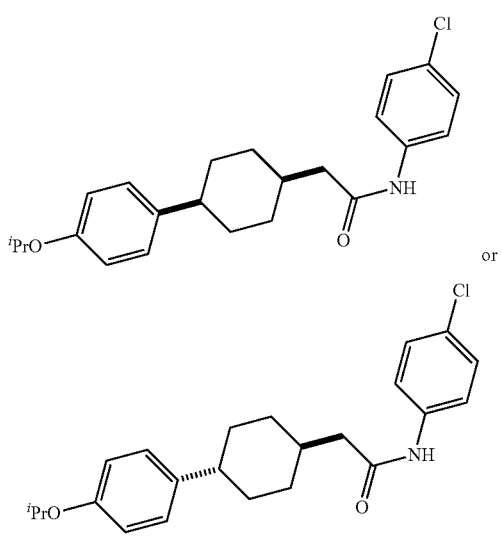

Further elution from the column in the previous example afforded the desired product as the second eluting isomer. $^1$H NMR (400 MHz, $CDCl_3$) δ 7.50 (d, J=8.8 Hz, 2H), 7.33-7.27 (m, 2H), 7.27-7.05 (m, 3H), 6.95-6.78 (m, 2H), 4.51 (dt, J=12.1, 6.1 Hz, 1H), 2.43 (t, J=12.1 Hz, 1H), 2.28 (d, J=6.6 Hz, 2H), 2.09-1.80 (m, 5H), 1.61-1.40 (m, 2H), 1.37-1.31 (m, 6H), 1.31-1.12 (m, 2H). m/z 386.3 $(M+H)^+$.

Example 71 cis-N-(4-Fluorophenyl)-2-(4-(4-isopropoxyphenyl)cyclohexyl)acetamide, or trans-N-(4-Fluorophenyl)-2-(4-(4-isopropoxyphenyl)cyclohexyl)acetamide (Relative Stereochemistry not Determined)

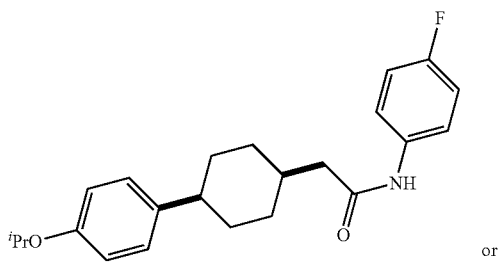

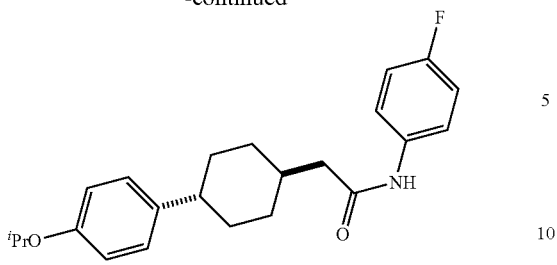

Prepared using General Procedures A, B and G. General Procedure A employed ethyl 2-(4-((((trifluoromethyl)sulfonyl)oxy)cyclohex-3-en-1-yl)acetate and (4-isopropoxyphenyl)boronic acid. The product was hydrogenated using General Procedure B with 10% Pd/C as catalyst and acetic acid as solvent. General Procedure G used ethyl 2-(4-(4-isopropoxyphenyl)cyclohexyl)acetate and 4-fluoroaniline. Purified using silica gel chromatography (0-20% EtOAc in hexanes) to afford the desired product as the first eluting isomer. $^1$H NMR (400 MHz, CDCl$_3$) δ 7.69 (s, 1H), 7.60-7.43 (m, 2H), 7.13 (t, J=5.8 Hz, 2H), 6.98 (dd, J=14.8, 5.9 Hz, 2H), 6.89-6.79 (m, 2H), 4.51 (dq, J=12.1, 6.1 Hz, 1H), 2.82-2.44 (m, 1H), 2.41 (d, J=9.7 Hz, 3H), 1.87-1.48 (m, 8H), 1.35 (t, J=5.2 Hz, 6H). m/z 370.3 (M+H)$^+$.

Example 72 cis-N-(4-Fluorophenyl)-2-(4-(4-isopropoxyphenyl)cyclohexyl)acetamide, or trans-N-(4-Fluorophenyl)-2-(4-(4-isopropoxyphenyl)cyclohexyl)acetamide (Relative Stereochemistry not Determined)

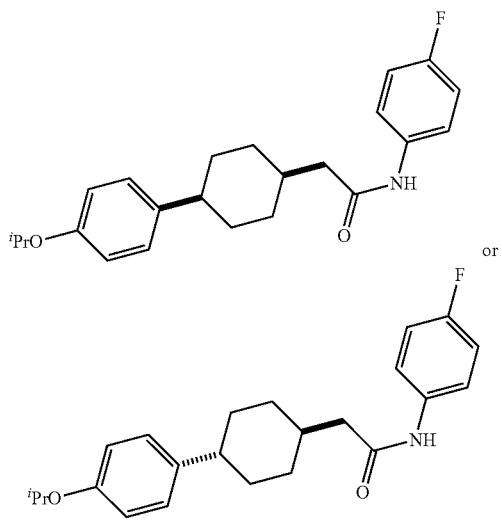

Further elution from the column in the previous example afforded the desired product as the second eluting isomer. $^1$H NMR (400 MHz, CDCl$_3$) δ 7.54-7.45 (m, 2H), 7.20-6.98 (m, 5H), 6.86-6.78 (m, 2H), 4.51 (dt, J=12.2, 6.0 Hz, 1H), 2.43 (dd, J=13.8, 10.4 Hz, 1H), 2.27 (d, J=6.6 Hz, 2H), 2.07-1.80 (m, 4H), 1.60-1.41 (m, 2H), 1.33 (t, J=5.1 Hz, 6H), 1.29-1.12 (m, 2H). m/z 370.3 (M+H)$^+$.

Example 73 cis-N-(4-Fluorophenyl)-2-(4-(4-ethoxyphenyl)cyclohexyl)acetamide

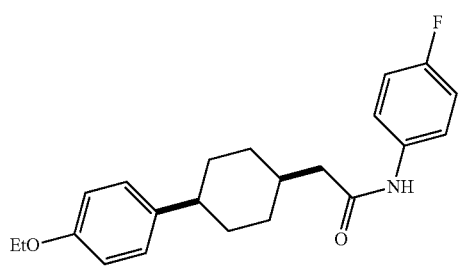

Example 73 was prepared using General Procedures A, B, and G. General Procedure A employed ethyl 2-(4-(((trifluoromethyl)sulfonyl)oxy) cyclohex-3-en-1-yl)acetate and (4-ethoxyphenyl)boronic acid. The product was hydrogenated using General Procedure B with 10% Pd/C as catalyst and acetic acid as solvent. General Procedure G used ethyl 2-(4-(4-ethoxyphenyl)cyclohexyl)acetate and 4-fluoroaniline. Purified using silica gel chromatography (0-20% EtOAc in hexanes) to afford the desired product as the first eluting isomer. $^1$H NMR (400 MHz, CDCl$_3$) δ 7.53-7.43 (m, 2H), 7.16 (t, J=6.0 Hz, 3H), 7.09-6.95 (m, 2H), 6.92-6.77 (m, 2H), 4.03 (q, J=7.0 Hz, 2H), 2.60 (d, J=9.2 Hz, 1H), 2.48-2.35 (m, 3H), 1.73 (ddd, J=21.7, 13.6, 9.0 Hz, 8H), 1.42 (t, J=7.0 Hz, 3H). m/z 356.2 (M+H)$^+$.

Example 74 trans-N-(4-Fluorophenyl)-2-(4-(4-ethoxyphenyl)cyclohexyl)acetamide

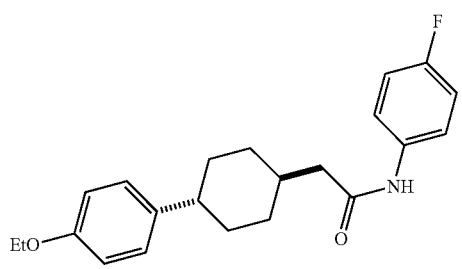

Further elution from the column in the previous example afforded the desired product as the second eluting isomer. $^1$H NMR (400 MHz, CDCl$_3$) δ 7.53-7.40 (m, 2H), 7.18 (s, 1H), 7.10 (d, J=8.6 Hz, 2H), 7.05-6.93 (m, 2H), 6.91-6.74 (m, 2H), 4.00 (q, J=7.0 Hz, 2H), 2.53-2.35 (m, 1H), 2.26 (d, J=6.7 Hz, 2H), 1.93 (dd, J=19.4, 13.2 Hz, 5H), 1.57-1.29 (m, 5H), 1.26-1.08 (m, 2H). m/z 356.2 (M+H)$^1$.

Example 75 cis-N-(4-Chlorophenyl)-2-(4-(4-(methylsulfonyl)phenyl)cyclohexyl)acetamide

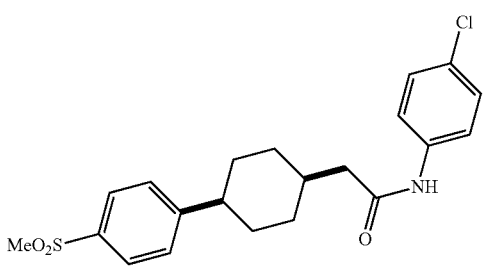

Prepared using General Procedures A, B and G. General Procedure A employed ethyl 2-(4-(((trifluoromethyl)sulfonyl)oxy)cyclohex-3-en-1-yl)acetate and (4-(methylsulfonyl)phenyl)-boronic acid. The product was hydrogenated using General Procedure B with 10% Pd/C as catalyst and acetic acid as solvent. General Procedure G used ethyl 2-(4-(4-(methylsulfonyl)-phenyl))cyclohexyl acetate and 4-chloroaniline. Purified using silica gel chromatography (20-50% EtOAc in hexanes) to afford the desired product as the first eluting isomer. $^1$H NMR (400 MHz, CDCl$_3$) δ 8.11 (br s, 1H), 7.86-7.73 (m, 2H), 7.56-7.49 (m, 2H), 7.49-7.42 (m, 1H), 7.38 (d, J=10.8 Hz, 1H), 7.24 (ddd, J=8.6, 6.2, 4.6 Hz, 2H), 3.05 (s, 3H), 2.68 (br s, 1H), 2.50-2.33 (m, 3H), 2.14 (d, J=1.6 Hz, 2H), 1.92 (br s, 1H), 1.67 (dd, J=19.9, 9.2 Hz, 5H). m/z 406.1 (M+H)$^+$.

Example 76 trans-N-(4-Chlorophenyl)-2-(4-(4-(methylsulfonyl)phenyl)cyclohexyl)acetamide

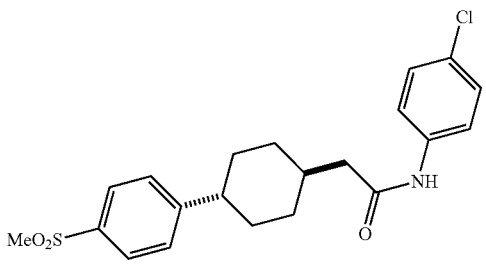

Further elution from the column in the previous example afforded the desired product as the second eluting isomer. $^1$H NMR (400 MHz, CDCl$_3$) δ 7.90-7.83 (m, 2H), 7.50 (t, J=10.4 Hz, 3H), 7.41-7.35 (m, 2H), 7.29 (d, J=8.3 Hz, 2H), 3.06 (s, 3H), 2.57 (tt, J=12.1, 3.3 Hz, 1H), 2.29 (d, J=6.6 Hz, 2H), 1.96 (ddd, J=22.7, 20.2, 18.6 Hz, 5H), 1.52 (qd, J=12.9, 2.8 Hz, 2H), 1.36-1.10 (m, 2H). m/z 406.2 (M+H)$^+$.

Example 77 cis-N-(4-Fluorophenyl)-2-(4-(4-(methylsulfonyl)phenyl)cyclohexyl)acetamide

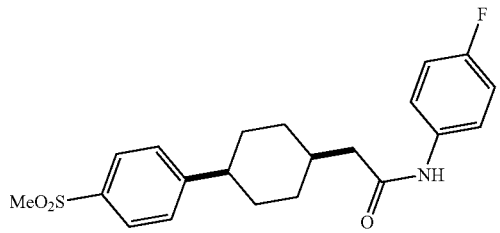

Prepared using General Procedures A, B and G. General Procedure A employed ethyl 2-(4-(((trifluoromethyl)sulfonyl)oxy)cyclohex-3-en-1-yl)acetate and (4-(methylsulfonyl)phenyl)boronic acid. The product was hydrogenated using General Procedure B with 10% Pd/C as catalyst and acetic acid as solvent. General Procedure G used ethyl 2-(4-(4-(methylsulfonyl)phenyl))cyclohexyl acetate and 4-fluoroaniline. Purified using silica gel chromatography (15-55% EtOAc in hexanes) to afford the desired product as the first eluting isomer. 390.2 m/z (M+H)$^+$.

Example 78 trans-N-(4-Fluorophenyl)-2-(4-(4-(methylsulfonyl)phenyl)cyclohexyl)acetamide

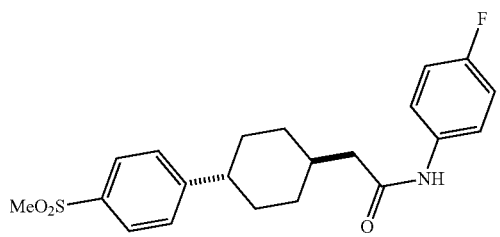

Further elution from the column in the previous example afforded the desired product as the second eluting isomer. 390.2 m/z (M+H)$^+$.

Example 79 cis-4-(-4-(2-((4-Chlorophenyl)amino)-2-oxoethyl)cyclohexyl)benzoic Acid

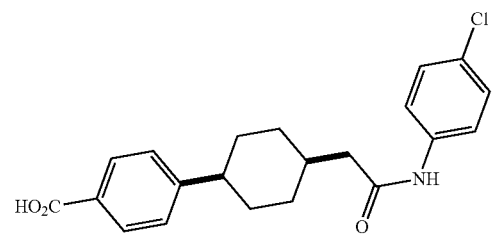

Prepared using General Procedures A, B, and G. General Procedure A employed 4-(tert-butoxycarbonyl)phenylboronic acid and ethyl 2-(4-(((trifluoromethyl)sulfonyl) oxy) cyclohex-3-en-1-yl)acetate. The product was hydrogenated using General Procedure B with 10% Pd(OH)$_2$/C as catalyst and acetic acid as solvent. General Procedure G used text-butyl 4-(4-(2-ethoxy-2-oxoethyl)cyclohexyl)benzoate and 4-chloroaniline. Purification by silica gel chromatography (0%-60% EtOAc in hexanes) afforded the tert-butyl ester of the desired product as the first eluting isomer. The ester was removed by dissolving in 10:1 CH$_2$Cl$_2$:CF$_3$CO$_2$H and stirring for 15 h. The mixture was concentrated under reduced pressure and purified using silica gel chromatography (20% EtOAc in hexanes) to afford the desired product. $^1$H NMR (400 MHz, CD$_3$OD) δ 7.95 (d, J=8.3 Hz, 2H), 7.60-7.52 (m, 2H), 7.39 (d, J=8.3 Hz, 2H), 7.32-7.25 (m, 2H), 2.70 (s, 1H), 2.52 (d, J=7.8 Hz, 2H), 2.37 (s, 1H), 2.02-1.70 (m, 8H). m/z 372.1 (M+H)$^+$.

Example 80 trans-4-(4-(2-((4-Chlorophenyl)amino)-2-oxoethyl) cyclohexyl)benzoic acid

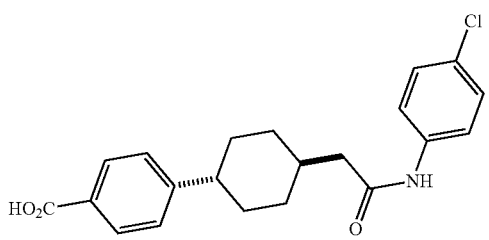

Prepared using General Procedures A, B, and G. General Procedure A employed 4-(tert-butoxycarbonyl)phenylboronic acid and ethyl 2-(4-(((trifluoromethyl)sulfonyl) oxy) cyclohex-3-en-1-yl)acetate. The product was hydrogenated using General Procedure B with 10% Pd(OH)$_2$/C as catalyst and acetic acid as solvent. General Procedure G used text-butyl 4-(4-(2-ethoxy-2-oxoethyl)cyclohexyl)benzoate and 4-chloroaniline. Purification by silica gel chromatography (0%-60% EtOAc in hexanes) afforded the tert-butyl ester of the desired product as the second eluting isomer. The ester was removed by dissolving in 10:1 CH$_2$Cl$_2$:CF$_3$CO$_2$H and stirring for 15 h. The mixture was concentrated under reduced pressure and purified using silica gel chromatography (20% EtOAc in hexanes) to afford the desired product. $^1$H NMR (400 MHz, CD$_3$OD) δ 7.93 (d, J=8.4 Hz, 2H), 7.57 (d, J=8.9 Hz, 2H), 7.31 (dd, J=12.5, 8.6 Hz, 4H), 2.59 (s, 1H), 2.30 (d, J=6.8 Hz, 2H), 1.93 (t, J=11.1 Hz, 5H), 1.58 (d, J=10.1 Hz, 2H), 1.25 (d, J=14.0 Hz, 2H). m/z 372.2 (M+H)$^+$.

Example 81 cis-4-(4-(2-((4-Chlorophenyl)amino)-2-oxoethyl) cyclohexyl)benzamide, or trans-4-(4-(2-((4-Chlorophenyl)amino)-2-oxoethyl)cyclohexyl)benzamide
Example 73 was Prepared using General Procedures A, B, and G

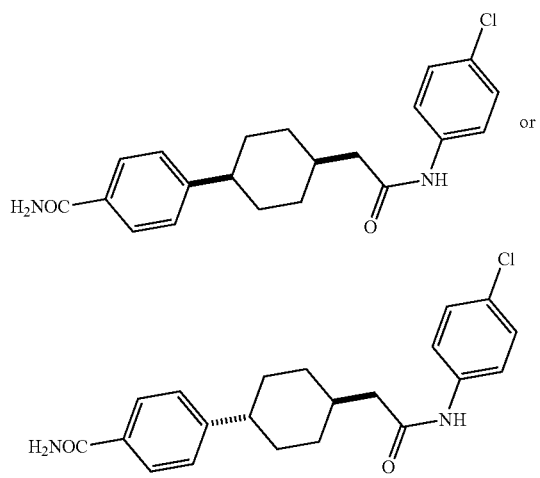

To a stirred solution of cis- or trans-4-(-4-(2-((4-chlorophenyl)amino)-2-oxoethyl) cyclohexyl)benzoic acid (50 mg, 0.134 mmol) in THF (0.8 mL) was added diisopropylethylamine (35 μL, 0.19 mmol) and ethyl chloroformate (15 μL, 0.17 mmol). The mixture was stirred for 30 min after which aqueous ammonium hydroxide (40 μL) was added and the solution was stirred for 30 minutes. The mixture was concentrated under reduced pressure and purified by silica gel chromatography (10-100% EtOAc in hexanes) to afford the desired product. $^1$H NMR (400 MHz, CD$_3$OD) δ 7.94 (d, 0.1=8.3 Hz, 1H), 7.81 (d, J=8.5 Hz, 1H), 7.56 (d, J=9.0 Hz, 2H), 7.39 (d, J=8.3 Hz, 2H), 7.33-7.25 (m, 2H), 2.69 (br s, 1H), 2.52 (d, J=7.7 Hz, 2H), 2.38 (br s, 1H), 1.88-1.69 (m, 8H). m/z 371.2 (M+H)$^+$.

Example 82 cis-4-(4-(2-((4-Chlorophenyl)amino)-2-oxoethyl) cyclohexyl)benzamide, or trans-4-(4-(2-((4-Chlorophenyl)amino)-2-oxoethyl)cyclohexyl)benzamide
(Relative Stereochemistry not Determined)

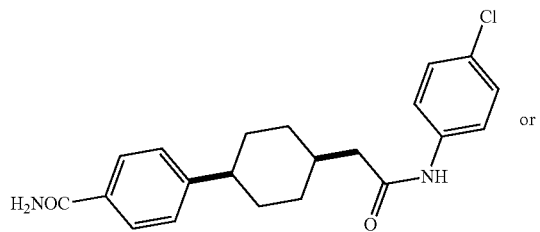

-continued

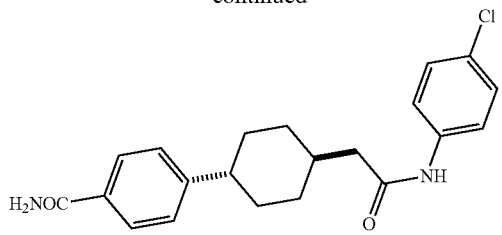

To a stirred solution of cis- or trans-4-(-4-(2-((4-chlorophenyl)amino)-2-oxoethyl) cyclohexyl)benzoic acid (50 mg, 0.134 mmol) in THF (0.8 mL) was added diisopropylethylamine (35 μL, 0.19 mmol) and ethyl chloroformate (15 μL, 0.17 mmol). The mixture was stirred for 30 min after which aqueous ammonium hydroxide (40 μL) was added and the solution was stirred for 30 minutes. The mixture was concentrated under reduced pressure and purified by silica gel chromatography (10-100% EtOAc in hexanes) to afford the desired product. m/z 371.2 (M+H)+.

Example 83 cis-4-(4-(2-((4-Fluorophenyl)amino)-2-oxoethyl) cyclohexyl)benzamide, or trans-4-(4-(2-((4-Fluorophenyl)amino)-2-oxoethyl)cyclohexyl)benzamide (Relative Stereochemistry not Determined)

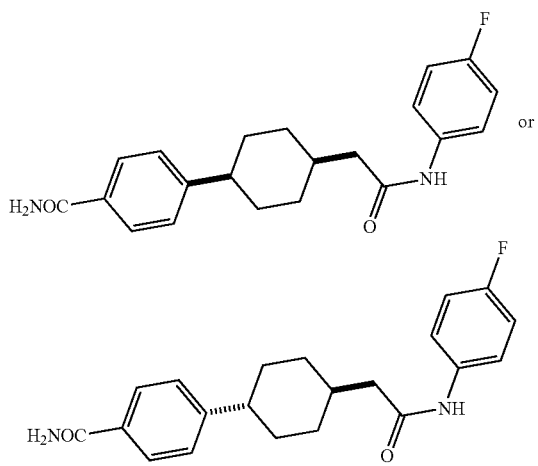

Prepared using General Procedures A, B, and G. General Procedure A employed 4-(tert-butoxycarbonyl)phenylboronic acid and ethyl 2-(4-(((trifluoromethyl)sulfonyl) oxy) cyclohex-3-en-1-yl)acetate. The product was hydrogenated using General Procedure B with 10% Pd(OH)$_2$/C as catalyst and acetic acid as solvent. General Procedure G used tert-butyl 4-(4-(2-ethoxy-2-oxoethyl)cyclohexyl)benzoate and 4-fluoroaniline. Purification by silica gel chromatography (0%-60% EtOAc in hexanes) afforded the tert-butyl ester of the product as the first eluting isomer. The ester was cleaved to the acid by dissolving in 10:1 CH$_2$Cl$_2$:CF$_3$CO$_2$H and stirring for 15 h. The mixture was concentrated under reduced pressure and purified using silica gel chromatography (20% EtOAc in hexanes) to afford cis- or trans-4-(-4-(2-((4-fluorophenyl)amino)-2-oxoethyl)cyclohexyl)benzoic acid. To a stirred solution of cis- or trans-4-(-4-(2-((4-fluorophenyl)amino)-2-oxoethyl)cyclohexyl) benzoic acid (50 mg, 0.14 mmol) in THF (0.7 mL) was added diisopropylethylamine (34 μL, 0.2 mmol) and ethyl chloroformate (16 μL, 0.17 mmol). The mixture was stirred for 30 min after which aqueous ammonium hydroxide (36 μL) was added and the solution was stirred for 30 minutes. The mixture was concentrated under reduced pressure and purified using silica gel chromatography (10-100% EtOAc in hexanes) to afford the desired product. $^1$H NMR (400 MHz, CD$_3$OD) δ 7.94 (d, J=8.3 Hz, 1H), 7.85-7.78 (m, 1H), 7.59-7.51 (m, 2H), 7.39 (dd, J=8.3, 1.7 Hz, 2H), 7.10-6.99 (m, 2H), 2.69 (br s, 1H), 2.55-2.49 (m, 2H), 2.37 (br s, 1H), 2.14-1.51 (m, 8H). m/z 355.2 (M+H)+.

Example 84 cis-4-(4-(2-((4-Fluorophenyl)amino)-2-oxoethyl) cyclohexyl)benzamide, or trans-4-(4-(2-((4-Fluorophenyl)amino)-2-oxoethyl)cyclohexyl)benzamide (Relative Stereochemistry not Determined)

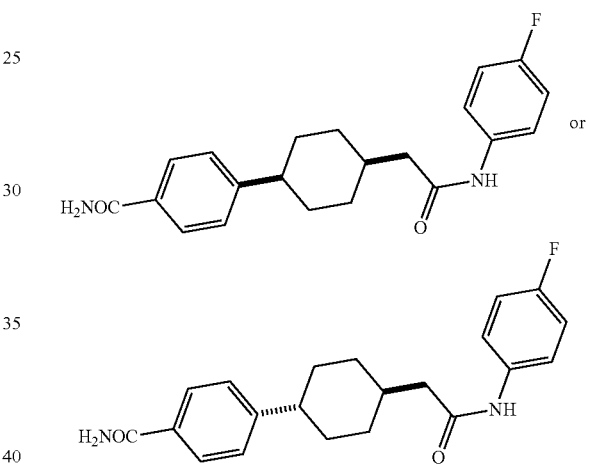

Prepared using General Procedures A, B, and G. General Procedure A employed 4-(tert-butoxycarbonyl)phenylboronic acid and ethyl 2-(4-(((trifluoromethyl)sulfonyl) oxy) cyclohex-3-en-1-yl)acetate. The product was hydrogenated using General Procedure B with 10% Pd(OH)$_2$/C as catalyst and acetic acid as solvent. General Procedure G used tert-butyl 4-(4-(2-ethoxy-2-oxoethyl)cyclohexyl)benzoate and 4-fluoroaniline. Purification by silica gel chromatography (0%-60% EtOAc) afforded the tert-butyl ester of the product as the second eluting isomer. The ester was removed by dissolving in 10:1 CH$_2$Cl$_2$:CF$_3$CO$_2$H and stirring for 15 h. The mixture was concentrated under reduced pressure and purified using silica gel chromatography (20% EtOAc in hexanes) to afford cis- or trans-4-(-4-(2-((4-fluorophenyl) amino)-2-oxoethyl)cyclohexyl)benzoic acid. To a stirred solution of cis- or trans-4-(-4-(2-((4-fluorophenyl)amino)-2-oxoethyl)cyclohexyl) benzoic acid (50 mg, 0.14 mmol) in THF (0.7 mL) was added diisopropylethylamine (34 μL, 0.2 mmol) and ethyl chloroformate (16 μL, 0.17 mmol). The mixture was stirred for 30 min after which aqueous ammonium hydroxide (36 μL) was added and the solution was stirred for 30 minutes. The mixture was concentrated under reduced pressure and purified using silica gel chromatography (10-100% EtOAc in hexanes) to afford the desired product. m/z 355.3 (M+H)+.

Example 86 cis-N-(4-Cyanophenyl)-2-((1,4)-4-(4-(trifluoromethoxy)phenyl)cyclohexyl)-acetamide

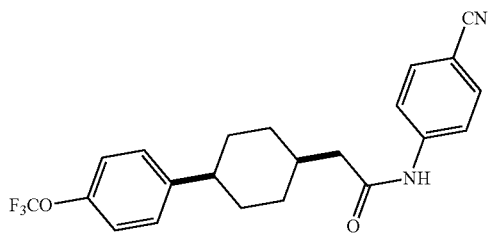

86A. Ethyl 2-(4'-(trifluoromethoxy)-2,3,4,5-tetrahydro-[1,1'-biphenyl]-4-yl)acetate

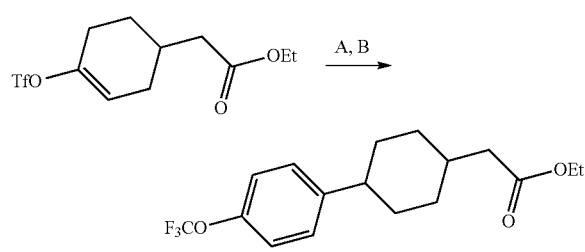

Prepared with General Procedure A employing ethyl 2-(4-(((trifluoromethyl) sulfonyl)oxy)cyclohex-3-en-1-yl)acetate (949 mg, 3.0 mmol), (4-(trifluoromethoxy) phenyl) boronic acid (740 mg, 3.6 mmol), $K_3PO_4$ (954 mg, 4.5 mmol), KBr (393 mg, 3.3 mmol) and $Pd(PPh_3)_4$ (347 mg, 0.3 mmol) in 1,4-dioxane (12 mL) and water (1.2 mL). Purified employing silica gel chromatography (0% to 5% EtOAc in hexanes) to afford the desired product as a clear oil. Ethyl 2-(4'-(trifluoromethoxy)-2,3,4,5-tetrahydro-[1,1'-biphenyl]-4-yl)acetate (492 mg, 1.5 mmol) was hydrogenated with General Procedure B employing Pd/C (10% Pd, 50 mg, 10 wt. %), in AcOH (3.0 mL) as solvent and purified employing silica gel chromatography (0% to 5% EtOAc in hexanes) to afford the desired cis and trans product mixture as a clear oil.

Example 86: cis-N-(4-Cyanophenyl)-2-((1,4)-4-(4-(trifluoromethoxy)phenyl)cyclohexyl)-acetamide Prepared with General Procedure G employing ethyl 2-(4-(4-(trifluoromethoxy)-phenyl)cyclohexyl)acetate (Preparation 86A) (66 mg, 0.2 mmol), 4-cyanoaniline (47 mg, 0.4 mmol), $^iPrMgCl$ (200 μL, 0.4 mmol) in THF (1.0 mL). Purified using silica gel chromatography (5% to 20% EtOAc in hexanes) to afford the desired product as a white solid. $^1H$ NMR (400 MHz; $CDCl_3$): δ 7.70-7.66 (m, 2H), 7.61 (s, 1H), 7.60-7.57 (m, 2H), 7.26-7.22 (m, 2H), 7.13-7.11 (m, 2H), 2.68-2.61 (m, 1H), 2.51-2.49 (m, 2H), 2.45-2.39 (m, 1H), 1.79-1.64 (m, 8H). m/z 403.2 $(M+H)^+$.

Example 87 trans-N-(4-Cyanophenyl)-2-((1,4)-4-(4-(trifluoromethoxy)phenyl)cyclohexyl)-acetamide

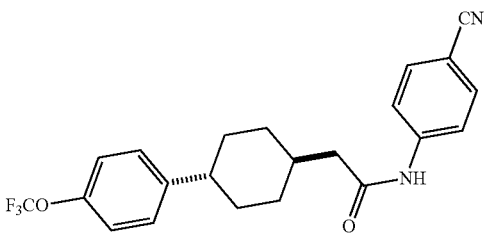

Further elution from the column in the previous example afforded the desired product as a white solid and the second eluting isomer. $^1H$ NMR (400 MHz; $CDCl_3$): δ 7.71-7.68 (m, 2H), 7.63 (s, 1H), 7.62-7.59 (m, 2H), 7.21-7.17 (m, 2H), 7.12 (d, J=8.6 Hz, 2H), 2.48 (tt, J=12.2, 3.2 Hz, 1H), 2.33 (d, J=6.7 Hz, 2H), 2.02-1.88 (m, 5H), 1.49 (qd, J=12.6, 2.5 Hz, 2H), 1.26-1.15 (m, 2H). m/z 403.2 $(M+H)^+$.

Example 88 cis-N-(4-Fluorophenyl)-2-((1,4)-4-(4-(trifluoromethoxy)phenyl)cyclohexyl)-acetamide

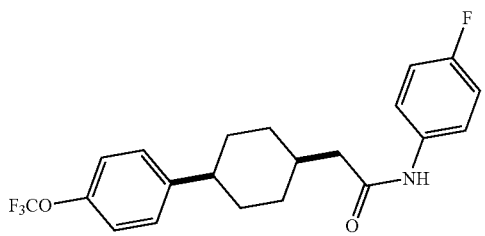

Prepared with General Procedure G employing ethyl 2-(4-(4-(trifluoromethoxy) phenyl)cyclohexyl)acetate (Preparation 86A) (66 mg, 0.2 mmol), 4-fluoroaniline (44 mg, 0.4 mmol), $^iPrMgCl$ (200 μL, 0.4 mmol) in THF (1.0 mL). Purified using silica gel chromatography (5% to 15% EtOAc in hexanes) to afford the desired product as a white solid. $^1H$ NMR (400 MHz; $CDCl_3$): δ 7.54-7.45 (m, 2H), 7.23-7.16 (m, 2H), 7.16-7.09 (m, 2H), 7.06-6.98 (m, 2H), 2.27 (d, J=6.6 Hz, 2H), 2.01-1.89 (m, 5H), 1.54-1.44 (m, 2H), 1.25-1.14 (m, 2H). m/z 396.2 $(M+H)^+$.

Example 89 trans-N-(4-Fluorophenyl)-2-((1,4)-4-(4-(trifluoromethoxy)phenyl)cyclohexyl)-acetamide

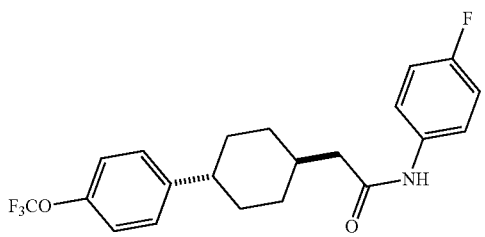

Further elution from the column in the previous example afforded the desired product as a white solid and the second eluting isomer. $^1$H NMR (400 MHz; CDCl$_3$): δ 7.48-7.45 (m, 2H), 7.25 (d, J=8.4 Hz, 3H), 7.14 (d, J=8.1 Hz, 2H), 7.02-6.98 (m, 2H), 2.68-2.61 (m, 1H), 2.46-2.37 (m, 3H), 1.77-1.63 (m, 8H). m/z 396.2 (M+H)$^+$.

Example 90 cis-N-(4-Chlorophenyl)-2-((1,4)-4-(4-(trifluoromethoxy)phenyl)cyclohexyl)-acetamide

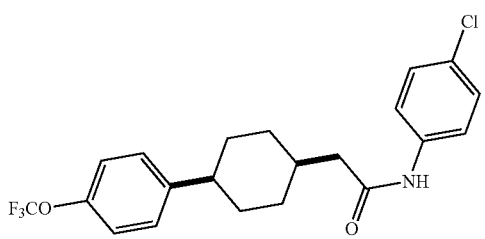

Prepared with General Procedure G employing ethyl 2-(4-(4-(trifluoromethoxy)phenyl)cyclohexyl)acetate (Preparation 86A) (66 mg, 0.2 mmol), 4-chloroaniline (51 mg, 0.4 mmol), $^i$PrMgCl (200 µL, 0.4 mmol) in THF (1.0 mL). Purified using silica gel chromatography (5% to 15% EtOAc in hexanes) to afford the desired product as a white solid. $^1$H NMR (400 MHz; CDCl$_3$): δ 7.49-7.44 (m, 2H), 7.28-7.23 (m, 4H), 7.17-7.12 (m, 3H), 2.68-2.61 (m, 1H), 2.46-2.37 (m, 3H), 1.79-1.64 (m, 8H). m/z 412.2 (M+H)$^+$.

Example 91 trans-N-(4-Chlorophenyl)-2-((1,4)-4-(4-(trifluoromethoxy)phenyl)cyclohexyl)-acetamide

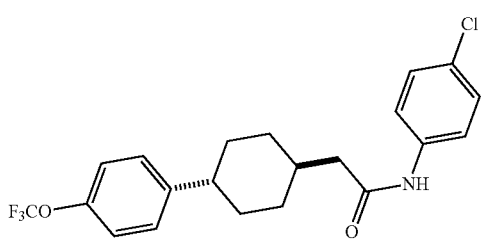

Further elution from the column in the previous example afforded the desired product as a white solid and the second eluting isomer. $^1$H NMR (400 MHz; CDCl$_3$): δ 7.50-7.47 (m, 2H), 7.41 (s, 1H), 7.29-7.27 (m, 2H), 7.20-7.17 (m, 2H), 7.13-7.11 (m, 2H), 2.48 (tt, J=12.2, 3.1 Hz, 1H), 2.27 (d, J=6.6 Hz, 2H), 1.96-1.88 (m, 5H), 1.52-1.42 (m, 2H), 1.25-1.13 (m, 2H). m/z 412.2 (M+H)$^+$.

Example 92 cis-N-(4-Chlorophenyl)-2-(4-(4-ethoxyphenyl)cyclohexyl)acetamide or trans-N-(4-Chlorophenyl)-2-(4-(4-ethoxyphenyl)cyclohexyl)acetamide (Relative Stereochemistry not Determined)

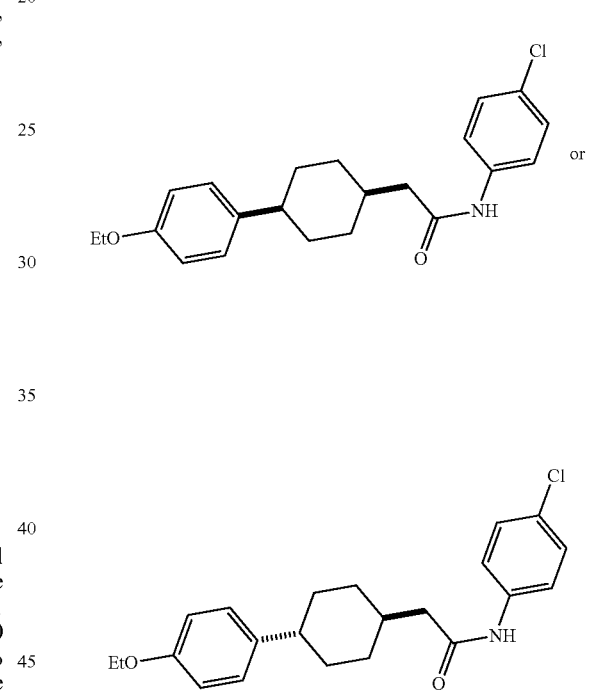

Prepared using General Procedures A, B and G. General Procedure A employed ethyl 2-(4-(((trifluoromethyl)sulfonyl)oxy)cyclohex-3-en-1-yl)acetate and (4-ethoxyphenyl)boronic acid. The product was hydrogenated using General Procedure B with 10% Pd/C as catalyst and acetic acid as solvent. General Procedure G used ethyl 2-(4-(4-ethoxyphenyl)cyclohexyl)acetate and 4-chloroaniline. Purified using silica gel chromatography (0-15% EtOAc in hexanes) to afford the desired product as the first eluting isomer. $^1$H NMR (400 MHz, CDCl$_3$) δ 7.48 (d, J=8.8 Hz, 2H), 7.33-7.22 (m, 2H), 7.16 (d, J=8.6 Hz, 3H), 6.98-6.72 (m, 2H), 4.03 (q, J=7.0 Hz, 2H), 2.59 (d, J=5.6 Hz, 1H), 2.49-2.32 (m, 3H), 1.72 (dt, J=18.6, 12.8 Hz, 8H), 1.42 (t, J=7.0 Hz, 3H). m/z 372.2 (M+H)$^+$.

Example 93 cis-N-(4-Chlorophenyl)-2-(4-(3-cyanophenyl)cyclohexyl)acetamide

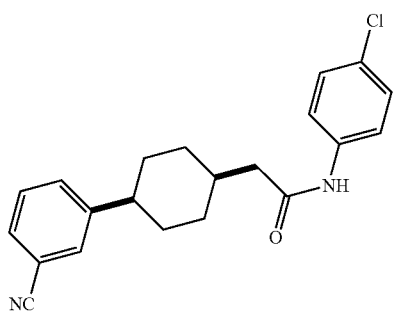

Prepared using General Procedures A, B and G. General Procedure A employed ethyl 2-(4-(((trifluoromethyl)sulfonyl)oxy)cyclohex-3-en-1-yl)acetate and (3-cyanophenyl)boronic acid. The product was hydrogenated using General Procedure B with 10% Pd/C as catalyst and acetic acid as solvent. General Procedure G used ethyl 2-(4-(3-cyanophenyl)cyclohexyl)acetate and 4-chloroaniline. Purified using silica gel chromatography (25% EtOAc in hexanes) to afford the desired product as the first eluting isomer. $^1$H NMR (400 MHz, CDCl$_3$) δ 7.63-7.45 (m, 5H), 7.45-7.36 (m, 1H), 7.34-7.19 (m, 3H), 2.69 (s, 1H), 2.46 (s, 3H), 1.73 (dt, J=18.3, 11.4 Hz, 8H). m/z 353.2 (M+H)$^+$.

Example 94 trans-N-(4-Chlorophenyl)-2-(4-(3-cyanophenyl)cyclohexyl)acetamide

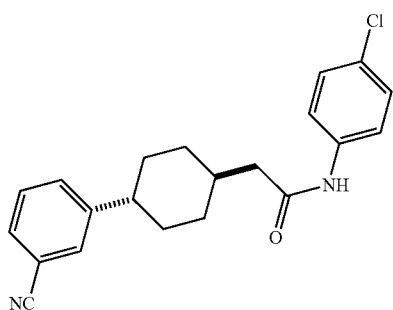

Further elution from the column in the previous example afforded the desired product as the second eluting isomer. $^1$H NMR (400 MHz, CDCl$_3$) δ 7.54-7.47 (m, 4H), 7.42 (dt, J=15.6, 7.0 Hz, 2H), 7.30 (d, J=8.8 Hz, 2H), 7.12 (s, 1H), 2.53 (t, J=12.3 Hz, 1H), 2.30 (d, J=6.5 Hz, 2H), 2.11-1.81 (m, 5H), 1.63-1.42 (m, 2H), 1.39-1.06 (m, 2H). m/z 353.2 (M+H)$^+$.

Example 95 cis-N-(4-Fluorophenyl)-2-(4-(3-cyanophenyl)cyclohexyl)acetamide

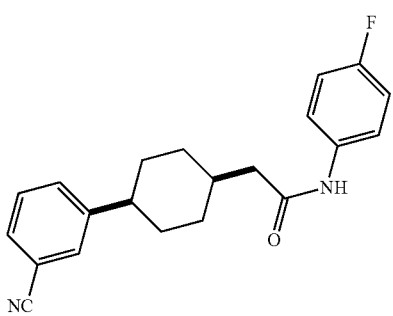

Prepared using General Procedures A, B and G. General Procedure A employed ethyl 2-(4-(((trifluoromethyl)sulfonyl)oxy)cyclohex-3-en-1-yl)acetate and (3-cyanophenyl)boronic acid. The product was hydrogenated using General Procedure B with 10% Pd/C as catalyst and acetic acid as solvent. General Procedure G used ethyl 2-(4-(3-cyanophenyl)cyclohexyl)acetate and 4-fluoroaniline. Purified using silica gel chromatography (25% EtOAc in hexanes) to afford the desired product as the first eluting isomer. $^1$H NMR (400 MHz, CDCl$_3$) δ 7.56 (s, 1H), 7.50 (ddd, J=6.7, 3.7, 1.6 Hz, 4H), 7.46-7.38 (m, 1H), 7.22 (d, J=5.7 Hz, 1H), 7.08-6.97 (m, 2H), 2.67 (d, J=22.1 Hz, 2H), 2.45 (d, J=5.6 Hz, 3H), 1.90-1.63 (m, 9H). m/z 337.2 (M+H)$^+$.

Example 96 trans-N-(4-Fluorophenyl)-2-(4-(3-cyanophenyl)cyclohexyl)acetamide

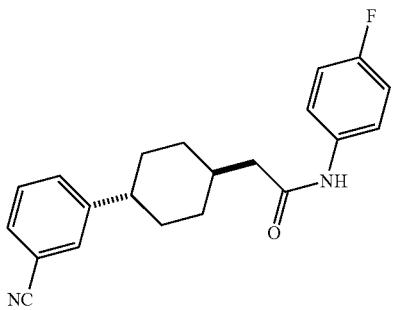

Further elution from the column in the previous example afforded the desired product as the second eluting isomer. $^1$H NMR (400 MHz, CDCl$_3$) δ 7.55-7.47 (m, 4H), 7.47-7.36 (m, 2H), 7.16 (s, 1H), 7.08-6.97 (m, 2H), 2.53 (ddd, J=12.3, 8.9, 3.3 Hz, 1H), 2.29 (d, J=6.6 Hz, 2H), 2.10-1.85 (m, 5H), 1.70-1.44 (m, 2H), 1.24 (dt, J=25.1, 9.8 Hz, 2H). m/z 337.2 (M+H)$^+$.

Example 97 cis-N-(4-Cyanophenyl)-2-(4-(3-cyanophenyl)cyclohexyl)acetamide

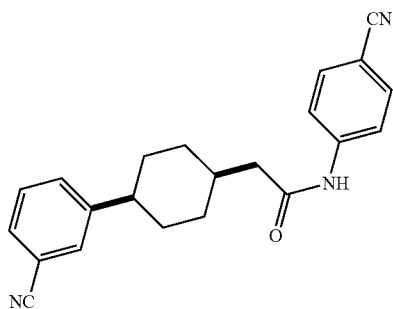

Prepared using General Procedures A, B and G. General Procedure A employed ethyl 2-(4-(((trifluoromethyl)sulfonyl)oxy)cyclohex-3-en-1-yl)acetate and (3-cyanophenyl)boronic acid. The product was hydrogenated using General Procedure B with 10% Pd/C as catalyst and acetic acid as solvent. General Procedure G used ethyl 2-(4-(3-cyanophenyl)cyclohexyl)acetate and 4-cyanoaniline. Purified using silica gel chromatography (60-75% methyl tert-butyl ether in hexanes) to afford the desired product as the first eluting isomer. $^1$H NMR (400 MHz, CDCl$_3$) δ 7.74-7.66 (m, 2H), 7.65-7.58 (m, 2H), 7.55 (t, J=1.7 Hz, 1H), 7.52-7.45 (m, 2H), 7.42 (dt, J=10.5, 5.7 Hz, 2H), 2.70 (s, 1H), 2.55-2.39 (m, 3H), 1.85-1.62 (m, 8H). m/z 344.3 (M+)$^+$.

Example 98 trans-N-(4-Cyanophenyl)-2-(4-(3-cyanophenyl)cyclohexyl)acetamide

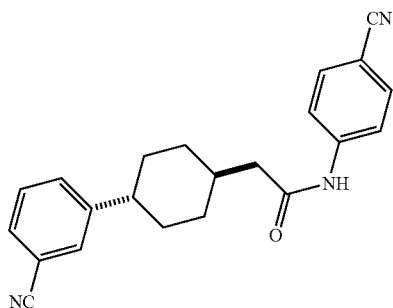

Further elution from the column in the previous example afforded the desired product as the second eluting isomer. $^1$H NMR (400 MHz, CDCl$_3$) δ 7.72-7.57 (m, 4H), 7.52-7.47 (m, 2H), 7.42 (ddd, J=15.6, 9.3, 7.0 Hz, 2H), 7.31 (d, J=5.0 Hz, 1H), 2.60-2.48 (m, 1H), 2.34 (d, J=6.5 Hz, 2H), 2.10-1.87 (m, 4H), 1.66-1.43 (m, 3H), 1.37-1.16 (m, 2H). m/z 344.2 (M+H)$^+$.

Example 99 cis-N-(4-Chlorophenyl)-2-(4-(3-((2-oxopyrrolidin-1-yl)methyl)phenyl) cyclohexyl)acetamide, or trans-N-(4-Chlorophenyl)-2-(4-(3-((2-oxopyrrolidin-1-yl)methyl)phenyl) cyclohexyl)acetamide (Relative Stereochemistry not Determined)

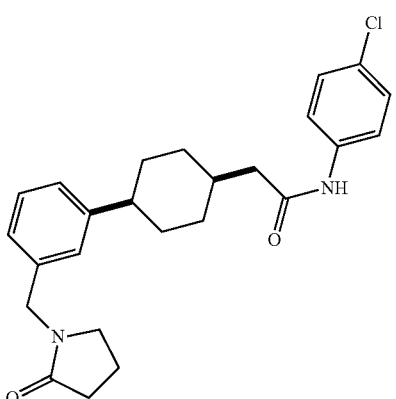

or

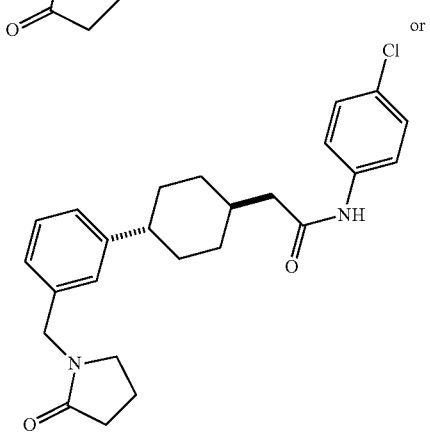

Prepared using General Procedures H, B and G. General Procedure H employed ethyl 2-(4-(4,4,5,5-tetramethyl-1,3,2-dioxaborolan-2-yl)cyclohex-3-en-1-yl)acetate and 1-(3-bromobenzyl)pyrrolidin-2-one. (Buerli, Roland from PCT Publication No. WO 2010/052448 (May 14, 2010), "Preparation of fused pyrazines as phosphoinositide 3-kinase (PI3K) inhibitors".) The product was hydrogenated using General Procedure B with 10% Pd/C as catalyst and acetic acid as solvent. General Procedure G used ethyl 2-(4-(3-((2-oxopyrrolidin-1-yl)methyl)phenyl)cyclohexyl)acetate and 4-chloroaniline. Purified using silica gel chromatography (60-75% EtOAc in hexanes) to afford the desired product as the first eluting isomer. $^1$H NMR (400 MHz, CDCl$_3$) δ 7.74 (s, 1H), 7.58-7.50 (m, 1H), 7.39-7.20 (m, 5H), 7.16 (d, J=5.9 Hz, 1H), 7.06 (d, J=7.6 Hz, 1H), 4.45 (d, J=10.5 Hz, 2H), 3.31-3.24 (m, 2H), 2.63 (d, J=10.0 Hz, 1H), 2.46 (dd, J=10.2, 6.1 Hz, 3H), 2.11-1.94 (m, 4H), 1.77-1.59 (m, 7H). m/z 425.3 (M+H)$^+$.

Further elution from the column in the previous example afforded a mixture. The mixture was recrystallized from acetone. The solid was purified using silica gel chromatography (75% EtOAc in hexanes) to afford the desired product. $^1$H NMR (400 MHz, CDCl$_3$) δ 7.50 (d, J=8.8 Hz, 2H), 7.32-7.20 (m, 4H), 7.08 (dd, J=25.7, 7.5 Hz, 3H), 4.42 (s, 2H), 3.31-3.22 (m, 2H), 2.46 (dd, J=17.1, 9.2 Hz, 3H), 2.28

(d, J=6.6 Hz, 2H), 2.07-1.91 (m, 7H), 1.51 (dt, J=22.9, 11.4 Hz, 2H), 1.43-1.09 (m, 2H). m/z 425.3 (M+H)+.

Example 100 cis-N-(4-Fluorophenyl)-2-(4-(3-((2-oxopyrrolidin-1-yl)methyl)phenyl) cyclohexyl)acetamide, or trans-N-(4-Fluorophenyl)-2-(4-(3-((2-oxopyrrolidin-1-yl)methyl)phenyl) cyclohexyl)acetamide (Relative Stereochemistry not Determined)

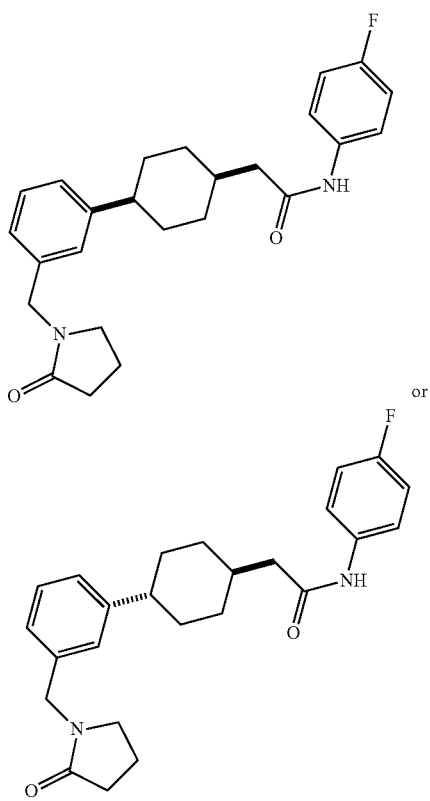

Prepared using General Procedures H, B and G. General Procedure H employed ethyl 2-(4-(4,4,5,5-tetramethyl-1,3,2-dioxaborolan-2-yl)cyclohex-3-en-1-yl)acetate and 1-(3-bromobenzyl)pyrrolidin-2-one. (Buerli, Roland from PCT Publication No. WO 2010/052448 (May 14, 2010), "Preparation of fused pyrazines as phosphoinositide 3-kinase (PI3K) inhibitors".The product was hydrogenated using General Procedure B with 10% Pd/C as catalyst and acetic acid as solvent. General Procedure G used ethyl 2-(4-(3-((2-oxopyrrolidin-1-yl)methyl)phenyl)cyclohexyl)acetate and 4-fluoroaniline. Purified using silica gel chromatography (75-100% EtOAc in hexanes) to afford the desired product as the first eluting isomer. 1H NMR (400 MHz, CDCl3) δ 7.57-7.38 (m, 2H), 7.38-7.21 (m, 4H), 7.17 (d, J=6.3 Hz, 1H), 7.10-6.97 (m, 2H), 4.45 (d, J=8.5 Hz, 2H), 3.28 (dd, J=14.5, 7.5 Hz, 2H), 2.64 (s, 1H), 2.46 (dd, J=9.8, 6.5 Hz, 4H), 2.08-1.94 (m, 4H), 1.72 (d, 0.1=6.0 Hz, 7H). m/z 409.3 (M+H)+.

Further elution from the column in the previous example afforded the desired product as the second eluting isomer. 1H NMR (400 MHz, CDCl3) δ 7.55-7.48 (m, 2H), 7.39 (s, 1H), 7.32-7.21 (m, 2H), 7.16-6.97 (m, 5H), 4.43 (s, 2H), 3.32-3.23 (m, 2H), 2.46 (dd, J=10.3, 5.9 Hz, 3H), 2.28 (d, J=6.7 Hz, 2H), 2.08-1.80 (m, 7H), 1.57-1.42 (m, 2H), 1.37-1.09 (m, 2H). m/z 409.3 (M+H)+.

Example 101 cis-N-(4-Cyanophenyl)-2-(4-(3-((2-oxopyrrolidin-1-yl)methyl)phenyl) cyclohexyl)acetamide, or trans-N-(4-Cyanophenyl)-2-(4-(3-((2-oxopyrrolidin-1-yl)methyl)phenyl) cyclohexyl)acetamide (Relative Stereochemistry not Determined)

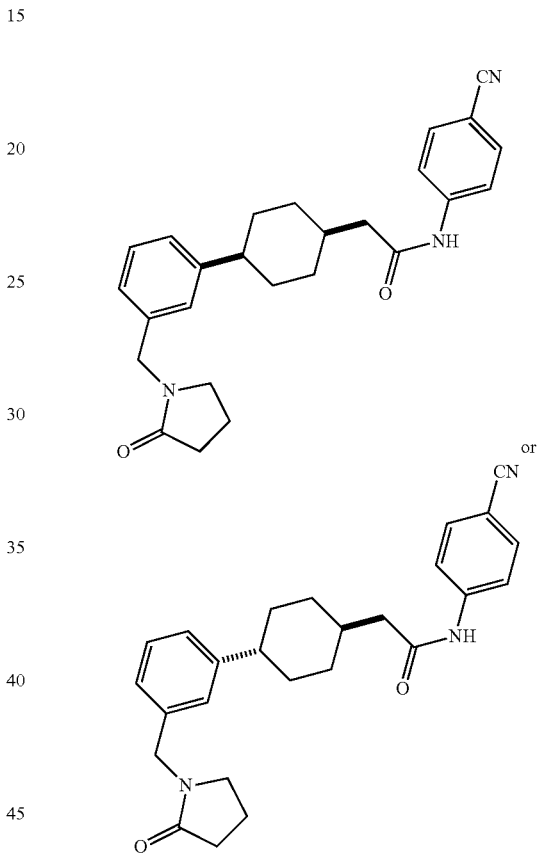

Prepared using General Procedures H, B and G. General Procedure H employed ethyl 2-(4-(4,4,5,5-tetramethyl-1,3,2-dioxaborolan-2-yl)cyclohex-3-en-1-yl)acetate and 1-(3-bromobenzyl)pyrrolidin-2-one. The product was hydrogenated using General Procedure B with 10% Pd/C as catalyst and acetic acid as solvent. General Procedure G used ethyl 2-(4-(3-((2-oxopyrrolidin-1-yl)methyl)phenyl)cyclohexyl)acetate and 4-cyanoaniline. Purified using silica gel chromatography (75-100% EtOAc in hexanes) to afford the desired product as the first eluting isomer. 1H NMR (400 MHz, CDCl3) δ 8.49 (s, 1H), 7.82-7.71 (m, 1H), 7.63-7.51 (m, 1H), 7.41-7.20 (m, 3H), 7.15 (d, J=10.4 Hz, 1H), 7.04 (d, J=7.2 Hz, 1H), 4.44 (d, J=14.1 Hz, 2H), 3.29 (dt, J=14.2, 7.0 Hz, 2H), 2.61 (s, 1H), 2.55-2.38 (m, 4H), 2.00 (dd, J=11.2, 7.1 Hz, 2H), 1.82 (s, 3H), 1.78-1.56 (m, 6H). m/z 416.3 (M+H)+.

Further elution from the column in the previous example afforded the desired product as the second eluting isomer. 1H NMR (400 MHz, DMSO) δ 10.36 (s, 1H), 7.77 (q, J=9.1 Hz, 4H), 7.24 (t, J=7.5 Hz, 1H), 7.14 (d, J=8.0 Hz, 1H), 7.06 (s, 1H), 7.00 (d, J=7.7 Hz, 1H), 4.32 (s, 2H), 3.32 (d, J=9.4 Hz, 2H), 3.25-3.16 (m, 2H), 2.28 (t, J=8.0 Hz, 4H), 1.98-1.78 (m, 6H), 1.46 (d, J=12.6 Hz, 2H), 1.15 (d, J=14.1 Hz, 2H). m/z 416.3 (M+H)$^+$.

Example 102 cis-N-(4-Chlorophenyl)-2-(4-(3-fluorophenyl)cyclohexyl)acetamide

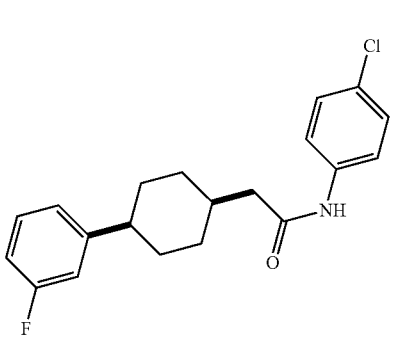

Prepared using General Procedures A, B and G. General Procedure A employed ethyl 2-(4-((((trifluoromethyl)sulfonyl)oxy)cyclohex-3-en-1-yl)acetate and (3-fluorophenyl) boronic acid. The product was hydrogenated using General Procedure B with 10% Pd/C as catalyst and acetic acid as solvent. General Procedure G used ethyl 2-(4-(3-fluorophenyl)cyclohexyl)acetate and 4-chloroaniline. Purified using silica gel chromatography (0-35% EtOAc in hexanes) to afford the desired product as the first eluting isomer. $^1$H NMR (400 MHz, CDCl$_3$) δ 7.49 (d, J=8.8 Hz, 2H), 7.35-7.22 (m, 3H), 7.11 (d, J=8.9 Hz, 1H), 7.03 (d, J=7.5 Hz, 1H), 6.96 (d, J=10.6 Hz, 1H), 6.93-6.86 (m, 1H), 2.67 (s, 1H), 2.45 (d, J=5.4 Hz, 3H), 1.84-1.63 (m, 8H). m/z 346.2 (M+H)$^+$.

Example 103 trans-N-(4-Chlorophenyl)-2-(4-(3-fluorophenyl)cyclohexyl)acetamide

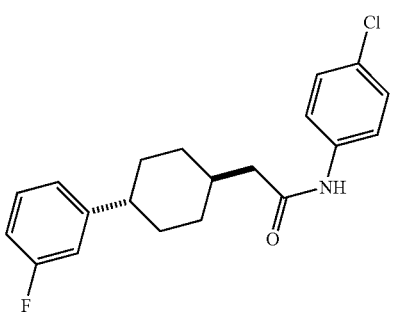

Further elution from the column in the previous example afforded the desired product as the second eluting isomer. $^1$H NMR (400 MHz, CDCl$_3$) δ 7.49 (d, J=8.8 Hz, 2H), 7.33-7.20 (m, 3H), 7.11 (s, 1H), 6.98 (d, J=7.8 Hz, 1H), 6.89 (ddd, J=14.0, 8.2, 1.7 Hz, 2H), 2.50 (t, J=12.2 Hz, 1H), 2.29 (d, J=6.6 Hz, 2H), 1.96 (dd, J=20.5, 8.6 Hz, 4H), 1.59-1.42 (m, 3H), 1.33-1.11 (m, 2H). m/z 346.1 (M+H)$^+$.

Example 104 cis-N-(4-Fluorophenyl)-2-(4-(3-fluorophenyl)cyclohexyl)acetamide

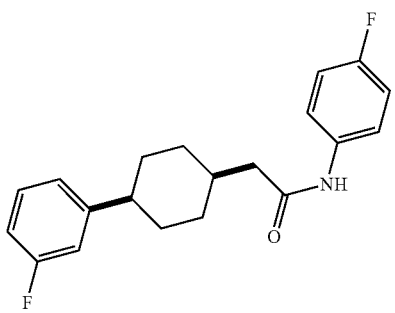

Prepared using General Procedures A, B and G. General Procedure A employed ethyl 2-(4-((((trifluoromethyl)sulfonyl)oxy)cyclohex-3-en-1-yl)acetate and (3-fluorophenyl) boronic acid. The product was hydrogenated using General Procedure B with 10% Pd/C as catalyst and acetic acid as solvent. General Procedure G used ethyl 2-(4-(3-fluorophenyl)cyclohexyl)acetate and 4-fluoroaniline. Purified using silica gel chromatography (0-35% EtOAc in hexanes) to afford the desired product as the first eluting isomer. m/z 330.2 (M+H)$^+$.

Example 105 trans-N-(4-Fluorophenyl)-2-(4-(3-fluorophenyl)cyclohexyl)acetamide

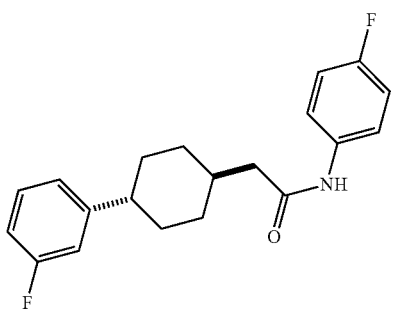

Further elution from the column in the previous example afforded the desired product as the second eluting isomer. $^1$H NMR (400 MHz, CDCl$_3$) δ 7.54-7.45 (m, 2H), 7.32-7.20 (m, 2H), 7.14-7.01 (m, 2H), 7.01-6.95 (m, 1H), 6.94-6.83 (m, 2H), 2.50 (t, J=12.1 Hz, 1H), 2.28 (d, J=6.7 Hz, 2H), 2.12-1.83 (m, 4H), 1.60-1.44 (m, 3H), 1.35-1.08 (m, 2H). m/z 330.2 (M+H)$^+$.

Example 106 cis-N-(4-Cyanophenyl)-2-(4-(3-carboxyphenyl)cyclohexyl)acetamide

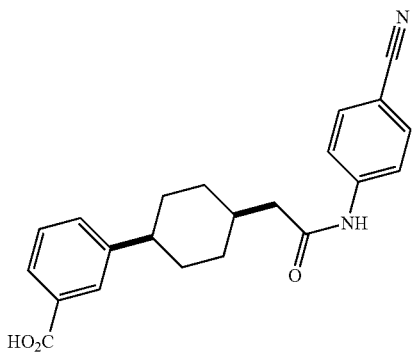

Prepared using General Procedures H, B, and G. General Procedure H employed tert-butyl 3-bromobenzoate and ethyl 2-(4-(4,4,5,5-tetramethyl-1,3,2-dioxaborolan-2-yl)cyclohex-3-en-1-yl)acetate. The product was hydrogenated using General Procedure B with 10% Pd(OH)$_2$/C as catalyst and acetic acid as solvent. General Procedure G used ethyl 2-(4-(tert-butyl 3-carboxybenzoate)cyclohexyl)acetate and 4-cyanoaniline. Purification by silica gel chromatography (0%-60% EtOAc) afforded the tert-butyl ester of the desired product as the first eluting isomer. The ester was removed by dissolving in 10:1 CH$_2$Cl$_2$:CF$_3$CO$_2$H and stirring for 15 h. The reaction was concentrated under reduced pressure and purified by silica gel chromatography (50%-100% EtOAc in hexanes) to afford the desired product as a white crystalline solid. $^1$H NMR (400 MHz, CD$_3$OD) δ 7.97 (t, J=1.7 Hz, 1H), 7.84 (dt, J=8.0, 1.7 Hz, 1H), 7.82-7.76 (m, 2H), 7.70-7.62 (m, 2H), 7.52 (d, J=7.7 Hz, 1H), 7.40 (t, J=7.7 Hz, 1H), 2.76-2.62 (m, 1H), 2.58 (d, J=7.7 Hz, 2H), 2.47-2.32 (m, 1H), 1.92-1.64 (m, 8H).

Example 107 trans-N-(4-Cyanophenyl)-2-(4-(3-carboxyphenyl)cyclohexyl)acetamide

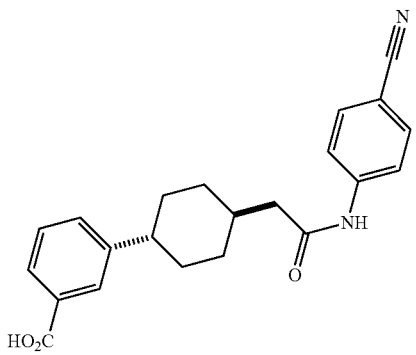

Prepared using General Procedures H, B, G and ester hydrolysis. General Procedure H employed text-butyl 3-bromobenzoate and ethyl 2-(4-(4,4,5,5-tetramethyl-1,3,2-dioxaborolan-2-yl)cyclohex-3-en-1-yl)acetate. The product was hydrogenated using General Procedure B with 10% Pd(OH)$_2$/C as catalyst and acetic acid as solvent. General Procedure G used ethyl 2-(4-(tert-butyl 3-carboxybenzoate)cyclohexyl)acetate and 4-cyanoaniline. Purification by silica gel chromatography (0%-60% EtOAc) afforded the tert-butyl ester of the desired product as the second eluting isomer. The ester was removed by dissolving in 10:1 CH$_2$Cl$_2$:CF$_3$CO$_2$H and stirring for 15 h. The reaction was concentrated under reduced pressure and purified by silica gel chromatography (50%-100% EtOAc in hexanes) to afford the desired product as a white crystalline solid. $^1$H NMR (400 MHz, CD$_3$OD) δ 7.88 (d, J=1.7 Hz, 1H), 7.83 (dt, J=7.7, 1.4 Hz, 1H), 7.81-7.77 (m, 2H), 7.71-7.64 (m, 2H), 7.46 (d, J=7.9 Hz, 1H), 7.41-7.34 (m, 1H), 2.64-2.52 (m, 1H), 2.35 (d, J=6.8 Hz, 2H), 2.01-1.88 (m, 5H), 1.65-1.50 (m, 2H), 1.34-1.20 (m, 2H).

Example 108 cis-N-(4-Chlorophenyl)-2-(4-(3-carboxyphenyl)cyclohexyl)acetamide

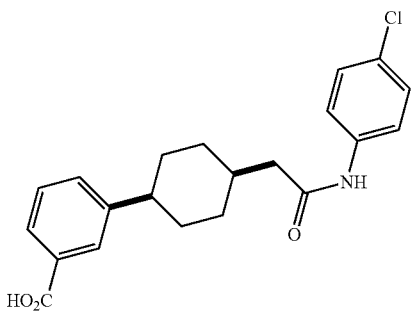

Prepared using General Procedures H, B, G and ester hydrolysis. General Procedure H employed tert-butyl 3-bromobenzoate and ethyl 2-(4-(4,4,5,5-tetramethyl-1,3,2-dioxaborolan-2-yl)cyclohex-3-en-1-yl)acetate. The product was hydrogenated using General Procedure B with 10% Pd(OH)$_2$/C as catalyst and acetic acid as solvent. General Procedure G used ethyl 2-(4-(tert-butyl 3-carboxybenzoate)cyclohexyl)acetate and 4-chloroaniline. Purification by silica gel chromatography (0%-60% EtOAc) afforded the tert-butyl ester of the desired product as the first eluting isomer. The ester was removed by dissolving in 10:1 CH$_2$Cl$_2$:CF$_3$CO$_2$H and stirring for 15 h. The reaction was concentrated under reduced pressure and purified by silica gel chromatography (50%-100% EtOAc in hexanes) to afford the desired product as a white crystalline solid. $^1$H NMR (400 MHz, CD$_3$OD) δ 7.97 (t, J=1.7 Hz, 1H), 7.84 (dt, J=7.7, 1.4 Hz, 1H), 7.61-7.54 (m, 2H), 7.54-7.48 (m, 1H), 7.39 (t, J=7.7 Hz, 1H), 7.33-7.24 (m, 2H), 2.76-2.61 (m, 1H), 2.53 (d, J=7.8 Hz, 2H), 2.39 (d, J=3.8 Hz, 1H), 1.99-1.60 (m, 8H).

Example 109 trans-N-(4-Chlorophenyl)-2-(4-(3-carboxyphenyl)cyclohexyl)acetamide

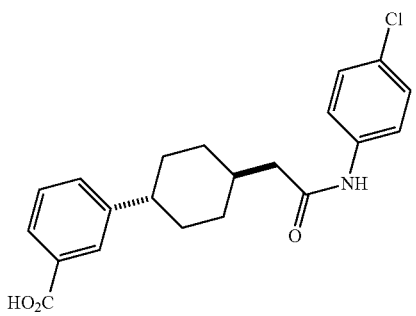

Prepared using General Procedures H, B, G and ester hydrolysis. General Procedure H employed tert-butyl 3-bromobenzoate and ethyl 2-(4-(4,4,5,5-tetramethyl-1,3,2-dioxaborolan-2-yl)cyclohex-3-en-1-yl)acetate. The product was hydrogenated using General Procedure B with 10% Pd(OH)$_2$/C as catalyst and acetic acid as solvent. General Procedure G used ethyl 2-(4-(tert-butyl 3-carboxybenzoate)cyclohexyl)acetate and 4-chloroaniline. Purification by silica gel chromatography (0%-60% EtOAc) afforded the tert-butyl ester of the desired product as the second eluting isomer. The ester was removed by dissolving in 10:1 CH$_2$Cl$_2$:CF$_3$CO$_2$H and stirring for 15 h. The reaction was concentrated under reduced pressure and purified by silica gel chromatography (50%-100% EtOAc in hexanes) to afford the desired product as a white crystalline solid. $^1$H NMR (400 MHz, CD$_3$OD) δ 7.88 (s, 1H), 7.82 (dt, J=7.6, 1.5 Hz, 1H), 7.61-7.54 (m, 2H), 7.46 (d, J=7.9 Hz, 1H), 7.37 (t, J=7.6 Hz, 1H), 7.33-7.26 (m, 2H), 2.65-2.49 (m, 1H), 2.31 (d, J=6.8 Hz, 2H), 2.00-1.87 (m, 5H), 1.66-1.50 (m, 2H), 1.36-1.21 (m, 2H).

Example 110 cis-N-(4-Fluorophenyl)-2-(4-(3-carboxyphenyl)cyclohexyl)acetamide

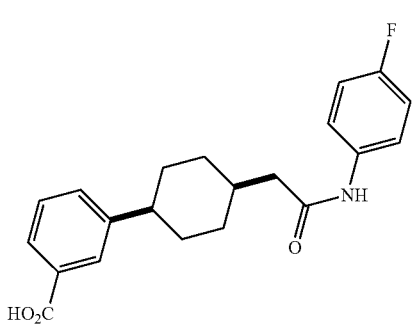

Prepared using General Procedures H, B, G and ester hydrolysis. General Procedure H employed tert-butyl 3-bromobenzoate and ethyl 2-(4-(4,4,5,5-tetramethyl-1,3,2-dioxaborolan-2-yl)cyclohex-3-en-1-yl)acetate. The product was hydrogenated using General Procedure B with 10% Pd(OH)$_2$/C as catalyst and acetic acid as solvent. General Procedure G used ethyl 2-(4-(tert-butyl 3-carboxybenzoate)cyclohexyl)acetate and 4-fluoroaniline. Purification by silica gel chromatography (0%-60% EtOAc) afforded the tert-butyl ester of the desired product as the first eluting isomer. The ester was removed by dissolving in 10:1 CH$_2$Cl$_2$:CF$_3$CO$_2$H and stirring for 15 h. The reaction was concentrated under reduced pressure and purified by silica gel chromatography (50%-100% EtOAc in hexanes) to afford the desired product as a white crystalline solid. $^1$H NMR (400 MHz, CD$_3$OD) δ 7.97 (t, J=1.6 Hz, 1H), 7.85 (dt, J=7.7, 1.4 Hz, 1H), 7.61-7.49 (m, 3H), 7.39 (d, J=7.7 Hz, 1H), 7.08-6.99 (m, 2H), 2.75-2.62 (m, 1H), 2.53 (d, J=7.8 Hz, 2H), 2.44-2.34 (m, 1H), 1.92-1.64 (m, 8H).

Example 111 trans-N-(4-Fluorophenyl)-2-(4-(3-carboxyphenyl)cyclohexyl)acetamide

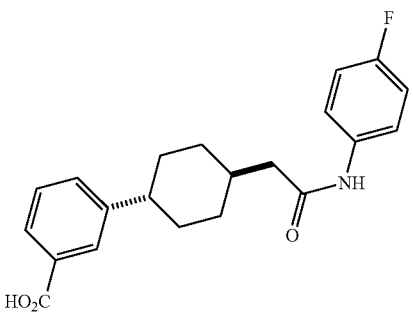

Prepared using General Procedures H, B, G and ester hydrolysis. General Procedure H employed tert-butyl 3-bromobenzoate and ethyl 2-(4-(4,4,5,5-tetramethyl-1,3,2-dioxaborolan-2-yl)cyclohex-3-en-1-yl)acetate. The product was hydrogenated using General Procedure B with 10% Pd(OH)$_2$/C as catalyst and acetic acid as solvent. General Procedure G used ethyl 2-(4-(tert-butyl 3-carboxybenzoate)cyclohexyl)acetate and 4-fluoroaniline. Purification by silica gel chromatography (0%-60% EtOAc) afforded the tert-butyl ester of the desired product as the second eluting isomer. The ester was removed by dissolving in 10:1 CH$_2$Cl$_2$:CF$_3$CO$_2$H and stirring for 15 h. The reaction was concentrated under reduced pressure and purified by silica gel chromatography (50%-100% EtOAc in hexanes) to afford the desired product as a white crystalline solid. $^1$H NMR (400 MHz, CD$_3$OD) δ 7.89 (s, 1H), 7.83 (d, J=7.7 Hz, 1H), 7.61-7.52 (m, 2H), 7.46 (d, J=7.8 Hz, 1H), 7.37 (t, J=7.7 Hz, 1H), 7.09-7.00 (m, 2H), 2.65-2.49 (m, 1H), 2.30 (d, J=6.8 Hz, 2H), 2.01-1.87 (m, 5H), 1.67-1.49 (m, 2H), 1.28 (t, J=12.7 Hz, 2H).

Example 112 cis-N-(4-Cyanophenyl)-2-(4-(3-carboxamidophenyl)cyclohexyl)acetamide

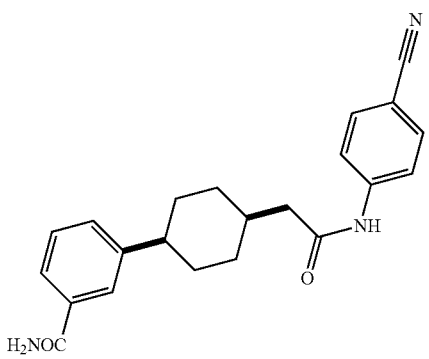

To a stirred solution of cis-N-(4-cyanophenyl)-2-(4-(3-carboxyphenyl)cyclohexyl) acetamide (Example 106) (50 mg, 0.14 mmol) in THF (0.7 mL) was treated with diisopropylethylamine (34 µL, 0.2 mmol) and ethyl chloroformate (16 µL, 0.17 mmol). The reaction was stirred for 30 min after which aqueous ammonium hydroxide (40 µL) was added and the solution was stirred for 30 minutes. Reaction mixture was concentrated under reduced pressure and purified by silica gel chromatography (50%-100% EtOAc in hexanes) to give the desired product as a white crystalline solid. $^1$H NMR (400 MHz, CD$_3$OD, Amide rotamers) δ 7.96 (t, J=1.7 Hz, 1H), 7.87-7.76 (m, 6H), 7.71-7.63 (m, 5H), 7.48 (t, J=8.0 Hz, 2H), 7.38 (td, J=7.7, 1.9 Hz, 2H), 2.76-2.63 (m, 2H), 2.57 (d, J=7.7 Hz, 4H), 2.45-2.35 (m, 2H), 1.92-1.61 (m, 16H).

Example 113 trans-N-(4-Cyanophenyl)-2-(4-(3-carboxamidophenyl)cyclohexyl)acetamide

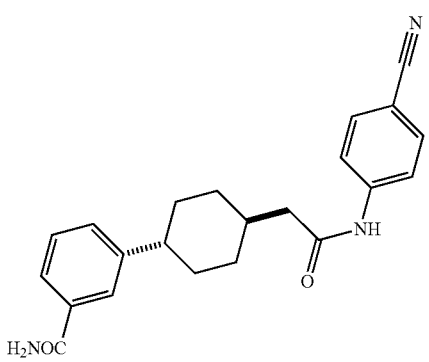

To a stirred solution of trans-N-(4-cyanophenyl)-2-(4-(3-carboxyphenyl) cyclohexyl)acetamide Example 107) (50 mg, 0.14 mmol) in THF (0.7 mL) was treated with diisopropylethylamine (34 µL, 0.2 mmol) and ethyl chloroformate (16 µL, 0.17 mmol). The reaction was stirred for 30 min after which aqueous ammonium hydroxide (40 µL) was added and the solution was stirred for 30 minutes. Reaction mixture was concentrated under reduced pressure and purified by silica gel chromatography (50%-100% EtOAc in hexanes) to give the desired product as a white crystalline solid. $^1$H NMR (400 MHz, CD$_3$OD) δ 7.88 (s, 1H), 7.85-7.73 (m, 3H), 7.71-7.63 (m, 2H), 7.49-7.31 (m, 2H), 2.58 (t, J=12.3 Hz, 1H), 2.35 (d, J=6.8 Hz, 2H), 1.94 (dd, J=12.7, 6.2 Hz, 5H), 1.58 (dd, =22.7, 12.6 Hz, 2H), 1.35-1.18 (m, 2H).

Example 114 cis-N-(4-Chlorophenyl)-2-(4-(3-carboxamidophenyl)cyclohexyl)acetamide

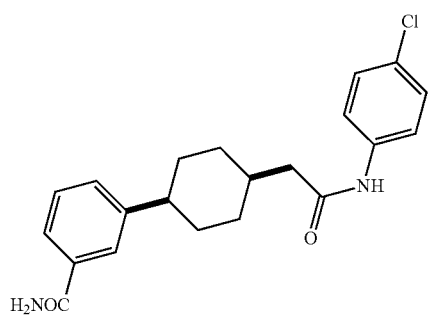

To a stirred solution of cis-N-(4-chlorophenyl)-2-(4-(3-carboxyphenyl) cyclohexyl)acetamide (Example 108) (50 mg, 0.14 mmol) in THF (0.7 mL) was treated with diisopropylethylamine (34 µL, 0.2 mmol) and ethyl chloroformate (16 µL, 0.17 mmol). The reaction was stirred for 30 min after which aqueous ammonium hydroxide (40 µL) was added and the solution was stirred for 30 minutes. Reaction mixture was concentrated under reduced pressure and purified by silica gel chromatography (50%-100% EtOAc in hexanes) to give the desired product as a white crystalline solid. $^1$H NMR (400 MHz, CD$_3$OD) δ 7.97 (t, J=1.8 Hz, 1H), 7.87-7.82 (m, 1H), 7.62-7.54 (m, 2H), 7.54-7.49 (m, 1H), 7.39 (t, J=7.7 Hz, 1H), 7.33-7.26 (m, 2H), 2.76-2.63 (m, 1H), 2.54 (d, J=7.8 Hz, 2H), 2.44-2.33 (m, 1H), 1.96-1.65 (m, 8H).

Example 115 trans-N-(4-Chlorophenyl)-2-(4-(3-carboxamidophenyl)cyclohexyl)acetamide

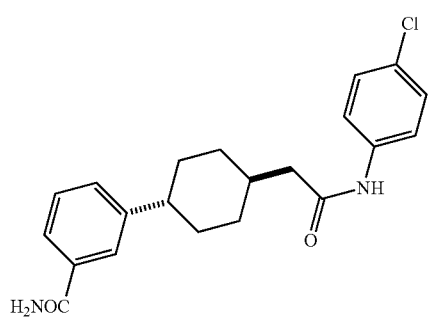

To a stirred solution of trans-N-(4-chlorophenyl)-2-(4-(3-carboxyphenyl) cyclohexyl)acetamide (Example 109) (50 mg, 0.14 mmol) in THF (0.7 mL) was treated with diisopropylethylamine (34 µL, 0.2 mmol) and ethyl chloroformate (16 µL, 0.17 mmol). The reaction was stirred for 30 min after which aqueous ammonium hydroxide (40 µL) was added and the solution was stirred for 30 minutes. Reaction mixture was concentrated under reduced pressure and purified by silica gel chromatography (50%-100% EtOAc in hexanes) to give the desired product as a white crystalline solid. $^1$H NMR (400 MHz, CD$_3$OD, amide rotamers) δ 7.88 (s, 1H), 7.82 (dt, J=7.6, 1.4 Hz, 1H), 7.75 (t, J=1.8 Hz, 1H), 7.70-7.65 (m, 1H), 7.61-7.54 (m, 4H), 7.47-7.40 (m, 2H), 7.40-7.33 (m, 2H), 7.32-7.26 (m, 4H), 2.65-2.50 (m, 2H), 2.31 (d, J=6.8 Hz, 4H), 2.02-1.85 (m, 10H), 1.68-1.49 (m, 4H), 1.34-1.19 (m, 4H).

Example 116 cis-N-(4-Fluorophenyl)-2-(4-(3-carboxamidophenyl)cyclohexyl)acetamide

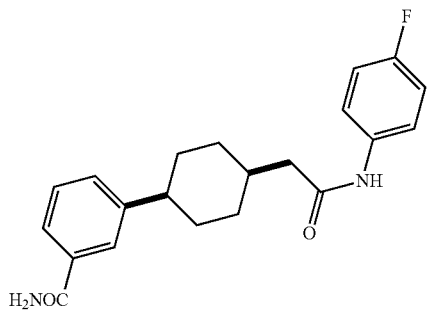

To a stirred solution of cis-N-(4-fluorophenyl)-2-(4-(3-carboxyphenyl) cyclohexyl)acetamide (Example 110) (50 mg, 0.14 mmol) in THF (0.7 mL) was treated with diisopropylethylamine (34 µL, 0.2 mmol) and ethyl chloroformate (16 µL, 0.17 mmol). The reaction was stirred for 30 min after which aqueous ammonium hydroxide (40 µL) was added and the solution was stirred for 30 minutes. Reaction mixture was concentrated under reduced pressure and purified by silica gel chromatography (50%-100% EtOAc in hexanes) to give the desired product as a white crystalline solid. $^1$H NMR (400 MHz, CD$_3$OD) δ 7.97 (t, 0.1=1.6 Hz, 1H), 7.85 (dt, 0.1=7.7, 1.4 Hz, 1H), 7.61-7.49 (m, 3H), 7.43-7.34 (m, 1H), 7.09-6.99 (m, 2H), 2.74-2.63 (m, 1H), 2.53 (d, J=7.8 Hz, 2H), 2.44-2.33 (m, 1H), 1.97-1.65 (m, 8H).

Example 117 trans-N-(4-Fluorophenyl)-2-(4-(3-carboxamidophenyl)cyclohexyl)acetamide

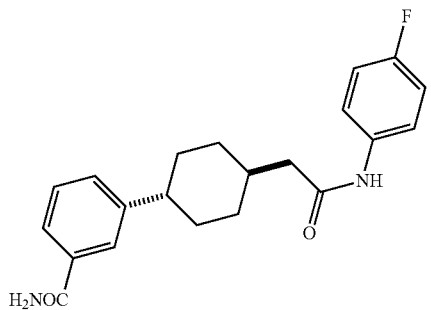

To a stirred solution of trans-N-(4-chlorophenyl)-2-(4-(3-carboxyphenyl) cyclohexyl)acetamide (Example 111) (50 mg, 0.14 mmol) in THF (0.7 mL) was treated with diisopropylethylamine (34 µL, 0.2 mmol) and ethyl chloroformate (16 µL, 0.17 mmol). The reaction was stirred for 30 min after which aqueous ammonium hydroxide (40 µL) was added and the solution was stirred for 30 minutes. Reaction mixture was concentrated under reduced pressure and purified by silica gel chromatography (50%-100% EtOAc in hexanes) to give the desired product as a white crystalline solid. $^1$H NMR (400 MHz, CD$_3$OD) δ 7.89 (s, 1H), 7.83 (d, J=7.7 Hz, 1H), 7.60-7.53 (m, 2H), 7.46 (d, J=7.8 Hz, 1H), 7.37 (t, J=7.7 Hz, 1H), 7.10-6.98 (m, 2H), 2.66-2.50 (m, 1H), 2.30 (d, J=6.8 Hz, 2H), 2.01-1.86 (m, 5H), 1.67-1.49 (m, 2H), 1.37-1.16 (m, 3H).

Example 118 cis-N-(4-Chlorophenyl)-2-(4-(2-fluorophenyl)cyclohexyl)acetamide

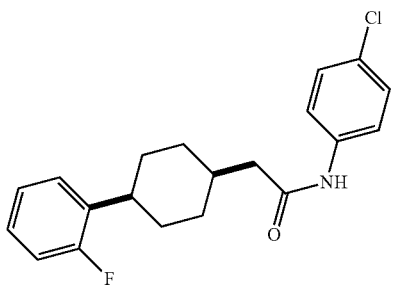

Prepared using General Procedures A, B and G. General Procedure A employed ethyl 2-(4-(((trifluoromethyl)sulfonyl)oxy)cyclohex-3-en-1-yl)acetate and (2-fluorophenyl)boronic acid. The product was hydrogenated using General Procedure B with 10% Pd/C as catalyst and acetic acid as solvent. General Procedure G used ethyl 2-(4-(2-fluorophenyl)cyclohexyl)acetate and 4-chloroaniline. Purified using silica gel chromatography (0-20% EtOAc in hexanes) to afford the desired product. $^1$H NMR (400 MHz, CDCl$_3$) δ 7.56-7.42 (m, 2H), 7.34-6.97 (m, 7H), 2.92 (s, 1H), 2.56-2.47 (m, 3H), 1.89-1.62 (m, 8H). m/z 346.2 (M+H)$^+$.

Example 119 cis-N-(4-Fluorophenyl)-2-(4-(2-fluorophenyl)cyclohexyl)acetamide

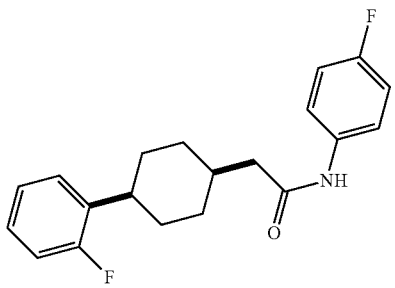

Prepared using General Procedures A, B and G. General Procedure A employed ethyl 2-(4-(((trifluoromethyl)sulfonyl)oxy)cyclohex-3-en-1-yl)acetate and (2-fluorophenyl) boronic acid. The product was hydrogenated using General Procedure B with 10% Pd/C as catalyst and acetic acid as solvent. General Procedure G used ethyl 2-(4-(2-fluorophenyl)cyclohexyl)acetate and 4-fluoroaniline. Purified using silica gel chromatography (0-20% EtOAc in hexanes) to afford the desired product. $^1$H NMR (400 MHz, CDCl$_3$) δ 7.54-7.45 (m, 2H), 7.33-6.97 (m, 7H), 2.92 (t, J=7.3 Hz, 1H), 2.55-2.30 (m, 3H), 1.97-1.60 (m, 8H). m/z 330.2 (M+H)$^+$.

Example 120 cis-N-(4-Chlorophenyl)-2-(4-(3-methoxyphenyl)cyclohexyl)acetamide

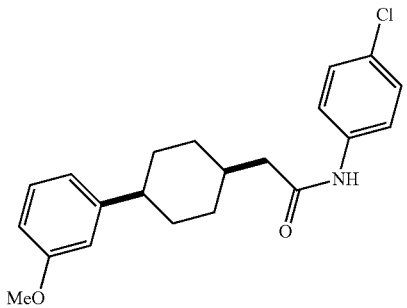

Prepared using General Procedures A, B, E and F employing 4-(3-methoxyphenylcyclohexyl) acetic acid and 4-chloroaniline. Purified using silica gel chromatography (0% to 20% EtOAc in hexanes) to afford the first eluting isomer as the desired product as a white solid. $^1$H NMR (400 MHz; CDCl$_3$): δ 7.48 (d, J=8.8 Hz, 2H), 7.31-7.24 (m, 2H), 7.22 (d, J=7.9 Hz, 1H), 7.11 (s, 1H), 6.85 (d, J=7.6 Hz, 1H), 6.80 (s, 1H), 6.74 (dd, J=8.2, 2.6 Hz, 1H), 3.81 (s, 3H), 2.65-2.57 (m, 1H), 2.50-2.35 (m, 3H), 1.83-1.63 (m, 8H).

Example 121 trans-N-(4-Chlorophenyl)-2-(4-(3-methoxyphenyl)cyclohexyl)acetamide

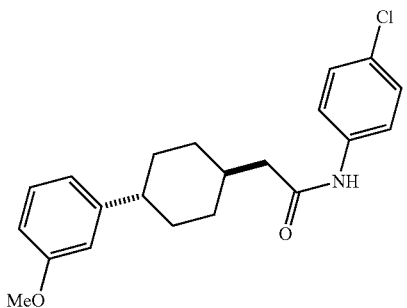

Further elution from the column in the previous example afforded the desired product as the second eluting isomer as a white solid. $^1$H NMR (400 MHz; CDCl$_3$): δ 7.49-7.47 (m, 2H), 7.29-7.26 (m, 2H), 7.21 (t, J=7.8 Hz, 1H), 7.13 (s, 14H), 6.80 (d, J=7.6 Hz, 1H), 6.75-6.72 (m, 2H), 3.79 (s, 3H), 2.46 (m, 1H), 2.27 (d, J=6.6 Hz, 2H), 1.94 (t, J=12.5 Hz, 4H), 1.76-1.64 (m, 1H), 1.55-1.48 (m, 2H), 1.25-1.11 (m, 2H).

Example 122 cis-N-(4-Chloro-3-fluorophenyl)-2-(4-(3-methoxyphenyl)cyclohexyl)acetamide

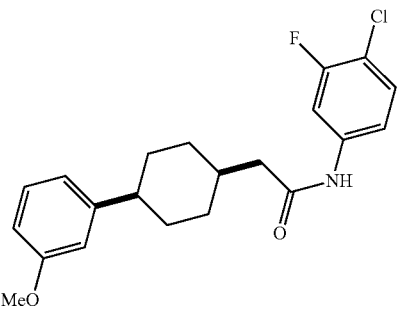

Prepared using General Procedures A, B, E and F employing 2-(4-(3-methoxyphenyl) cyclohexyl)acetic acid and 4-chloro-3-fluoroaniline. Purified using silica gel chromatography (0% to 20% EtOAc in hexanes) to afford the first eluting isomer as the desired product as a white solid. $^1$H NMR (400 MHz; CDCl$_3$): δ 7.48 (d, J=8.8 Hz, 2H), 7.29-7.26 (m, 2H), 7.23 (t, =7.9 Hz, 1H), 7.11 (s, 1H), 6.85 (d, =7.6 Hz, 1H), 6.80 (s, 1H), 6.74 (dd, J=8.2, 2.6 Hz, 1H), 3.81 (s, 3H), 2.64-2.59 (m, 1H), 2.45-2.38 (m, 3H), 1.78-1.66 (m, 8H).

Example 123 trans-N-(4-Chloro-3-fluorophenyl)-2-(4-(3-methoxyphenyl)cyclohexyl)acetamide

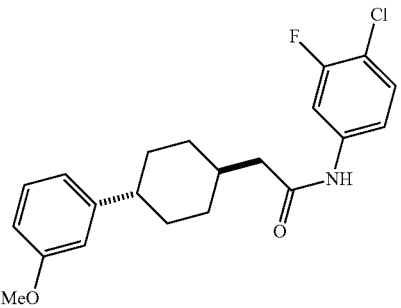

Further elution from the column in the previous example afforded the desired product as the second eluting isomer as a white solid. $^1$H NMR (400 MHz; CDCl$_3$): δ 7.65 (dd, J=11.0, 2.3 Hz, 1H), 7.38-7.28 (m, 2H), 7.21 (t, J=7.7 Hz, 1H), 7.12 (dd, J=9.9, 1.2 Hz, 1H), 6.79 (d, J=7.6 Hz, 1H), 6.7-6.69 (m, 2H), 3.79 (s, 3H), 2.45 (tt, J=12.0, 3.2 Hz, 1H), 2.28 (d, J=6.6 Hz, 2H), 2.0-1.87 (m, 5H), 1.59-1.43 (m, 2H), 1.32-1.07 (m, 2H).

Example 124 cis-N-(4-Cyanophenyl)-2-(4-(3-methoxyphenyl)cyclohexyl)acetamide

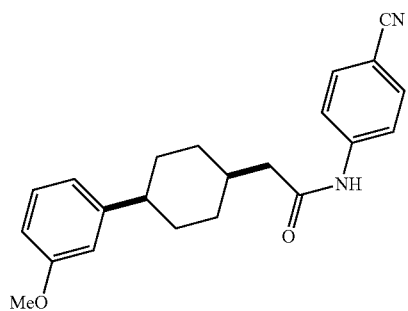

Prepared using General Procedures A, B, E and F employing 2-(4-(3-methoxyphenyl) cyclohexyl)acetic acid and 4-cyanoaniline. Purified using silica gel chromatography (0% to 20% EtOAc in hexanes) to afford the desired product as a white solid. $^1$H NMR (400 MHz; CDCl$_3$): δ 7.71-7.64 (m, 2H), 7.65-7.55 (m, 2H), 7.22 (t, =7.9 Hz, 1H), 6.84 (d, J=7.7 Hz, 1H), 6.81-6.77 (m, 1H), 6.74 (dd, J=8.1, 2.6 Hz, 1H), 3.81 (s, 3H), 2.63-2.61 (m, 1H), 2.49-2.37 (m, 3H), 1.80-1.55 (m, 8H).

Example 125 cis-N-(4-Fluorophenyl)-2-(4-(3-methoxyphenyl)cyclohexyl)acetamide

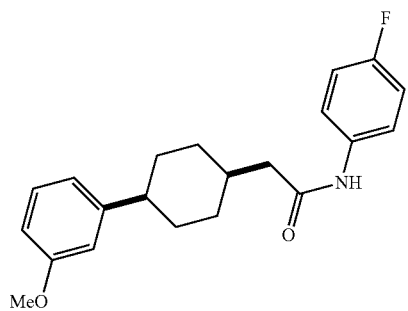

Prepared using General Procedures A, B, E and F employing 2-(4-(3-methoxyphenyl) cyclohexyl)acetic acid and 4-fluoroaniline. Purified using silica gel chromatography (0% to 20% EtOAc in hexanes) to afford the first eluting isomer as the desired product as a white solid. $^1$H NMR (400 MHz; CDCl$_3$): δ 7.56-7.38 (m, 2H), 7.23 (t, J=7.9 Hz, 1H), 7.16 (s, 1H), 7.01 (t, J=8.7 Hz, 2H), 6.85 (d, J=7.6 Hz, 1H), 6.80 (s, 1H), 6.74 (dd, J=8.1, 2.4 Hz, 1H), 3.81 (s, 3H), 2.62 (t, J=8.7 Hz, 1H), 2.50-2.36 (m, 3H), 1.82-1.63 (m, 8H).

Example 126 trans-N-(4-Fluorophenyl)-2-(4-(3-methoxyphenyl)cyclohexyl)acetamide

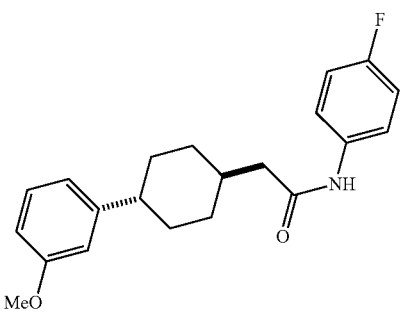

Further elution from the column in the previous example afforded the desired product as the second eluting isomer as a white solid. $^1$H NMR (400 MHz; CDCl$_3$): δ 7.54-7.43 (m, 2H), 7.21 (t, J=7.8 Hz, 1H), 7.18 (s, 1H), 7.10-6.93 (m, 2H), 6.80 (d, J=7.9 Hz, 1H), 6.76-6.70 (m, 2H), 3.79 (s, 3H), 2.46 (tt, J=12.0, 3.1 Hz, 1H), 2.27 (d, J=6.7 Hz, 2H), 1.94 (t, J=13.3 Hz, 5H), 1.59-1.51 (m, 2H), 1.21-1.15 (m, 2H).

Example 127 cis-N-(4-Chlorophenyl)-2-(4-(2-methoxyphenyl)cyclohexyl)acetamide

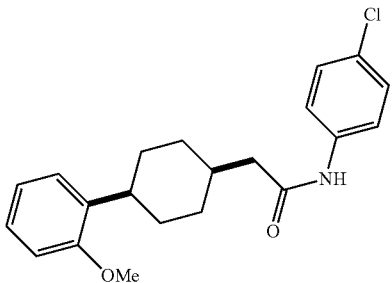

Prepared using General Procedures A, B, E and F employing 2-(4-(2-methoxyphenyl) cyclohexyl)acetic acid and 4-chloroaniline. Purified using silica gel chromatography (0% to 20% EtOAc in hexanes) to afford the first eluting isomer as the desired product as a white solid. $^1$H NMR (400 MHz; CDCl$_3$): δ 7.55-7.46 (m, 2H), 7.29-7.26 (m, 2H), 7.23-7.07 (m, 3H), 6.95-6.89 (m, 1H), 6.87-6.84 (m, 1H), 3.82 (s, 3H), 3.03-2.97 (m, 1H), 2.53-2.40 (m, 3H), 1.82-1.55 (m, 8H).

Example 128 trans-N-(4-Chlorophenyl)-2-(4-(2-methoxyphenyl)cyclohexyl)acetamide

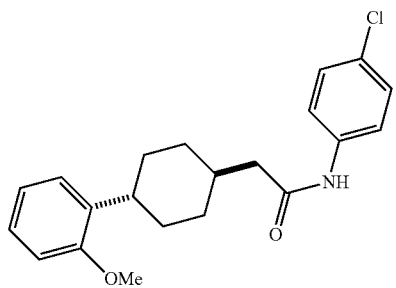

Further elution from the column in the previous example afforded the desired product as the second eluting isomer as a white solid. $^1$H NMR (400 MHz; CDCl$_3$): δ 7.49 (dd, J=9.1, 2.4 Hz, 2H), 7.31-7.23 (m, 3H), 7.19-7.12 (m, 2H), 6.95-6.83 (m, 2H), 3.81 (s, 3H), 2.92 (tt, J=12.1, 3.2 Hz, 1H), 2.27 (d, J=6.8 Hz, 2H), 2.00-1.83 (m, 4H), 1.79-1.38 (m, 5H).

Example 129 cis-N-(4-Cyanophenyl)-2-(4-(2-methoxyphenyl)cyclohexyl)acetamide

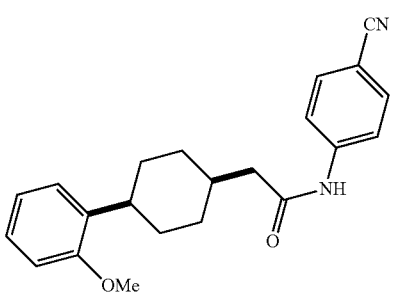

Prepared using General Procedures A, B, E and F employing 2-(4-(2-methoxyphenyl) cyclohexyl)acetic acid and 4-cyanoaniline. Purified using silica gel chromatography (0% to 20% EtOAc in hexanes) to afford the first eluting isomer as the desired product as a white solid. $^1$H NMR (400 MHz; CDCl$_3$): δ 7.77-7.64 (m, 2H), 7.63-7.57 (m, 2H), 7.39 (s, 1H), 7.19 (ddd, J=9.7, 8.4, 1.6 Hz, 2H), 6.92 (dd, J=7.5, 6.5 Hz, 1H), 6.87-6.83 (m, 1H), 3.82 (s, 3H), 3.00 (t, J=11.3 Hz, 1H), 2.55 (d, J=7.7 Hz, 2H), 2.49-2.44 (m, 1H), 1.87-1.54 (m, 8H).

Example 130 cis-N-(4-Cyanophenyl)-2-(4-(2-methoxyphenyl)cyclohexyl)acetamide

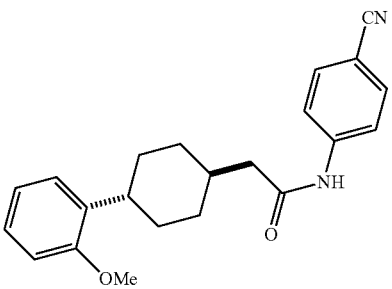

Further elution from the column in the previous example afforded the desired product as the second eluting isomer as a white solid. $^1$H NMR (400 MHz; CDCl$_3$): δ 7.49 (dd, J=9.1, 2.4 Hz, 2H), 7.31-7.23 (m, 3H), 7.15 (dd, J=6.2, 1.6 Hz, 2H), 6.92 (td, J=7.5, 1.1 Hz, 1H), 6.87-6.81 (m, 1H), 3.81 (s, 3H), 2.92 (tt, J=12.1, 3.2 Hz, 1H), 2.27 (d, J=6.8 Hz, 2H), 2.00-1.81 (m, 4H), 1.81-1.38 (m, 5H).

Example 131 cis-N-(4-Fluorophenyl)-2-(4-(2-methoxyphenyl)cyclohexyl)acetamide

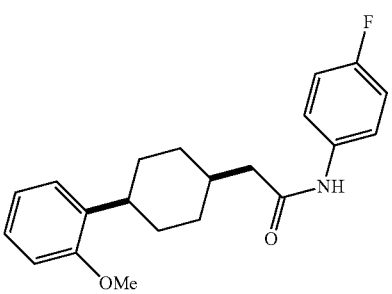

Prepared using General Procedures A, B, E and F employing 2-(4-(2-methoxyphenyl) cyclohexyl)acetic acid and 4-fluoroaniline. Purified using silica gel chromatography (0% to 20% EtOAc in hexanes) to afford the first eluting isomer as the desired product as a white solid. $^1$H NMR (400 MHz; CD$_3$OD): δ 7.62-7.53 (m, 2H), 7.25 (d, J=7.8 Hz, 1H), 7.16-7.10 (m, 1H), 7.10-6.98 (m, 2H), 6.90-6.87 (m, 2H), 3.81 (s, 3H), 2.99-2.96 (m, 1H), 2.54 (d, J=7.8 Hz, 2H), 2.42-2.36 (m, 1H), 1.79-1.58 (m, 8H).

Example 132 trans-N-(4-Fluorophenyl)-2-(4-(2-methoxyphenyl)cyclohexyl)acetamide

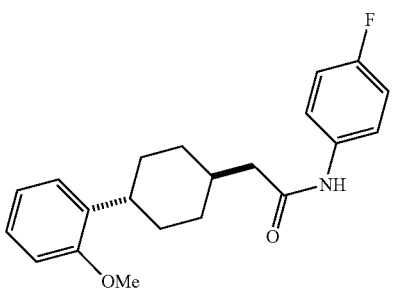

Further elution from the column in the previous example afforded the desired product as the second eluting isomer as a white solid. $^1$H NMR (400 MHz; CD$_3$OD): δ 7.55 (ddd, J=9.2, 4.8, 2.3 Hz, 2H), 7.18-7.08 (m, 2H), 7.08-6.97 (m, 2H), 6.93-6.80 (m, 2H), 3.80 (s, 3H), 2.94 (ddd, J=12.2, 7.5, 3.2 Hz, 1H), 2.28 (d, J=6.8 Hz, 2H), 1.99-1.96 (m, 1H), 1.95-1.56 (m, 6H), 1.49 (dt, J=14.5, 11.2 Hz, 2H).

Example 133 cis-N-(4-Chlorophenyl)-2-((1,4)-4-(thiazol-5-yl)cyclohexyl)acetamide

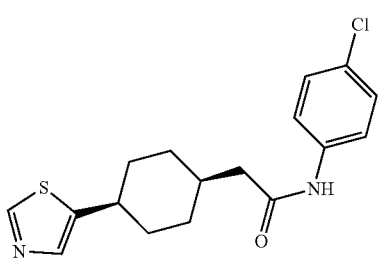 [SMILES: O=C(C[C@H]1CC[C@@H](c2cncs2)CC1)Nc1ccc(Cl)cc1]

Preparation 133A: Ethyl 2-(4-(thiazol-2-yl)cyclohexyl)acetate

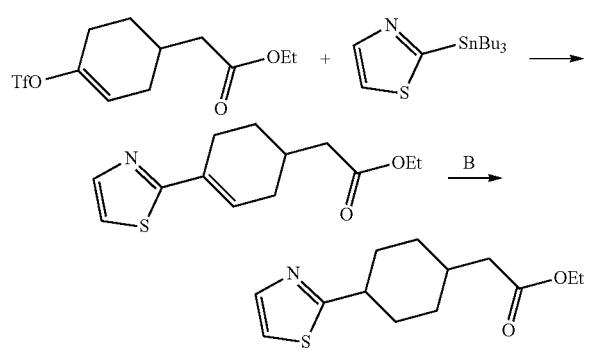

To a solution of ethyl 2-(4-(((trifluoromethyl)sulfonyl)oxy)cyclohex-3-en-1-yl)acetate (316 mg, 1.0 mmol), 2-(tributylstannyl)thiazole (486 mg, 1.3 mmol), LiCl (64 mg, 1.5 mmol) and CuI (38 mg, 0.2 mmol) in 1,4-dioxane was added Pd(PPh$_3$)$_4$ (110 mg, 0.1 mmol). The reaction mixture was heated to 100° C. for 16 h, upon which the reaction mixture was concentrated. The resulting solid was diluted with EtOAc (25 mL) and water (25 mL) and the layers were separated. The aqueous layer was extracted with EtOAc (3×25 mL). The combined organic extracts were dried over anhydrous MgSO$_4$, filtered, and concentrated under reduced pressure. The crude reaction mixture was purified employing silica gel chromatography (0% to 20% EtOAc in hexanes) to afford the desired product as a yellow oil (232 mg, 92%). Ethyl 2-(4-(thiazol-2-yl)cyclohex-3-en-1-yl)acetate (125 mg, 0.5 mmol) was hydrogenated with General Procedure B employing Pd(OH)$_2$ (13 mg, 10 wt. % Pd) in AcOH (1.0 mL) and purified employing silica gel chromatography (5% to 25% EtOAc in hexanes) to afford the desired cis and trans product mixture as a yellow oil.

Preparation 133B: Ethyl 2-(4-(thiazol-5-yl)cyclohexyl)acetate

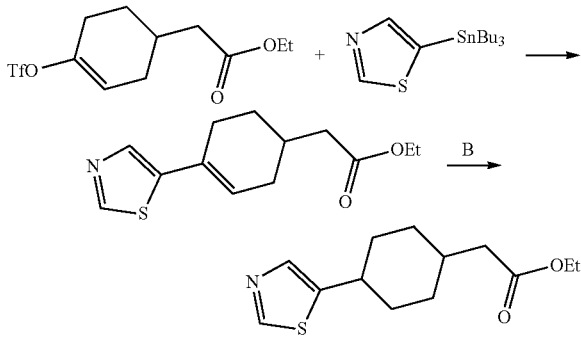

To a solution of Preparation 133A (316 mg, 1.0 mmol), 4-(tributylstannyl)thiazole (486 mg, 1.3 mmol), LiCl (64 mg, 1.5 mmol) and CuI (38 mg, 0.2 mmol) in 1,4-dioxane was added Pd(PPh$_3$)$_4$ (110 mg, 0.1 mmol). The reaction mixture was heated to 100° C. for 16 h, upon which the reaction mixture was concentrated. The resulting solid was diluted with EtOAc (25 mL) and water (25 mL) and the layers were separated. The aqueous layer was extracted with EtOAc (3×25 mL). The combined organic extracts were dried over anhydrous MgSO$_4$, filtered, and concentrated under reduced pressure. The crude reaction mixture was purified employing silica gel chromatography (0% to 20% EtOAc in hexanes) to afford the desired product as a yellow oil. Ethyl 2-(4-(thiazol-5-yl)cyclohex-3-en-1-yl)acetate (125 mg, 0.5 mmol) was hydrogenated with General Procedure B employing Pd(OH)$_2$ (13 mg, 10 wt. % Pd) in AcOH (1.0 mL) and purified employing silica gel chromatography (5% to 25% EtOAc in hexanes) to afford Preparation 133B as a mixture of cis and trans isomers as a yellow oil.

Example 133: cis-N-(4-Chlorophenyl)-2-((1,4)-4-(thiazol-5-yl)cyclohexyl)acetamide Prepared with General Procedure G employing ethyl 2-(4-(thiazol-5-yl)cyclohexyl)acetate (25 mg, 0.1 mmol), 4-chloroaniline (26 mg, 0.2 mmol), $^i$PrMgCl (100 µL, 0.4 mmol) in THF (1.0 mL). Purified using silica gel chromatography (40% EtOAc in hexanes) to afford the desired product as a white solid. $^1$H NMR (400 MHz; CDCl$_3$): δ

8.77 (d, J=1.9 Hz, 1H), 7.47 (d, J=8.8 Hz, 2H), 7.29-7.25 (m, 2H), 7.00-6.98 (m, 1H), 3.00 (tt, J=8.1, 4.1 Hz, 1H), 2.38 (d, J=7.1 Hz, 2H), 2.34-2.29 (m, 1H), 2.03-1.92 (m, 2H), 1.92-1.83 (m, 2H), 1.77-1.69 (m, 2H), 1.58-1.50 (m, 2H). m/z 335.1 (M+H)+.

Example 136 trans-N-(4-Chlorophenyl)-2-((1,4)-4-(thiazol-5-yl)cyclohexyl)acetamide

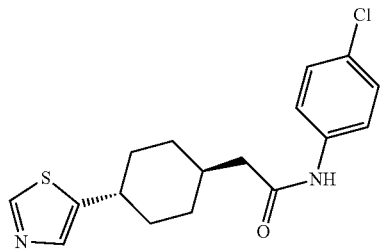 [SMILES: O=C(C[C@H]1CC[C@H](c2cncs2)CC1)Nc1ccc(Cl)cc1]

Further elution from the column in the previous example afforded the desired product as a white solid and the second eluting isomer. m/z 335.1 (M+H)+.

Example 137 cis-N-(4-Chlorophenyl)-2-(4-(2-thiazole)cyclohexyl)acetamide

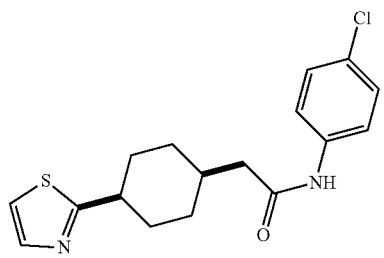 [SMILES: O=C(C[C@H]1CC[C@@H](c2nccs2)CC1)Nc1ccc(Cl)cc1]

Prepared using General Procedures A, B and G using ethyl 2-(4-(2-thiazole)cyclohexyl) acetate and 4-chloroaniline. Purification by silica gel chromatography (0%-80% EtOAc in hexanes) afforded the desired product as the first eluting isomer. m/z 335.1 (M+H)+.

Example 138 trans-N-(4-Chlorophenyl)-2-(4-(2-thiazole)cyclohexyl)acetamide

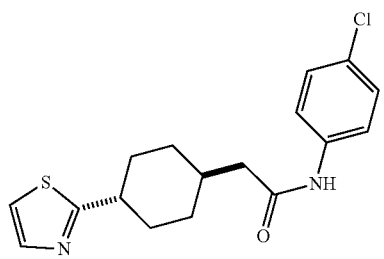 [SMILES: O=C(C[C@H]1CC[C@H](c2nccs2)CC1)Nc1ccc(Cl)cc1]

Further elution of the column in the previous example afforded the desired product as the second eluting isomer. $^1$H NMR (400 MHz, CDCl$_3$) δ 7.67 (d, J=3.3 Hz, 1H), 7.47 (d, J=8.8 Hz, 2H), 7.32-7.26 (m, 2H), 7.19 (d, J=3.3 Hz, 1H), 7.11 (s, 1H), 3.04-2.92 (m, 1H), 2.28 (d, J=6.6 Hz, 2H), 2.21 (d, J=12.9 Hz, 2H), 2.05-1.90 (m, 3H), 1.70-1.57 (m, 2H), 1.30-1.13 (m, 2H), m/z 335.1 (M+H)+.

Example 139 cis-N-(3-Fluoro-4-chlorophenyl)-2-(4-(2-thiazole)cyclohexyl)acetamide

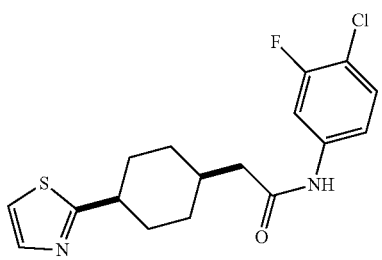 [SMILES: O=C(C[C@H]1CC[C@@H](c2nccs2)CC1)Nc1ccc(Cl)c(F)c1]

Prepared using General Procedure G using ethyl 2-(4-(2-thiazole)cyclohexyl) acetate and 3-fluoro-4-chloroaniline. Purification by silica gel chromatography (0%-80% EtOAc in hexanes) afforded the desired product as the first eluting isomer. m/z 353.1 (M+H)+.

Example 140 trans-N-(3-Fluoro-4-chlorophenyl)-2-(4-(2-thiazole)cyclohexyl)acetamide

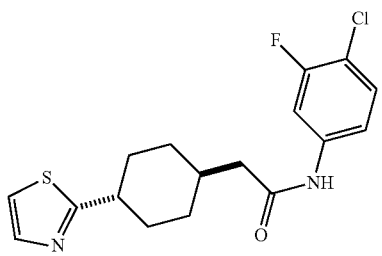

Further elution of the column in the previous example afforded the desired product as the second eluting isomer. $^1$H NMR (400 MHz, CDCl$_3$) δ 7.68 (d, J=3.3 Hz, 1H), 7.65 (dd, J=11.0, 2.4 Hz, 1H), 7.31 (t, J=8.4 Hz, 1H), 7.20 (d, J=3.3 Hz, 1H), 7.17 (s, 1H), 7.13-7.07 (m, 1H), 3.06-2.93 (m, 1H), 2.29 (d, J=6.7 Hz, 2H), 2.22 (d, J=12.5 Hz, 2H), 2.05-1.93 (m, 3H), 1.70-1.58 (m, 2H), 1.31-1.15 (m, 2H). LC/MS 2.92 min, m/z 353.1 (M+H)+.

Example 141

N-(4-Fluorophenyl)-2-(4-(3-pyridyl)cyclohexyl)acetamide

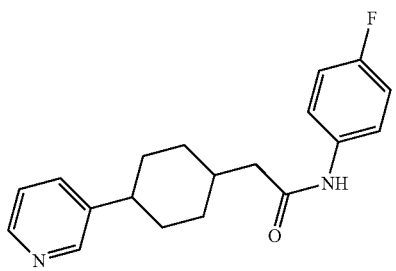 [SMILES: O=C(CC1CCC(c2cccnc2)CC1)Nc1ccc(F)cc1]

Prepared using General Procedures H, B and G. General Procedure H employed 3-bromopyridine and ethyl 2-(4-(4,4,5,5-tetramethyl-1,3,2-dioxaborolan-2-yl)cyclohex-3-en-1-yl)acetate. The product was hydrogenated using General Procedure B with 10% Degussa Pd/C as catalyst and acetic acid as solvent. General Procedure G used ethyl 2-(4-(3-pyridyl)cyclohexyl)acetate and 4-fluoroaniline and the reaction was quenched with saturated aqueous NaHCO$_3$. Purification by silica gel chromatography (20%-100% EtOAc in hexanes) afforded the desired product as a mixture of diastereomers. $^1$H NMR (400 MHz, CDCl$_3$, 1:1 mixture of diastereomers) δ 8.52 (s, 1H), 8.49-8.40 (m, 3H), 7.60-7.42 (m, 6H), 7.25-7.17 (m, 3H), 7.13 (s, 1H), 7.02 (td, J=8.6, 2.0 Hz, 4H), 2.76-2.63 (m, 1H), 2.59-2.47 (m, 1H), 2.47-2.40 (m, 3H), 2.29 (d, J=6.7 Hz, 2H), 2.07-1.87 (m, 5H), 1.85-1.64 (m, 8H), 1.61-1.46 (m, 2H), 1.32-1.14 (m, 2H).

Example 142

N-(4-Chlorophenyl)-2-(4-(3-pyridyl)cyclohexyl)acetamide

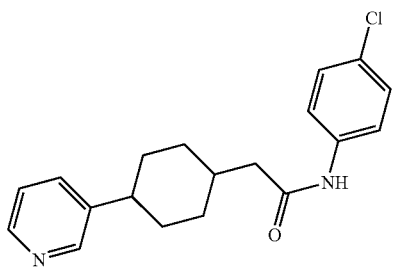 [SMILES: O=C(CC1CCC(c2cccnc2)CC1)Nc1ccc(Cl)cc1]

Prepared using General Procedures H, B and G. General Procedure H employed 3-bromopyridine and ethyl 2-(4-(4,4,5,5-tetramethyl-1,3,2-dioxaborolan-2-yl)cyclohex-3-en-1-yl)acetate. The product was hydrogenated using General Procedure B with 10% Degussa Pd/C as catalyst and acetic acid as solvent. General Procedure G used ethyl 2-(4-(3-pyridyl)cyclohexyl)acetate and 4-chloroaniline and the reaction was quenched with saturated aqueous NaHCO$_3$. Purification by silica gel chromatography (20%-100% EtOAc in hexanes) afforded the desired product as a mixture of diastereomers. $^1$H NMR (400 MHz, CDCl$_3$, 5:2 mixture of diastereomers) δ 8.52 (s, 5H), 8.49-8.40 (m, 9H), 7.59-7.42 (m, 21H), 7.35-7.18 (m, 21H), 2.69 (s, 5H), 2.56-2.48 (m, 2H), 2.44 (s, 15H), 2.29 (d, J=6.5 Hz, 4H), 2.05-1.87 (m, 10H), 1.85-1.62 (m, 40H), 1.57-1.46 (m, 4H), 1.31-1.16 (m, 4H).

Example 143

N-(4-Chlorophenyl)-2-(4-(3-pyridyl)cyclohexyl)acetamide

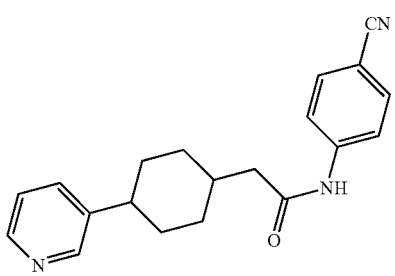 [SMILES: N#Cc1ccc(NC(=O)CC2CCC(c3cccnc3)CC2)cc1]

Prepared using General Procedures H, B and G. General Procedure H employed 3-bromopyridine and ethyl 2-(4-(4,4,5,5-tetramethyl-1,3,2-dioxaborolan-2-yl)cyclohex-3-en-1-yl)acetate. The product was hydrogenated using General Procedure B with 10% Degussa Pd/C as catalyst and acetic acid as solvent. General Procedure G used ethyl 2-(4-(3-pyridyl)cyclohexyl)acetate and 4-chloroaniline and the reaction was quenched with saturated aqueous NaHCO$_3$. Purification by silica gel chromatography (20%-100% EtOAc in hexanes) afforded the desired product as a mixture of diastereomers. $^1$H NMR (400 MHz, CDCl$_3$, 2:1 mixture of diastereomers) δ 8.51 (s, 2H), 8.49-8.41 (m, 4H), 7.74-7.64 (m, 6H), 7.64-7.57 (m, 6H), 7.57-7.48 (m, 3H), 7.40 (s, 1H), 7.25-7.19 (m, 3H), 2.69 (s, 2H), 2.60-2.38 (m, 7H), 2.33 (d, J=6.5 Hz, 2H), 1.98 (dd, J=33.9, 17.2 Hz, 5H), 1.86-1.45 (m, 18H), 1.33-1.14 (m, 2H).

Example 144

4-(1H-Pyrazol-1-yl)cyclohexan-1-one

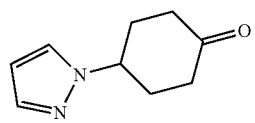 [SMILES: O=C1CCC(n2cccn2)CC1]

In an oven-dried vial, NaH (192 mg) was dissolved in dimethylformamide (6.4 mL) and cooled to 0° C. To this solution, pyrazole (436 mg) was added and the reaction stirred for 10 min. After this time 4,4-ethylenedioxycyclohexyl toluene-p-sulfonate (1 g) (*J. Chem. Soc., Perkin Trans.* 1, 2251-2255 (2002)) was added, the vial was capped and heated to 60° C. for 3 h. The reaction was quenched by the addition of H$_2$O. The aqueous layer was extracted with EtOAc (3×20 mL) and dried with anhydrous Na$_2$SO$_4$ and concentrated under reduced pressure. The crude residue was taken up in MeOH (20 mL) and 1 M HCl (10 mL) and stirred for 16 h. The reaction mixture was basified with 2.5 M NaOH to pH 14 and extracted with EtOAc (3×30 mL). The organic extracts were dried with anhydrous Na$_2$SO$_4$ and concentrated under reduced pressure to afford the desired product contaminated with pyrazole. $^1$H NMR (400 MHz, CDCl$_3$) δ 7.50 (d, J=1.7 Hz, 1H), 7.42 (t, 0.1=3.3 Hz, 1H), 6.24 (t, 0.1=2.1 Hz, 1H), 4.67-4.51 (m, 1H), 2.59-2.15 (m, 8H).

Example 145 cis-2-(4-(1H-Pyrazol-1-yl)cyclohexyl-N-(4-fluorophenyl)acetamide

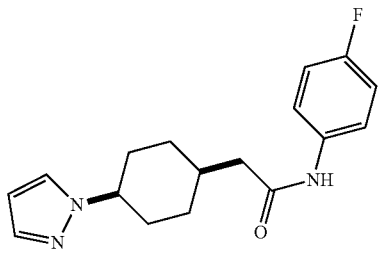

Prepared by General Procedures C, D and G. 4-(1H-Pyrazol-1-yl)cyclohexan-1-one was olefinated then reduced with General Procedures C and D without modification. The desired product was formed by General Procedure G using ethyl 2-(4-(1H-pyrazol-1-yl)cyclohexyl)acetate and 4-fluoroaniline and the reaction was quenched with saturated aqueous NaHCO$_3$. Purification by silica gel chromatography (0%-100% EtOAc in hexanes) afforded the desired compound as the first eluting isomer. $^1$H NMR (400 MHz; CDCl$_3$): δ 7.56-7.44 (m, 4H), 7.05-6.96 (m, 2H), 6.25 (s, 1H), 4.22 (tt, J=8.3, 3.9 Hz, 1H), 2.44-2.32 (m, 3H), 2.22 (ddd, J=14.8, 11.9, 4.8 Hz, 2H), 1.99-1.86 (m, 2H), 1.82-1.55 (m, 4H).

Example 146 trans-2-(4-(1H-Pyrazol-1-yl)cyclohexyl-N-(4-fluorophenyl)acetamide

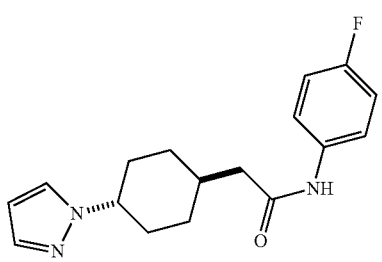

Further elution from the column in the previous example afforded the desired product as the second eluting isomer. $^1$H NMR (400 MHz; CDCl$_3$): δ 7.50 (d, J=1.8 Hz, 1H), 7.50-7.44 (m, 2H), 7.41 (d, 0.1=2.3 Hz, 1H), 7.11 (s, 1H), 7.02 (t, 0.1=8.6 Hz, 2H), 6.24 (t, J=2.0 Hz, 1H), 4.22-4.05 (m, 1H), 2.29 (d, J=6.7 Hz, 2H), 2.25-2.18 (m, 2H), 2.08-1.97 (m, 3H), 1.88-1.75 (m, 2H), 1.33-1.17 (m, 2H).

Example 147 cis-2-(4-(1H-Pyrazol-1-yl)cyclohexyl-N-(4-chlorophenyl)acetamide

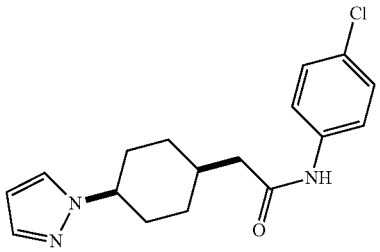

Prepared by General Procedures C, D and G. 4-(1H-Pyrazol-1-yl)cyclohexan-1-one was olefinated then reduced with General Procedures C and D without modification. The desired product was formed by General Procedure G using ethyl 2-(4-(1H-pyrazol-1-yl)cyclohexyl)acetate and 4-chloroaniline and the reaction was quenched with saturated aqueous NaHCO$_3$. Purification by silica gel chromatography (0%-100% EtOAc in hexanes) afforded the desired compound as the first eluting isomer. $^1$H NMR (400 MHz; CDCl$_3$): δ 7.52 (dd, J=9.2, 2.3 Hz, 1H), 7.47 (dd, J=7.2, 4.9 Hz, 2H), 7.37-7.26 (m, 3H), 6.25 (t, J=2.1 Hz, 1H), 4.27-4.15 (m, 1H), 2.41 (d, J=6.8 Hz, 2H), 2.36 (s, 1H), 2.21 (dd, J=12.2, 7.9 Hz, 2H), 2.02-1.88 (m, 2H), 1.81-1.68 (m, 2H), 1.67-1.55 (m, 2H).

Example 148 trans-2-(4-(1H-Pyrazol-1-yl)cyclohexyl-N-(4-chlorophenyl)acetamide

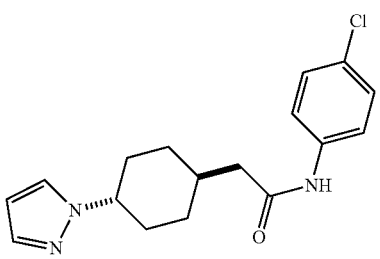

Further elution from the column in the previous example afforded the desired product as the second eluting isomer. $^1$H NMR (400 MHz; CDCl$_3$): δ 7.50 (d, J=1.7 Hz, 1H), 7.47 (d, J=8.8 Hz, 2H), 7.41 (d, J=2.3 Hz, 1H), 7.32-7.27 (m, 2H), 7.11-7.05 (s, 1H), 6.24 (t, J=2.2 Hz, 1H), 4.20-4.05 (m, 1H), 2.29 (d, J=6.4 Hz, 2H), 2.26-2.17 (m, 2H), 2.07-1.98 (m, 3H), 1.87-175 (m, 2H), 1.32-1.17 (m, 2H).

Example 149 cis-2-(4-(1H-Pyrazol-1-yl)cyclohexyl-N-(4-cyanophenyl)acetamide

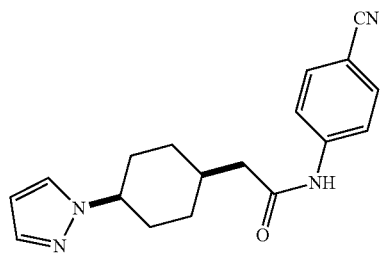

Prepared by General Procedures C, D and G. 4-(1H-Pyrazol-1-yl)cyclohexan-1-one was olefinated then reduced with General Procedures C and D without modification. The desired product was formed by General Procedure G using ethyl 2-(4-(1H-pyrazol-1-yl)cyclohexyl)acetate and 4-cyanoaniline and the reaction was quenched with saturated aqueous NaHCO$_3$. Purification by silica gel chromatography (0%-100% EtOAc in hexanes) afforded the desired compound as the first eluting isomer. $^1$H NMR (400 MHz, CDCl$_3$) δ 7.69-7.57 (m, 4H), 7.54 (d, J=1.9 Hz, 1H), 7.45 (d, J=2.2 Hz, 1H), 6.25 (t, =1.9 Hz, 1H), 4.26-4.16 (m, 1H), 2.47 (d, J=7.8 Hz, 2H), 2.43-2.29 (m, 1H), 2.28-2.16 (m, 2H), 1.99-1.87 (m, 2H), 1.79-1.68 (m, 2H), 1.68-1.52 (m, 2H).

Example 150 trans-2-(4-(1H-Pyrazol-1-yl)cyclohexyl-N-(4-cyanophenyl)acetamide

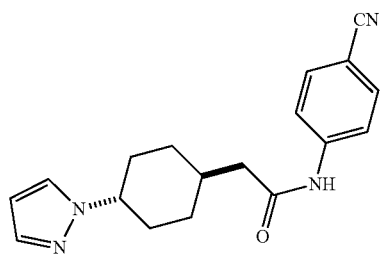

Further elution from the column in the previous example afforded the desired product as the second eluting isomer. $^1$H NMR (400 MHz; CDCl$_3$): δ 7.71-7.58 (m, 4H), 7.50 (d, J=1.8 Hz, 1H), 7.41 (d, J=2.3 Hz, 1H), 6.24 (t, J=2.0 Hz, 1H), 4.18-4.07 (m, 1H), 2.33 (d, J=6.5 Hz, 2H), 2.26-2.17 (m, 2H), 2.07-1.98 (m, 3H), 1.89-1.75 (m, 2H), 1.34-1.18 (m, 2H).

Example 151 trans-N-(4-Chlorophenyl)-2-(4-(pyridin-4-yl)cyclohexyl)acetamide

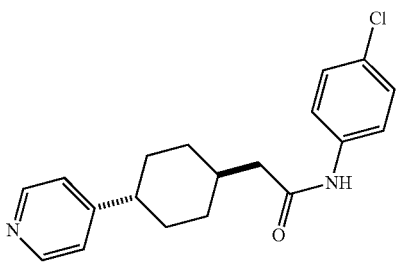

Prepared using General Procedure H, B, and G. General Procedure H employed 1 g (3.4 mmol) of the boronic ester, 661 mg (3.4 mmol) of 4-bromopyridine, 196 mg (5 mol. %) of Pd(PPh$_3$)$_4$, and 1.08 g (10.2 mmol) of sodium carbonate. General Procedure B employed 10 wt. % Pd/C and MeOH as a solvent. General Procedure G employed 100 mg ethyl 2-(4-(pyridin-4-yl)cyclohexyl)acetate (mixture of diastereomers), and 102 mg 4-chloroaniline. Purified using silica gel chromatography (0% to 50% EtOAc in diethyl ether) to afford the desired product as a trans-diastereomer as the first eluting isomer. $^1$H NMR (400 MHz; CDCl$_3$): δ 8.48-8.51 (m, 2H), 7.46-7.51 (m, 2H), 7.26-7.31 (m, 2H), 7.23 (bs, 1H), 7.10-7.14 (m, 2H), 2.49 (tt, J=12.1 Hz, J=3.3 Hz, 1H), 2.28 (d, J=6.6 Hz, 2H), 1.88-2.03 (m, 5H), 1.45-1.68 (m, 2H), 1.13-1.27 (m, 2H) ppm. m/z 329.1 (M+H)$^+$.

Example 152 cis-N-(4-Chlorophenyl)-2-(4-(pyridin-4-yl)cyclohexyl)acetamide

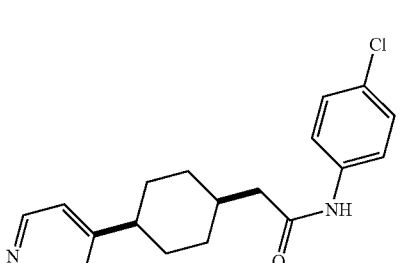

Further elution from the column afforded the desired cis-diastereomer as the second eluting isomer. $^1$H NMR (400 MHz; CDCl$_3$): δ 8.47-8.52 (m, 2H), 7.99 (bs, 1H), 7.48-7.55 (m, 2H), 7.26-7.30 (m, 2H), 7.13-7.18 (m, 2H), 2.62-2.71 (m, 1H), 2.41 (s, 2H), 1.66-1.80 (m, 7H), 1.55-1.65 (m, 2H) ppm. m/z 329.1 (M+H)$^+$.

Example 153 trans-N-(4-Fluorophenyl)-2-(4-(pyridin-4-yl)cyclohexyl)acetamide

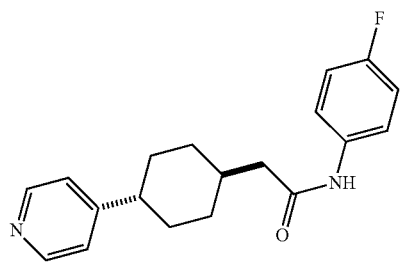

Prepared using General Procedure H, B, and G. General Procedure H employed 1 g (3.4 mmol) of the boronic ester, 661 mg (3.4 mmol) of 4-bromopyridine, 196 mg (5 mol. %) of Pd(PPh$_3$)$_4$, and 1.08 g (10.2 mmol) of sodium carbonate. General Procedure B employed 10 wt. % Pd/C and MeOH as a solvent. General Procedure G employed 100 mg ethyl 2-(4-(pyridin-4-yl)cyclohexyl)acetate (mixture of diastereomers), and 89 mg 4-fluoroaniline. Purified using silica gel chromatography (0% to 50% EtOAc in diethyl ether) to afford the desired product as a trans-diastereomer as the first eluting isomer. $^1$H NMR (400 MHz; CDCl$_3$): δ 8.47-8.51 (m, 2H), 7.45-7.51 (m, 2H), 7.21 (bs, 1H), 7.10-7.14 (m, 2H), 6.98-7.05 (m, 2H), 2.48 (tt, J=12.3 Hz, J=3.5 Hz, 1H), 2.28 (d, J=6.7 Hz, 2H), 1.88-2.04 (m, 5H), 1.45-1.58 (m, 2H), 1.14-1.27 (m, 2H) ppm. m/z 313.2 (M+H)$^+$.

Example 154 cis-N-(4-Fluorophenyl)-2-(4-(pyridin-4-yl)cyclohexyl)acetamide

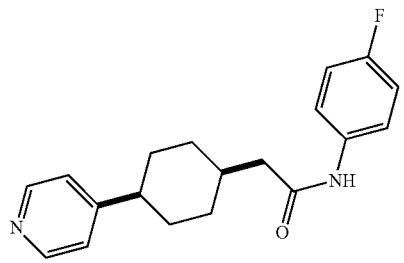

Further elution from the column afforded the desired cis-diastereomer as the second eluting isomer. $^1$H NMR (400 MHz; CDCl$_3$): δ 8.47-8.51 (m, 2H), 8.34 (bs, 1H), 7.50-7.56 (m, 2H), 7.13-7.17 (m, 2H), 7.96-7.03 (m, 2H), 2.61-2.71 (m, 1H), 2.42 (s, 2H), 1.55-1.81 (m, 9H) ppm. m/z 313.2 (M+H)$^+$.

Example 155 trans-N-(4-Cyanophenyl)-2-(4-(pyridin-4-yl)cyclohexyl)acetamide

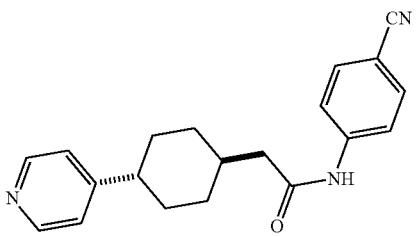

Prepared using General Procedure H, B, and G. General Procedure H employed 1 g (3.4 mmol) of the boronic ester, 661 mg (3.4 mmol) of 4-bromopyridine, 196 mg (5 mol. %) of Pd(PPh$_3$)$_4$, and 1.08 g (10.2 mmol) of sodium carbonate. General Procedure B employed 10 wt. % Pd/C and MeOH as a solvent. General Procedure G employed 100 mg ethyl 2-(4-(pyridin-4-yl)cyclohexyl)acetate (mixture of diastereomers), and 95 mg 4-cyanoaniline. Purified using silica gel chromatography (0% to 50% EtOAc in diethyl ether) to afford the desired product as a trans-diastereomer as the first eluting isomer. $^1$H NMR (400 MHz; CDCl$_3$): δ 8.48-8.51 (m, 2H), 7.66-7.72 (m, 2H), 7.58-7.63 (m, 2H), 7.11-0.715 (m, 2H), 2.48 (tt, J=12.0 Hz, J=3.2 Hz, 1H), 2.33 (d, J=6.6 Hz, 2H), 1.89-2.04 (m, 6H), 1.45-1.57 (m, 2H), 1.14-1.26 (m, 2H) ppm. m/z 320.2 (M+H)$^+$.

Example 156 cis-N-(4-Cyanoophenyl)-2-(4-(pyridin-4-yl)cyclohexyl)acetamide

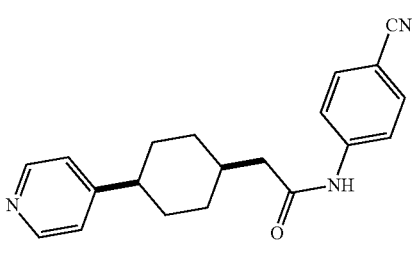

Further elution from the column afforded the desired cis-diastereomer as the second eluting isomer. $^1$H NMR (400 MHz; CDCl$_3$): δ 8.48-8.52 (m, 2H), 7.70-7.75 (m, 2H), 7.57-7.64 (m, 2H), 7.14-7.18 (m, 2H), 2.62-2.72 (m, 1H), 2.45 (s, 2H), 1.56-1.82 (m, 9H) ppm. m/z 320.2 (M+H)$^+$.

Example 157 cis-2-(4-(2-Chloro-4-methoxyphenyl)cyclohexyl)-N-(4-chlorophenyl)acetamide

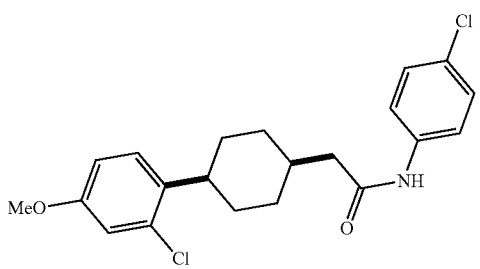

Prepared using General Procedures A, B and G. General Procedure A employed ethyl 2-(4-(((trifluoromethyl)sulfonyl)oxy)cyclohex-3-en-1-yl)acetate and (2-chloro-4-methoxyphenyl)boronic acid. The product was hydrogenated using General Procedure B with 10% Pd/C as catalyst and acetic acid as solvent. General Procedure G used ethyl 2-(4-(2-chloro-4-methoxyphenyl)cyclohexyl)acetate and 4-chloroaniline. Purified using silica gel chromatography (0-20% EtOAc in hexanes) to afford the desired product as the first eluting isomer. $^1$H NMR (400 MHz, CDCl$_3$) δ 7.59-7.44 (m, 2H), 7.34-7.25 (m, 2H), 7.25-7.12 (m, 2H), 6.93 (dd, J=5.5, 2.7 Hz, 1H), 6.81 (dd, J=8.6, 2.7 Hz, 1H), 3.80 (s, 3H), 2.97 (dd, J=23.7, 12.2 Hz, 1H), 2.57-2.47 (m, 2H), 1.78 (t, J=16.3 Hz, 5H), 1.64-1.19 (m, 4H). m/z 392.2 (M+H)$^+$.

Example 158 cis-2-(4-(2-Chloro-4-methoxyphenyl)cyclohexyl)-N-(4-fluorophenyl)acetamide

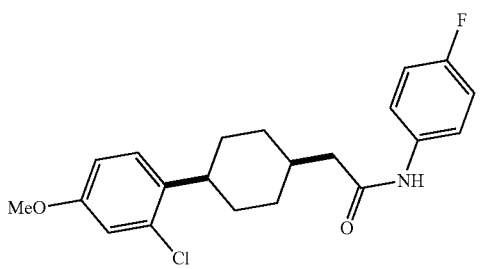

Prepared using General Procedures A, B and G. General Procedure A employed ethyl 2-(4-(((trifluoromethyl)sulfonyl)oxy)cyclohex-3-en-1-yl)acetate and (2-chloro-4-methoxyphenyl)boronic acid. The product was hydrogenated using General Procedure B with 10% Pd/C as catalyst and acetic acid as solvent. General Procedure G used ethyl 2-(4-(2-chloro-4-methoxyphenyl)cyclohexyl)acetate and 4-fluoroaniline. Purified using silica gel chromatography (0-20% EtOAc in hexanes) to afford the desired product as the first eluting isomer. $^1$H NMR (400 MHz, CDCl$_3$) δ 7.55-7.43 (m, 2H), 7.16 (dd, J=20.5, 8.6 Hz, 2H), 7.02 (dd, J=11.9, 5.5 Hz, 2H), 6.90 (dd, J=5.6, 2.7 Hz, 1H), 6.79 (dd, J=8.6, 2.6 Hz, 1H), 3.78 (s, 3H), 3.02-2.91 (m, 1H), 2.55-2.43 (m, 2H), 1.76 (dd, J=18.1, 14.8 Hz, 5H), 1.61-1.18 (m, 4H). m/z 376.2 (M+H)$^+$.

Example 159 cis-2-(4-(4-Chloro-2-fluorophenyl)cyclohexyl)-N-(4-chlorophenyl)acetamide, or trans-2-(4-(4-Chloro-2-fluorophenyl)cyclohexyl)-N-(4-chlorophenyl)acetamide (Relative Stereochemistry not Determined)

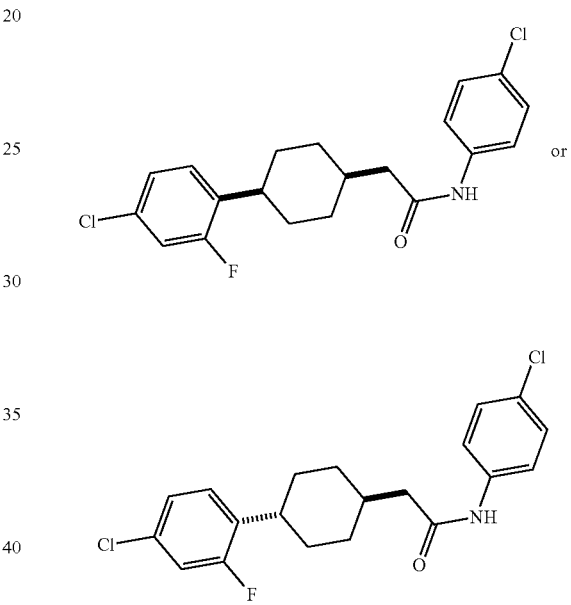

Prepared using General Procedures A, B and G. General Procedure A employed ethyl 2-(4-(((trifluoromethyl)sulfonyl)oxy)cyclohex-3-en-1-yl)acetate and (4-chloro-2-fluorophenyl)boronic acid. The product was hydrogenated using General Procedure B with 10% Pd/C as catalyst and acetic acid as solvent. General Procedure G used ethyl 2-(4-(4-chloro-2-fluorophenyl)cyclohexyl)acetate and 4-chloroaniline. Purified using silica gel chromatography (0-20% EtOAc in hexanes) to afford the desired product as the first eluting isomer. $^1$H NMR (400 MHz, CDCl$_3$) δ 7.48 (d, J=8.8 Hz, 2H), 7.39-7.24 (m, 3H), 7.18 (t, J=8.1 Hz, 1H), 7.06 (ddd, J=12.3, 9.2, 2.1 Hz, 2H), 2.85 (dt, J=14.5, 5.0 Hz, 1H), 2.54-2.27 (m, 3H), 1.69 (ddd, J=24.3, 23.5, 12.7 Hz, 8H). m/z 380.2 (M+H)$^+$.

Further elution from the column in the previous example afforded the desired product as the second eluting isomer. $^1$H NMR (400 MHz, CDCl$_3$) δ 7.55-7.36 (m, 3H), 7.36-7.17 (m, 2H), 7.17-6.99 (m, 3H), 2.78 (tt, J=12.2, 3.2 Hz, 1H), 2.28 (d, J=6.7 Hz, 2H), 2.03-1.94 (m, 2H), 1.94-1.75 (m, 3H), 1.49 (qd, J=12.9, 2.8 Hz, 2H), 1.29-1.07 (m, 2H). m/z 380.2 (M+H)$^+$.

Example 160 cis-2-(4-(4-Chloro-2-fluorophenyl)cyclohexyl)-N-(4-fluorophenyl)acetamide, or trans-2-(4-(4-Chloro-2-fluorophenyl)cyclohexyl)-N-(4-fluorophenyl)acetamide (Relative Stereochemistry not Determined)

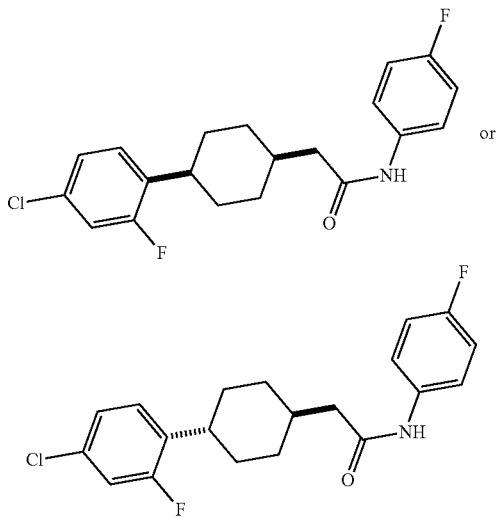

Prepared using General Procedures A, B and G. General Procedure A employed ethyl 2-(4-(((trifluoromethyl)sulfonyl)oxy)cyclohex-3-en-1-yl)acetate and (4-chloro-2-fluorophenyl)boronic acid. The product was hydrogenated using General Procedure B with 10% Pd/C as catalyst and acetic acid as solvent. General Procedure G used ethyl 2-(4-(4-chloro-2-fluorophenyl)cyclohexyl)acetate and 4-fluoroaniline. Purified using silica gel chromatography (0-20% EtOAc in hexanes) to afford the desired product as the first eluting isomer. $^1$H NMR (400 MHz, CDCl$_3$) δ 7.53-7.45 (m, 2H), 7.17 (dd, J=26.4, 18.2 Hz, 2H), 7.10-6.94 (m, 4H), 2.87 (ddd, J=14.4, 10.0, 4.3 Hz, 1H), 2.56-2.42 (m, 3H), 1.89-1.64 (m, 8H). m/z 364.2 (M+H)$^+$.

Further elution from the column in the previous example afforded the desired product as the second eluting isomer. $^1$H NMR (400 MHz, CDCl$_3$) δ 7.53-7.45 (m, 2H), 7.19-6.98 (m, 6H), 2.86-2.75 (m, 1H), 2.28 (d, =6.7 Hz, 2H), 1.99 (t, =11.5 Hz, 3H), 1.88 (d, J=12.3 Hz, 2H), 1.59-1.43 (m, 4H), 1.41-1.14 (m, 2H). m/z 364.2 (M+H)$^+$.

Example 161 cis-2-(4-(4-Chloro-3-fluorophenyl)cyclohexyl)-N-(4-chlorophenyl)acetamide

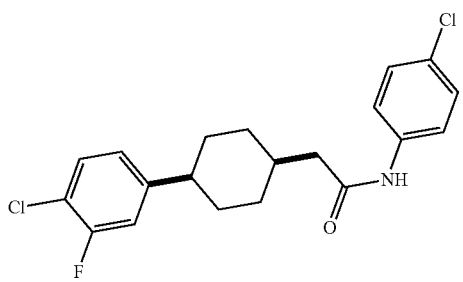

Prepared from general Procedures A, B and G. General Procedure A employed ethyl 2-(4-(((trifluoromethyl)sulfonyl)oxy) cyclohex-3-en-1-yl)acetate and (4-chloro-3-fluorophenyl)boronic acid. The product was hydrogenated using General Procedure B with 10% Pd/C as catalyst and acetic acid as solvent. General Procedure G used ethyl 2-(4-(4-chloro-3-fluorophenyl)cyclohexyl) acetate and 4-chloroaniline. Purified using silica gel chromatography (0-35% EtOAc in hexanes) to afford the desired product as the first eluting isomer. $^1$H NMR (400 MHz, CDCl$_3$) δ 7.48 (d, J=8.8 Hz, 2H), 7.37-7.23 (m, 3H), 7.18 (s, 1H), 7.04 (dd, J=10.6, 1.8 Hz, 1H), 6.98 (d, J=8.2 Hz, 1H), 2.64 (br s, 1H), 2.53-2.33 (m, 3H), 1.87-1.61 (m, 8H). m/z 380.2 (M-FH)'.

Example 162 trans-2-(4-(4-Chloro-3-fluorophenyl)cyclohexyl)-N-(4-chlorophenyl)acetamide

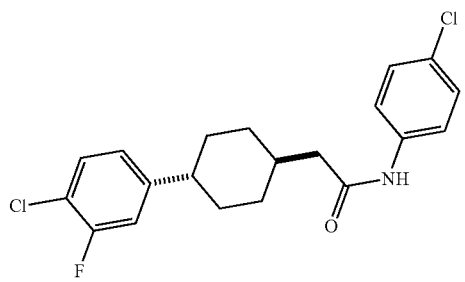

Further elution from the column in the previous example afforded the desired product as the second eluting isomer. m/z 380.2 (M+H)$^+$.

Example 163 cis-2-(4-(4-Chloro-3-fluorophenyl)cyclohexyl)-N-(4-fluorophenyl)acetamide

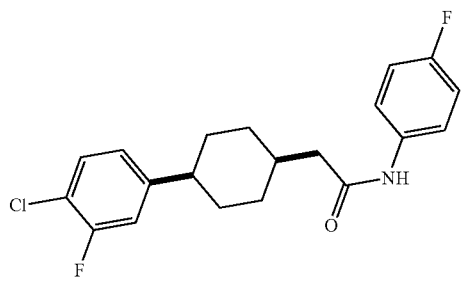

Prepared from General Procedures A, B, and G. General Procedure A employed ethyl 2-(4-(((trifluoromethyl)sulfonyl)oxy) cyclohex-3-en-1-yl)acetate and (4-chloro-3-fluorophenyl)boronic acid. The product was hydrogenated using General Procedure B with 10% Pd/C as catalyst and acetic acid as solvent. General Procedure G used ethyl 2-(4-(4-chloro-3-fluorophenyl)cyclohexyl) acetate and 4-fluoroaniline. Purified using silica gel chromatography (0-50% EtOAc in hexanes) to afford the desired product as the first eluting isomer. $^1$H NMR (400 MHz, CDCl$_3$) δ 7.58-7.42 (m, 2H), 7.36-7.26 (m, 1H), 7.20 (s, 1H), 7.07-6.95 (m, 4H), 2.65 (d, J=3.3 Hz, 1H), 2.49-2.32 (m, 3H), 1.85-1.48 (m, 8H). m/z 364.2 (M+H)+.

Example 164 trans-2-(4-(4-Chloro-3-fluorophenyl)cyclohexyl)-N-(4-fluorophenyl)acetamide

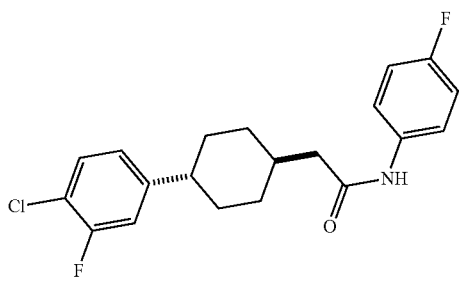

Further elution from the column in the previous example afforded the desired product as the second eluting isomer. $^1$H NMR (400 MHz, CDCl$_3$) δ 7.56-7.42 (m, 2H), 7.35-7.24 (m, 1H), 7.16 (s, 1H), 7.08-6.84 (m, 4H), 2.60-2.35 (m, 1H), 2.28 (d, J=6.6 Hz, 2H), 2.04-1.83 (m, 5H), 1.47 (tt, J=13.2, 6.5 Hz, 2H), 1.30-1.09 (m, 2H). m/z 364.2 (M+H)+.

Example 165

N-(4-Cyanophenyl)-2-(4-(2-fluoro-4-methoxyphenyl)cyclohexyl)acetamide

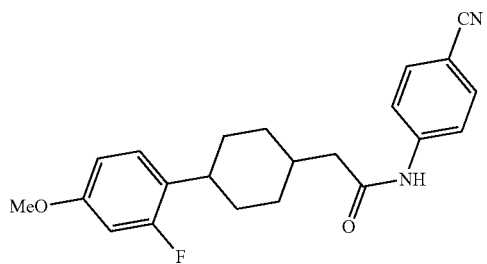 [SMILES: COc1ccc(C2CCC(CC(=O)Nc3ccc(C#N)cc3)CC2)c(F)c1]

Preparation 165A: Ethyl 2-(2'-fluoro-4'-methoxy-2,3,4,5-tetrahydro-[1,1'-biphenyl]-4-yl)acetate

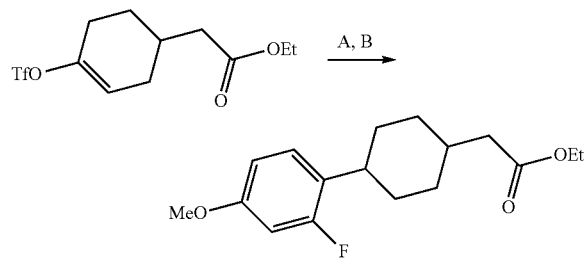

Prepared with General Procedure A employing ethyl 2-(4-(((trifluoromethyl) sulfonyl)oxy)cyclohex-3-en-1-yl)acetate (633 mg, 2.0 mmol) (2-fluoro-4-methoxyphenyl) boronic acid (408 mg, 2.4 mmol), K$_3$PO$_4$ (636 mg, 3.0 mmol), KBr (262 mg, 2.2 mmol) and Pd(PPh$_3$)$_4$ (231 mg, 0.2 mmol) in 1,4-dioxane (8 mL) and water (800 μL). Purified employing silica gel chromatography (0% to 10% EtOAc in hexanes) to afford the desired product as a clear oil. Ethyl 2-(2'-fluoro-4'-methoxy-2,3,4,5-tetrahydro-[1,1'-biphenyl]-4-yl)acetate (292 mg, 1.0 mmol) was hydrogenated with General Procedure B employing Pd/C (10 wt. % Pd, 29.0 mg), in AcOH (2.0 mL) as solvent and purified employing silica gel chromatography (0% to 10% EtOAc in hexanes) to afford Preparation 165A as a mixture of cis and trans isomers as a clear oil.

Example 165: N-(4-Cyanophenyl)-2-(4-(2-fluoro-4-methoxyphenyl)cyclohexyl)acetamide Prepared with General Procedure G employing Preparation 165A (59 mg, 0.2 mmol), 4-cyanoaniline (47 mg, 0.4 mmol), $^i$PrMgCl (200 μL, 0.4 mmol) in THF (1.0 mL). Purified using silica gel chromatography (5% to 15% EtOAc in hexanes) to afford the desired products as a 1.5:1 mixture of cis:trans diastereomers, as a white solid. Cis-isomer: $^1$H NMR (400 MHz; CDCl$_3$): δ 7.97 (s, 1H), 7.73-7.71 (m, 2H), 7.60-7.57 (m, 2H), 7.13-7.05 (m, 2H), 6.66-6.55 (m, 2H), 3.76 (s, 3H), 2.82-2.78 (m, 1H), 2.55 (d, J=7.4 Hz, 2H), 2.48-2.42 (m, 1H), 1.77-1.64 (m, 8H). Trans-isomer: $^1$H NMR (400 MHz; CDCl$_3$): δ 7.90 (s, 1H), 7.73-7.71 (m, 2H), 7.60-7.57 (m, 2H), 7.13-7.05 (m, 1H), 6.66-6.55 (m, 2H), 3.76 (s, 3H), 2.78-2.69 (m, 1H), 2.32 (d, J=6.8 Hz, 2H), 2.00-1.91 (m, 3H), 1.91-1.85 (m, 6H) 1.55-1.44 (m, 2H), 1.27-1.15 (m, 2H). m/z 367.2 (M+H)+.

Example 167

N-(4-Fluorophenyl)-2-(4-(2-fluoro-4-methoxyphenyl)cyclohexyl)acetamide

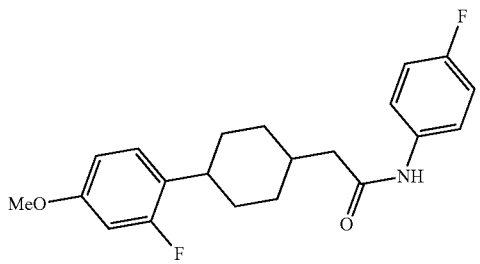 [SMILES: COc1ccc(C2CCC(CC(=O)Nc3ccc(F)cc3)CC2)c(F)c1]

Prepared with General Procedure G employing ethyl 2-(4-(2-fluoro-4-methoxyphenyl)cyclohexyl)acetate (Preparation 165A) (59 mg, 0.2 mmol), 4-fluoroaniline (44 mg, 0.4 mmol), $^i$PrMgCl (200 μL, 0.4 mmol) in THF (1.0 mL). Purified using silica gel chromatography (5% to 15% EtOAc in hexanes) to afford the desired products as a 1.5:1 mixture of cis:trans diastereomers, as a white solid. Cis-isomer: $^1$H NMR (400 MHz; CDCl$_3$): δ 7.52-7.45 (m, 2H), 7.18 (s, 1H), 7.17-7.06 (m, 1H), 7.05-6.98 (m, 2H), 6.65-6.55 (m, 2H), 3.78 (s, 3H), 2.85-2.78 (m, 1H), 2.50-2.42 (m, 3H), 1.78-1.64 (m, 8H). Trans-isomer: $^1$H NMR (400 MHz; CDCl$_3$): δ 7.52-7.45 (m, 2H), 7.17 (s, 1H), 7.17-7.06 (m, 1H), 7.05-6.98 (m, 2H), 6.65-6.55 (m, 2H), 3.77 (s, 3H), 2.79-2.71 (m, 1H), 2.26 (d, J=6.8 Hz, 2H), 2.00-1.83 (m, 6H), 1.58-1.46 (m, 2H), 1.26-1.15 (m, 2H). m/z 360.2 (M+H)+.

Example 168

N-(4-Chlorophenyl)-2-(4-(2-fluoro-4-methoxyphenyl)cyclohexyl)acetamide

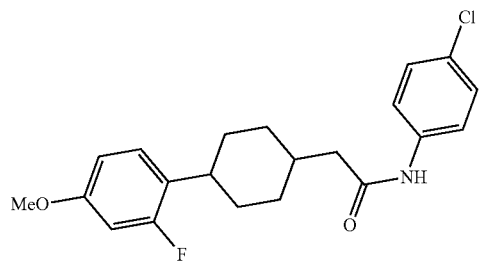 [SMILES: COc1ccc(C2CCC(CC(=O)Nc3ccc(Cl)cc3)CC2)c(F)c1]

Prepared with General Procedure G employing ethyl 2-(4-(2-fluoro-4-methoxyphenyl)cyclohexyl)acetate (Preparation 165A) (59 mg, 0.2 mmol), 4-chloroaniline (51 mg, 0.4 mmol), $^i$PrMgCl (200 µL, 0.4 mmol) in THF (1.0 mL). Purified using silica gel chromatography (5% to 15% EtOAc in hexanes) to afford the desired products as a 1.5:1 mixture of cis:trans diastereomers, as a white solid. Cis-isomer: $^1$H NMR (400 MHz; CDCl$_3$): δ 7.52-7.45 (m, 2H), 7.32-7.27 (m, 2H), 7.17-7.14 (m, 1H), 7.13-7.07 (m, 1H), 6.65-6.55 (m, 2H), 3.77 (s, 3H), 2.85-2.76 (m, 1H), 2.50-2.42 (m, 3H), 1.80-1.62 (m, 8H). Trans-isomer: $^1$H NMR (400 MHz; CDCl$_3$): δ 7.52-7.45 (m, 2H), 7.32-7.27 (m, 2H), 7.17-7.14 (m, 1H), 7.13-7.07 (m, 1H), 6.65-6.55 (m, 2H), 3.78 (s, 3H), 2.78-2.72 (m, 1H), 2.27 (d, J=6.8 Hz, 2H), 2.00-1.84 (m, 6H), 1.56-1.46 (m, 2H), 1.26-1.15 (m, 2H). m/z 376.2 (M+H)$^+$.

Example 169 cis-N-(4-Chlorophenyl)-2-(4-(3-chloro-4-methoxyphenyl)cyclohexyl) Acetamide

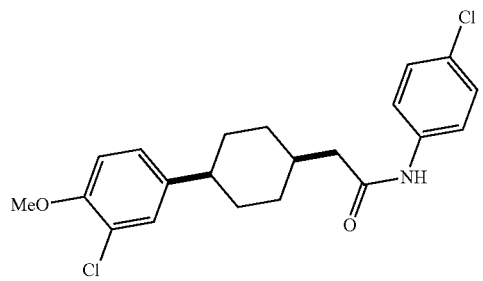

Prepared using General Procedure F employing 2-(4-(3-chloro-4-methoxyphenyl) cyclohexyl)acetic acid and 4-chloroaniline with heating at 55° C. Purified using silica gel chromatography (0% to 25% EtOAc in hexanes) to afford the first eluting isomer as the desired product as a white solid. $^1$H NMR (400 MHz; CDCl$_3$): δ 7.48 (d, J=8.7 Hz, 2H), 7.38 (s, 1H), 7.31-7.21 (m, 3H), 7.08 (dd, 0.1=8.4, 2.0 Hz, 1H), 6.86 (d, J=8.4 Hz, 1H), 3.88 (s, 3H), 2.63-2.48 (m, 1H), 2.47-2.34 (m, 3H), 1.79-1.59 (m, 8H).

Example 170 trans-N-(4-Chlorophenyl)-2-(4-(3-chloro-4-methoxyphenyl)cyclohexyl) Acetamide

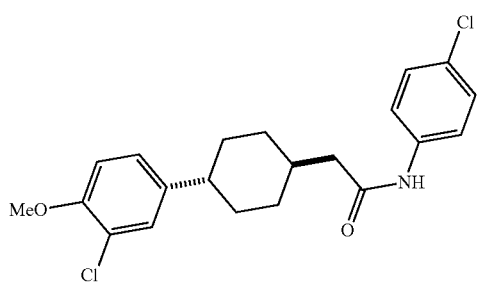

Further elution from the column in the previous example afforded the desired product as the second eluting isomer as a white solid. $^1$H NMR (400 MHz; CDCl$_3$): δ 7.52-7.42 (m, 2H), 7.32-7.22 (m, 3H), 7.19 (d, J=2.2 Hz, 1H), 7.04 (dd, J=8.5, 2.2 Hz, 1H), 6.85 (d, J=8.5 Hz, 1H), 3.87 (s, 3H), 2.40 (tt, J=12.0, 3.3 Hz, 1H), 2.27 (d, J=6.6 Hz, 2H), 1.99-1.82 (m, 5H), 1.46 (qd, J=13.0, 3.0 Hz, 2H), 1.15 (tt, J=9.0, 3.6 Hz, 2H).

Example 171 cis-N-(4-Cyanophenyl)-2-(4-(3-chloro-4-methoxyphenyl)cyclohexyl) acetamide

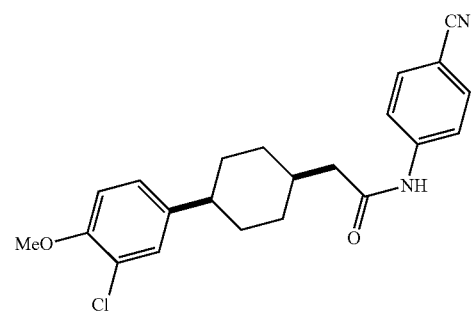

Prepared using General Procedure F employing 2-(4-(3-chloro-4-methoxyphenyl) cyclohexyl)acetic acid and 4-cyanoaniline with heating at 55° C. Purified using silica gel chromatography (0% to 25% EtOAc in hexanes) to afford the first eluting isomer as the desired product as a white solid. $^1$H NMR (400 MHz; CDCl$_3$): δ 7.71-7.65 (m, 2H), 7.62-7.55 (m, 3H), 7.24 (d, J=2.2 Hz, 1H), 7.08 (dd, J=8.4, 2.3 Hz, 1H), 6.86 (d, J=8.5 Hz, 1H), 3.88 (s, 3H), 2.63-2.52 (m, 1H), 2.51-2.47 (m, 2H), 2.41 (d, J=4.9 Hz, 1H), 1.80-1.56 (m, 8H).

Example 172 trans-N-(4-Cyanophenyl)-2-(4-(3-chloro-4-methoxyphenyl)cyclohexyl) acetamide

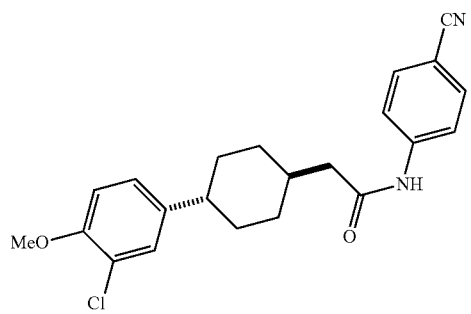

Further elution from the column in the previous example afforded the desired product as the second eluting isomer as a white solid. $^1$H NMR (400 MHz, CDCl$_3$) δ 7.75-7.64 (m, 2H), 7.64-7.57 (m, 3H), 7.19 (d, J=2.2 Hz, 1H), 7.03 (dd, J=8.5, 2.2 Hz, 1H), 6.85 (d, J=8.5 Hz, 1H), 3.86 (s, 3H), 2.40 (tt, J=12.2, 3.3 Hz, 1H), 2.31 (d, J=6.6 Hz, 2H), 1.99-1.81 (m, 5H), 1.53-1.38 (m, 3H), 1.23-1.08 (m, 4H).

Example 173 cis-N-(4-Fluorophenyl)-2-(4-(3-chloro-4-methoxyphenyl)cyclohexyl) acetamide

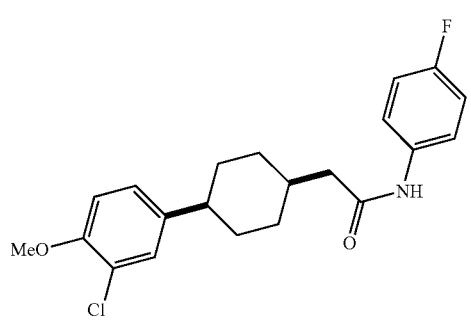

Prepared using General Procedure F employing 2-(4-(3-chloro-4-methoxyphenyl) cyclohexyl)acetic acid and 4-fluoroaniline with heating at 55° C. Purified using silica gel chromatography (0% to 25% EtOAc in hexanes) to afford the first eluting isomer as the desired product as a white solid. $^1$H NMR (400 MHz; CDCl$_3$): δ 7.55-7.44 (m, 2H), 7.37 (s, 1H), 7.24 (d, J=2.2 Hz, 1H), 7.08 (dd, J=8.5, 2.2 Hz, 1H), 7.05-6.93 (m, 2H), 6.86 (d, J=8.5 Hz, 1H), 3.88 (s, 3H), 2.66-2.51 (m, 1H), 2.47-2.31 (m, 3H), 1.82-1.56 (m, 8H).

Example 174 trans-N-(4-Fluorophenyl)-2-(4-(3-chloro-4-methoxyphenyl)cyclohexyl) acetamide

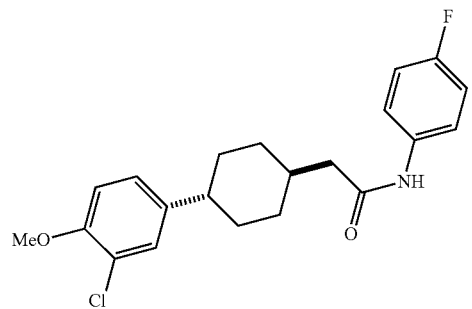

Further elution from the column in the previous example afforded the desired product as the second eluting isomer as a white solid. $^1$H NMR (400 MHz, CDCl$_3$) δ 7.53-7.43 (m, 2H), 7.20 (d, J=2.2 Hz, 1H), 7.15 (s, 1H), 7.09-6.97 (m, 3H), 6.85 (d, J=8.5 Hz, 1H), 3.87 (s, 3H), 2.41 (tt, J=12.0, 3.4 Hz, 1H), 2.27 (d, J=6.6 Hz, 2H), 1.92 (ddd, J=16.8, 12.3, 3.2 Hz, 5H), 1.47 (qd, J=13.0, 2.9 Hz, 2H), 1.22-1.09 (m, 2H).

Example 175

N-(4-Fluorophenyl)-2-(3-phenylcyclobutyl)acetamide (Diastereomeric Mixture)

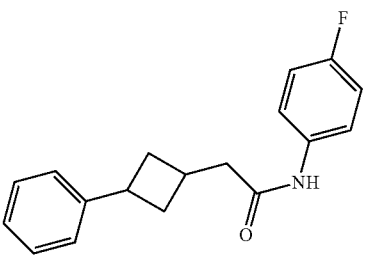 [SMILES: O=C(CC1CC(c2ccccc2)C1)Nc1ccc(F)cc1]

Prepared using General Procedure C, B, and G. General Procedure C employed 5.0 g (34 mmol) of 3-phenylcyclobutanone, 9.2 g (41 mmol) of ethyl 2-(diethoxyphosphoryl) acetate, and 2.04 g (51 mmol) of 60% sodium hydride. General Procedure B employed 10 wt. % Pd/C and MeOH as a solvent. General Procedure G employed 400 mg 2-(4-phenylcyclobutyl)acetic acid ethyl ester (mixture of diastereomers), and 407 mg 4-fluoroaniline. Purified using silica gel chromatography (0% to 100% EtOAc in hexanes) to afford the desired product as mixture of diastereomers. $^1$H NMR of mixture of diastereomers (400 MHz; CDCl$_3$): δ 7.43-7.50 (m, 2.0H), 7.27-7.35 (m, 2H), 7.13-7.25 (m, 4H), 6.97-7.05 (m, 2H), 3.60-3.72 (m, 0.3H), 3.39-3.50 (m, 0.7H), 2.70-2.90 (m, 1H), 2.60-2.69 (m, 2H), 2.40-2.52 (m, 2H), 2.21-2.30 (m, 0.7H), 1.84-1.94 (m, 1.3H) ppm. m/z 284.1 (M+H)$^+$.

Example 176

N-(4-Chlorophenyl)-2-(3-phenylcyclobutyl)acetamide (Diastereomeric Mixture)

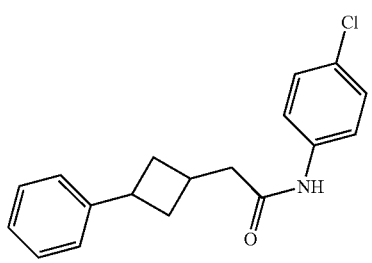

Prepared using General Procedure C, B, and G. General Procedure C employed 5.0 g (34 mmol) of 3-phenylcyclobutanone, 9.2 g (41 mmol) of ethyl 2-(diethoxyphosphoryl)acetate, and 2.04 g (51 mmol) of 60% sodium hydride. General Procedure B employed 10 wt. % Pd/C and MeOH as a solvent. General Procedure G employed 400 mg 2-(4-phenylcyclobutyl)acetic acid ethyl ester (mixture of diastereomers), and 467 mg 4-chloroaniline. Purified using silica gel chromatography (0% to 100% EtOAc in hexanes) to afford the desired product as mixture of diastereomers. $^1$H NMR of mixture of diastereomers (400 MHz; CDCl$_3$): δ 7.43-7.50 (m, 2.0H), 7.12-7.35 (m, 8H), 3.61-3.71 (m, 0.3H), 3.40-3.50 (m, 0.7H), 2.70-2.88 (m, 1H), 2.60-2.70 (m, 2H), 2.40-2.52 (m, 2H), 2.20-2.30 (m, 0.7H), 1.83-1.94 (m, 1.3H) ppm. m/z 300.1 (M+H)$^+$.

Example 177

N-(4-Cyanophenyl)-2-(3-phenylcyclobutyl)acetamide (Diastereomeric Mixture)

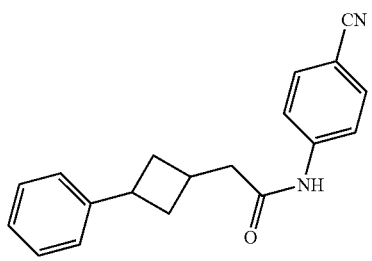 [SMILES: N#Cc1ccc(NC(=O)CC2CC(c3ccccc3)C2)cc1]

Prepared using General Procedure C, B, and G. General Procedure C employed 5.0 g (34 mmol) of 3-phenylcyclobutanone, 9.2 g (41 mmol) of ethyl 2-(diethoxyphosphoryl)acetate, and 2.04 g (51 mmol) of 60% sodium hydride. General Procedure B employed 10 wt. % Pd/C and MeOH as a solvent. General Procedure G employed 400 mg 2-(4-phenylcyclobutyl)acetic acid ethyl ester (mixture of diastereomers), and 432 mg 4-chloroaniline. Purified using silica gel chromatography (0% to 100% EtOAc in hexanes) to afford the desired product as mixture of diastereomers. $^1$H NMR of mixture of diastereomers (400 MHz; CDCl$_3$): δ 7.81 (bs, 0.3H), 7.75 (bs, 0.7H), 7.64-7.70 (m, 2.0H), 7.56-7.61 (m, 2H), 7.26-7.33 (m, 2H), 7.16-7.25 (m, 3H), 3.60-3.70 (m, 0.3H), 3.40-3.50 (m, 0.7H), 2.60-2.88 (m, 3H), 2.53 (d, J=7.3 Hz, 1.3H), 2.40-2.49 (m, 0.7H), 2.20-2.29 (m, 0.7H), 1.83-1.93 (m, 1.3H) ppm. m/z 391.1 (M+H)$^+$.

Example 178

N-(4-Chlorophenyl)-2-((3R)-3-phenylcyclopentyl)acetamide (Diastereomeric Mixture)

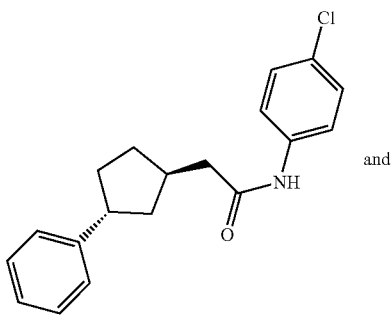

and

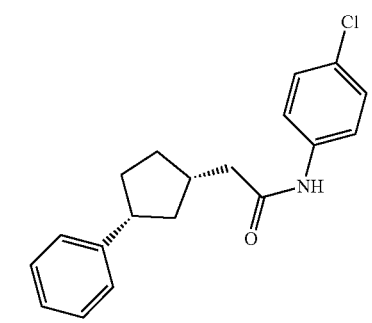

Prepared in a four step process starting with the procedure of Hayashi (*J. Am. Chem. Soc.*, 120:5579-5580 (1998)) using cyclopentanone and phenyl boronic acid with R-BINAP as ligand. The ketone was submitted to General Procedure C then hydrogenated with 10% Pd/C in MeOH according to General Procedure B. The desired product was isolated after using General Procedure G using ethyl 2-((3R)-2-phenylcyclopentyl)acetate and 4-chloroaniline. Purification by silica gel chromatography (0%-40% EtOAc in hexanes) afforded the desired product as a white crystalline product. $^1$H NMR (400 MHz, CDCl$_3$) δ 7.47 (d, J=7.3 Hz, 4H), 7.33-7.15 (m, 14H), 7.12 (s, 1H), 3.25-3.06 (m, 2H), 2.76-2.62 (m, 1H), 2.62-2.49 (m, 1H), 2.49-2.40 (m, 4H), 2.40-2.29 (m, 1H), 2.23-1.93 (m, 5H), 1.91-1.62 (m, 3H), 1.55-1.50 (m, 1H), 1.45-1.19 (m, 2H).

Example 179

N-(4-Fluorophenyl)-2-((3R)-3-phenylcyclopentyl) acetamide (Diastereomeric Mixture)

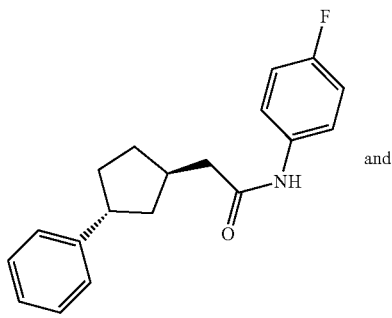

and

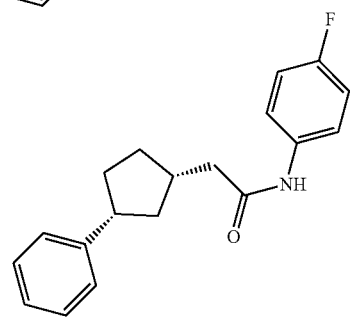

Was prepared in a four step process starting with the procedure of Hayashi (*J. Am. Chem. Soc.*, 120:5579-5580 (1998)) using cyclopentanone and phenyl boronic acid with R-BINAP as ligand. The ketone was submitted to General Procedure C then hydrogenated with 10% Pd/C in MeOH according to General Procedure B. The desired product was isolated after using General Procedure G using ethyl 2-((3R)-2-phenylcyclopenyl)acetate and 4-fluoroaniline. Purification by silica gel chromatography (0%-40% EtOAc in hexanes) afforded the desired product as a white crystalline product. $^1$H NMR (400 MHz, CDCl$_3$) δ 7.52-7.42 (m, 4H), 7.33-7.14 (m, 10H), 7.10 (s, 2H), 7.06-6.96 (m, 4H), 3.25-3.05 (m, 2H), 2.76-2.63 (m, 1H), 2.63-2.50 (m, 1H), 2.50-2.40 (m, 4H), 2.35 (dt, J=12.7, 6.4 Hz, 1H), 2.24-1.92 (m, 5H), 1.91-1.63 (m, 3H), 1.55-1.47 (m, 1H), 1.47-1.22 (m, 2H).

Example 180

N-(4-Cyanophenyl)-2-((3R)-3-phenylcyclopentyl) acetamide

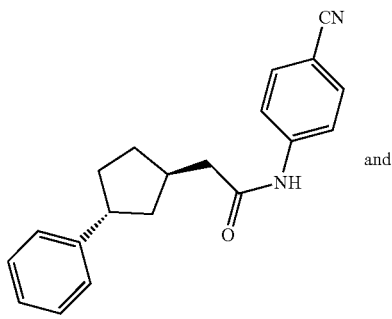

and

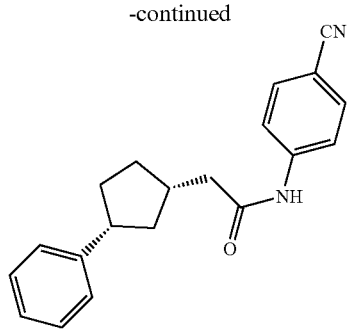

Was prepared in a four step process starting with the procedure of Hayashi (*J. Am. Chem. Soc.*, 120:5579-5580 (1998)) using cyclopentanone and phenyl boronic acid with R-BINAP as ligand. The ketone was submitted to General Procedure C then hydrogenated with 10% Pd/C in MeOH according to General Procedure B. The desired product was isolated after using General Procedure G using ethyl 2-((3R)-2-phenylcyclopentyl)acetate and 4-cyanoaniline. Purification by silica gel chromatography (0%-60% EtOAc in hexanes) afforded the desired product as a white crystalline product. $^1$H NMR (400 MHz, CDCl$_3$) δ 7.70-7.56 (m, 8H), 7.34-7.13 (m, 12H), 3.26-3.06 (m, 2H), 2.76-2.52 (m, 2H), 2.52-2.45 (m, 4H), 2.40-2.30 (m, 1H), 2.23-1.95 (m, 5H), 1.89-1.65 (m, 3H), 1.55-1.47 (m, 1H), 1.45-1.25 (m, 2H).

Example 181

N-(4-Chlorophenyl)-2-((3 S)-3-phenylcyclopentyl) acetamide

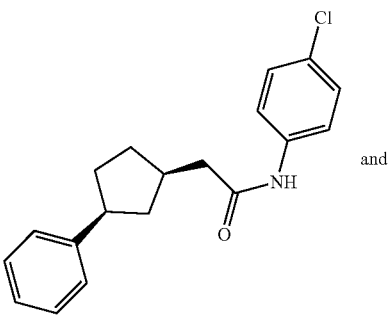

and

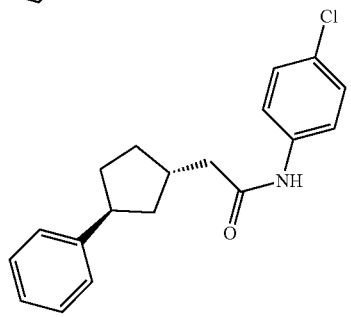

Was prepared in a four step process starting with the procedure of Hayashi (*J. Am. Chem. Soc.*, 120:5579-5580 (1998)) using cyclopentanone and phenyl boronic acid with S-BINAP as ligand. The ketone was submitted to General Procedure C then hydrogenated with 10% Pd/C in MeOH according to General Procedure B. The desired product was isolated after using General Procedure G using ethyl 2-((3R)-2-phenylcyclopentyl)acetate and 4-chloroaniline. Purification by silica gel chromatography (0%-40% EtOAc in hexanes) afforded the desired product as a white crystalline product. $^1$H NMR (400 MHz, CDCl$_3$) δ 7.47 (d, J=7.3 Hz, 4H), 7.33-7.15 (m, 14H), 7.12 (s, 1H), 3.25-3.06 (m, 2H), 2.76-2.62 (m, 1H), 2.62-2.49 (m, 1H), 2.49-2.40 (m, 4H), 2.40-2.29 (m, 1H), 2.23-1.93 (m, 5H), 1.91-1.62 (m, 3H), 1.55-1.50 (m, 1H), 1.45-1.19 (m, 2H).

Example 182

N-(4-Fluorophenyl)-2-((3S)-3-phenylcyclopentyl)acetamide

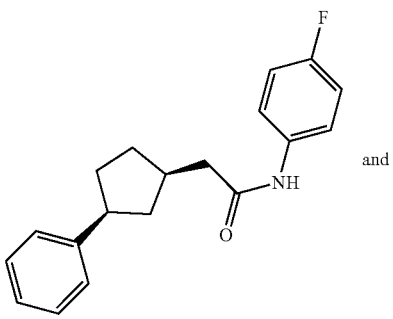

and

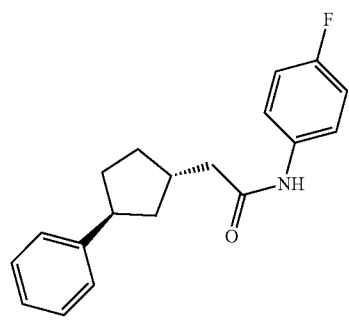

Was prepared in a four step process starting with the procedure of Hayashi (*J. Am. Chem. Soc.*, 120:5579-5580 (1998)) using cyclopentanone and phenyl boronic acid with S-BINAP as ligand. The ketone was submitted to General Procedure C then hydrogenated with 10% Pd/C in MeOH according to General Procedure B. The desired product was isolated after using General Procedure G using ethyl 2-((3R)-2-phenylcyclopenyl)acetate and 4-fluoroaniline. Purification by silica gel chromatography (0%-40% EtOAc in hexanes) afforded the desired product as a white crystalline product. $^1$H NMR (400 MHz, CDCl$_3$) δ 7.52-7.42 (m, 4H), 7.33-7.14 (m, 10H), 7.10 (s, 2H), 7.06-6.96 (m, 4H), 3.25-3.05 (m, 2H), 2.76-2.63 (m, 1H), 2.63-2.50 (m, 1H), 2.50-2.40 (m, 4H), 2.35 (dt, J=12.7, 6.4 Hz, 1H), 2.24-1.92 (m, 5H), 1.91-1.63 (m, 3H), 1.55-1.47 (m, 1H), 1.47-1.22 (m, 2H).

Example 183

N-(4-Cyanophenyl)-2-((3S)-3-phenylcyclopentyl)acetamide

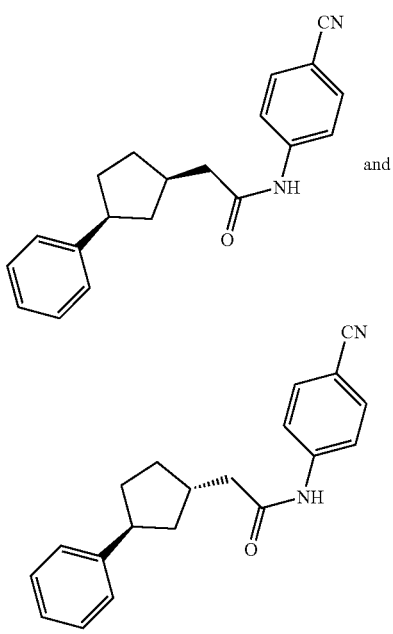

and

Prepared in a four step process starting with the procedure of Hayashi (*J. Am. Chem. Soc.*, 120:5579-5580 (1998)) using cyclopentanone and phenyl boronic acid with S-BINAP as ligand. The ketone was submitted to General Procedure C then hydrogenated with 10% Pd/C in MeOH according to General Procedure B. The desired product was isolated after using General Procedure G using ethyl 2-((3R)-2-phenylcyclopenyl)acetate and 4-cyanoaniline. Purification by silica gel chromatography (0%-60% EtOAc in hexanes) afforded the desired product as a white crystalline product. $^1$H NMR (400 MHz, CDCl$_3$) δ 7.70-7.56 (m, 8H), 7.34-7.13 (m, 12H), 3.26-3.06 (m, 2H), 2.76-2.52 (m, 2H), 2.52-2.45 (m, 4H), 2.40-2.30 (m, 1H), 2.23-1.95 (m, 5H), 1.89-1.65 (m, 3H), 1.55-1.47 (m, 1H), 1.45-1.25 (m, 2H).

Example 184 cis-N-(4-Cyanophenyl)-2,2-di fluoro-2-(1-hydroxy-4-phenylcyclohexyl)acetamide

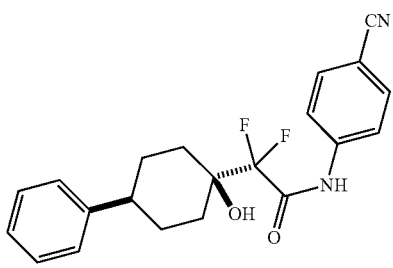 [SMILES: N#Cc1ccc(NC(=O)C(F)(F)[C@]2(O)CC[C@@H](c3ccccc3)CC2)cc1]

Prepared using General Procedure I and G. General Procedure I employed 1.0 g (5.74 mmol) of 4-phenylcyclohexanone and ethyl bromodifluoroacetate. Cis-isomer ethyl of 2,2-difluoro-2-(1-hydroxy-4-phenylcyclohexyl)acetate eluted first (0% to 40% EtOAc in hexanes). Further elution of the column afforded trans-isomer of ethyl 2,2-difluoro-2-(1-hydroxy-4-phenylcyclohexyl)acetate. General Procedure G employed 50 mg of ethyl cis-2,2-difluoro-2-(1-hydroxy-4-phenylcyclohexyl)acetate, and 51 of mg 4-cyanoaniline. Purified using silica gel chromatography (0% to 50% EtOAc in hexanes) to afford the desired product as a cis-isomer. $^1$H NMR (400 MHz; CDCl$_3$): δ 8.47 (s, 1H), 7.71-7.76 (m, 2H), 7.65-7.70 (m, 2H), 7.29-7.34 (m, 2H), 7.19-7.25 (m, 3H), 2.61 (s, 1H), 2.50-2.60 (m, 1H), 1.82-2.12 (m, 8H) ppm. m/z 371.2 (M+H)$^+$.

Example 185 cis-N-(4-Chlorophenyl)-2,2-difluoro-2-(1-hydroxy-4-phenylcyclohexyl)acetamide

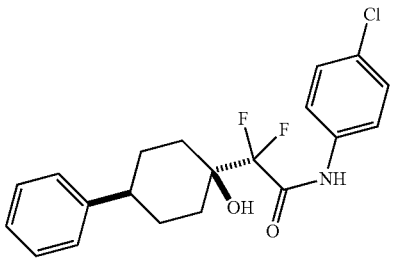 [SMILES: O=C(Nc1ccc(Cl)cc1)C(F)(F)[C@]1(O)CC[C@@H](c2ccccc2)CC1]

Prepared using General Procedure I and G. General Procedure I employed 1.0 g (5.74 mmol) of 4-phenylcyclohexanone and ethyl bromodifluoroacetate. Cis-isomer ethyl of 2,2-difluoro-2-(1-hydroxy-4-phenylcyclohexyl)acetate eluted first (0% to 40% EtOAc in hexanes). Further elution of the column afforded trans-isomer of ethyl 2,2-difluoro-2-(1-hydroxy-4-phenylcyclohexyl)acetate. General Procedure G employed 50 mg ethyl cis-2,2-difluoro-2-(1-hydroxy-4-phenylcyclohexyl)acetate, and 55 mg 4-chloroaniline. Purified using silica gel chromatography (0% to 30% EtOAc in hexanes) to afford the desired product as a cis-isomer. $^1$H NMR (400 MHz; CDCl$_3$): δ 8.24 (s, 1H), 7.51-7.56 (m, 2H), 7.28-7.37 (m, 4H), 7.18-7.26 (m, 3H), 2.84 (s, 1H), 2.50-2.60 (m, 1H), 1.78-2.02 (m, 8H) ppm. m/z 378.1 (M+H)$^+$.

Example 186 cis-N-(4-Fluorophenyl)-2,2-difluoro-2-(1-hydroxy-4-phenylcyclohexyl)acetamide

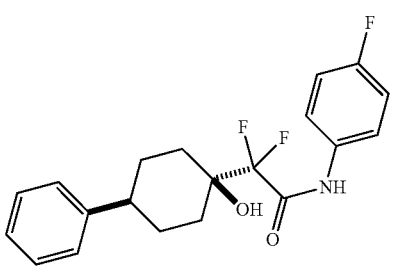

Prepared using General Procedure I and G. General Procedure I employed 1.0 g (5.74 mmol) of 4-phenylcyclohexanone and ethyl bromodifluoroacetate. Cis-isomer ethyl of 2,2-difluoro-2-(1-hydroxy-4-phenylcyclohexyl)acetate eluted first (0% to 40% EtOAc in hexanes). Further elution of the column afforded trans-isomer of ethyl 2,2-difluoro-2-(1-hydroxy-4-phenylcyclohexyl)acetate. General Procedure G employed 50 mg ethyl cis-2,2-difluoro-2-(1-hydroxy-4-phenylcyclohexyl)acetate, and 48 mg 4-fluoroaniline. Purified using silica gel chromatography (0% to 30% EtOAc in hexanes) to afford the desired product as a cis-isomer. $^1$H NMR (400 MHz; CDCl$_3$): δ 8.21 (s, 1H), 7.52-7.58 (m, 2H), 7.28-7.34 (m, 2H), 7.18-7.26 (m, 3H), 7.04-7.12 (m, 2H), 2.91 (s, 1H), 2.50-2.60 (m, 1H), 1.79-2.02 (m, 8H) ppm. m/z 364.1 (M+H)$^+$.

Example 187 trans-N-(4-Cyanophenyl)-2,2-difluoro-2-(1-hydroxy-4-phenylcyclohexyl)acetamide

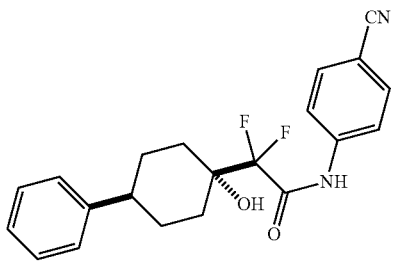

Prepared using General Procedure I and G. General Procedure I employed 1.0 g (5.74 mmol) of 4-phenylcyclohexanone and ethyl bromodifluoroacetate. Cis-isomer ethyl of 2,2-difluoro-2-(1-hydroxy-4-phenylcyclohexyl)acetate eluted first (0% to 40% EtOAc in hexanes). Further elution of the column afforded trans-isomer of ethyl 2,2-difluoro-2-(1-hydroxy-4-phenylcyclohexyl)acetate. General Procedure G employed 50 mg ethyl trans-2,2-difluoro-2-(1-hydroxy-4-phenylcyclohexyl)acetate, and 51 mg 4-cyanoaniline. Purified using silica gel chromatography (0% to 50% EtOAc in hexanes) to afford the desired product as a cis-isomer. $^1$H NMR (400 MHz; CDCl$_3$): δ ppm. m/z 8.46 (s, 1H), 7.64-7.74 (m, 4H), 7.25-7.35 (m, 4H), 7.18-7.24 (m, 1H), 2.77-2.86 (m, 1H), 2.64 (s, 1H), 2.20-2.29 (m, 2H), 1.95-2.05 (m, 4H), 1.64-1.73 (m, 2H) ppm. m/z 371.2 (M+H)$^+$.

Example 188 cis-N-(4-Chlorophenyl)-2,2-difluoro-2-(1-hydroxy-4-phenylcyclohexyl)acetamide

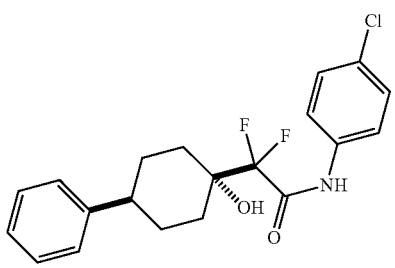

Prepared using General Procedure I and G. General Procedure I employed 1.0 g (5.74 mmol) of 4-phenylcyclohexanone and ethyl bromodifluoroacetate. Cis-isomer ethyl of 2,2-difluoro-2-(1-hydroxy-4-phenylcyclohexyl)acetate eluted first (0% to 40% EtOAc in hexanes). Further elution of the column afforded trans-isomer of ethyl 2,2-difluoro-2-(1-hydroxy-4-phenylcyclohexyl)acetate. General Procedure G employed 50 mg ethyl trans-2,2-difluoro-2-(1-hydroxy-4-phenylcyclohexyl)acetate, and 55 mg 4-chloroaniline. Purified using silica gel chromatography (0% to 30% EtOAc in hexanes) to afford the desired product as a cis-isomer. $^1$H NMR (400 MHz; CDCl$_3$): δ 8.22 (s, 1H), 7.50-1.55 (m, 2H), 7.26-7.36 (m, 6H), 7.17-7.24 (m, 1H), 2.93 (s, 1H), 2.78-2.87 (m, 1H), 2.18-2.27 (m, 2H), 1.95-2.05 (m, 4H), 1.63-1.73 (m, 2H) ppm. m/z 378.1 (M+H)$^+$.

Example 189 trans-N-(4-Fluorophenyl)-2,2-difluoro-2-(1-hydroxy-4-phenylcyclohexyl)acetamide

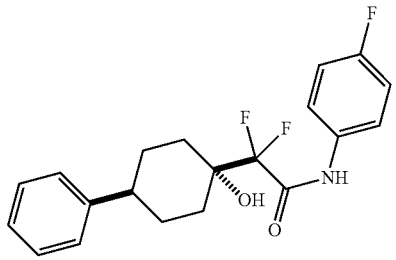

Prepared using General Procedure I and G. General Procedure I employed 1.0 g (5.74 mmol) of 4-phenylcyclohexanone and ethyl bromodifluoroacetate. Cis-isomer ethyl of 2,2-difluoro-2-(1-hydroxy-4-phenylcyclohexyl)acetate eluted first (0% to 40% EtOAc in hexanes). Further elution of the column afforded trans-isomer of ethyl 2,2-difluoro-2-(1-hydroxy-4-phenylcyclohexyl)acetate. General Procedure G employed 50 mg ethyl trans-2,2-difluoro-2-(1-hydroxy-4-phenylcyclohexyl)acetate, and 48 mg 4-fluoroaniline. Purified using silica gel chromatography (0% to 30% EtOAc in hexanes) to afford the desired product as a cis-isomer. $^1$H NMR (400 MHz; CDCl$_3$): δ 8.20 (s, 1H), 7.50-7.57 (m, 2H), 7.26-7.35 (m, 4H), 7.17-7.24 (m, 1H), 7.03-7.10 (m, 2H), 3.04 (s, 1H), 2.75-2.87 (m, 1H), 2.17-2.26 (m, 2H), 1.95-2.05 (m, 4H), 1.62-1.75 (m, 2H) ppm. m/z 364.1 (M+H)$^+$.

Example 190 trans-N-(4-Fluorophenyl)-2-(1-hydroxy-4-phenylcyclohexyl)acetamide

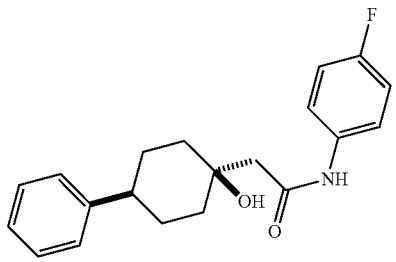

Prepared using General Procedure I and G. General Procedure I employed 1.0 g (5.74 mmol) of 4-phenylcyclohexanone and ethyl bromoacetate. Trans-isomer of 2-(1-hydroxy-4-phenylcyclohexyl)acetate eluted first (0% to 30% EtOAc in hexanes). Further elution of the column afforded cis-isomer of 2-(1-hydroxy-4-phenylcyclohexyl)acetate. General Procedure G employed 100 mg ethyl trans-2-(1-hydroxy-4-phenylcyclohexyl) acetate, and 85 mg 4-fluoroaniline. Purified using silica gel chromatography (0% to 100% EtOAc in hexanes) to afford the desired product as a trans-isomer. $^1$H NMR (400 MHz; CDCl$_3$): δ 8.06 (bs, 1H), 7.45-7.52 (m, 2H), 7.27-7.34 (m, 2H), 7.17-7.26 (m, 3H), 6.98-7.06 (m, 2H), 3.55 (bs, 1H), 2.53 (s, 2H), 2.49 (tt, J=12.2 Hz, J=3.4 Hz, 1H), 1.83-2.01 (m, 4H), 1.71-1.80 (m, 2H), 1.54 (dt, J=13.2 Hz, J=3.8 Hz, 2H) ppm. m/z 328.2 (M+H)$^+$.

Example 191 trans-N-(4-Chlorophenyl)-2-(1-hydroxy-4-phenylcyclohexyl)acetamide

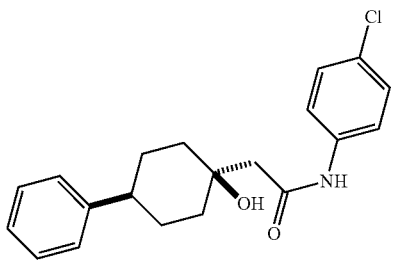

Prepared using General Procedure I and G. General Procedure I employed 1.0 g (5.74 mmol) of 4-phenylcyclohexanone and ethyl bromoacetate. Trans-isomer of 2-(1-hydroxy-4-phenylcyclohexyl)acetate eluted first (0% to 30% EtOAc in hexanes). Further elution of the column afforded cis-isomer of 2-(1-hydroxy-4-phenylcyclohexyl)acetate. General Procedure G employed 100 mg ethyl trans-2-(1-hydroxy-4-phenylcyclohexyl) acetate, and 97 mg 4-chloroaniline. Purified using silica gel chromatography (0% to 100% EtOAc in hexanes) to afford the desired product as a trans-isomer. $^1$H NMR (400 MHz; CDCl$_3$): δ 8.17 (bs, 1H), 7.46-7.51 (m, 2H), 7.17-7.34 (m, 7H), 3.43 (bs, 1H), 2.54 (s, 2H), 2.49 (tt, J=11.9 Hz, J=3.3 Hz, 1H), 1.82-2.00 (m, 4H), 1.72-1.81 (m, 2H), 1.55 (dt, J=13.1 Hz, J=3.7 Hz, 2H) ppm. m/z 344.1 (M+H)$^+$.

Example 192 trans-N-(4-Cyanophenyl)-2-(1-hydroxy-4-phenylcyclohexyl)acetamide

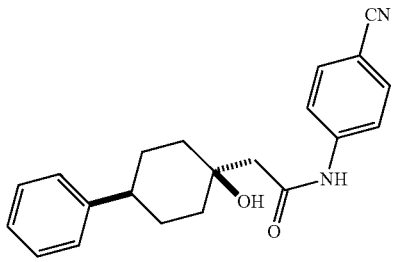

Prepared using General Procedure I and G. General Procedure I employed 1.0 g (5.74 mmol) of 4-phenylcyclohexanone and ethyl bromoacetate. Trans-isomer of 2-(1-hydroxy-4-phenylcyclohexyl)acetate eluted first (0% to 30% EtOAc in hexanes). Further elution of the column afforded cis-isomer of 2-(1-hydroxy-4-phenylcyclohexyl)acetate. General Procedure G employed 100 mg ethyl trans-2-(1-hydroxy-4-phenylcyclohexyl) acetate, and 90 mg 4-cyanoaniline. Purified using silica gel chromatography (0% to 100% EtOAc in hexanes) to afford the desired product as a trans-isomer. $^1$H NMR (400 MHz; CDCl$_3$): δ 8.59 (bs, 1H), 7.65-7.70 (m, 2H), 7.59-7.63 (m, 2H), 7.28-7.34 (m, 2H), 7.18-7.25 (m, 3H), 2.95 (s, 1H), 2.59 (s, 2H), 2.51 (tt, J=11.2 Hz, J=4.5 Hz, 1H), 1.76-2.00 (m, 6H), 1.55-1.65 (m, 2H) ppm. m/z 335.2 (M+H)$^+$.

Example 193 cis-N-(4-Fluorophenyl)-2-(1-hydroxy-4-phenylcyclohexyl)acetamide

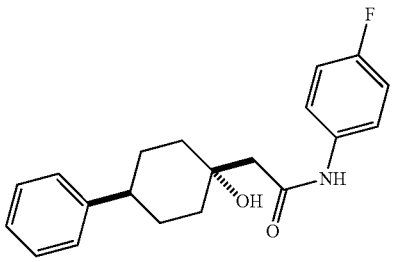

Prepared using General Procedure I and G. General Procedure I employed 1.0 g (5.74 mmol) of 4-phenylcyclohexanone and ethyl bromoacetate. Trans-isomer of 2-(1-hydroxy-4-phenylcyclohexyl)acetate eluted first (0% to 30% EtOAc in hexanes). Further elution of the column afforded cis-isomer of 2-(1-hydroxy-4-phenylcyclohexyl)acetate. General Procedure G employed 100 mg ethyl cis-2-(1-hydroxy-4-phenylcyclohexyl) acetate, and 85 mg 4-fluoroaniline. Purified using silica gel chromatography (0% to 100% EtOAc in hexanes) to afford the desired product as a cis-isomer. $^1$H NMR (400 MHz; CDCl$_3$): δ 8.28 (bs, 1H), 7.45-7.52 (m, 2H), 7.27-7.33 (m, 2H), 7.17-7.24 (m, 3H), 6.97-7.05 (m, 2H), 3.35 (bs, 1H), 2.74 (s, 2H), 2.55-2.65 (m, 1H), 1.88-2.07 (m, 4H), 1.55-1.73 (m, 4H) ppm. m/z 328.2 (M+H)$^+$.

Example 194 cis-N-(4-Chlorophenyl)-2-(1-hydroxy-4-phenylcyclohexyl)acetamide

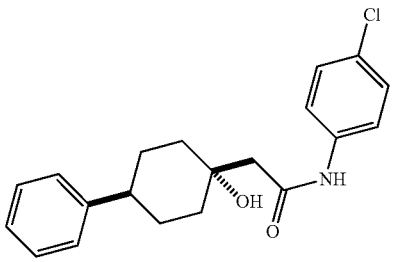

Prepared using General Procedure I and G. General Procedure I employed 1.0 g (5.74 mmol) of 4-phenylcyclohexanone and ethyl bromoacetate. Trans-isomer of 2-(1-hydroxy-4-phenylcyclohexyl)acetate eluted first (0% to 30% EtOAc in hexanes). Further elution of the column afforded cis-isomer of 2-(1-hydroxy-4-phenylcyclohexyl)acetate. General Procedure G employed 100 mg ethyl cis-2-(1-hydroxy-4-phenylcyclohexyl) acetate, and 97 mg 4-chloroaniline. Purified using silica gel chromatography (0% to 100% EtOAc in hexanes) to afford the desired product as a cis-isomer. $^1$H NMR (400 MHz; CDCl$_3$): δ 8.34 (bs, 1H), 7.46-7.51 (m, 2H), 7.26-7.33 (m, 4H), 7.17-7.24 (m, 3H), 3.12 (bs, 1H), 2.74 (s, 2H), 2.55-2.65 (m, 1H), 2.00-2.07 (m, 2H), 1.88-1.96 (m, 2H), 1.55-1.73 (m, 4H) ppm. m/z 344.1 (M+H)$^+$.

Example 195 cis-N-(4-Cyanophenyl)-2-(1-hydroxy-4-phenylcyclohexyl)acetamide

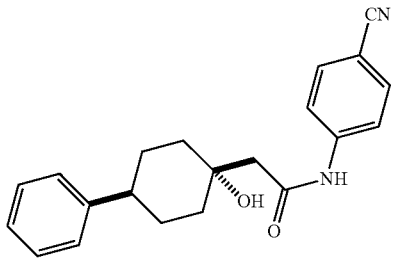

Prepared using General Procedure I and G. General Procedure I employed 1.0 g (5.74 mmol) of 4-phenylcyclohexanone and ethyl bromoacetate. Trans-isomer of 2-(1-hydroxy-4-phenylcyclohexyl)acetate eluted first (0% to 30% EtOAc in hexanes). Further elution of the column afforded cis-isomer of 2-(1-hydroxy-4-phenylcyclohexyl)acetate. General Procedure G employed 100 mg ethyl cis-2-(1-hydroxy-4-phenylcyclohexyl) acetate, and 90 mg 4-cyanoaniline. Purified using silica gel chromatography (0% to 100% EtOAc in hexanes) to afford the desired product as a cis-isomer. $^1$H NMR (400 MHz; CDCl$_3$): δ 8.82 (bs, 1H), 7.65-7.70 (m, 2H), 7.58-7.63 (m, 2H), 7.27-7.33 (m, 2H), 7.18-7.25 (m, 3H), 2.78 (m, 2H), 2.67 (bs, 1H), 2.54-2.64 (m, 1H), 2.01-2.07 (m, 2H), 1.88-1.97 (m, 2H), 1.59-1.71 (m, 4H) ppm. m/z 335.2 (M+H)$^+$.

Example 196 cis-N-(4-Chlorophenyl)-2-(1-hydroxy-4-phenylcyclohexyl)propanamide

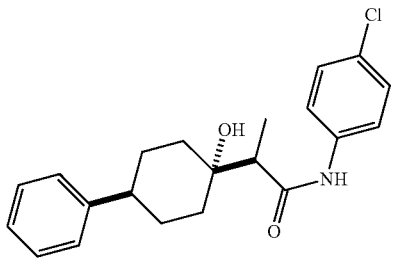 [SMILES: C[C@@H](C(=O)Nc1ccc(Cl)cc1)[C@]1(O)CC[C@H](c2ccccc2)CC1]

Prepared using General Procedure I and G. General Procedure I employed 1.0 g of 4-phenylcyclohexanone and 1.05 g of methyl 2-bromopropanoate. General Procedure G employed 80 mg methyl cis-2-(1-hydroxy-4-phenylcyclohexyl)propanoate, and 119 mg 4-chloroaniline. Purified using silica gel chromatography (0% to 50% EtOAc in hexanes) to afford the desired product as a cis-diastereomer. $^{1}$H NMR (400 MHz; CDCl$_{3}$): δ 8.17 (bs, 1H), 7.46-7.51 (m, 2H), 7.26-7.33 (m, 4H), 7.17-7.25 (m, 3H), 3.17 (bs, 1H), 2.90 (q, J=7.2 Hz, 1H), 2.59-2.69 (m, 1H), 2.02-2.11 (m, 2H), 1.87-1.95 (m, 2H), 1.48-1.74 (m, 4H), 1.35 (d, J=7.2 Hz, 3H) ppm. m/z 358.1 (M+H)$^{+}$.

Example 197 cis-N-(4-Fluorophenyl)-2-(1-hydroxy-4-phenylcyclohexyl)propanamide

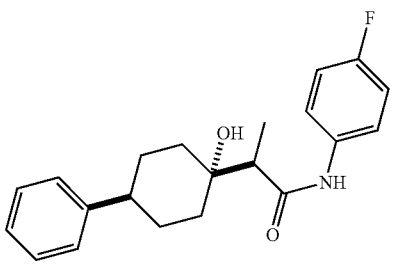 [SMILES: C[C@@H](C(=O)Nc1ccc(F)cc1)[C@]1(O)CC[C@H](c2ccccc2)CC1]

Prepared using General Procedure I and G. General Procedure I employed 1.0 g of 4-phenylcyclohexanone and 1.05 g of methyl 2-bromopropanoate. General Procedure G employed 80 mg methyl cis-2-(1-hydroxy-4-phenylcyclohexyl)propanoate, and 103 mg 4-fluoroaniline. Purified using silica gel chromatography (0% to 50% EtOAc in hexanes) to afford the desired product as a cis-diastereomer. $^{1}$H NMR (400 MHz; CDCl$_{3}$): δ 8.09 (s, 1H), 7.45-7.51 (m, 2H), 7.27-7.33 (m, 2H), 7.17-7.25 (m, 3H), 6.97-7.05 (m, 2H), 3.37 (s, 1H), 2.89 (q, J=7.1 Hz, 1H), 2.59-2.69 (m, 1H), 2.02-2.11 (m, 2H), 1.87-1.96 (m, 2H), 1.47-1.75 (m, 4H), 1.35 (d, J=7.1 Hz, 3H) ppm. m/z 342.2 (M+H)$^{+}$.

Example 198 cis-N-(4-Cyanophenyl)-2-(1-hydroxy-4-phenylcyclohexyl)propanamide

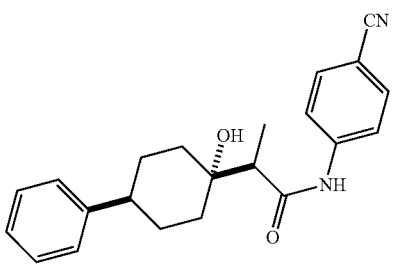 [SMILES: C[C@@H](C(=O)Nc1ccc(C#N)cc1)[C@]1(O)CC[C@H](c2ccccc2)CC1]

Prepared using General Procedure I and G. General Procedure I employed 1.0 g of 4-phenylcyclohexanone and 1.05 g of methyl 2-bromopropanoate. General Procedure G employed 80 mg methyl cis-2-(1-hydroxy-4-phenylcyclohexyl)propanoate, and 110 mg 4-cyanoaniline. Purified using silica gel chromatography (0% to 50% EtOAc in hexanes) to afford the desired product as a cis-diastereomer. $^{1}$H NMR (400 MHz; CDCl$_{3}$): δ 8.73 (bs, 1H), 7.65-7.69 (m, 2H), 7.56-7.62 (m, 2H), 7.27-7.33 (m, 2H), 7.17-7.25 (m, 3H), 2.98 (q, J=7.2 Hz, 1H), 2.58-2.68 (m, 2H), 2.03-2.15 (m, 2H), 1.86-1.95 (m, 2H), 1.48-1.78 (m, 4H), 1.36 (d, J=7.2 Hz, 3H) ppm. m/z 349.2 (M+H)$^{+}$.

Example 201 cis-N-(4-Cyanophenyl)-2-((1,4)-4-(4-methoxyphenyl)cyclohexyl)propanamide

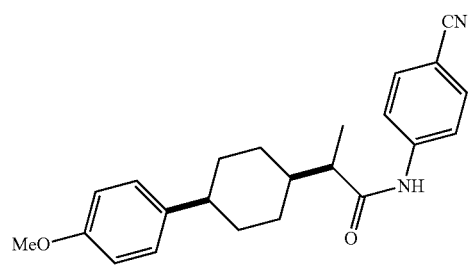

Preparation 201A: Ethyl 2-(4-(4-methoxyphenyl)cyclohexyl)propanoate

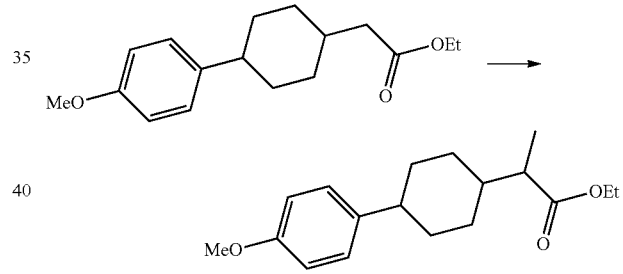

To a solution of ethyl 2-(4-(4-methoxyphenyl)cyclohexyl) acetate (691 mg, 2.5 mmol) in THF (5.0 mL), at 0° C. was added NaHMDS solution (2.75 mL, 1M/THF). The resulting yellow solution was stirred at 0° C. for 5 min and MeI (390 mg, 171 μL, 2.75 mmol) was added. The reaction mixture was stirred at 0° C. for 30 min and was poured onto a saturated solution of NH$_{4}$Cl. EtOAc (50 mL) was added and the layer were separated. The aqueous layer was extracted with EtOAc (3×25 mL). The combined organic extracts were dried over anhydrous MgSO$_{4}$, filtered, and concentrated under reduced pressure. The crude reaction mixture was purified employing silica gel chromatography (5% EtOAc in hexanes) to afford the desired products as a 1:2 mixture of cis:trans diastereomers, as a yellow oil.

Example 201: cis-N-(4-Cyanophenyl)-2-((1,4)-4-(4-methoxyphenyl)cyclohexyl)-propanamide Prepared with General Procedure G employing Preparation 201A (174 mg, 0.6 mmol), 4-cyanoaniline (142 mg, 1.2 mmol), $^{i}$PrMgCl (600 μL, 1.2 mmol) in THF (3.0 mL). Purified using silica gel chromatography (5% to 20% EtOAc in hexanes) to afford the desired product as a white solid and the first eluting isomer. $^1$H NMR (400 MHz; CDCl$_3$): δ 7.70-7.67 (m, 2H), 7.60-7.57 (m, 2H), 7.54 (s, 1H), 7.18-7.15 (m, 2H), 6.85-6.82 (m, 2H), 3.79 (s, 3H), 2.69-2.63 (m, 1H), 2.56-2.49 (m, 1H), 1.98-1.95 (m, 1H), 1.79-1.56 (m, 10H), 1.24 (d, J=6.8 Hz, 3H). m/z 363.3 (M+H)$^+$.

Example 202 trans-N-(4-Cyanophenyl)-2-((1,4)-4-(4-methoxyphenyl)cyclohexyl)propanamide

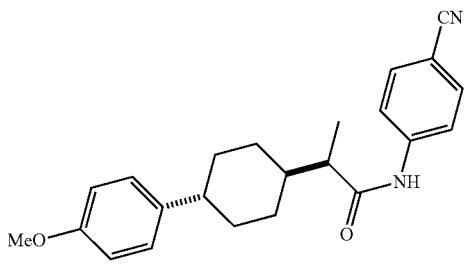

Further elution from the column in the previous example afforded the desired product as a white solid and the second eluting isomer. $^1$H NMR (400 MHz; CDCl$_3$): δ 7.73-7.70 (m, 2H), 7.63-7.60 (m, 2H), 7.56 (s, 1H), 7.12-7.08 (m, 2H), 6.85-6.81 (m, 2H), 3.78 (s, 3H), 2.45-2.37 (m, 1H), 2.20-2.13 (m, 1H), 2.02-1.86 (m, 4H), 1.74-1.65 (m, 2H), 1.50-1.40 (m, 2H), 1.28-1.09 (m, 5H). m/z 363.3 (M+H)$^+$.

Example 203 cis-N-(4-Fluorophenyl)-2-((1,4)-4-(4-methoxyphenyl)cyclohexyl)propanamide

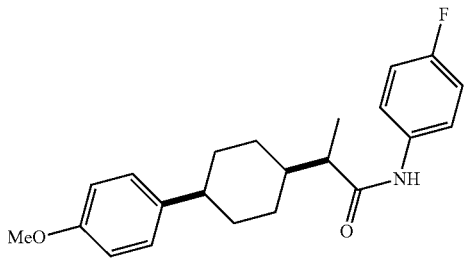

Prepared with General Procedure G employing ethyl 2-(4-(4-methoxyphenyl) cyclohexyl)propanoate (174 mg, 0.6 mmol), 4-fluoroaniline (133 mg, 1.2 mmol), $^i$PrMgCl (600 µL, 1.2 mmol) in THF 3.0 mL). Purified using silica gel chromatography (5% to 20% EtOAc in hexanes) to afford the desired product as a white solid and the first eluting isomer. $^1$H NMR (400 MHz; CDCl$_3$): δ 7.48 (ddd, J=9.5, 5.0, 2.6 Hz, 2H), 7.19-7.16 (m, 3H), 7.03-6.98 (m, 2H), 6.87-6.84 (m, 2H), 3.80 (s, 3H), 2.67-2.63 (m, 1H), 2.50-2.42 (m, 1H), 1.98-1.94 (m, 1H), 1.77-1.62 (m, 9H), 1.23 (d, J=6.8 Hz, 3H). m/z 356.2 (M+H)$^+$.

Example 204 cis-N-(4-Chlorophenyl)-2-((1,4)-4-(4-methoxyphenyl)cyclohexyl)propanamide

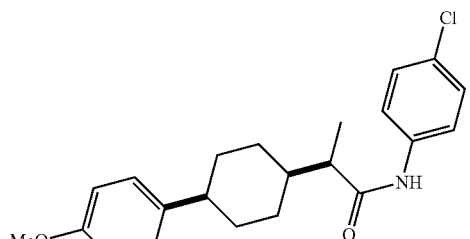

Prepared with General Procedure G employing ethyl 2-(4-(4-methoxyphenyl) cyclohexyl)propanoate (58 mg, 0.2 mmol), 4-chloroaniline (51 mg, 0.4 mmol), $^i$PrMgCl (200 µL, 0.4 mmol) in THF (1.0 mL). Purified using silica gel chromatography (5% to 20% EtOAc in hexanes) to afford the desired product as a white solid and the first eluting isomer. $^1$H NMR (400 MHz; CDCl$_3$): δ 7.50-7.46 (m, 2H), 7.29-7.26 (m, 2H), 7.17 (dd, J=9.2, 2.5 Hz, 3H), 6.87-6.83 (m, 2H), 3.80 (s, 3H), 2.68-2.63 (m, 1H), 2.50-2.42 (m, 1H), 1.99-1.93 (m, 1H), 1.77-1.62 (m, 8H), 1.23 (d, J=6.8 Hz, 3H). m/z 372.2 (M+H)$^+$.

Example 205 trans-N-(4-Chlorophenyl)-2-((1,4)-4-(4-methoxyphenyl)cyclohexyl)propanamide

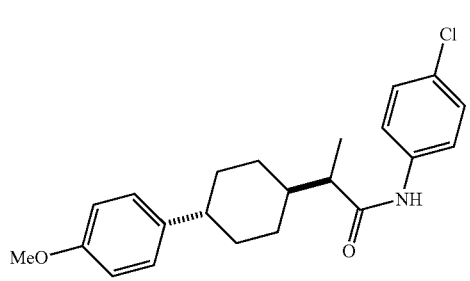

Further elution from the column in the previous example afforded the desired product as a white solid and the second eluting isomer. $^1$H NMR (400 MHz; CDCl$_3$): δ 7.52-7.49 (m, 2H), 7.30-7.26 (m, 2H), 7.18 (s, 1H), 7.12-7.09 (m, 2H), 6.85-6.81 (m, 2H), 3.78 (s, 3H), 2.45-2.37 (m, 1H), 2.13-2.06 (m, 1H), 2.02-1.94 (m, 2H), 1.94-1.85 (m, 3H), 1.75-1.65 (m, 2H), 1.50-1.40 (m, 2H), 1.25 (d, J=6.8 Hz, 3H), 1.20-1.08 (m, 1H). m/z 372.2 (M+H)$^+$.

Example 206 cis-N-(4-Cyanophenyl)-2-((1,4)-4-phenylcyclohexyl)propanamide

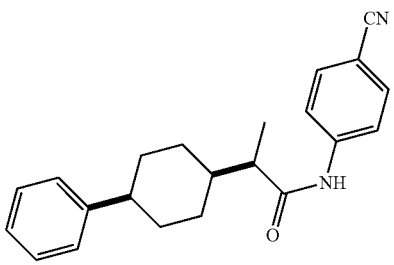

Preparation 206A: Ethyl 2-(4-phenylcyclohexyl)propanoate

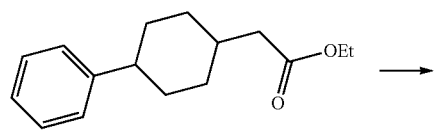

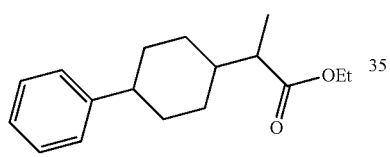

To a solution of ethyl 2-(4-phenylcyclohexyl)acetate (266 mg 1.0 mmol) in THF (10 mL) at −78° C. was added a solution of LiHMDS (1.1 mL, 1M/THF) The resulting yellow reaction mixture was stirred at −78° C. for 15 min and MeI (156 mg, 68 µL, 1.1 mmol) was added. The reaction mixture was stirred at −78° C. for 8 h and was poured onto a saturated solution of $NH_4Cl$. EtOAc (50 mL) was added and the layer were separated. The aqueous layer was extracted with EtOAc (3×25 mL). The combined organic extracts were dried over anhydrous $MgSO_4$, filtered, and concentrated under reduced pressure. The crude reaction mixture was purified employing silica gel chromatography (0% to 10% EtOAc in hexanes) to afford the desired products as a 1:1 mixture of cis:trans diastereomers, as a yellow oil.

Example 206: cis-N-(4-Cyanophenyl)-2-((1,4)-4-phenylcyclohexyl)propanamide

Prepared with General Procedure G employing Preparation 206A (26 mg, 0.1 mmol), 4-cyanoaniline (24 mg, 0.2 mmol), $^iPrMgCl$ (100 µL, 0.2 mmol) in THF 1.0 ml). Purified using silica gel chromatography (5% to 25% EtOAc in hexanes) to afford the desired product as a white solid and the first eluting isomer. $^1H$ NMR (400 MHz; $CDCl_3$): δ 7.68-7.66 (m, 2H), 7.61-7.59 (m, 2H), 7.29 (dt, J=16.8, 8.0 Hz, 5H), 7.22-7.18 (m, 1H), 2.75-2.68 (m, 1H), 2.55-2.47 (m, 1H), 2.01-1.95 (m, 1H), 1.80-1.61 (m, 7H), 1.25 (d, J=6.8 Hz, 3H). m/z 333.2 $(M+H)^+$.

Example 207 trans-N-(4-Cyanophenyl)-2-((1,4)-4-phenylcyclohexyl)propanamide

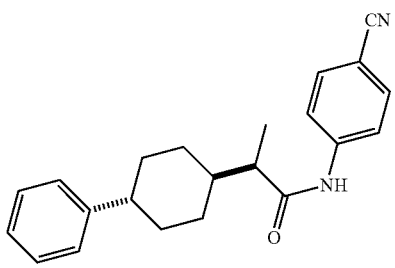

Further elution from the column in the previous example afforded the desired product as a white solid and the second eluting isomer. $^1H$ NMR (400 MHz; $CDCl_3$): δ 7.72-7.67 (m, 2H), 7.64-7.60 (m, 2H), 7.35-7.26 (m, 4H), 7.22-7.16 (m, 3H), 2.51-2.41 (m, 1H), 2.19-2.11 (m, 1H), 2.04-1.86 (m, 4H), 1.77-1.64 (m, 2H), 1.55-1.43 (m, 2H), 1.27 (d, J=6.9 Hz, 3H), 1.24-1.10 (m, 1H). m/z 333.2 $(M+H)^+$.

Example 208 cis-N-(4-Fluorophenyl)-2-((1,4)-4-phenylcyclohexyl)propanamide

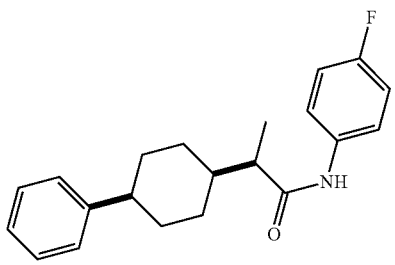

Prepared with General Procedure G employing ethyl 2-(4-phenylcyclohexyl) propanoate (26 mg, 0.1 mmol), 4-fluoroaniline (22 mg, 0.2 mmol), $^iPrMgCl$ (100 µL, 0.2 mmol) in THF (1.0 mL). Purified using silica gel chromatography (5% to 15% EtOAc in hexanes) to afford the desired product as a white solid and the first eluting isomer. $^1H$ NMR (400 MHz; $CDCl_3$): δ 7.50-7.47 (m, 2H), 7.33-7.27 (m, 4H), 7.22-7.18 (m, 1H), 7.12 (s, 1H), 7.04-6.98 (m, 2H), 2.75-2.68 (m, 1H), 2.52-2.44 (m, 1H), 2.01-1.96 (m, 1H), 1.81-1.64 (m, 8H), 1.25 (d, J=6.8 Hz, 3H). m/z 326.3 $(M+H)^+$.

Example 209 trans-N-(4-Fluorophenyl)-2-((1,4)-4-phenylcyclohexyl)propanamide

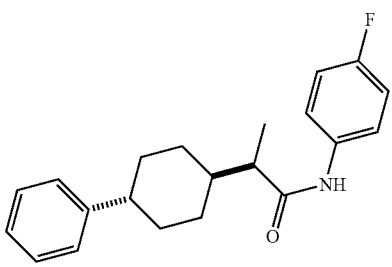

Further elution from the column in the previous example afforded the desired product as a white solid and the second eluting isomer. $^1$H NMR (400 MHz; CDCl$_3$): δ 7.54-7.48 (m, 2H), 7.31-7.27 (m, 2H), 7.22-7.16 (m, 4H), 7.05-6.99 (m, 2H), 2.47 (tt, J=12.2, 3.1 Hz, 1H), 2.14-2.07 (m, 1H), 2.06-1.88 (m, 4H), 1.74-1.64 (m, 1H), 1.56-1.45 (m, 2H), 1.26 (t, J=6.1 Hz, 3H), 1.24-1.11 (m, 2H). m/z 326.2 (M+H)$^+$.

Example 210 cis-N-(4-Chlorophenyl)-2-((1,4)-4-phenylcyclohexyl)propanamide

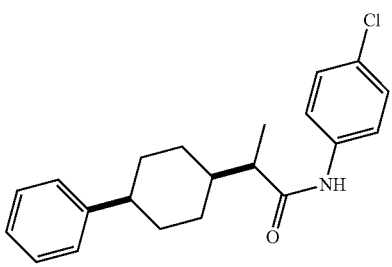

Prepared with General Procedure G employing ethyl 2-(4-phenylcyclohexyl) propanoate (26 mg, 0.1 mmol), 4-chloroaniline (26 mg, 0.2 mmol), $^i$PrMgCl (100 μL, 0.2 mmol) in THF (1.0 mL). Purified using silica gel chromatography (5% to 15% EtOAc in hexanes) to afford the desired product as a white solid and the first eluting isomer. $^1$H NMR (400 MHz; CDCl$_3$): δ 7.50-7.47 (m, 2H), 7.33-7.26 (m, 8H), 7.22-7.18 (m, 1H), 7.14 (s, 1H), 2.75-2.68 (m, 1H), 2.52-2.44 (m, 1H), 2.00-1.96 (m, 1H), 1.80-1.62 (m, 8H), 1.24 (d, J=6.8 Hz, 3H). m/z 342.2 (M+H)$^+$.

Example 211 trans-N-(4-Chlorophenyl)-2-((1,4)-4-phenylcyclohexyl)propanamide

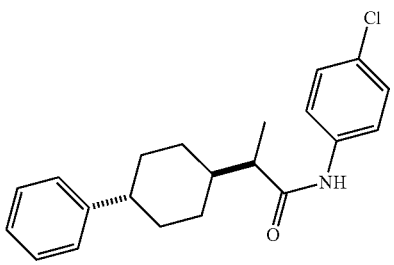

Further elution from the column in the previous example afforded the desired product as a white solid and the second eluting isomer. $^1$H NMR (400 MHz; CDCl$_3$): δ 7.53-7.49 (m, 2H), 7.31-7.27 (m, 4H), 7.22-7.16 (m, 4H), 2.47 (tt, J=12.1, 3.0 Hz, 1H), 2.11 (quintet, J=7.3 Hz, 1H), 2.05-1.88 (m, 4H), 1.74-1.64 (m, 1H), 1.56-1.45 (m, 2H), 1.26 (d, J=6.9 Hz, 3H), 1.24-1.11 (m, 2H). m/z 342.3 (M+H)$^+$.

Example 212

N-(4-Chlorophenyl)-2-(4-fluoro-4-phenylcyclohexyl)acetamide

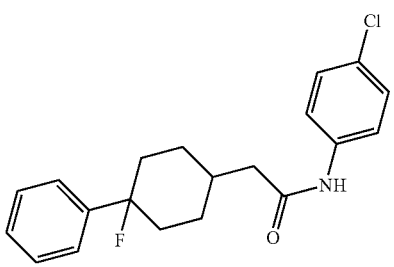 [SMILES: O=C(CC1CCC(F)(c2ccccc2)CC1)Nc1ccc(Cl)cc1]

Prepared in three steps from ethyl 2-(4-cyclohexanone) acetate. N-(4-chlorophenyl)-2-(4-cyclohexanone)acetamide was prepared by General Procedure G using ethyl 2-(4-cyclohexanone)acetate and 4-chloroaniline. To a stirred solution of N-(4-chlorophenyl)-2-(4-cyclohexanone)acetamide was added phenyl magnesium bromide to form N-(4-chlorophenyl)-2-(4-(phenyl)-4'-(hydroxy)cyclohexyl)acetamide. The tertiary alcohol was treated with diaminosulfur trifluoride then mCPBA to afford the desired product as a single diastereomer. $^1$H NMR (400 MHz, CDCl$_3$) δ 7.56-7.11 (m, 9H), 2.48-2.29 (m, 2H), 2.29-2.00 (m, 3H), 2.00-1.86 (m, 1H), 1.86-1.72 (m, 2H), 1.72-1.39 (m, 3H).

Example 213 cis-N-(3-Chlorophenyl)-2-((1,4)-4-(cyclohexyl)cyclohexyl)acetamide

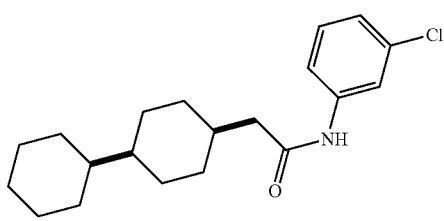

Preparation 213A: Ethyl 2-([1,1'-bi(cyclohexan)]-4-yl)acetate

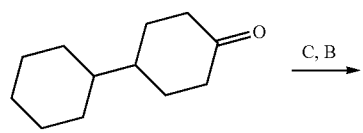

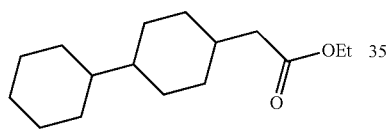

Prepared with General Procedure C employing [1,1'-bi(cyclohexan)]-4-one (1.80 g, 10.0 mmol), triethyl phosphonoacetate (2.47 g, 11 mmol), and NaO$^t$Bu (1.06 g, 11 mmol) in THF (40 mL). The resulting crude reaction mixture was purified using silica gel chromatography (0% to 5% EtOAc in hexanes) to afford the desired product as an oil. The unsaturated ester (2.50 g, 10 mmol) was reduced with General Procedure B employing Pd/C (250 mg, 10 wt. % Pd) in MeOH (10 mL). The crude ester was used directly after filtration through silica with Et$_2$O.

Example 213: cis-N-(3-Chlorophenyl)-2-((1,4)-4-(cyclohexyl)cyclohexyl)acetamide

Prepared with General Procedure G employing Preparation 213A (252 mg, 1.0 mmol), 3-chloroaniline (255 mg, 2.0 mmol), $^i$PrMgCl (1.0 mL, 2.0 mmol) in THF (5.0 mL). Purified using silica gel chromatography (0% to 15% EtOAc in hexanes) to afford the desired product as a white solid. $^1$H NMR (400 MHz; CDCl$_3$): δ 7.65 (t, J=1.7 Hz, 1H), 7.36-7.33 (m, 1H), 7.23 (t, J=8.1 Hz, 1H), 7.11 (s, 1H), 7.08-7.06 (m, 1H), 2.33 (d, J=7.5 Hz, 2H), 2.22-2.15 (m, 1H), 1.76-1.69 (m, 4H), 1.66-1.61 (m, 1H), 1.57-1.35 (m, 10H), 1.26-1.09 (m, 6H), 0.93-0.83 (m, 2H). m/z 334.2 (M+H)$^+$.

Example 215

2-cis((1,4)-[1,1'-Bi(cyclohexan)]-4-yl)-N-(3,4-difluorophenyl)acetamide

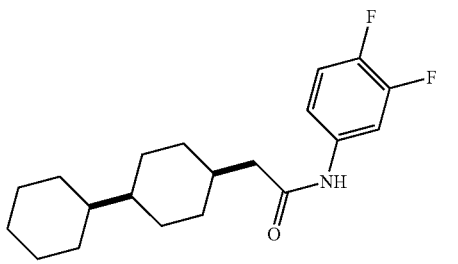

Prepared with General Procedure G employing ethyl 2-([1,1'-bi(cyclohexan)]-4-yl)acetate (252 mg, 1.0 mmol), 3,4-difluoroaniline (258 mg, 2.0 mmol), $^i$PrMgCl (1.0 mL, 2.0 mmol) in THF (5.0 mL). Purified using silica gel chromatography (0% to 15% EtOAc in hexanes) to afford the desired product as a white solid. $^1$H NMR (400 MHz; CDCl$_3$): δ 7.66-7.61 (m, 1H), 7.12-7.03 (m, 3H), 2.32 (d, J=7.5 Hz, 2H), 2.20-2.16 (m, 1H), 1.73 (dd, J=12.4, 2.9 Hz, 4H), 1.68-1.60 (m, 2H), 1.42-1.37 (m, 8H), 1.26-1.06 (m, 5H), 0.93-0.84 (m, 2H). m/z 336.3 (M+H)$^+$.

Example 216 cis-N-(4-Chlorophenyl)-2-((1,4)-4-(cyclohexyl)cyclohexyl)acetamide

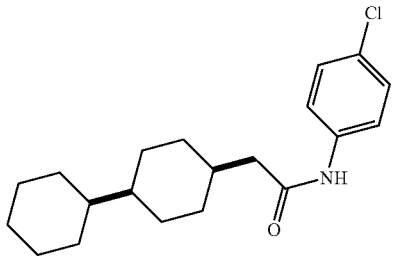

Prepared with General Procedure G employing ethyl 2-([1,1'-bi(cyclohexan)]-4-yl)acetate (252 mg, 1.0 mmol), 4-chloroaniline (255 mg, 2.0 mmol), $^i$PrMgCl (1.0 mL, 2.0 mmol, 2 M/THF) in THF (5 mL). Purified using silica gel chromatography (0% to 15% EtOAc in hexanes) to afford the desired product as a white solid. $^1$H NMR (400 MHz; CDCl$_3$): δ 7.48-7.44 (m, 2H), 7.31-7.28 (m, 2H), 7.07 (s, 1H), 2.32 (d, J=7.5 Hz, 2H), 2.20-2.17 (m, 1H), 1.75-1.72 (m, 4H), 1.66-1.59 (m, 1H), 1.47-1.35 (m, 8H), 1.21-1.13 (m, 5H), 0.93-0.84 (m, 2H). m/z 334.1 (M+H)$^+$.

Example 217

Ethyl 2-(4-(benzo[d][1,3]dioxol-5-yl)cyclohex-3-en-1-yl)acetate

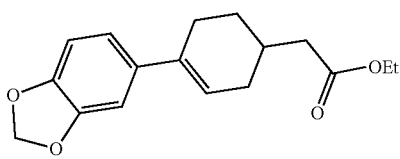 [SMILES: CCOC(=O)CC1CC=C(c2ccc3c(c2)OCO3)CC1]

Prepared using General Procedure A employing benzo[d][1,3]dioxol-5-ylboronic acid (0.76 g, 4.6 mmol) and ethyl 2-(4-(((trifluoromethyl)sulfonyl)oxy)cyclohex-3-en-1-yl)acetate (1.2 g, 3.8 mmol). Purified using silica gel chromatography (0% to 30% EtOAc in hexanes) to afford the desired product (1.02 g, 94%). $^1$H NMR (400 MHz; CDCl$_3$): δ 6.88 (d, J=1.8 Hz, 1H), 6.85-6.80 (m, 1H), 6.77-6.63 (m, 1H), 6.00-5.81 (m, 3H), 4.15 (q, J=7.2 Hz, 2H), 2.45-2.34 (m, 3H), 2.31 (d, J=7.0 Hz, 2H), 2.38-2.15 (m, 1H), 1.96-1.75 (m, 2H), 1.50-1.39 (m, 1H), 1.27 (t, J=7.2 Hz, 3H).

Example 218

Ethyl 2-(4-(benzo[d][1,3]dioxol-5-yl)cyclohexyl)acetate

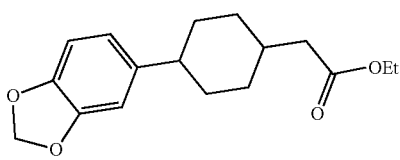 [SMILES: CCOC(=O)CC1CCC(c2ccc3c(c2)OCO3)CC1]

Prepared using General Procedure B employing ethyl 2-(4-(benzo[d][1,3]dioxol-5-yl)cyclohex-3-en-1-yl)acetate (1.02 g, 3.54 mmol) and wet Pd/C (3.75 g, 3.54 mmol) in acetic acid. The desired product was afforded in a 1.5:1 diastereomeric mixture. $^1$H NMR (400 MHz; CDCl$_3$): δ 6.79-6.60 (m, 4.6H), 5.91 (s, 3H), 4.14 (q, J=7.2 Hz, 3.5H), 2.58-2.44 (m, 1H), 2.44-2.40 (m, 2.4H), 2.35-2.26 (m, 1.4H), 2.22 (d, J=6.8 Hz, 1.5H), 1.87 (d, J=11.1 Hz, 3.7H), 1.76-1.55 (m, 7.8H), 1.55-1.35 (m, 1.6H), 1.34-1.20 (m, 5.3H), 1.21-1.05 (m, 1.2H).

Example 219 cis-2-((1,4)-4-(Benzo[d][1,3]dioxol-5-yl)cyclohexyl)-N-(4-chlorophenyl)acetamide

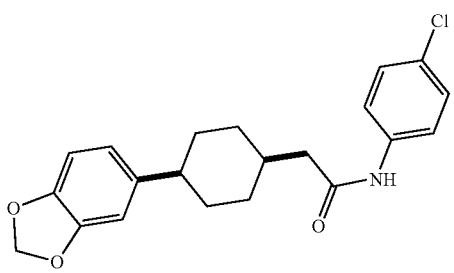

Prepared using General Procedure G employing ethyl 2-(4-(benzo[d][1,3]dioxol-5-yl)cyclohexyl)acetate (300 mg, 1.03 mmol) and 4-chloroaniline (263 mg, 2.06 mmol). Purified using silica gel chromatography (20% EtOAc in hexanes) to afford the first eluting isomer as the desired product. $^1$H NMR (400 MHz; CDCl$_3$): δ 7.48 (d, J=8.8 Hz, 2H), 7.39 (br s, 1H), 7.27 (d, J=8.8 Hz, 2H), 6.76-6.67 (m, 3H), 5.92 (s, 2H), 2.58-2.51 (m, 1H), 2.46-2.34 (m, 3H), 1.78-1.56 (m, 8H); m/z 372.2 (M+H)$^+$.

Example 220 trans-2-((1,4)-4-(Benzo[d][1,3]dioxol-5-yl)cyclohexyl)-N-(4-chlorophenyl)acetamide

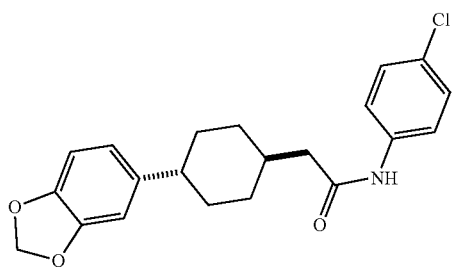

Further elution from the column in the previous example afforded the desired product as the second eluting isomer. $^1$H NMR (400 MHz; CDCl$_3$): δ 7.49 (d, J=8.8 Hz, 2H), 7.33-7.20 (m, 3H), 6.75-6.63 (m, 3H), 5.92 (s, 2H), 2.45-2.35 (m, 1H), 2.27 (d, J=6.6 Hz, 2H), 2.00-1.84 (m, 5H), 1.55-1.41 (m, 2H), 1.35-1.12 (m, 2H); m/z 372.2 (M+H)$^+$.

Example 221 cis-2-((1,4)-4-(Benzo[d][1,3]dioxol-5-yl)cyclohexyl)-N-(4-cyanophenyl)acetamide

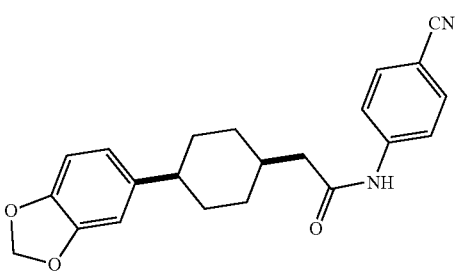

Prepared using General Procedure G employing ethyl 2-(4-(benzo[d][1,3]dioxol-5-yl)cyclohexyl)acetate (300 mg, 1.03 mmol) and 4-cyanoaniline (243 mg, 2.06 mmol). Purified using silica gel chromatography (20% EtOAc in hexanes) to afford the first eluting isomer as the desired product. $^1$H NMR (400 MHz; CDCl$_3$): δ 7.70-7.67 (m, 2H), 7.62-7.58 (m, 3H), 6.75-6.73 (m, 2H), 6.69-6.67 (m, 1H), 5.92 (s, 2H), 2.57-2.55 (m, 1H), 2.53-2.48 (m, 2H), 2.43-2.40 (m, 1H), 1.77-1.61 (m, 6H), 1.35-1.21 (m, 2H); m/z 438.3 (M+H)$^+$.

Example 222 trans-2-((1,4)-4-(Benzo[d][1,3]dioxol-5-yl)cyclohexyl)-N-(4-cyanophenyl)acetamide

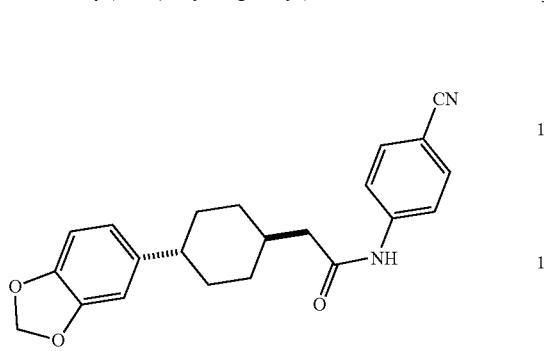

Further elution from the column in the previous example afforded the desired product as the second eluting isomer. $^1$H NMR (400 MHz; CDCl$_3$): δ 7.72-7.66 (m, 3H), 7.62-7.58 (m, 2H), 6.74-6.67 (m, 2H), 6.65-6.62 (m, 1H), 5.91 (s, 2H), 2.43-2.39 (m, 1H), 2.37-2.30 (m, 2H), 1.99-1.83 (m, 5H), 1.49-1.41 (m, 2H), 1.34-1.15 (m, 2H); m/z 438.3 (M+H)$^+$.

Example 223 cis-2-((1,4)-4-(Benzo[d][1,3]dioxol-5-yl)cyclohexyl)-N-(4-fluorophenyl)acetamide

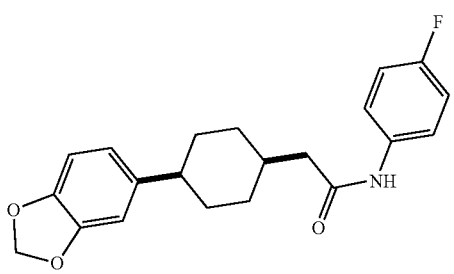

Prepared using General Procedure G employing ethyl 2-(4-(benzo[d][1,3]dioxol-5-yl)cyclohexyl)acetate (300 mg, 1.03 mmol) and 4-fluoroaniline (0.195 mL, 2.06 mmol). Purified using silica gel chromatography (20% EtOAc in hexanes) to afford the first eluting isomer as the desired product. $^1$H NMR (400 MHz; CDCl$_3$): δ 7.79 (s, 1H), 7.48 (dd, J=4.9, 9.0 Hz, 2H), 6.97 (t, J=8.7 Hz, 2H), 6.74 (d, J=5.5 Hz, 2H), 6.68-6.65 (m, 1H), 5.92 (s, 2H), 2.56-2.50 (m, 1H), 2.45-2.36 (m, 3H), 1.72-1.57 (m, 8H); m/z 356.2 (M+H)$^+$.

Example 224 trans-2-((1,4)-4-(Benzo[d][1,3]dioxol-5-yl)cyclohexyl)-N-(4-fluorophenyl)acetamide

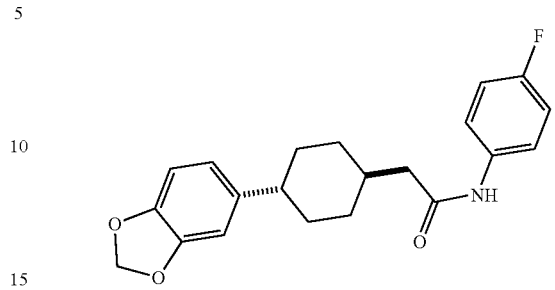

Further elution from the column in the previous example afforded the desired product as the second eluting isomer. $^1$H NMR (400 MHz; CDCl$_3$): δ 7.52-7.46 (m, 2H), 7.37 (br s, 1H), 7.05-6.97 (m, 2H), 6.73-6.63 (m, 3H), 5.91 (s, 2H), 2.45-2.36 (m, 1H), 2.25 (d, J=7.0 Hz, 2H), 1.98-1.86 (m, 5H), 1.53-1.01 (m, 2H), 1.23-1.13 (m, 2H); m/z 356.2 (M+H)$^+$.

Example 225

Ethyl 2-(4-(2,2-difluorobenzo[d][1,3]dioxol-5-yl)cyclohex-3-en-1-yl)acetate

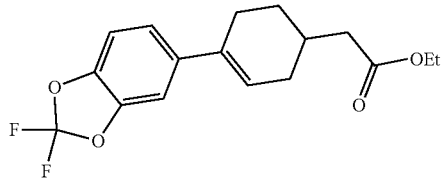 [SMILES: CCOC(=O)CC1CC=C(c2ccc3c(c2)OC(F)(F)O3)CC1]

Prepared using General Procedure A employing (2,2-difluorobenzo[d][1,3]dioxol-5-yl)boronic acid (1.00 mg, 4.95 mmol) and (4-(((trifluoromethyl)sulfonyl)oxy)cyclohex-3-en-1-yl)acetate (1.305 g, 4.13 mmol). Purified using silica gel chromatography (0% to 30% EtOAc in hexanes) to afford the desired product as a clear, colorless oil (1.34 g, 99%). $^1$H NMR (400 MHz; CDCl$_3$): δ 7.36-7.29 (m, 1H), 7.10-7.02 (m, 2H), 7.02-6.92 (m, 1H), 5.99 (t, J=3.1 Hz, 1H), 4.22-4.05 (m, 2H), 2.47-2.36 (m, 2H), 2.32 (d, J=7.2 Hz, 2H), 2.23-2.07 (m, 1H), 2.01-1.85 (m, 2H), 1.53-1.35 (m, 1H), 1.33-1.22 (m, 3H); m/z 325.2 (M+H)$^+$.

Example 226

Ethyl 2-(4-(2,2-difluorobenzo[d][1,3]dioxol-5-yl)cyclohexyl)acetate

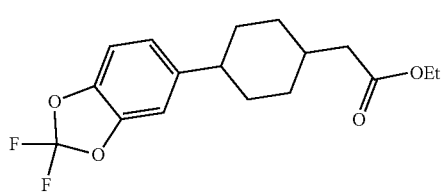 [SMILES: CCOC(=O)CC1CCC(c2ccc3c(c2)OC(F)(F)O3)CC1]

Prepared using General Procedure B employing ethyl 2-(4-(2,2-difluorobenzo[d][1,3]dioxol-5-yl)cyclohex-3-en-1-yl)acetate (1.34 g, 4.13 mmol) and wet Pd/C (4.4 g, 4.13 mmol) in acetic acid. The desired product was afforded in a 1.5:1 diastereomeric mixture as a light yellow oil (1.01 g, 75% yield). $^1$H NMR (400 MHz; CDCl$_3$): δ 6.97-6.86 (m, 7.5H), 4.17-4.10 (m, 5H), 2.60-2.53 (m, 1.2H), 2.49-2.44 (m, 1.4H), 2.43-2.39 (m, 2H), 1.93-1.79 (m, 5.4H), 1.73-1.54 (m, 12H), 1.50-1.39 (m, 2H), 1.26 (t, =7.1 Hz, 8H), 1.20-1.05 (m, 2H).

Example 227 cis-N-(4-Chlorophenyl)-2-((1,4)-4-(2,2-difluorobenzo[d][1,3]dioxol-5-yl)cyclohexyl)acetamide

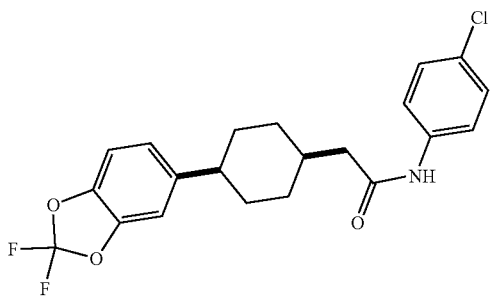

Prepared using General Procedure G employing ethyl 2-(4-(2,2-difluorobenzo[d][1,3]dioxol-5-yl)cyclohexyl)acetate (0.33 g, 1.0 mmol) and 4-chloroaniline (0.258 g, 2.0 mmol). Purified using silica gel chromatography (0% to 25% EtOAc in hexanes) to afford the first eluting isomer as the desired product. $^1$H NMR (400 MHz; CDCl$_3$): δ 7.48 (d, J=8.6 Hz, 2H), 7.33 (br s, 1H), 7.30-7.21 (m, 2H), 6.98-6.91 (m, 3H), 2.66-2.59 (m, 1H), 2.49-2.37 (m, 3H), 1.83-1.59 (m, 8H).

Example 228 trans-N-(4-Chlorophenyl)-2-((1,4)-4-(2,2-difluorobenzo[d][1,3]dioxol-5-yl)cyclohexyl)acetamide

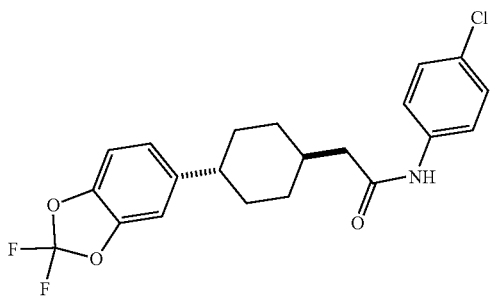

Further elution from the column in the previous example afforded the desired product as the second eluting isomer. $^1$H NMR (400 MHz; CDCl$_3$): δ 7.50 (d, J=8.6 Hz, 3H), 7.28 (d, J=9.2 Hz, 2H), 7.01-6.92 (m, 1H), 6.90-6.86 (m, 2H), 2.44 (d, J=8.8 Hz, 1H), 2.27 (d, J=6.6 Hz, 2H), 2.02-1.82 (m, 5H), 1.53-1.37 (m, 2H), 1.23-1.12 (m, 2H).

Example 229 cis-N-(4-Cyanophenyl)-2-((1,4)-4-(2,2-difluorobenzo[d][1,3]dioxol-5-yl)cyclohexyl)acetamide

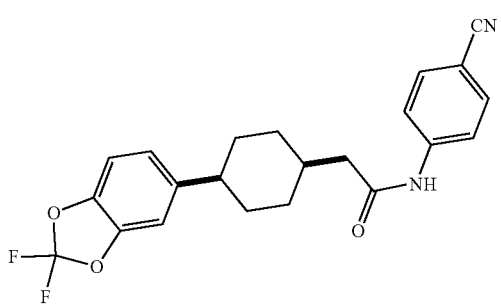

Prepared using General Procedure G employing ethyl 2-(4-(2,2-difluorobenzo[d][1,3]dioxol-5-yl)cyclohexyl)acetate (0.33 g, 1.0 mmol) and 4-cyanoaniline (0.240 g, 2.0 mmol). Purified using silica gel chromatography (0% to 25% EtOAc in hexanes) to afford the first eluting isomer as the desired product. $^1$H NMR (400 MHz; CDCl$_3$): δ 8.48 (s, 1H), 7.74 (d, J=8.8 Hz, 2H), 7.55 (d, J=8.6 Hz, 2H), 6.98-6.85 (m, 3H), 2.57 (br. s., 1H), 2.53 (d, J=7.6 Hz, 2H), 2.47-2.40 (m, 1H), 1.76-1.59 (m, 8H).

Example 230 trans-N-(4-Cyanophenyl)-2-((1,4)-4-(2,2-difluorobenzo[d][1,3]dioxol-5-yl)cyclohexyl)acetamide

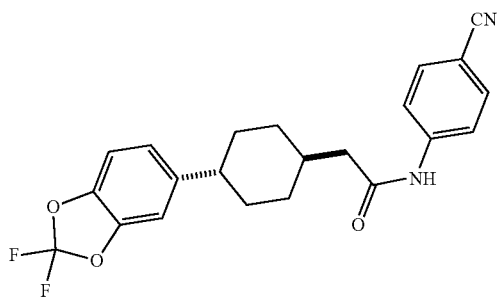

Further elution from the column in the previous example afforded the desired product as the second eluting isomer. $^1$H NMR (400 MHz; CDCl$_3$): δ 7.92 (s, 1H), 7.73 (d, J=8.4 Hz, 2H), 7.60 (d, J=8.6 Hz, 2H), 6.95-6.93 (m, 1H), 6.89-6.85 (m, 2H), 2.49-2.42 (m, 1H), 2.33 (d, J=6.6 Hz, 2H), 1.99-1.85 (m, 5H), 1.52-1.38 (m, 2H), 1.19 (q, J=12.6 Hz, 2H).

Example 231 cis-N-(4-Fluorophenyl)-2-((1,4)-4-(2,2-difluorobenzo[d][1,3]dioxol-5-yl)cyclohexyl)acetamide

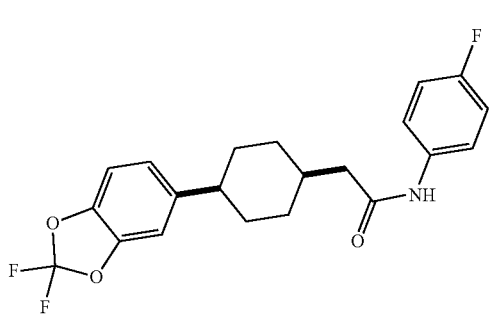

Prepared using General Procedure G employing ethyl 2-(4-(2,2-difluorobenzo[d][1,3]dioxol-5-yl)cyclohexyl)acetate (0.33 g, 1.0 mmol) and 4-fluoroaniline (0.191 mL, 2.0 mmol). Purified using silica gel chromatography (0% to 25% EtOAc in hexanes) to afford the first eluting isomer as the desired product. $^1$H NMR (400 MHz; CDCl$_3$): δ 7.55 (br s, 1H), 7.52-7.45 (m, 2H), 7.01-6.90 (m, 5H), 2.64-2.58 (m, 1H), 2.46-2.38 (m, 3H), 1.75-1.53 (m, 8H).

Example 232 trans-N-(4-Fluorophenyl)-2-((1,4)-4-(2,2-difluorobenzo[d][1,3]dioxol-5-yl)cyclohexyl)acetamide

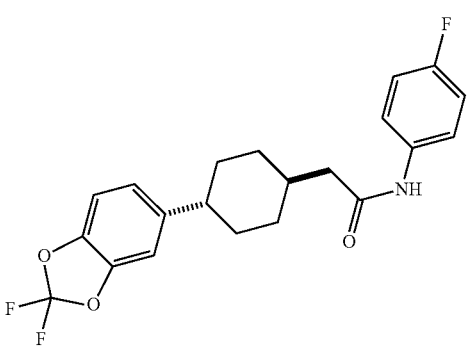

Further elution from the column in the previous example afforded the desired product as the second eluting isomer. $^1$H NMR (400 MHz; CDCl$_3$): δ 7.49 (dd, J=4.8, 9.1 Hz, 2H), 7.37 (s, 1H), 7.01 (t, J=8.6 Hz, 2H), 6.96-6.94 (m, 1H), 6.90-6.86 (m, 2H), 2.51-2.43 (m, 1H), 2.27 (d, J=6.6 Hz, 2H), 2.09-1.86 (m, 5H), 1.45 (q, 13.0 Hz, 2H), 1.25-1.13 (m, 2H).

Example 233

2-Chloro-N-(4-chlorophenyl)acetamide

Prepared with General Procedure J employing chloroacetyl chloride (2.82 g, 25 mmol), 4-chloroaniline (3.06 g, 24 mmol), saturated NaOAc (12.5 mL), water (12.5 mL) in HOAc (15 mL). Product obtained as a white solid.

Example 234

2-Chloro-N-(4-fluorophenyl)acetamide

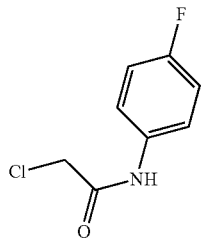 [SMILES: O=C(CCl)Nc1ccc(F)cc1]

Prepared with General Procedure J employing chloroacetyl chloride (2.82 g, 25 mmol), 4-fluoroaniline (2.67 g, 24 mmol), saturated NaOAc (12.5 mL), water (12.5 mL) in HOAc (15 mL). Product obtained as a white solid.

Example 235

2-Chloro-N-(4-cyanophenyl)acetamide

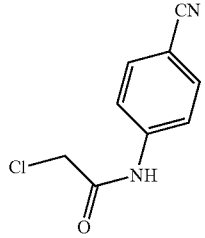 [SMILES: N#Cc1ccc(NC(=O)CCl)cc1]

Prepared with General Procedure J employing chloroacetyl chloride (2.82 g, 25 mmol), 4-cyanoaniline (2.67 g, 24 mmol), saturated NaOAc (12.5 mL), water (12.5 mL) in HOAc (15 mL). Product obtained as a white solid.

Example 236

N-(4-Chlorophenyl)-2-(4-(4-methoxyphenyl)piperidin-1-yl)acetamide

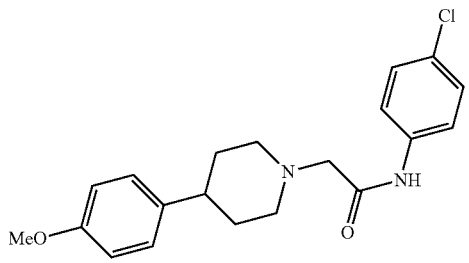

A mixture of 2-chloro-N-(4-chlorophenyl)acetamide (20 mg, 0.1 mmol), 4-(4-methoxyphenyl)piperidine (25 mg, 0.11 mmol), and $^i$Pr$_2$NEt (65 mg, 0.5 mmol) in PhMe (200 μL) was heated to 100° C., upon which the reaction mixture was diluted with EtOAc (5 mL). The resulting slurry was filtered through a small plug of silica washing with additional EtOAc (10 mL). The filtrate was concentrated under reduced pressure and purified using silica gel chromatography (15% to 40% EtOAc in hexanes) to afford the desired product as an oil. $^1$H NMR (400 MHz; CDCl$_3$): δ 9.26 (s, 1H), 7.58-7.54 (m, 2H), 7.32-7.29 (m, 2H), 7.20-7.16 (m, 2H), 6.90-6.86 (m, 2H), 3.81 (s, 3H), 3.16 (s, 2H), 3.03-3.01 (m, 2H), 2.56-2.48 (m, 1H), 2.40 (td, J=11.8, 2.4 Hz, 2H), 1.93-1.89 (m, 2H), 1.83-1.73 (m, 2H). m/z 359.2 (M+H)$^+$.

Example 237

N-(4-Cyanophenyl)-2-(4-(4-methoxyphenyl)piperidin-1-yl)acetamide

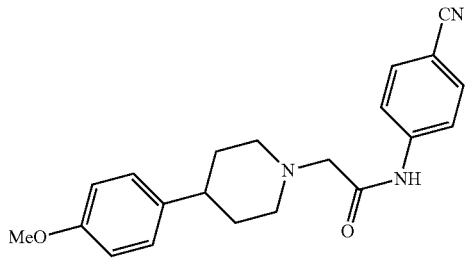 [SMILES: COc1ccc(C2CCN(CC(=O)Nc3ccc(C#N)cc3)CC2)cc1]

A mixture of 2-chloro-N-(4-cyanophenyl)acetamide (19 mg, 0.1 mmol), 4-(4-methoxyphenyl)piperidine (25 mg, 0.11 mmol), and $^i$Pr$_2$NEt (65 mg, 0.5 mmol) in PhMe (200 μL) was heated to 100° C., upon which the reaction mixture was diluted with EtOAc (5 mL). The resulting slurry was filtered through a small plug of silica washing with additional EtOAc (10 mL). The filtrate was concentrated under reduced pressure and purified using silica gel chromatography (15% to 40% EtOAc in hexanes) to afford the desired product as an oil. $^1$H NMR (400 MHz; CDCl$_3$): δ 9.22 (s, 1H), 7.59-7.54 (m, 2H), 7.20-7.16 (m, 2H), 7.07-7.01 (m, 2H), 6.90-6.86 (m, 2H), 3.81 (s, 3H), 3.16 (s, 2H), 3.03 (dd, 0.1=9.4, 2.1 Hz, 2H), 2.52 (tt, 0.1=12.0, 3.8 Hz, 1H), 2.40 (td, 0.1=11.8, 2.4 Hz, 2H), 1.93-1.89 (m, 2H), 1.80 (td, J=12.4, 3.6 Hz, 2H). m/z 350.2 (M+H)$^+$.

Example 238

N-(4-Chlorophenyl)-2-(4-phenylpiperidin-1-yl)acetamide

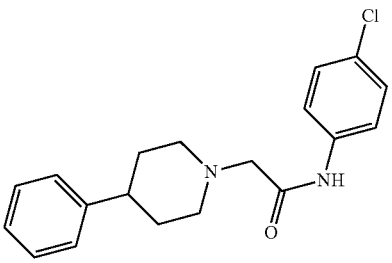 [SMILES: O=C(CN1CCC(c2ccccc2)CC1)Nc1ccc(Cl)cc1]

A mixture of 2-chloro-N-(4-chlorophenyl)acetamide (204 mg, 1.0 mmol), and 4-phenylpiperidine (323 mg, 2.0 mmol) in PhMe (1 mL) were heated to 100° C. Upon cooling to rt, the reaction mixture was diluted with NaOH solution (1M, 5 mL) and EtOAc (5 mL). The layers were separated, and the organic layer was extracted with EtOAc (3×25 mL). The combined organic extracts were dried over anhydrous MgSO$_4$, filtered, and concentrated under reduced pressure. The crude reaction mixture was purified using silica gel chromatography (10% to 40% EtOAc in hexanes) to afford the desired product as a white solid (308 mg, 94%). $^1$H NMR (400 MHz; CDCl$_3$): δ 9.26 (s, 1H), 7.58-7.54 (m, 2H), 7.36-7.29 (m, 3H), 7.27-7.22 (m, 4H), 3.17 (s, 2H), 3.04 (dd, J=9.6, 2.0 Hz, 2H), 2.57 (tt, J=12.0, 3.8 Hz, 1H), 2.42 (td, J=11.8, 2.5 Hz, 2H), 1.96-1.92 (m, 2H), 1.88-1.77 (m, 2H). m/z 329.2 (M+H)$^+$.

Example 239

N-(4-Cyanophenyl)-2-(4-phenylpiperidin-1-yl)acetamide

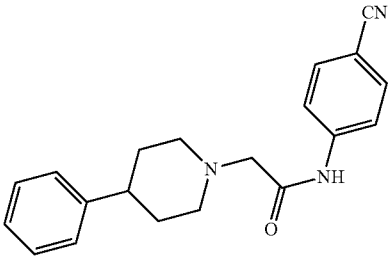 [SMILES: N#Cc1ccc(NC(=O)CN2CCC(c3ccccc3)CC2)cc1]

A mixture of 2-chloro-N-(4-cyanophenyl)acetamide (195 mg, 1.0 mmol), and 4-phenylpiperidine (323 mg, 2.0 mmol) in PhMe (1 mL) were heated to 100° C. Upon cooling to rt, the reaction mixture was diluted with NaOH solution (1M, 5 mL) and EtOAc (5 mL). The layers were separated, and the organic layer was extracted with EtOAc (3×25 mL). The combined organic extracts were dried over anhydrous MgSO$_4$, filtered, and concentrated under reduced pressure. Purified using silica gel chromatography (10% to 40% EtOAc in hexanes) to afford the desired product as a white solid (306 mg, 96%). $^1$H NMR (400 MHz; CDCl$_3$): δ 9.51 (s, 1H), 7.76-7.72 (m, 2H), 7.65-7.62 (m, 2H), 7.37-7.32 (m, 2H), 7.27-7.22 (m, 3H), 3.20 (s, 2H), 3.05-3.02 (m, 2H), 2.58 (tt, J=12.1, 3.8 Hz, 1H), 2.44 (td, J=11.9, 2.5 Hz, 2H), 1.98-1.93 (m, 2H), 1.88-1.78 (m, 2H). m/z 320.2 (M+H)+.

Example 240

N-(4-Fluorophenyl)-2-(4-phenylpiperidin-1-yl)acetamide

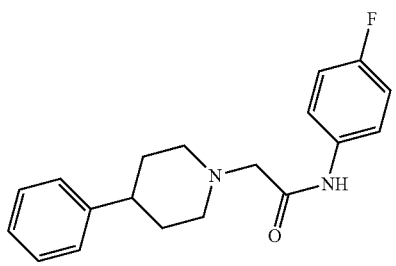 [SMILES: O=C(CN1CCC(c2ccccc2)CC1)Nc1ccc(F)cc1]

A mixture of 2-chloro-N-(4-fluorophenyl)acetamide (188 mg, 1.0 mmol), and 4-phenylpiperidine (323 mg, 2.0 mmol) in PhMe (1 mL) were heated to 100° C. Upon cooling to rt, the reaction mixture was diluted with NaOH solution (1M, 5 mL) and EtOAc (5 mL). The layers were separated, and the organic layer was extracted with EtOAc (3×25 mL). The combined organic extracts were dried over anhydrous MgSO4, filtered, and concentrated under reduced pressure. The crude reaction mixture was purified using silica gel chromatography. (10% to 40% EtOAc in hexanes) to afford the desired product as a white solid. ¹H NMR (400 MHz; CDCl3): δ 9.22 (s, 1H), 7.59-7.54 (m, 2H), 7.36-7.32 (m, 2H), 7.27-7.22 (m, 3H), 7.07-7.01 (m, 2H), 3.17 (s, 2H), 3.06-3.02 (m, 2H), 2.57 (tt, J=12.0, 3.8 Hz, 1H), 2.42 (td, J=11.8, 2.6 Hz, 2H), 1.96-1.92 (m, 2H), 1.88-1.78 (m, 2H). m/z 313.2 (M+H)+.

Example 241 cis-N-(3,4-Difluorophenyl)-2-(4-propylcyclohexyl)acetamide

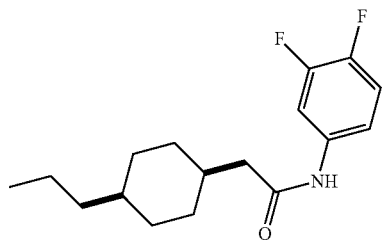

Intermediate 241A:

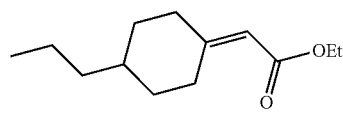

Ethyl 2-(4-propylcyclohexylidene)acetate: Sodium tert-butoxide (1.50 g, 15.7 mmol) was dissolved in THF (19 mL) and cooled to 0° C. Triethylphosphonoacetate (3.10 mL, 15.7 mmol) was added dropwise, and the solution was allowed to warm to rt. The reaction was cooled to 0° C. and a THF (19 mL) solution of 4-propyl-cyclohexanone (2.00 g, 14.3 mmol) was added dropwise. The reaction was warmed to rt and stirred for 1 h, after which the reaction was concentrated under reduced pressure. The residue was dissolved in EtOAc (50 mL), and the organic layer was washed with sat. aqueous NaHCO3 (50 mL). The organic layer was dried over anhydrous sodium sulfate, and the crude α,β-unsaturated ester was utilized without further purification.

Intermediate 241B:

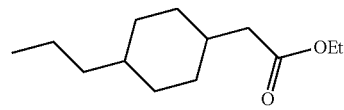

Ethyl 2-(4-propylcyclohexyl)acetate: To a stirred solution of the crude α,β-unsaturated ester (2.0 g, 14 mmol) in ethanol (30 mL) was added 10% Pd/C Degussa type (1.5 g). The resulting mixture was bubbled with hydrogen for 5 min after which an atmosphere of hydrogen was maintained with a balloon. The reaction was stirred for 15 h, after which time the hydrogen atmosphere was removed by bubbling with argon, and the reaction was filtered through a pad of CELITE®. The CELITE® was washed with EtOAc and the filtrate was concentrated under reduced pressure. The crude residue was purified using silica gel chromatography (0% to 50% EtOAc in hexanes) to afford the desired product as a clear oil (2.6 g, 86% two steps).

Example 241: cis-N-(3,4-Difluorophenyl)-2-(4-propylcyclohexyl)acetamide

Prepared using General Procedure G employing ethyl 2-(4-propylcyclohexyl) acetate and 3,4-difluoroaniline. Purification by silica gel chromatography (0% to 40% EtOAc in hexanes) afforded the desired product as the first eluting isomer. LC/MS t, 3.42 min, m/z 296.2 (M+H+).

Example 242 trans-N-(3,4-Difluorophenyl)-2-(4-propylcyclohexyl)acetamide

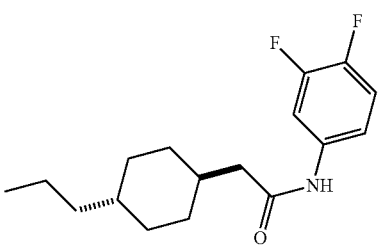

Further elution from the column in the previous example afforded the desired product as the second eluting isomer. LC/MS t, 3.37 min, m/z 296.3 (M+H+).

Example 243

Methyl 4-(2-((3-chlorophenyl)amino)-2-oxoethyl)cyclohexane-1-carboxylate

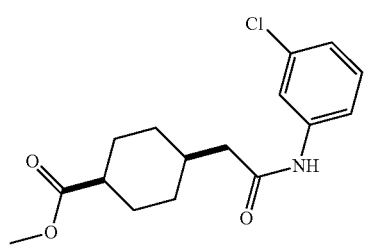

Prepared using General Procedures C and G, as well as hydrogenation and esterification. General Procedure C employed 4-oxocyclohexane-1-carboxylic acid and 2.1 equivalents of sodium tert-butoxide. The product was hydrogenated using the following procedure: To a solution of 4-(2-methoxy-2-oxoethylidene)cyclohexane-1-carboxylic acid (5.72 g, 28.9 mmol) in methanol was added $PtO_2$ (327 mg, 1.44 mmol). The reaction solution was sparged with a balloon of $H_2$ gas and stirred overnight under an atmosphere of hydrogen for 2 days. The reaction mixture was filtered through CELITE® and concentrated under reduced pressure afforded the desired product as a waxy, black solid (4.85 g, 84%). This product was subjected to General Procedure G employing 3-chloroaniline, which was converted to the methyl ester using the following procedure: To a solution of 4-(2-((3-chlorophenyl)amino)-2-oxoethyl)cyclohexane-1-carboxylic acid (1.23 g, 4.16 mmol) in methanol (25 mL) was added 3 drops of concentrated $H_2SO_4$. This solution was refluxed for 16 h before cooling to rt and treating with sat. aqueous $NaHCO_3$ to pH~8. The solution was extracted with EtOAc (2×30 mL), washed with brine, dried over anhydrous $MgSO_4$, filtered, and concentrated under reduced pressure. The crude residue was purified by silica gel chromatography (15% to 25% EtOAc in hexanes) to afford the desired product as an off-white solid (467 mg, 39%). $^1$H NMR (400 MHz; $CDCl_3$): δ 7.65 (t, J=1.8 Hz, 1H), 7.47-7.28 (m, 2H), 7.21 (t, J=8.1 Hz, 1H), 7.06 (dd, J=8.0, 1.0 Hz, 1H), 3.68 (s, 3H), 2.58 (m, 1H), 2.25 (d, J=7.3 Hz, 2H), 2.11-1.89 (m, 3H), 1.72-1.52 (m, 4H), 1.37-1.26 (m, 2H); m/z 310.1 (M+H$^+$).

Example 244 cis-N-(4-Chloro-phenyl)-2-(4-(tert-butyl)cyclohexyl)acetamide

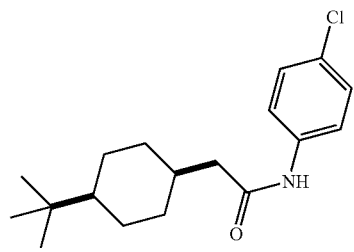

Prepared using General Procedures C, D, and G. General Procedure C employed 4-t-butylcyclohexane-1-one. The product was hydrogenated using General Procedure D. Procedure G employed methyl 2-(4-(tert-butyl)cyclohexyl)acetate and 4-chloroaniline. Purification by silica gel chromatography (0% to 20% EtOAc in hexanes) afforded the desired product as the first eluting isomer. $^1$H NMR (400 MHz; $CDCl_3$): δ 7.47 (d, J=8.8 Hz, 2H), 7.27 (d, J=8.8 Hz, 2H), 7.21 (s, 1H), 2.45-2.29 (m, 3H), 1.69 (d, J=13.7 Hz, 2H), 1.61-1.48 (m, 4H), 1.18-0.93 (m, 3H), 0.86 (s, 9H); m/z 308.2 (M+H$^+$).

Example 245 trans-N-(4-Chloro-phenyl)-2-(4-(tert-butyl)cyclohexyl)acetamide

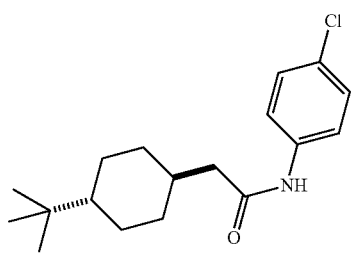

Further elution from the column in the previous example afforded the desired product as the second eluting isomer. $^1$H NMR (400 MHz; $CDCl_3$): δ 7.51-7.41 (m, 2H), 7.31-7.26 (m, 2H), 7.17 (s, 1H), 2.20 (d, J=7.0 Hz, 2H), 1.86 (d, J=9.6 Hz, 2H), 1.77 (d, J=11.5 Hz, 3H), 1.09-0.91 (m, 5H), 0.83 (s, 9H); m/z 308.2 (M+H$^+$).

Example 246 cis-N-(4-Chloro-3-fluorophenyl)-2-(4-(tert-butyl)cyclohexyl)acetamide

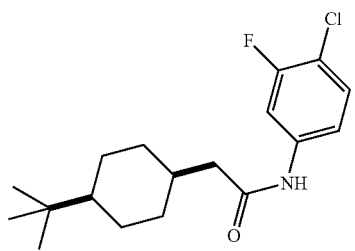

Prepared using General Procedures C, D, and G. General Procedure C employed 4-text-butylcyclohexane-1-one. The product was hydrogenated using General Procedure D. Procedure G employed methyl 2-(4-(tert-butyl)cyclohexyl)acetate and 4-chloro-3-fluoroaniline. Purification by silica gel chromatography (0% to 20% EtOAc in hexanes) afforded the desired product as the first eluting isomer. $^1$H NMR (400 MHz; $CDCl_3$): δ 7.64 (dd, J=11.1, 2.3 Hz, 1H), 7.30 (t, J=8.4 Hz, 1H), 7.13 (s, 1H), 7.10 (ddd, J=8.7, 2.4, 1.2 Hz, 1H), 2.46-2.27 (m, 3H), 1.69 (d, J=13.6 Hz, 2H), 1.63-1.47 (m, 4H), 1.19-0.95 (m, 3H), 0.85 (s, 9H); m/z 326.2 (M+H$^+$).

Example 247 trans-N-(4-Chloro-3-fluorophenyl)-2-(4-(tert-butyl)cyclohexyl)acetamide

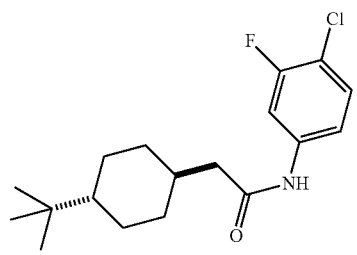

Further elution from the column in the previous example afforded the desired product as the second eluting isomer. ¹H NMR (400 MHz; CDCl₃): δ 7.63 (dd, J=11.0, 2.3 Hz, 1H), 7.28 (t, J=8.3 Hz, 1H), 7.14 (s, 1H), 7.09 (ddd, J=8.7, 2.3, 1.1 Hz, 1H), 2.20 (d, J=6.9 Hz, 2H), 1.86 (d, J=10.6 Hz, 2H), 1.77 (d, J=9.2 Hz, 3H), 1.15-0.86 (m, 5H), 0.83 (s, 9H); m/z 326.2 (M+H⁺).

Example 248

N-(4-Chlorophenyl)-2-(4,4-difluorocyclohexyl)acetamide

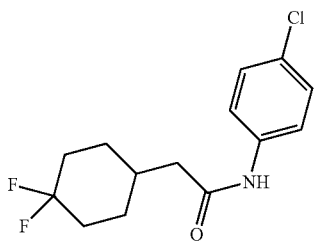 [SMILES: O=C(CC1CCC(F)(F)CC1)Nc1ccc(Cl)cc1]

Prepared using General Procedures C and G. General Procedure C employed 4,4-difluorocyclohexan-1-one. The product was hydrogenated using the following procedure: To a solution of methyl 2-(4,4-difluorocyclohexylidene)acetate (6.22 g, 32.7 mmol) in methanol (110 mL) was added 10% Pd/C Degussa type (700 mg, 10 wt. %). The reaction mixture was sparged with H₂ gas and then stirred under an atmosphere of H₂ for 7 h. The mixture was filtered through CELITE® and concentrated under reduced pressure afforded the desired product as a clear oil. Procedure G employed methyl 2-(4,4-difluorocyclohexyl)acetate and 4-chloroaniline. Purification by silica gel chromatography (0% to 60% EtOAc in hexanes) afforded the desired product. ¹H NMR (400 MHz; CDCl₃): δ 7.50-7.39 (m, 2H), 7.33-7.23 (m, 2H), 7.19 (s, 1H), 2.27 (d, J=7.1 Hz, 2H), 2.18-1.94 (m, 3H), 1.93-1.53 (m, 4H), 1.42-1.23 (m, 2H); m/z 288.1 (M+H⁺).

Example 249 cis-N-(4-Chlorophenyl)-2-(4-(2-hydroxypropan-2-yl)cyclohexyl)acetamide

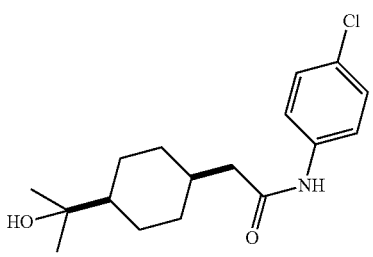

Prepared using General Procedures C, E, and F. General Procedure C employed 4-oxocyclohexane-1-carboxylic acid. The product was hydrogenated using the following procedure: To a solution of 4-(2-methoxy-2-oxoethylidene)cyclohexane-1-carboxylic acid (5.72 g, 28.9 mmol) in methanol was added PtO₂ (327 mg, 1.44 mmol). The reaction solution was sparged with a balloon of H₂ gas and stirred overnight under an atmosphere of H₂ gas for 2 d. The reaction mixture was filtered through a pad of CELITE® and concentrated under reduced pressure to afford the desired product as a waxy, black solid (4.85 g, 84%). This product was subjected to General Procedure G employing 4-chloroaniline. General Procedure F employed 4-(2-((4-chlorophenyl)amino)-2-oxoethyl)cyclohexane-1-carboxylic acid and N,O-dimethylhydroxylamine hydrochloride. The Weinreb amide, 4-(2-((4-chlorophenyl)amino)-2-oxoethyl)-N-methoxy-N-methylcyclohexane-1-carboxamide, was converted to the tertiary alcohol in the following procedure: To a 0° C. solution of 4-(2-((4-chlorophenyl)amino)-2-oxoethyl)-N-methoxy-N-methylcyclohexane-1-carboxamide (240 mg, 0.71 mmol) in THF (3.5 mL) was added methylmagnesium bromide (2.0 M, 0.64 mL, 1.28 mmol). The solution was stirred cold for 2 h before slow quenching with NH₄Cl (3 mL). The mixture was extracted with EtOAc (3×20 mL), washed with brine, dried over anhydrous MgSO₄, filtered, and concentrated under reduced pressure. The crude residue was purified using silica gel chromatography (0% to 50% EtOAc in hexanes) to afford the pure cis-diastereomer as the first eluting product (150 mg, 0.51 mmol). Next, to a solution of cis-2-(4-acetylcyclohexyl)-N-(4-chlorophenyl)acetamide (8.0 mg, 0.26 mmol) in THF (2.0 mL) was added methylmagnesium bromide (2.0 M, 0.64 mL, 1.28 mmol). The solution was stirred for 2 h before quenching with NH₄Cl (3 mL). The mixture was extracted with EtOAc (3×20 mL), washed with brine, dried over anhydrous MgSO₄, filtered, and concentrated under reduced pressure. The crude residue was purified using silica gel chromatography (0% to 60% EtOAc in hexanes) to afford the desired product. ¹H NMR (400 MHz; CDCl₃): δ 7.48 (d, J=8.8 Hz, 2H), 7.40 (s, 1H), 7.32-7.22 (m, 2H), 2.40 (s, 3H), 1.85-1.46 (m, 6H), 1.37-1.13 (m, 9H); m/z 310.1 (M+H⁺).

Example 250 cis-N-(4-Chlorophenyl)-2-(4-(1-hydroxy-1-phenyl-ethyl)cyclohexyl)acetamide

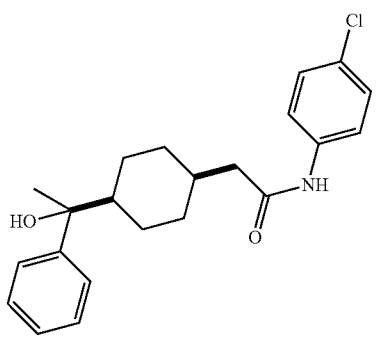

Intermediate ketone, cis-2-(4-acetylcyclohexyl)-N-(4-chlorophenyl)acetamide, was prepared as previously described and converted to the desired product by the following procedure: To a solution of cis-2-(4-acetylcyclo-hexyl)-N-(4-chlorophenyl) acetamide (50 mg, 0.17 mmol) in THF (2 mL) at 0° C. was added phenylmagnesium bromide (2.0 M, 0.2 mL, 0.34 mmol). The solution was allowed to warm to rt and stirred for 2 h before quenching with 3 M HCl (5 mL). The reaction solution was extracted with EtOAc (3×10 mL), washed sequentially with water and brine, dried over anhydrous MgSO$_4$, filtered, and concentrated under reduced pressure. The crude residue was purified using silica gel chromatography (0% to 60% EtOAc in hexanes) to afford the desired product as a white foam. $^1$H NMR (400 MHz; CDCl$_3$): δ 7.45 (d, J=8.8 Hz, 2H), 7.42-7.36 (m, 2H), 7.34 (dd, J=10.3, 5.1 Hz, 2H), 7.29-7.21 (m, 3H), 7.20 (s, 1H), 2.35 (s, 3H), 1.77-1.43 (m, 9H), 1.38-1.11 (m, 3H); m/z 372.2 (M+H$^+$).

Example 251

N-(4-Chlorophenyl)-2-(4-(hydroxymethyl)cyclohexyl)acetamide

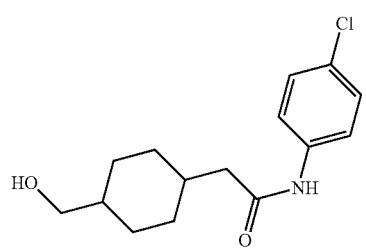 [SMILES: O=C(CC1CCC(CO)CC1)Nc1ccc(Cl)cc1]

4-(2-((4-Chlorophenyl)amino)-2-oxoethyl)cyclohexane-1-carboxylic acid was prepared as previously described and was converted to the methyl ester using the following procedure: To a solution of 4-(2-((4-chlorophenyl)amino)-2-oxoethyl) cyclohexane-1-carboxylic acid (43 mg, 0.34 mmol) in CH$_2$Cl$_2$ (1.0 mL) and methanol (1.0 mL) was added trimethylsilyldiazomethane (0.34 mL, 0.68 mmol). The reaction was stirred for 15 min followed by the addition of silica gel. The resulting slurry was filtered and concentrated under reduced pressure to afford the methyl ester. The crude product mixture was reduced to the primary alcohol using the following procedure: To a solution of methyl 4-(2-((4-chlorophenyl)amino)-2-oxoethyl)cyclohexane-1-carboxylate (40 mg, 0.13 mmol) in diethyl ether (1.3 mL) and ethanol (1.3 mL) was added LiBH$_4$ (42 mg, 1.92 mmol) in 3 portions at 0° C. over 30 min. The mixture was warmed to rt and stirred for 3 h, at which time the solution formed an unstirrable gel. The reaction was quenched by addition of diethyl ether (10 mL), followed by 1 M HCl (5 mL). The aqueous phase was extracted with EtOAc (3×20 mL), and the combined organic layers were dried over sodium sulfate and concentrated under reduced pressure. The crude residue was purified using silica gel chromatography (0% to 90% EtOAc in hexanes) to afford a 1.3:1 mixture of diastereomers as a white solid. $^1$H NMR (400 MHz; CDCl$_3$): δ 7.47 (d, J=8.9 Hz, 2H), 7.29 (d, J=2.0 Hz, 2H), 7.14 (d, J=10.4 Hz, 1H), 3.57 (d, J=6.8 Hz, 1.4H), 3.46 (d, J=6.8 Hz, 0.90H), 2.32 (d, J=7.4 Hz, 1.1H), 2.24-2.17 (m, 1.4H), 1.95-1.76 (m, 2H), 1.74-1.52 (m, 3.1H), 1.52-1.35 (m, 3.1H), 1.03 (q, J=9.0 Hz, 1.7H); m/z 282.1 (M+H$^+$).

Example 252

N-Cyclopropyl-2-(4-phenylcyclohexyl)acetamide

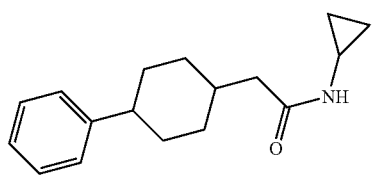 [SMILES: O=C(CC1CCC(c2ccccc2)CC1)NC1CC1]

Prepared using General Procedure F employing 2-(4-phenylcyclohexyl)acetic acid (100 mg, 0.46 mmol) and cyclopropylamine (0.060 mL, 0.92 mmol). Purification using silica gel chromatography (0% to 50% EtOAc in hexanes) afforded the desired product in a 1.2:1 mixture of diastereomers. $^1$H NMR (400 MHz; CDCl$_3$): δ 7.28-7.09 (m, 5H), 5.75 (s, 1H), 2.79-2.65 (m, 1H), 2.65-2.53 (m, 0.31H), 2.51-2.38 (m, 1.2H), 2.28-2.23 (m, 0.38H), 2.11-2.00 (m, 1.81H), 1.90-1.85 (m, 4.43H), 1.68-1.45 (m, 3.14H), 1.20-1.01 (m, 1.74H), 0.91-0.69 (m, 2.04H), 0.62-0.43 (m, 1.9H); m/z 259.2 (M+H$^+$).

Example 253

N-Cyclopentyl-2-(4-phenylcyclohexyl)acetamide

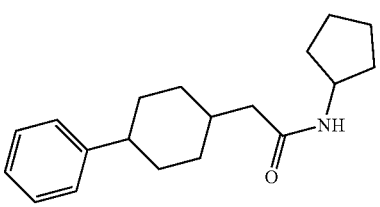 [SMILES: O=C(CC1CCC(c2ccccc2)CC1)NC1CCCC1]

Prepared using General Procedure F employing 2-(4-phenylcyclohexyl)acetic acid (100 mg, 0.46 mmol) and cyclopentylamine (0.090 mL, 0.92 mmol). Purification using silica gel chromatography (0% to 50% EtOAc in hexanes) afforded the desired product as a 1.1:1 mixture of diastereomers. $^1$H NMR (400 MHz; CDCl$_3$): δ 7.36-7.13 (m, 11H), 5.41 (s, 2H), 4.30-4.17 (m, 2.2H), 2.64-2.47 (m, 1.2H), 2.45 (t, J=6.1 Hz, 1H), 2.43-2.25 (m, 1.94H), 2.25-2.18 (m, 1.6H), 2.04-1.94 (m, 4.2H), 1.94-1.83 (m, 5.9H), 1.79-1.40 (m, 19.4H), 1.40-1.30 (m, 4.1H), 1.21-1.02 (m, 2.2H), 0.93-0.81 (m, 1.3H); m/z 286.2 (M+H$^+$).

Example 254

N-Cyclohexyl-2-(4-phenylcyclohexyl)acetamide

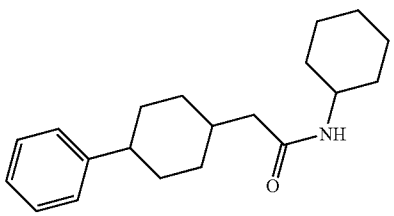 [SMILES: O=C(CC1CCC(c2ccccc2)CC1)NC1CCCCC1]

Prepared using General Procedure F employing 2-(4-phenylcyclohexyl)acetic acid (100 mg, 0.46 mmol) and cyclohexylamine (0.080 mL, 0.92 mmol). Purification using silica gel chromatography (0% to 50% EtOAc in hexanes) afforded the desired product as a 1.3:1 mixture of diastereomers. $^1$H NMR (400 MHz; CDCl$_3$): δ 7.35-7.13 (m, 5H), 5.31 (d, J=7.4 Hz, 1H), 3.86-3.74 (m, 1H), 2.62-2.60 (m, 0.35H), 2.46 (tt, J=12.2, 3.1 Hz, 0.52H), 2.40-2.17 (m, 1.27H), 2.12-2.04 (m, 1.12H), 1.91 (dd, J=11.7, 9.9 Hz, 4.6H), 1.86-1.03 (m, 14H); m/z 300.2 (M+H$^+$).

Example 255

2-(4-(4-Methoxyphenyl)cyclohexyl)acetic Acid

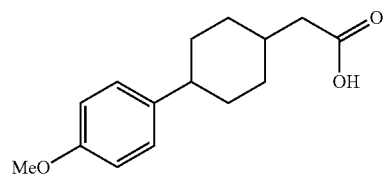 [SMILES: COc1ccc(C2CCC(CC(=O)O)CC2)cc1]

Prepared using General Procedure E employing ethyl 2-(4-(4-methoxyphenyl) cyclohexyl)acetate.

Example 256

N-Cyclopropyl-2-(4-(4-methoxyphenyl)cyclohexyl) acetamide

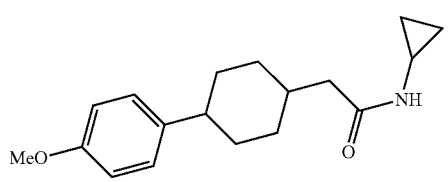 [SMILES: COc1ccc(C2CCC(CC(=O)NC3CC3)CC2)cc1]

To a solution of 2-(4-(4-methoxyphenyl)cyclohexyl)acetic acid (110 mg, 0.46 mmol) in CH$_2$Cl$_2$ (4 mL) was added oxalyl chloride (0.050 mL, 0.55 mmol) and triethylamine (0.13 mL, 0.92 mmol). The reaction was stirred at rt for 1 h followed by the addition of cyclopropylamine (0.08 mL, 0.92 mmol). The reaction was deposited on silica gel and purified using silica gel chromatography (0% to 50% EtOAc in hexanes) to afford the desired product as a 1.4:1 mixture of diastereomers. $^1$H NMR (400 MHz; CDCl$_3$): δ 7.20-7.07 (m, 2H), 6.84 (ddd, J=9.6, 6.0, 2.8 Hz, 2H), 5.61 (s, 1H), 3.82-3.76 (m, 3H), 2.86-2.64 (m, 1.3H), 2.56 (d, J=7.3 Hz, 0.8H), 2.40 (t, J=12.2 Hz, 0.56H), 2.30-2.27 (m, 0.57H), 2.21 (d, J=7.1 Hz, 1.14H), 2.04 (d, J=7.4 Hz, 0.82H), 1.87 (d, J=10.1 Hz, 1.9H), 1.70-1.54 (m, 4.4H), 1.46 (q, J=12.8 Hz, 0.81H), 1.10 (q, J=12.8 Hz, 0.71H), 0.90-0.81 (m, 1.27H), 0.81-0.73 (m, 1.69H), 0.65-0.57 (m, 1.17H), 0.53-0.42 (m, 1.56H); m/z 288.2 (M+H$^+$).

Example 257

N-Cyclopentyl-2-(4-(4-methoxyphenyl)cyclohexyl) acetamide

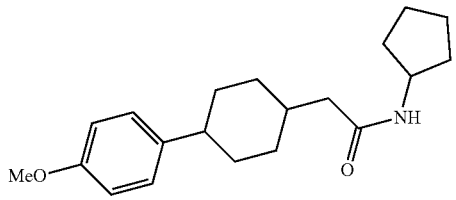 [SMILES: COc1ccc(C2CCC(CC(=O)NC3CCCC3)CC2)cc1]

To a solution of 2-(4-(4-methoxyphenyl)cyclohexyl)acetic acid (110 mg, 0.46 mmol) in CH$_2$Cl$_2$ (4 mL) was added oxalyl chloride (0.050 mL, 0.55 mmol) and triethylamine (0.13 mL, 0.92 mmol). The reaction was stirred at rt for 1 h followed by the addition of cyclopentylamine (0.08 mL, 0.92 mmol). The reaction was deposited on silica gel and purified using silica gel chromatography (0% to 30%, then 30% to 50% EtOAc in hexanes) to afford the desired product as a 1:1 mixture of diastereomers. $^1$H NMR (400 MHz; CDCl$_3$): δ 7.24-7.07 (m, 2H), 6.89-6.79 (m, 2H), 5.37 (s, 1H), 4.29-4.16 (m, 1H), 3.77 (s, 3H), 2.60-2.50 (m, 0.5H), 2.41 (tt, 0.1=11.6, 2.9 Hz, 0.5H), 2.30-2.27 (m, 0.5H), 2.25-2.18 (m, 1H), 2.08-1.93 (m, 3H), 1.88 (d, J=9.3 Hz, 2.6H), 1.75-1.22 (m, 12H), 1.21-1.04 (m, 1H); m/z 316.2 (M+H$^+$).

Example 258

N-Cyclohexyl-2-(4-(4-methoxyphenyl)cyclohexyl) acetamide

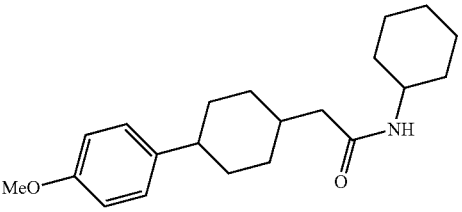 [SMILES: COc1ccc(C2CCC(CC(=O)NC3CCCCC3)CC2)cc1]

To a solution of 2-(4-(4-methoxyphenyl)cyclohexyl)acetic acid (110 mg, 0.46 mmol) in CH$_2$Cl$_2$ (4 mL) was added oxalyl chloride (0.050 mL, 0.55 mmol) and triethylamine (0.13 mL, 0.92 mmol). The reaction was stirred at rt for 1 h followed by the addition of cyclohexylamine (0.08 mL, 0.92 mmol). The reaction was deposited on silica gel and purified using silica gel chromatography (0% to 30%, then 30% to 50% EtOAc in hexanes) to afford the desired product as a 1.1:1 mixture of diastereomers. $^1$H NMR (400 MHz; CDCl$_3$): δ 7.20-7.08 (m, 2H), 6.89-6.79 (m, 2H), 5.28 (d, J=7.4 Hz, 1H), 3.79 (s, 1.5H), 3.78 (s, 1.5H), 2.59-2.52 (m, 0.4H), 2.45-2.36 (m, 0.4H), 2.30-2.15 (m, 1.5H), 2.09-2.01 (m, 2.3H), 1.96-1.79 (m, 4.6H), 1.79-1.60 (m, 7.2H), 1.51-1.32 (m, 3.72H), 1.23-1.02 (m, 4H); m/z 330.2 (M+H$^+$).

Example 259

Ethyl 4-benzylcyclohexane-1-carboxylate

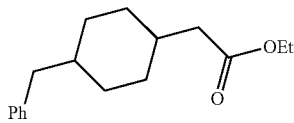 [SMILES: CCOC(=O)CC1CCC(Cc2ccccc2)CC1]

To a solution of NaH (60% on mineral oil, 590 mg, 14.7 mmol) in DMSO (15 mL) was added benzyltriphenylphosphonium bromide (6.36 g, 14.7 mmol) slowly at rt. The reaction was stirred for 30 min at rt, then the reaction was heated to 50° C. for 30 min. The solution turned a dark red, then ethyl 4-oxocyclohexane-1-carboxylate (2.28 g, 13.3 mmol) was added as a solution in DMSO (20 mL). The reaction was stirred at 50° C. for 16 h. The reaction was cooled to rt and quenched with sat. NH$_4$Cl (50 mL), extracted with EtOAc (3×20 mL), washed with brine, dried over anhydrous MgSO$_4$, filtered, and concentrated under reduced pressure to provide ethyl 4-benzylidenecyclohexan-1-carboxylate (2.36 g, 73%). Ethyl 4-benzylidenecyclohexane-1-carboxylate was diluted in ethanol (25 mL) and treated with 10% Pd/C (300 mg, 10 wt. %). The reaction mixture was sparged with H$_2$ gas and was stirred under H$_2$ atmosphere for 6 h. The reaction mixture was filtered through CELITE® and concentrated to provide an inseparable mixture of diastereomers as a clear oil which is used without further purification.

Example 260

Ethyl 2-(4-hydroxycyclohexyl)acetate

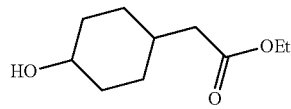 [SMILES: CCOC(=O)CC1CCC(O)CC1]

To a solution of ethyl (2-(4-oxocyclohexane)acetate (1.0 g, 5.4 mmol) in methanol (40 mL) at rt was added NaBH$_4$ (0.60 g, 16 mmol). The resulting solution was stirred open to air for 13 h, after which it was diluted with CH$_2$Cl$_2$ (60 mL), washed with 1 M HCl (3×30 mL), dried over anhydrous MgSO$_4$, filtered, and concentrated under reduced pressure to afford the desired product as a 1:3 mixture of diastereomers, clear, colorless oil (1.0 g, 99% yield).

Example 261

Ethyl 2-(4-phenoxycyclohexyl)acetate

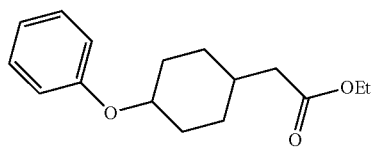 [SMILES: CCOC(=O)CC1CCC(Oc2ccccc2)CC1]

To a solution of PPh$_3$ (5.97 g, 22.8 mmol) in THF (18 mL) under argon cooled to 0° C. was added DEAD (0.936 mL, 5.97 mmol). The solution was stirred for 5 min before adding ethyl 2-(4-hydroxycyclohexyl)acetate (1.01 g, 5.43 mmol) as a solution in THF (4 mL) and phenol (767 mg, 8.15 mmol). After 20 min, the ice bath was removed, and the reaction was allowed to warm to rt over 1 h. The reaction mixture was diluted with EtOAc (50 mL), washed with 1 M NaOH (30 mL), dried over anhydrous MgSO$_4$, filtered, and concentrated under reduced pressure. The crude residue was purified using silica gel chromatography (1%, then 10% to 30% EtOAc in hexanes) to afford the desired product as a clear, colorless oil and mixture of diastereomers. m/z 263.2 (M+H$^+$).

General Procedure K: Preparation of Cyclohexylethers

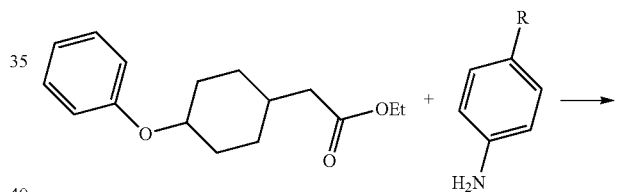

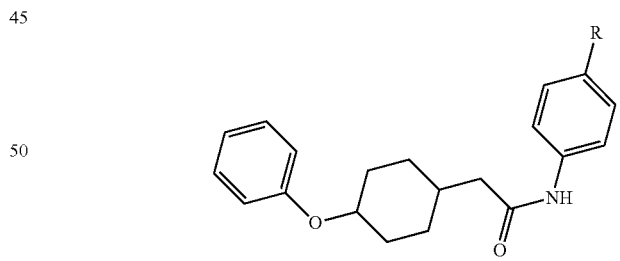

To a solution of aniline (2.0 equiv) in THF (0.2 M) was added iPrMgCl (2.0 M solution in THF, 2.0 equiv) dropwise over 2 min. The resulting solution was stirred at rt for 20 min and became darker in color. To this solution was added the ester of interest (1.0 equiv) as a solution in THF (0.5 M). After 12 h, the reaction solution was diluted with EtOAc, washed with 3 M HCl (2×), washed with brine, dried over anhydrous MgSO$_4$, filtered, and concentrated under reduced pressure. The crude reaction mixture was purified using silica gel chromatography (EtOAc and hexanes) to afford the desired product(s).

Example 262 cis-N-(4-Chlorophenyl)-2-(4-phenoxycyclohexyl)acetamide

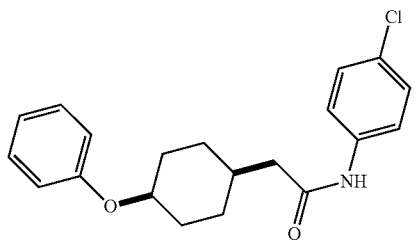

Prepared using General Procedure K employing ethyl 2-(4-phenoxycyclohexyl) acetate (168 mg, 0.641 mmol) and 4-chloroaniline (163 mg, 1.28 mmol). Purification using silica gel chromatography (15% to 30% EtOAc in hexanes) afforded the cis-diastereomer as the first eluting isomer as a thin film: $^1$H NMR (400 MHz; CDCl$_3$): δ 7.73 (s, 1H), 7.57-7.39 (m, 2H), 7.32-7.14 (m, 4H), 6.98-6.83 (m, 3H), 4.53 (br s, 1H), 2.29 (d, J=7.2 Hz, 2H), 2.12-1.90 (m, 3H), 1.69-1.40 (m, 6H); m/z 344.2 (M+H$^+$).

Example 263 trans-N-(4-Chlorophenyl)-2-(4-phenoxycyclohexyl)acetamide

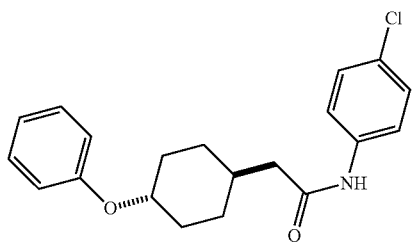

Further elution from the column in the previous example afforded the trans-diastereomer as a thin film. $^1$H NMR (400 MHz; CDCl$_3$): δ 7.48 (d, J=8.8 Hz, 2H), 7.35-7.12 (m, 4H), 7.18 (br s, 1H), 6.99-6.79 (m, 3H), 4.23-4.08 (m, 1H), 2.27 (d, J=6.6 Hz, 2H), 2.18 (d, J=10.3 Hz, 2H), 2.03-1.87 (m, 3H), 1.57-1.42 (m, 2H), 1.24-1.06 (m, 2H); m/z 344.2 (M+H$^+$).

Example 264 cis-N-(4-Cyanophenyl)-2-(4-phenoxycyclohexyl)acetamide

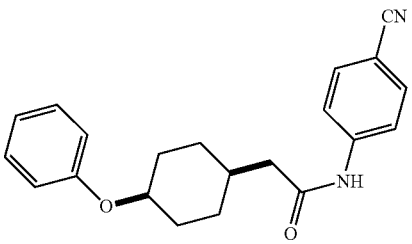 [SMILES: N#Cc1ccc(NC(=O)C[C@H]2CC[C@@H](Oc3ccccc3)CC2)cc1]

Prepared using General Procedure K employing ethyl 2-(4-phenoxycyclohexyl) acetate (165 mg, 0.630 mmol) and 4-cyanoaniline (150 mg, 1.26 mmol). Purification using silica gel chromatography (15% to 35% EtOAc in hexanes) afforded the cis-diastereomer as the first eluting desired product as a thin film. $^1$H NMR (400 MHz; CDCl$_3$): δ 7.68 (app d, J=8.5 Hz, 3H), 7.59 (d, J=8.5 Hz, 2H), 7.32-7.22 (m, 2H), 6.97-6.84 (m, 3H), 4.53 (br s, 1H), 2.34 (d, J=7.0 Hz, 2H), 2.10-1.97 (m, 3H), 1.66-1.45 (m, 6H); m/z 335.2 (M+H$^+$).

Example 265 trans-N-(4-Cyanophenyl)-2-(4-phenoxycyclohexyl)acetamide

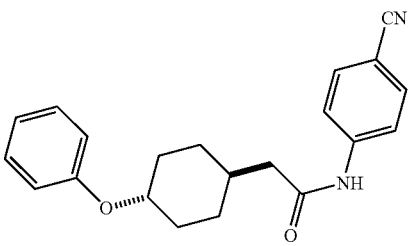 [SMILES: N#Cc1ccc(NC(=O)C[C@H]2CC[C@H](Oc3ccccc3)CC2)cc1]

Further elution from the column in the previous example afforded the trans-diastereomer as a thin film. $^1$H NMR (400 MHz; CDCl$_3$): δ 7.70-7.64 (d, J=7.5 Hz, 2H), 7.64-7.57 (d, J=7.5 Hz, 2H), 7.48 (br s, 1H), 7.30-7.21 (m, 2H), 6.96-6.85 (m, 3H), 4.22-4.12 (m, 1H), 2.31 (d, J=6.6 Hz, 2H), 2.16 (m, 2H), 1.98-1.89 (m, 3H), 1.54-1.48 (m, 2H), 1.24-1.18 (m, 2H); m/z 335.2 (M+H).

Example 266 cis-N-(4-Fluorophenyl)-2-(4-phenoxycyclohexyl)acetamide

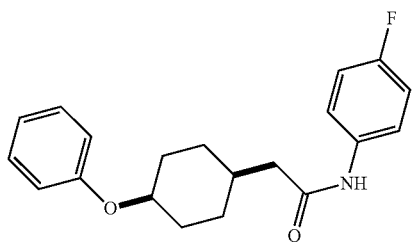 [SMILES: O=C(C[C@H]1CC[C@@H](Oc2ccccc2)CC1)Nc1ccc(F)cc1]

Prepared using General Procedure K employing ethyl 2-(4-phenoxycyclohexyl) acetate (165 mg, 0.630 mmol) and 4-fluoroaniline (0.120 mL, 1.26 mmol). Purification using silica gel chromatography (15% to 30% EtOAc in hexanes) afforded the cis-diastereomer as the first eluting isomer as a thin film. $^1$H NMR (400 MHz; CDCl$_3$): δ 7.76 (s, 1H), 7.54-7.44 (m, 2H), 7.31-7.22 (m, 2H), 7.04-6.82 (m, 5H), 4.52 (br s, 1H), 2.28 (d, J=7.2 Hz, 2H), 2.09-1.94 (m, 3H), 1.69-1.41 (m, 6H).

Example 267 trans-N-(4-Fluorophenyl)-2-(4-phenoxycyclohexyl)acetamide

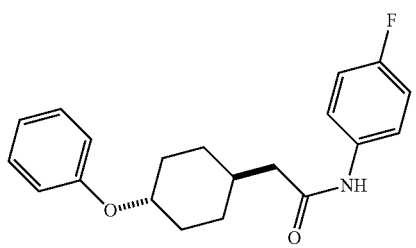 [SMILES: O=C(C[C@H]1CC[C@H](Oc2ccccc2)CC1)Nc1ccc(F)cc1]

Further elution from the column in the previous example afforded the trans-diastereomer as a thin film. $^1$H NMR (400 MHz; CDCl$_3$): δ 7.53-7.43 (m, 2H), 7.43-7.34 (br s, 1H), 7.26 (m, 2H), 7.05-6.96 (m, 2H), 6.96-6.83 (m, 3H), 4.19-4.09 (m, 1H), 2.29-2.22 (d, J=6.8 Hz, 2H), 2.20-2.10 (m, 2H), 2.00-1.89 (m, 3H), 1.56-1.39 (m, 2H), 1.20-1.04 (m, 2H).

General Procedure L: Preparation of Cyclohexylalcohols

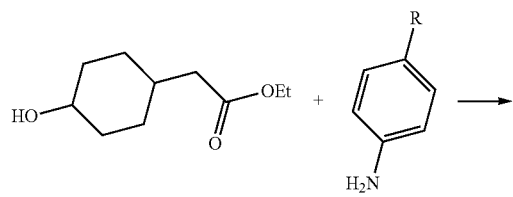

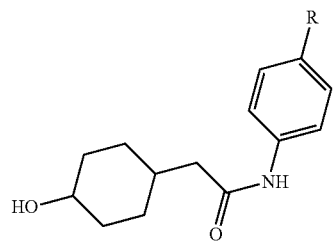

To a solution of aniline (2.0 equiv) in THF (2.0 M) cooled to 0° C. was added iPrMgCl (2.0 M in THF, 2.0 equiv). The solution was stirred at 0° C. for 30 min. In a separate reaction flask, ethyl 2-(4-hydroxycyclohexyl)acetate (1.0 equiv) in THF (0.4 M) was treated with iPrMgCl (2.0 M in THF, 1.0 equiv) and stirred at rt for 5 min. The ester solution was added to the anilide solution at 0° C. by syringe dropwise. The ice bath was then removed, and the reaction mixture was allowed to warm to rt and stir for 14 h. The reaction mixture was diluted with EtOAc, washed with 3 M HCl (2×), washed with brine, dried over anhydrous MgSO$_4$, filtered, and concentrated under reduced pressure to provide an off-white solid. The crude residue was purified using silica gel chromatography (50% to 100% EtOAc in hexanes) to afford the desired product(s).

Example 268

N-(4-Chlorophenyl)-2-(4-hydroxycyclohexyl)acetamide

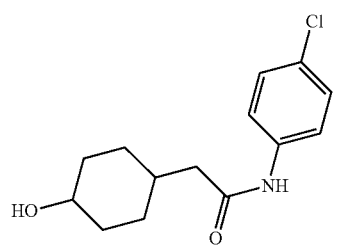

Prepared using General Procedure L employing ethyl 2-(4-hydroxycyclohexyl) acetate (1.0 g, 5.4 mmol) and 4-chloroaniline (1.4 g, 11 mmol). Purification using silica gel chromatography (50% to 100% EtOAc in hexanes) afforded the desired product as a 1:2 mixture of diastereomers, white solid (662 mg, 46%). $^1$H NMR (400 MHz; CDCl$_1$): δ 7.52-7.40 (m, 6H), 7.33-7.24 (m, 6H), 7.17-6.99 (m, 3H), 4.03 (br s, 1H), 3.57 (br s, 2H), 2.27 (d, J=7.0 Hz, 2H), 2.22 (d, J=6.6 Hz, 4H), 2.07-1.94 (m, 4H), 1.94-1.80 (m, 4H), 1.80-1.21 (m, 16H), 1.15-1.04 (m, 4H); m/z 268.2 (M+H$^+$).

Example 269

N-(4-Cyanophenyl)-2-(4-hydroxycyclohexyl)acetamide

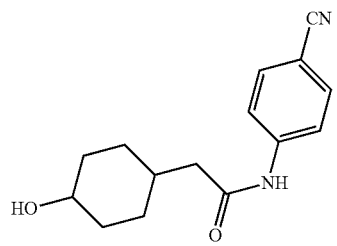 [SMILES: N#Cc1ccc(NC(=O)CC2CCC(O)CC2)cc1]

Prepared using General Procedure L employing ethyl 2-(4-hydroxycyclohexyl) acetate (1.0 g, 5.4 mmol) and 4-cyanoaniline (1.26 g, 11 mmol). Purification using silica gel chromatography (50% to 100% EtOAc in hexanes) afforded the desired product as a 1:2 mixture of diastereomers, white solid (888 mg, 64%).

Example 270

N-(4-Fluorophenyl)-2-(4-hydroxycyclohexyl)acetamide

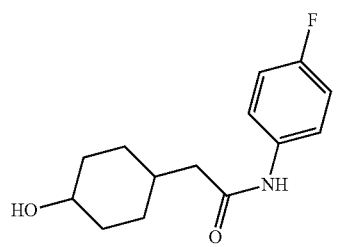 [SMILES: O=C(CC1CCC(O)CC1)Nc1ccc(F)cc1]

Prepared using General Procedure K employing ethyl 2-(4-hydroxycyclohexyl) acetate (1.0 g, 5.4 mmol) and 4-fluoroaniline (1.01 mL, 11 mmol). Purification using silica gel chromatography (50% to 100% EtOAc in hexanes) afforded the desired product as a 1:2 mixture of diastereomers, white solid (772 mg, 57%).

General Procedure M: Preparation of Cyclohexylacetamide Ethers

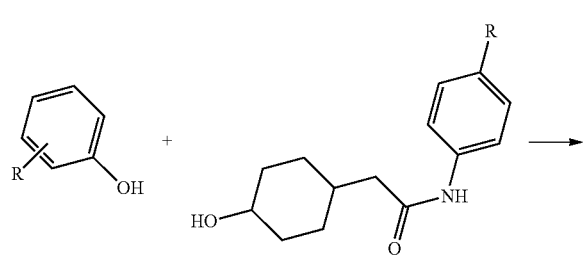

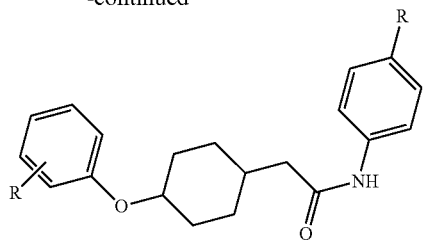

To a mixture of alcohol of interest (1.0 equiv), substituted phenol of interest (1.5 equiv), and polymer-bound PPh$_3$ (3.0 mmol/g, 3.0 equiv) cooled to 0° C. was added DEAD (1.5 equiv) dropwise. The ice bath was the removed, and the reaction mixture was allowed to warm to rt and stirred for 16 h. The mixture was then diluted with EtOAc, filtered through a pad of CELITE®, and concentrated under reduced pressure. The crude residue was purified using silica gel chromatography (EtOAc and hexanes) or semi-preparative reverse-phase HPLC to afford the desired product(s).

Example 271 cis-Methyl 4-((4-(2-((4-chlorophenyl)amino)-2-oxoethyl)cyclohexyl)oxy)benzoate

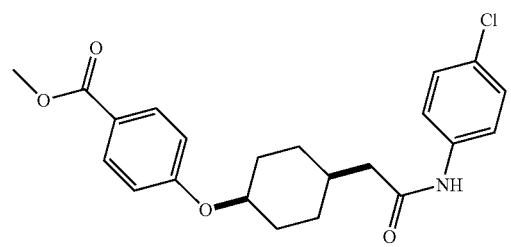 [SMILES: COC(=O)c1ccc(O[C@H]2CC[C@@H](CC(=O)Nc3ccc(Cl)cc3)CC2)cc1]

Prepared using General Procedure M employing N-(4-chlorophenyl)-2-(4-hydroxycyclohexyl)acetamide (200 mg, 0.747 mmol) and methyl 4-hydroxybenzoate (170 mg, 1.12 mmol). Purification using silica gel chromatography (0% to 30% EtOAc in hexanes) afforded the cis-diastereomer as the first eluting isomer. $^1$H NMR (400 MHz; CDCl$_3$): δ 7.97 (d, J=8.8 Hz, 2H), 7.47 (d, J=8.8 Hz, 2H), 7.34-7.23 (m, 3H), 6.89 (d, J=9.0 Hz, 2H), 4.63 (br s, 1H), 3.88 (s, 3H), 2.29 (d, J=7.2 Hz, 2H), 2.03 (app d, J=8.8 Hz, 3H), 1.70-1.58 (m, 4H), 1.56-1.42 (m, 2H); m/z 402.3 (M+H$^+$).

Example 272 trans-Methyl 4-((4-(2-((4-chlorophenyl)amino)-2-oxoethyl)cyclohexyl)oxy)benzoate

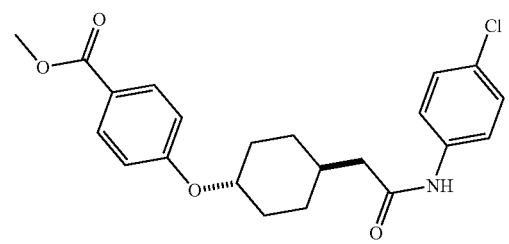

Further elution from the column in the previous example afforded the trans-diastereomer as the second eluting isomer with impurities. The trans-diastereomer was further purified by semi-preparative reverse-phase HPLC (PHENOMENEX® Gemini-NX, 10μ, C18, 110A, 250×30 mm, 20 mL/min, eluting with 0% to 100% acetonitrile in water gradient over the first 30 min of a 40 min run) to afford the desired product at 32 min as a thin film. $^1$H NMR (400 MHz; CDCl$_3$): δ 7.96 (d, J=9.0 Hz, 2H), 7.48 (d, J=8.8 Hz, 2H), 7.28 (d, J=9.0 Hz, 2H), 7.17 (s, 1H), 6.88 (d, J=8.8 Hz, 2H), 4.28-4.20 (m, 1H), 3.88 (s, 3H), 2.27 (d, J=6.6 Hz, 2H), 2.21-2.11 (m, 2H), 2.05-1.93 (m, 3H), 1.61-1.46 (m, 2H), 1.28-1.13 (m, 2H); m/z 402.3 (M+H$^+$).

Example 273 cis-Methyl 4-((4-(2-((4-chlorophenyl)amino)-2-oxoethyl)cyclohexyl)oxy)benzoate

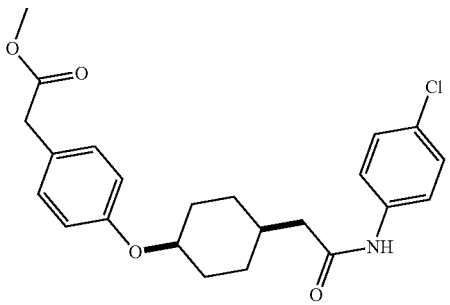

Prepared using General Procedure M employing N-(4-chlorophenyl)-2-(4-hydroxycyclohexyl)acetamide (200 mg, 0.747 mmol) and methyl 2-(4-hydroxyphenyl) acetate (186 mg, 1.12 mmol). Purification using silica gel chromatography (0% to 30% EtOAc in hexanes) afforded the cis-diastereomer as the first eluting isomer. $^1$H NMR (400 MHz; CDCl$_3$): δ 7.47 (d, J=8.2 Hz, 2H), 7.35-7.22 (m, 3H), 7.17 (d, J=8.0 Hz, 2H), 6.84 (d, J=7.6 Hz, 2H), 4.51 (br s, 1H), 3.69 (s, 3H), 3.56 (s, 2H), 2.27 (d, J=7.0 Hz, 2H), 2.00 (m, 3H), 1.67-1.40 (m, 6H); m/z 416.3 (M+H$^+$).

Example 274 trans-Methyl 4-((4-(2-((4-chlorophenyl)amino)-2-oxoethyl)cyclohexyl)oxy)benzoate

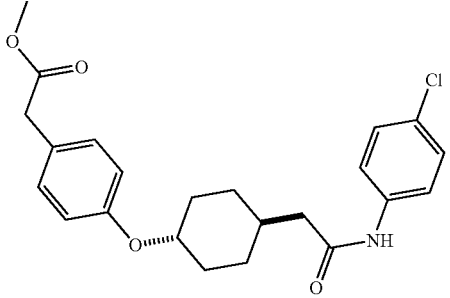

Further elution from the column in the previous example afforded the trans-diastereomer as the second eluting isomer with impurities. The trans-diastereomer was further purified by semi-preparative reverse-phase HPLC (PHENOMENEX® Gemini-NX, 10μ, C18, 110A, 250×30 mm, 20 mL/min, eluting with 0% to 100% acetonitrile in water gradient over the first 30 min of a 40 min run) to afford the desired product at 31.5 min as a thin film. $^1$H NMR (400 MHz; CDCl$_3$): δ 7.47 (d, J=8.8 Hz, 2H), 7.28 (d, J=8.8 Hz, 2H), 7.19-7.00 (m, 3H), 6.84 (d, J=8.6 Hz, 2H), 4.16-4.08 (m, 1H), 3.67 (br. s., 3H), 3.55 (s, 2H), 2.26 (d, J=6.4 Hz, 2H), 2.16 (br d, J=11.9 Hz, 2H), 1.94 (br d, =12.0 Hz, 3H), 1.54-1.43 (m, 2H), 1.27-1.10 (m, 2H); m/z 416.3 (M+H$^+$).

Example 275 cis-N-(4-Chlorophenyl)-2-(4-(3-methoxyphenoxy)cyclohexyl)acetamide

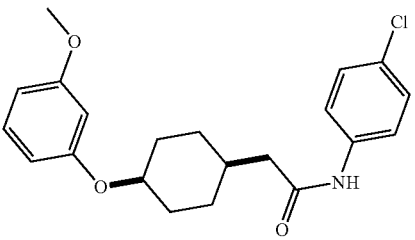

Prepared using General Procedure M employing N-(4-chlorophenyl)-2-(4-hydroxycyclohexyl)acetamide (200 mg, 0.747 mmol) and 3-methoxyphenol (0.139 mL, 1.12 mmol). Purification using silica gel chromatography (20% to 30% EtOAc in hexanes) afforded the cis-diastereomer as the first eluting isomer. $^1$H NMR (400 MHz; CDCl$_3$): δ 7.47 (d, J=8.8 Hz, 2H), 7.31-7.22 (m, 3H), 7.22-7.13 (m, 1H), 6.52-6.45 (m, 3H), 4.52 (br s, 1H), 3.79 (s, 3H), 2.28 (d, J=7.2 Hz, 2H), 2.07-1.97 (m, 3H), 1.67-1.44 (m, 6H); m/z 374.1 (M+H$^+$).

Example 276 trans-N-(4-Chlorophenyl)-2-(4-(3-methoxyphenoxy)cyclohexyl)acetamide

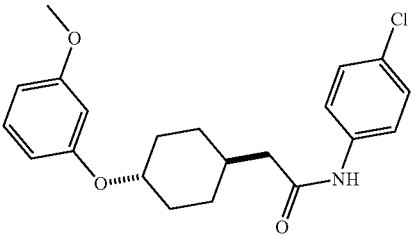

Further elution from the column in the previous example afforded the desired product as the second eluting isomer as a thin film. $^1$H NMR (400 MHz; CDCl$_3$): δ 7.47 (d, J=8.6 Hz, 2H), 7.30-7.21 (m, 3H), 7.21-7.13 (m, 1H), 6.51-6.39 (m, 3H), 4.22-4.08 (m, 1H), 3.78 (s, 3H), 2.25 (d, J=6.6 Hz, 2H), 2.07 (br d, J=13.0 Hz, 2H) 1.93 (br d, J=14.0 Hz, 3H), 1.53-1.42 (m, 2H), 1.20-1.09 (m, 2H); m/z 374.1 (M+H$^+$).

Example 277

Ethyl 2-(4-(4-fluorophenoxy)cyclohexyl)acetate

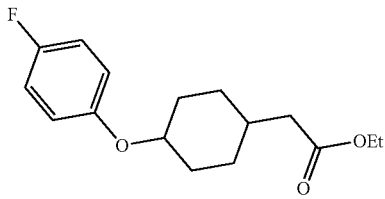 [SMILES: CCOC(=O)CC1CCC(Oc2ccc(F)cc2)CC1]

To a mixture of polymer-bound PPh₃ (3.0 mmol/g, 2.69 g, 8.07 mmol), ethyl 2-(4-hydroxycyclohexyl)acetate (1.01 g, 5.43 mmol), and 4-fluorophenol (452 mg, 4.03 mmol) in THF (13 mL) cooled to 0° C. was added DEAD (0.637 mL, 4.03 mmol). After 20 min, the ice bath was removed, and the reaction was allowed to warm to rt over 16 h. The reaction mixture was diluted with CH₂Cl₂ (40 mL), filtered through a pad of CELITE®, and concentrated under reduced pressure. The crude residue was purified using silica gel chromatography (30% EtOAc in hexanes) to afford the desired product as a mixture with excess 4-fluorophenol and was used without further purification.

Example 278 cis-N-(4-Chlorophenyl)-2-(4-(4-fluorophenoxy)cyclohexyl)acetamide

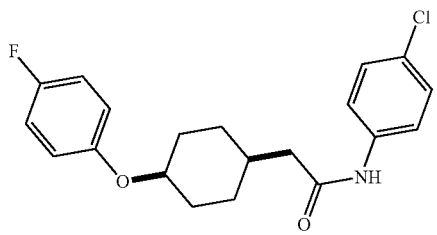

To a solution of 4-chloroaniline (137 mg, 1.07 mmol) in THF (2.5 mL) was added iPrMgCl (2.0 M solution in THF, 0.536 mL, 1.07 mmol) dropwise over 2 min. The resulting solution was stirred at rt for 20 min and became darker in color. To this solution was added ethyl 2-(4-(4-fluorophenoxy)cyclohexyl)acetate (200 mg, 0.536 mmol) as a solid. After 12 h, the reaction solution was diluted with EtOAc (30 mL), washed with 3 M HCl (2×15 mL), washed with brine, dried over anhydrous MgSO₄, filtered, and concentrated under reduced pressure. The crude reaction mixture was purified using silica gel chromatography (0% to 50% EtOAc in hexanes) to afford the cis-diastereomer desired product as a thin film with minor impurities. The desired product was further purified by semi-preparative reverse-phase HPLC (PHENOMENEX® Gemini-NX, 10μ, C18, 110A, 250×30 mm, 20 mL/min, eluting with 0% to 100% acetonitrile in water gradient over the first 30 min of a 40 min run) to afford the desired product at 32 min as a thin film. ¹H NMR (400 MHz; CDCl₃): δ 7.47 (d, J=8.8 Hz, 2H), 7.28 (d, J=8.8 Hz, 2H), 7.12 (br s, 1H), 7.04-6.92 (m, 2H), 6.84 (dd, J=4.4, 9.1 Hz, 2H), 4.45 (br s, 1H), 2.29 (d, J=7.0 Hz, 2H), 2.08-1.94 (m, 3H), 1.65-1.42 (m, 6H); m/z 362.1 (M+H⁺).

Example 279 trans-N-(4-Chlorophenyl)-2-(4-(4-fluorophenoxy)cyclohexyl)acetamide

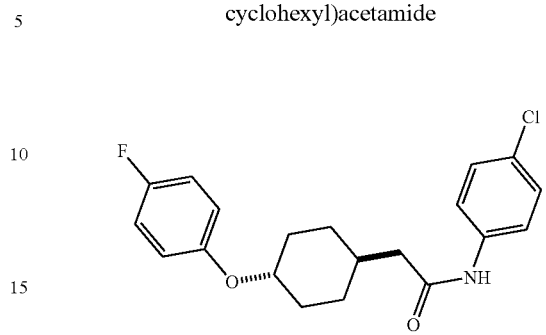

Further elution from the silica gel column in the previous example afforded the trans-diastereomer as the second eluting isomer with impurities, which was further purified by semi-preparative reverse-phase HPLC (PHENOMENEX® Gemini-NX, 10μ, C18, 110A, 250×30 mm, 20 mL/min, eluting with 0% to 100% acetonitrile in water gradient over the first 30 min of a 40 min run) to afford the desired product at 32 min as a thin film. ¹H NMR (400 MHz; CDCl₃): δ 7.46 (d, J=8.8 Hz, 2H), 7.27 (d, J=8.8 Hz, 2H), 7.08 (br s, 1H), 7.04-6.92 (m, 2H), 6.84 (dd, J=4.4, 9.1 Hz, 2H), 4.10-4.00 (br s, 1H), 2.28-2.24 (d, J=7.0 Hz, 2H), 2.18-2.14 (m, 2H), 1.98-1.91 (m, 3H), 1.53-1.46 (m, 2H), 1.22-1.10 (m, 2H); m/z 362.1 (M+H⁺).

Example 280 cis-N-(4-Fluorophenyl)-2-(4-(4-fluorophenoxy)cyclohexyl)acetamide

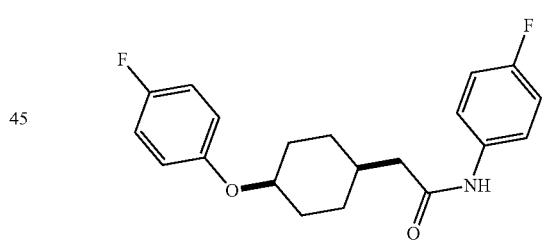

To a solution of 4-fluoroaniline (0.101 mL, 1.07 mmol) in THF (2.5 mL) was added iPrMgCl (2.0 M solution in THF, 0.536 mL, 1.07 mmol) dropwise over 2 min. The resulting solution was stirred at rt for 20 min and became darker in color. To this solution was added ethyl 2-(4-(4-fluorophenoxy)cyclohexyl)acetate (200 mg, ~0.536 mmol) as a solid. After 12 h, the reaction solution was diluted with EtOAc (30 mL), washed with 3 M HCl (2×15 mL), washed with brine, dried over anhydrous MgSO₄, filtered, and concentrated under reduced pressure. The crude reaction mixture was purified using silica gel chromatography (0% to 50% EtOAc in hexanes) afforded the cis-diastereomer desired product as a thin film. ¹H NMR (400 MHz; CDCl₃): δ 7.47 (dd, J=4.7, 9.0 Hz, 2H), 7.18 (br s, 1H), 7.06-6.92 (m, 4H), 6.84 (dd, J=4.4, 9.1 Hz, 2H), 4.44 (br s, 1H), 2.28 (d, J=7.0 Hz, 2H), 2.10-1.95 (m, 3H), 1.66-1.44 (m, 6H); m/z 346.2 (M+H⁺).

Example 281 trans-N-(4-Fluorophenyl)-2-(4-(4-fluorophenoxy)cyclohexyl)acetamide

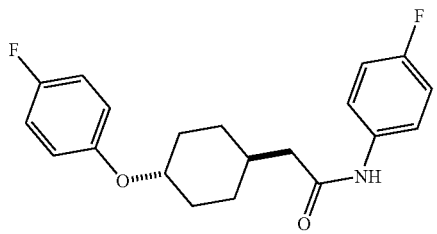

Further elution from the column in the previous example afforded the trans-diastereomer as the second eluting isomer with impurities, which was further purified by semi-preparative reverse-phase HPLC (PHENOMENEX® Gemini-NX, 10μ, C18, 110A, 250×30 mm, 20 mL/min, eluting with 0% to 100% acetonitrile in water gradient over the first 30 min of a 40 min run) to afford the desired product at 31 min as a thin film. $^1$H NMR (400 MHz; CDCl$_3$): δ 7.47 (dd, J=4.8, 9.1 Hz, 2H), 7.14-6.91 (m, 5H), 6.83 (dd, J=4.4, 9.1 Hz, 2H), 4.13-3.99 (m, 1H), 2.26 (d, J=6.6 Hz, 2H), 2.15 (br d, J=12.0 Hz, 2H), 1.95 (br d, J=12.0 Hz, 3H), 1.54-1.42 (m, 2H), 1.29-1.09 (m, 2H); m/z 346.2 (M+H$^+$).

Example 282 trans-N-(4-Cyanophenyl)-2-(4-(p-tolyloxy)cyclohexyl)acetamide

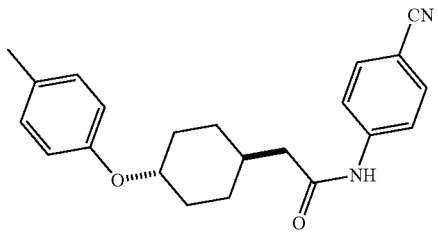

Prepared using General Procedure M employing N-(4-cyanophenyl)-2-(4-hydroxycyclohexyl)acetamide (200 mg, 0.775 mmol) and 4-methylphenol (0.121 mL, 1.16 mmol). Purification using silica gel chromatography (20% to 30% EtOAc in hexanes) afforded the trans-diastereomer as the only eluting isomer with impurities, which was further purified by semi-preparative reverse-phase HPLC (PHENOMENEX® Gemini-NX, 10μ, C18, 110A, 250×30 mm, 20 mL/min, eluting with 0% to 100% acetonitrile in water gradient over the first 30 min of a 40 min run) to afford the desired product at 31.5 min as a thin film. $^1$H NMR (400 MHz; CDCl$_3$): δ 7.79-7.59 (m, 4H), 7.29 (br s, 1H), 7.06 (d, J=8.2 Hz, 2H), 6.79 (d, J=8.6 Hz, 2H), 4.13-4.05 (m, 1H), 2.30 (d, J=7.0 Hz, 2H), 2.27 (s, 3H), 2.16 (d, J=9.8 Hz, 2H), 1.98-1.92 (m, 3H), 1.53-1.42 (m, 2H), 1.28-1.10 (m, 2H); m/z 349.2 (M+H$^+$).

Example 283 trans-N-(4-Cyanophenyl)-2-(4-(m-tolyloxy)cyclohexyl)acetamide

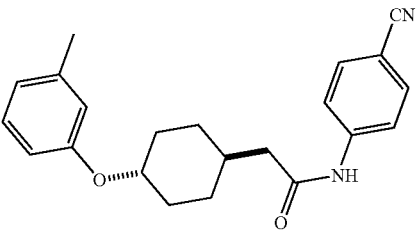

Prepared using General Procedure M employing N-(4-cyanophenyl)-2-(4-hydroxycyclohexyl)acetamide (200 mg, 0.775 mmol) and 3-methylphenol (0.121 mL, 1.16 mmol). Purification using silica gel chromatography (20% to 30% EtOAc in hexanes) afforded the trans-diastereomer as the only eluting isomer with impurities, which was further purified by semi-preparative reverse-phase HPLC (PHENOMENEX® Gemini-NX, 10μ, C18, 110A, 250×30 mm, 20 mL/min, eluting with 0% to 100% acetonitrile in water gradient over the first 30 min of a 40 min run) to afford the desired product at 31.5 min as a thin film. $^1$H NMR (400 MHz; CDCl$_3$): δ 7.81-7.59 (m, 4H), 7.34 (br s, 1H), 7.14 (t, J=7.7 Hz, 1H), 6.77-6.67 (m, 3H), 4.18-4.10 (m, 1H), 2.41-2.23 (m, 5H), 2.17 (d, J=13.9 Hz, 2H), 1.94 (d, J=12.9 Hz, 2H), 1.56-1.43 (m, 2H), 1.28-1.12 (m, 2H); m/z 349.3 (M+H$^+$).

Example 284 trans-N-(4-Cyanophenyl)-2-(4-(3,5-dimethylphenoxy)cyclohexyl)acetamide

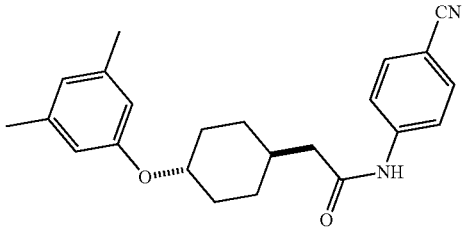

Prepared using General Procedure M employing N-(4-cyanophenyl)-2-(4-hydroxycyclohexyl)acetamide (200 mg, 0.747 mmol) and 3,5-dimethylphenol (142 mg, 1.16 mmol). Purification using silica gel chromatography (20% to 30% EtOAc in hexanes) afforded a white residue, which was further purified by semi-preparative reverse-phase HPLC (PHENOMENEX® Gemini-NX, 10μ, C18, 110A, 250×30 mm, 20 mL/min, eluting with 0% to 100% acetonitrile in water gradient over the first 30 min of a 40 min run) to afford the trans-diastereomer desired product at 32 min as a thin film and first eluting isomer. $^1$H NMR (400 MHz; CDCl$_3$): δ 7.69-7.60 (m, 4H), 7.36 (br s, 1H), 6.58 (s, 1H), 6.52 (s, 2H), 4.16-4.08 (m, 1H), 2.31 (d, J=6.6 Hz, 2H), 2.28-2.25 (m, 6H), 2.22-2.11 (m, 2H), 2.00-1.90 (m, 3H), 1.61-1.37 (m, 2H), 1.31-1.12 (m, 2H); m/z 363.4 (M+H$^+$).

Example 285 cis-N-(4-Cyanophenyl)-2-(4-(3,5-dimethylphenoxy)cyclohexyl)acetamide

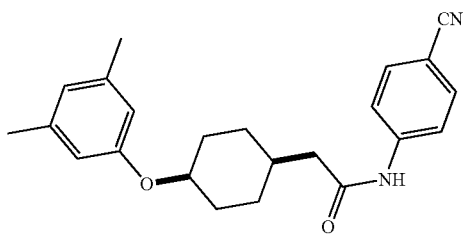

Further elution from the semi-preparative HPLC column in the previous example afforded the cis-diastereomer as the second eluting isomer at 33.5 min as a thin film. $^1$H NMR (400 MHz; CDCl$_3$): δ 7.68-7.59 (m, 4H), 7.35 (br s, 1H), 6.59-6.52 (m, 3H), 4.52 (br s, 1H), 2.33 (d, J=7.0 Hz, 2H), 2.27 (s, 6H), 2.12-1.93 (m, 3H), 1.64-1.59 (m, 4H), 1.59-1.46 (m, 2H); m/z 363.4 (M+H').

Example 286 cis-2-(4-(3-Chlorophenoxy)cyclohexyl)-N-(4-chlorophenyl)acetamide

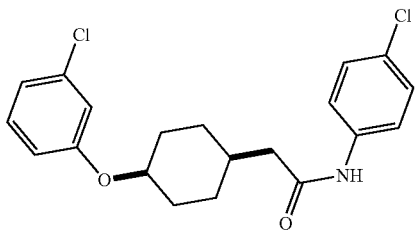

Prepared using General Procedure M employing N-(4-chlorophenyl)-2-(4-hydroxycyclohexyl)acetamide (220 mg, 0.822 mmol) and 3-chlorophenol (0.130 mL, 1.23 mmol). Purification using silica gel chromatography (20% to 30% EtOAc in hexanes) afforded the cis-diastereomer as the first eluting isomer. $^1$H NMR (400 MHz; CDCl$_3$): δ 7.47 (d, J=8.8 Hz, 2H), 7.29-7.15 (m, 4H), 6.91-6.88 (m, 2H), 6.78 (dd, J=0.9, 7.1 Hz, 1H), 4.52 (br s, 1H), 2.28 (d, J=7.0 Hz, 2H), 2.07-1.97 (m, 3H), 1.66-1.56 (m, 4H), 1.54-1.42 (m, 2H); m/z 378.2 (M+H).

Example 287

Methyl 2-phenylhex-5-enoate

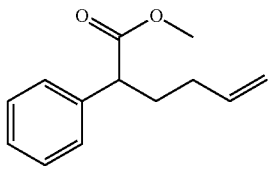

To a solution of methyl phenylacetate (4.0 g, 27 mmol) in DMF (75 mL) was added NaH (60% dispersion in mineral oil, 1.4 g, 35 mmol). The mixture was stirred for 1.5 h before adding 4-bromobutene (3.0 mL, 29 mmol) by syringe. After stirring at rt for 2 h, the reaction solution was diluted with EtOAc (100 mL) and NH$_4$Cl (30 mL). The organic layer was separated and washed with brine, dried over anhydrous MgSO$_4$, filtered, and concentrated to afford a light orange oil, which was purified by silica gel chromatography (0% to 10% EtOAc in hexanes) to afford the desired product as a clear colorless oil (2.08 g, 38%). $^1$H NMR (400 MHz; CDCl$_3$): δ 7.38-7.21 (m, 5H), 5.83-5.72 (m, 1H), 5.05-4.93 (m, 2H), 3.65 (s, 3H), 3.58 (t, J=7.6 Hz, 1H), 2.23-2.10 (m, 1H), 2.07-1.96 (m, 2H), 1.95-1.82 (m, 1H).

Example 288

2-Phenylhex-5-en-1-ol

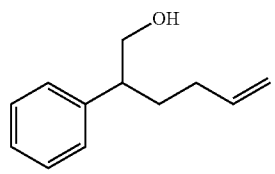

To a solution of methyl 2-phenylhex-5-enoate (2.08 g, 10.2 mmol) in CH$_2$Cl$_2$ (50 mL) cooled to 0° C. was added diisobutylaluminum hydride (DIBAL-H, 1 M in THF, 30.6 mL, 30.6 mmol) dropwise. The ice bath was removed after the addition was complete, and the reaction was allowed to warm to rt and stirred for 16 h. The reaction mixture was cooled to −78° C. and was quenched by the addition of 7.2 mL of a pH=8 buffer (buffer: 1.2 mL 30% NH$_4$OH in water and 20 mL sat. NH$_4$Cl). The cooling bath was then removed, and the reaction was allowed to warm to rt and stir for 45 min. Anhydrous MgSO$_4$ (6.4 g) was added to the mixture to form a white slurry. The mixture was filtered, and the organic solution was concentrated under reduced pressure to afford the desired product as a clear, colorless oil (1.8 g, quant.). $^1$H NMR (400 MHz; CDCl$_3$): δ 7.41-7.15 (m, 5H), 5.86-5.66 (m, 1H), 5.04-4.85 (m, 2H), 3.85-3.63 (m, 2H), 2.94-2.73 (m, 1H), 2.05-1.89 (m, 2H), 1.87-1.74 (m, 1H), 1.74-1.62 (m, 1H), 1.31 (br s, 1H).

Example 289

Ethyl (E)-7-hydroxy-6-phenylhept-2-enoate

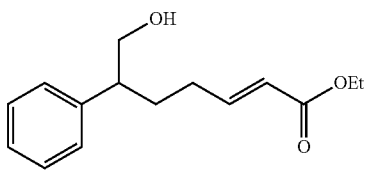 [SMILES: CCOC(=O)/C=C/CCC(CO)c1ccccc1]

A solution of 2-phenylhex-5-en-1-ol (1.9 g, 11 mmol) in CH$_2$Cl$_2$ (138 mL) was degassed for 5 min be sparging with argon before adding ethyl acrylate (4.7 mL, 44 mmol) and Grubbs II catalyst (190 mg, 0.22 mmol). The red solution was placed in a 40° C. oil bath for 30 min before adding additional Grubbs II catalyst (30 mg, 0.035 mmol). The reaction was stirred at 40° C. for an additional 45 min before cooling to rt and concentrated under reduced pressure. The crude residue was purified by silica gel chromatography (20% EtOAc in hexanes) to afford the desired product as a clear oil (2.0 g, 72%). $^1$H NMR (400 MHz; CDCl$_3$): δ 7.36-7.32 (m, 2H), 7.28-7.17 (m, 3H), 6.95-6.87 (m, 1H), 5.81-5.71 (m, 1H), 4.17 (q, J=7.0 Hz, 2H), 3.78-3.71 (m, 2H), 2.84-2.77 (m, 1H), 2.13-2.06 (m, 2H), 1.94-1.85 (m, 1H), 1.80-1.70 (m, 1H), 1.35 (br t, J=6.2 Hz, 1H), 1.28 (t, J=7.1 Hz, 3H).

Example 290

Ethyl 2-(5-phenyltetrahydro-2H-pyran-2-yl)acetate

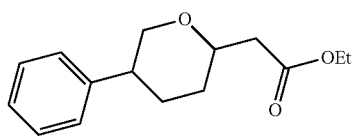 [SMILES: CCOC(=O)CC1CCC(c2ccccc2)CO1]

To a solution of ethyl (E)-7-hydroxy-6-phenylhept-2-enoate (1.25 g, 4.95 mmol) in 1,4-dioxane (165 mL) at rt was added NaH (60% dispersion in mineral oil, (396 mg, 9.90 mmol). The mixture was allowed to stir for 16 h at rt before diluting with EtOAc (30 mL), washing with sat. NH$_4$Cl (40 mL), washing with brine, drying over anhydrous MgSO$_4$, filtering, and concentrating under reduced pressure. The crude residue was purified using silica gel chromatography (0% to 10%, then 10% to 15%) to afford the desired product as a 1:1 mixture of diastereomers and clear, colorless oil (725 mg, 58%). $^1$H NMR (400 MHz; CDCl$_3$): δ 7.46-7.43 (m, 2H), 7.33-7.29 (m, 4H), 7.26-7.19 (m, 4H), 4.21-4.14 (m, 5H), 4.05-3.99 (m, 2H), 3.91-3.83 (m, 2H), 3.46 (t, J=11.2 Hz, 1H), 2.88-2.77 (m, 2H), 2.71-2.54 (m, 2H), 2.50-2.43 (m, 2H), 2.13-1.74 (m, 5H), 1.60-1.45 (m, 3H), 1.30-1.24 (m, 6H).

Example 291 cis-N-(4-Chlorophenyl)-2-(5-phenyltetrahydro-2H-pyran-2-yl)acetamide

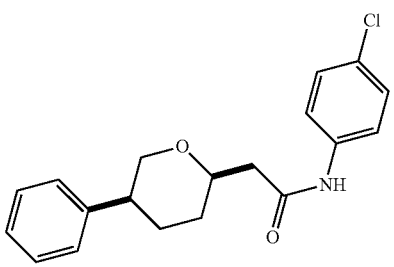

Prepared using General Procedure G employing ethyl 2-(5-phenyltetrahydro-2H-pyran-2-yl)acetate (361 mg, 1.45 mmol) and 4-chloroaniline (371 mg, 2.91 mmol). Purification employing silica gel chromatography (0% to 15%, then 15% to 20% EtOAc in pentanes) afforded the desired product as the first eluting isomer as a clear film. $^1$H NMR (400 MHz; CDCl$_3$): δ 8.51 (br s, 1H), 7.48-7.37 (m, 4H), 7.32-7.19 (m, 6H), 4.41 (d, J=11.9 Hz, 1H), 4.00-3.89 (m, 2H), 2.92 (br s, 1H), 2.65 (dd, J=8.5, 15.7 Hz, 1H), 2.57-2.46 (m, 1H), 2.14-2.04 (m, 2H), 1.70-1.50 (m, 3H).

General Procedure N: Coupling of Carboxylic Acid with Chiral Auxiliary

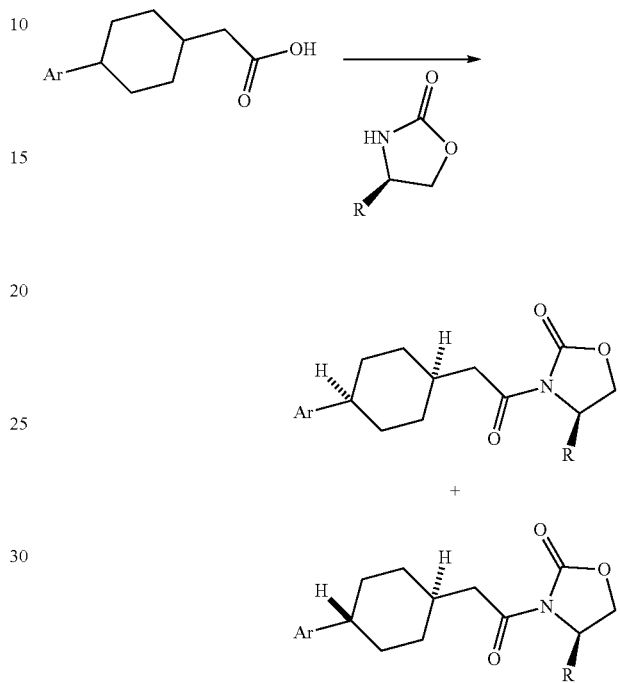

R = Bn, Ph

To an oven-dried round bottom flask (Flask #1) was added carboxylic acid (17.9 mmol, 1.0 equiv) as a mixture of diastereomers. The flask was evacuated and backfilled with nitrogen and subsequently charged with THF (70 mL) and triethylamine (5.00 mL, 35.8 mmol, 2.0 equiv). This solution was cooled to −78° C. before the slow addition of pivaloyl chloride (2.76 mL, 22.4 mmol, 1.25 equiv) over 15 minutes. The reaction was then stirred at 0° C. for one hour.

To a separate oven-dried round bottomed flask (Flask #2) was added chiral (R) or (S)-4-benzyl- or 4-phenyl-2-oxazolidinone (23.3 mmol, 1.3 equiv) and THF (70 mL). This solution was cooled to −78° C. before the careful addition of n-BuLi (2.5 M in hexanes, 23.3 mmol, 1.3 equiv). This reaction mixture was stirred at −78° C. for 15 minutes before being removed from the cold bath.

Flask #1 was then cooled back to −78° C. and the contents of Flask #2 were added to Flask #1 via cannula over the course of 15 minutes. After complete addition, the cold bath was removed and the reaction was allowed to stir for 3 hours at room temperature. The reaction was quenched by addition of saturated ammonium chloride solution (100 mL) and subsequent extraction with ethyl acetate (100 mL×3). The combined organics were washed with brine, dried over sodium sulfate, filtered and concentrated. The crude residue was purified using silica gel chromatography (10% to 20% EtOAc in methylene chloride) which allowed for the separation of diastereomers.

General Procedure O: Alkylation of Oxazalidinone-derived Imides

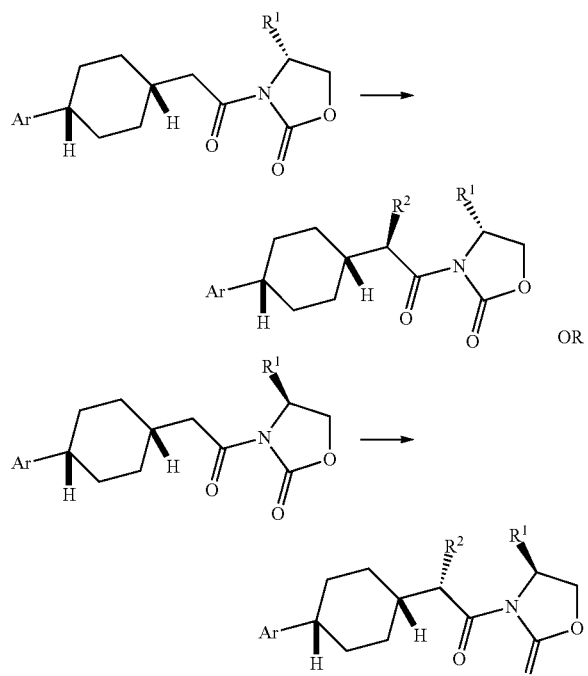

$R^1$ = Bn, Ph
$R^2$ = Alkyl group

A 2M Solution of NaHMDS (1.2 equiv) was added dropwise to 0.2 M solution of the imide (1.0 equiv) in anhydrous tetrahydrofuran at −50° C. The solution was stirred for 10 minutes at −50° C. and then neat alkylhalide was added dropwise. The reaction mixture was stirred for additional 2-48 hours at −50--20° C. and then quenched by adding saturated solution of ammonium chloride while still cold. Then reaction was allowed to warm to ambient temperature and was extracted 3 times with ethyl acetate. The combined organic phases were dried with $MgSO_4$, concentrated under reduced pressure, and subjected to flash chromatography using gradient 100% hexanes to 30% hexanes/70% ethyl acetate.

General Procedure P: Cleavage of Chiral Auxiliary

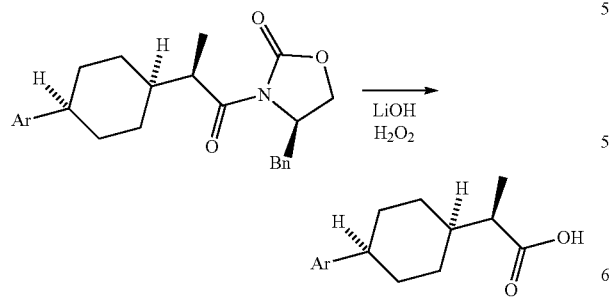

To a round bottom flask was added imide (1.0 equiv), THF (4.3 mL/mmol) and distilled water (1.0 mL/mmol). This solution was cooled to 0° C. before the slow addition of $H_2O_2$ (35 wt. % in water, 0.43 mL/mmol) followed by addition of LiOH (2.7 M in water; 1.6 equiv). The reaction was allowed to warm to rt. Reaction progress was followed by LC/MS, and the reaction was carefully quenched at 0° C. by the addition of saturated $Na_2SO_3$ (1 mL/mmol) once starting material had been consumed. The pH was adjusted to 5-6 with 1 N HCl, and then the mixture was extracted with EtOAc (5×) and methylene chloride (2×). The combined organics were dried over sodium sulfate, filtered, and concentrated. The crude product was purified using silica gel chromatography (10% to 50% EtOAc in methylene chloride) to afford a white solid.

General Procedure Q: Coupling of Carboxylic Acids and Anilines

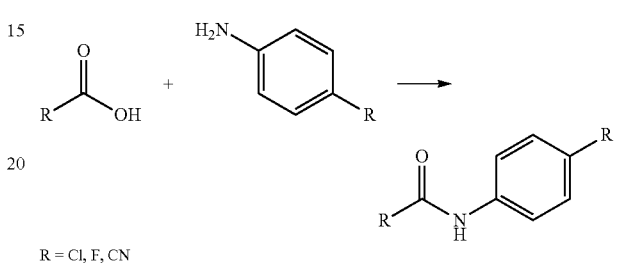

R = Cl, F, CN

Propylphosphonic anhydride (1.5 eq, 50 wt. % solution in ethyl acetate) was added to solution of carboxylic acid (1 equiv) and pyridine (3 equiv) in ethyl acetate (0.1 M) at ambient temperature. The reaction mixture was stirred for 5 min and then aniline (1.5 equiv) was added. The reaction was stirred at ambient temperature until complete consumption of the acid, which was determined by TLC and/or LC-MS. The reaction mixture was poured in water, 1M NaOH (10 equiv) was added, and aqueous layer was extracted with ethyl acetate 3 times. The combined organic phases was dried with $MgSO_4$, the solvent removed under reduced pressure, and the residue chromatographed on a silica gel column.

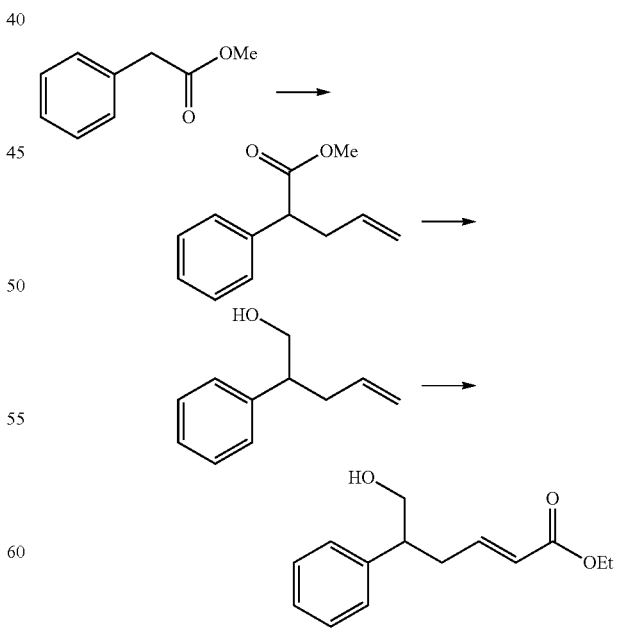

1-Ethyl 6-methyl (E)-5-phenylhex-2-enedioate: To a solution of methyl phenylacetate (4.0 g, 27 mmol, 1.0 equiv.) in DMF (75 mL, 0.36 M) at rt under argon was added NaH (60% dispersion in mineral oil, 1.4 g, 35 mmol, 1.3 equiv.). The mixture was stirred for 1 h before the addition of 4-bromobutene (2.97 mL, 29 mmol, 1.1 equiv.). The reaction mixture turned from light beige to orange/brown and was stirred for 2 h. The mixture was diluted with EtOAc (100 mL), and the organic layer was separated, washed with sat. NH₄Cl and brine, dried (MgSO₄), and concentrated. The crude residue was purified by silica gel chromatography (0% to 30% EtOAc in hexanes) to afford the desired product (2.08 g, 38%). Methyl 2-phenylpent-4-enoate (2.08 g, 10.2 mmol, 1.0 equiv.) was diluted in CH₂Cl₂ (51 mL) and cooled to −78° C. DIBAL-H (1 M in THF, 30.6 mL, 30.6 mmol, 3.0 equiv.) was added via syringe. The cold bath was removed after addition, and the clear, colorless reaction solution was allowed to warm to rt overnight. The reaction was then cooled to −78° C. before adding 7.2 mL of a buffer made from 1.2 mL NH₄OH and 10 mL sat. NH₄Cl. Some of the buffer froze upon addition. The cold bath was removed, and the reaction mixture was allowed to warm to rt before adding MgSO₄ (6.4 g). The mixture was filtered, rinsing with 30 mL of CH₂Cl₂. The solution was concentrated and used directly in the next reaction. 2-Phenylpent-4-en-1-ol (1.95 g, 11.1 mmol, 1.0 equiv.) was diluted in CH₂Cl₂ (138 mL) and degassed for 5 min. Ethyl acrylate (4.70 mL, 11.3 mmol, 4.0 equiv.) and Grubbs II catalyst (188 mg, 0.222 mmol, 0.02 equiv.) were added to the solution, and the reaction solution was placed in a 40° C. bath for 2 h. Additional Grubbs II (30 mg) was added, and the reaction was heated at 40° C. for an additional 14 h. The reaction was cooled to rt, concentrated by rotary evaporation, and purified by silica gel chromatography (0% to 20% EtOAc in hexanes) to afford the desired product (1.5 g, 54% yield).

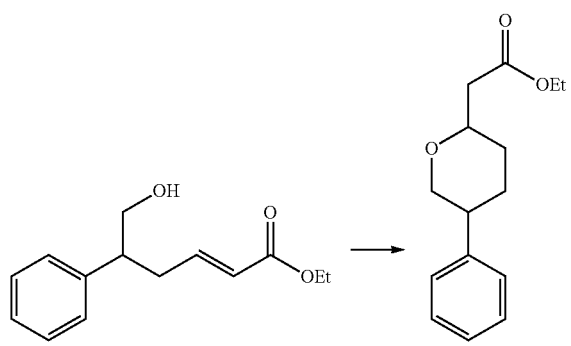 [SMILES: CCOC(=O)/C=C/CC(CO)c1ccccc1 ; CCOC(=O)CC1CCC(c2ccccc2)CO1]

Ethyl 2-(5-phenyltetrahydro-2H-pyran-2-yl)acetate: Ethyl (E)-6-hydroxy-5-phenylhex-2-enoate (500 mg, 2.0 mmol, 1.0 equiv.) was diluted in dioxane (66 mL) before adding NaH (60% dispersion in mineral oil, 160 mg, 4.0 mmol, 2.0 equiv.). The reaction was allowed to stir at rt overnight. The reaction was diluted with EtOAc (100 mL), washed with sat. NH₄Cl and brine, dried (MgSO₄), and concentrated. The crude residue was purified by silica gel chromatography (0% to 15% EtOAc in hexanes) to afford the desired product as a clear, colorless oil in a 1:1 cis/trans ratio (361 mg, 72% yield).

Example 292

N-(4-Fluorophenyl)-2-((2R,5S)-5-phenyltetrahydro-2H-pyran-2-yl)acetamide, and N-(4-Fluorophenyl)-2-((2S,5R)-5-phenyltetrahydro-2H-pyran-2-yl)acetamide

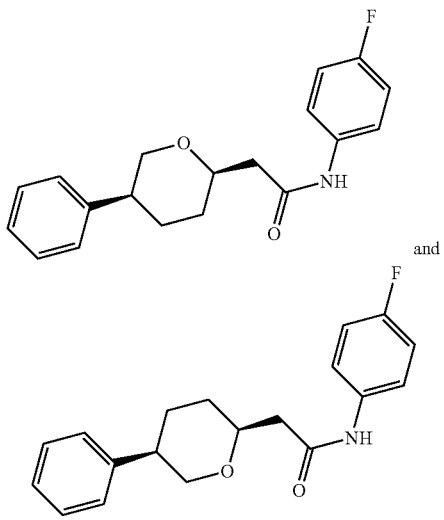

To a solution of 4-fluoroaniline (0.153 mL, 1.61 mmol, 2.0 equiv.) in THF (4 mL, 0.2 M) was added iPrMgCl (2 M in THF, 0.805 mL, 1.61 mmol, 2.0 equiv.). The reaction solution turned from clear and colorless to clear and orange/grey. The reaction was stirred for 20 min before adding ethyl 2-(5-phenyltetrahydro-2H-pyran-2-yl)acetate (200 mg, 0.805 mmol, 1.0 equiv.) as a solution in THF (2 mL). The reaction was stirred for 16 h and diluted with EtOAc (30 mL). The solution was washed with 3 M HCl (2×) and brine, dried (MgSO₄), and concentrated. The crude residue was purified twice by silica gel chromatography (0% to 35% EtOAc in hexane and 25% to 35% EtOAc in hexane) to afford the desired product. ¹H NMR (400 MHz; CDCl₃): δ 8.37-8.49 (m, 1H) 7.35-7.49 (m, 3H) 7.17-7.32 (m, 2H) 6.99 (t, J=8.7 Hz, 2H) 4.33-4.46 (m, 1H) 3.86-4.03 (m, 2H) 2.87-2.98 (m, 1H) 2.60-2.71 (m, 1H) 2.45-2.58 (m, 1H) 2.01-2.17 (m, 1H) 1.43-1.69 (m, 3H). m/z 314.2 (M+H)⁺.

Example 293 trans-N-(4-Chlorophenyl)-2-((4-(pyrimidin-5-yl)cyclohexyl)acetamide

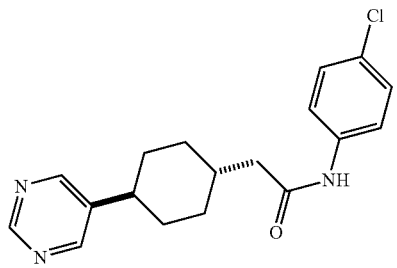

Prepared using General Procedures H, B, and G. For General Procedure H, 5-bromopyrimidine was employed. For General Procedure G, 4-chloroaniline was employed, and the residue was purified via preparative HPLC (Varian ProStar using Hamilton C18 PRP-1 column (15×250 mm) with flow rate of 20 mL/min, Mobile Phase A: 0.5% formic acid in water; Mobile Phase B: 0.5% formic acid in acetonitrile; 0% to 100% B gradient elution over 30 min) to afford the desired product. $^1$H NMR (400 MHz; CDCl$_3$): δ 9.15 (s, 1H), 8.70 (s, 2H), 7.50-7.46 (m, 2H), 7.31-7.26 (m, 2H), 7.15 (br s, 1H), 2.58-2.49 (m, 1H), 2.33-2.29 (m, 2H), 2.05-1.91 (m, 4H), 1.33-1.19 (m, 5H) ppm. m/z 330 (M+H)$^+$.

Example 294

(cis)-N-(4-Chlorophenyl)-2-(4-(2,4-dimethoxyphenyl)cyclohexyl)acetamide

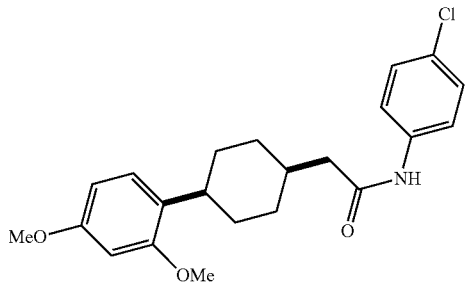

The title compound was prepared starting with General Procedure A employing ethyl 2-(4-(((trifluoromethyl)sulfonyl)oxy)cyclohex-3-en-1-yl)acetate and 2,4-dimethoxyphenylboronic acid. Next, General Procedure B was accomplished using 10% Pd/C as a hydrogenation catalyst. Ethyl 2-(4-(2,4-dimethoxyphenyl)cyclohexyl)acetate (333 mg, 1.09 mmol) was subjected to General Procedure G using 4-chloroaniline (292 mg, 2.29 mmol), iPrMgCl (1.1 mL, 2.17 mmol) in THF (14 mL). The reaction was purified using silica gel chromatography (5% to 35% EtOAc in hexanes) to afford the desired product as a white solid. $^1$H NMR (400 MHz; CDCl$_3$): δ 7.49-7.46 (m, 2H), 7.32-7.23 (m, 2H), 7.17-7.07 (m, 2H), 6.49-6.41 (m, 2H), 3.80 (s, 6H), 2.90 (tt, J=10.7, 3.6 Hz, 1H), 2.54-2.47 (m, 2H), 2.47-2.38 (m, 1H), 1.85-1.64 (m, 6H), 1.64-1.52 (m, 2H).

Example 295

(trans)-N-(4-Chlorophenyl)-2-(4-(2,4-dimethoxyphenyl)cyclohexyl)-acetamide

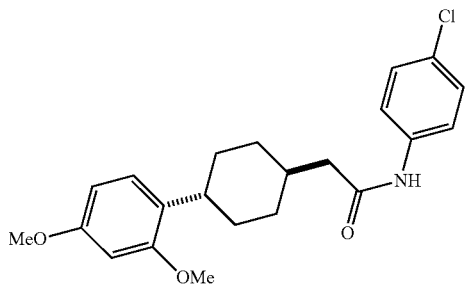

Further elution from the column in the previous example afforded the desired product as a white solid and the second eluting isomer. $^1$H NMR (400 MHz; CDCl$_3$): δ 7.50-7.46 (m, 2H), 7.29-7.25 (m, 2H), 7.18-7.02 (m, 2H), 6.49-6.41 (m, 2H), 3.81-3.75 (m, 6H), 2.86-2.75 (m, 1H), 2.27 (d, J=6.9 Hz, 2H), 1.98-1.84 (m, 5H), 1.51-1.41 (m, 2H), 1.28-1.16 (m, 2H).

Example 296

(cis)-N-(4-Cyanophenyl)-2-(4-(2,4-dimethoxyphenyl)cyclohexyl)acetamide

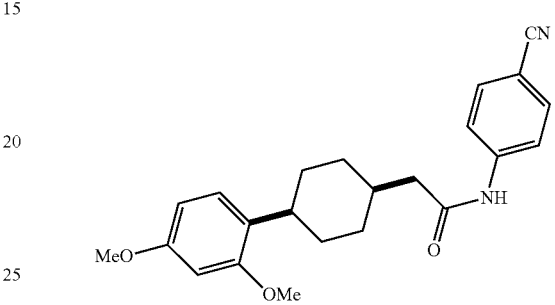

The title compound was prepared starting with General Procedure A employing ethyl 2-(4-(((trifluoromethyl)sulfonyl)oxy)cyclohex-3-en-1-yl)acetate and 2,4-dimethoxyphenylboronic acid. Next, General Procedure B was accomplished using 10% Pd/C as hydrogenation catalyst. Ethyl 2-(4-(2,4-dimethoxyphenyl)cyclohexyl)acetate (333 mg, 1.09 mmol) was subjected to General Procedure G using 4-cyanoaniline (270 mg, 2.29 mmol) and iPrMgCl (1.1 mL, 2.2 mmol) in THF (14 mL). The reaction was purified using silica gel chromatography (5% to 75% EtOAc in hexanes) to afford the desired product as a white solid. $^1$H NMR (400 MHz; CDCl$_3$): δ 7.72-7.63 (m, 2H), 7.63-7.55 (m, 2H), 7.50 (s, 1H), 7.09 (d, J=8.0 Hz, 1H), 6.49-6.39 (m, 2H), 2.89 (tt, J=11.2, 3.4 Hz, 1H), 2.54 (d, J=7.4 Hz, 2H), 2.49-2.38 (m, 1H), 1.85-1.47 (m, 8H).

Example 297

(cis)-N-(4-Fluorophenyl)-2-(4-(2,4-dimethoxyphenyl)cyclohexyl)acetamide

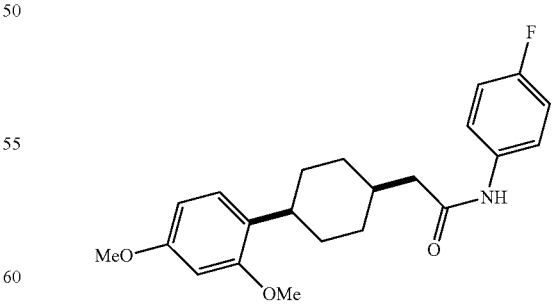

The title compound was prepared starting with General Procedure A employing ethyl 2-(4-(((trifluoromethyl)sulfonyl)oxy)cyclohex-3-en-1-yl)acetate and 2,4-dimethoxyphenylboronic acid. Next, General Procedure B was accomplished using 10% Pd/C as hydrogenation catalyst. Ethyl 2-(4-(2,4-dimethoxyphenyl)cyclohexyl)acetate (333 mg, 1.09 mmol) was subjected to General Procedure G using 4-fluoroaniline (0.22 mL, 2.29 mmol) and iPrMgCl (1.1 mL, 2.2 mmol) in THF (14 mL). The reaction was purified using silica gel chromatography (5% to 40% EtOAc in hexanes) to afford the desired product as a white solid. $^1$H NMR (400 MHz; CDCl$_3$): δ 7.55-7.39 (m, 2H), 7.18 (s, 1H), 7.13-7.07 (m, 1H), 7.04-6.97 (m, 2H), 6.48-6.42 (m, 2H), 3.80 (s, 6H), 2.90 (tt, J=10.9, 3.5 Hz, 1H), 2.53-2.35 (m, 3H), 1.85-1.64 (m, 6H), 1.63-1.49 (m, 2H).

Example 298

2-(4-(4-Acetamidophenyl)cyclohexyl)-N-(4-chlorophenyl)-acetamide

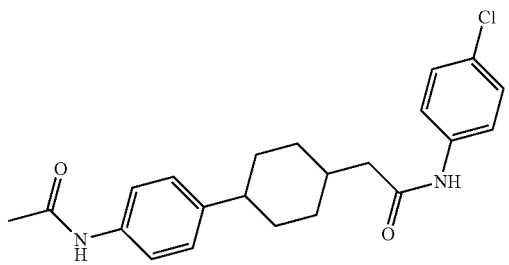 [SMILES: CC(=O)Nc1ccc(C2CCC(CC(=O)Nc3ccc(F)cc3)CC2)cc1]

Prepared using General Procedures H, B, E, and F. 4-Acetamidophenyl boronic acid was employed in Procedure H, and 4-chloroaniline was employed in Procedure G. Purified using silica gel chromatography (0% to 100% EtOAc in hexanes) to afford the desired product as a mixture of cis- and trans-isomers. m/z 385.3 (M+H)$^+$.

Example 299

2-(4-(4-A cetamidophenyl)cyclohexyl)-N-(4-fluorophenyl)-acetamide

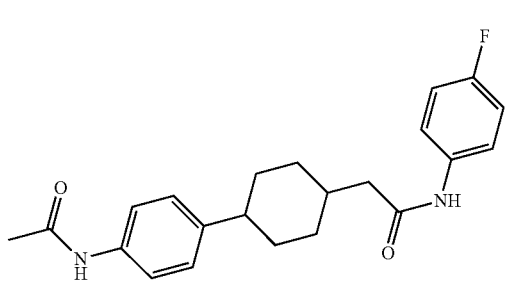

Prepared using General Procedures H, B, E, and F. 4-Acetamidophenyl boronic acid was employed in Procedure H, and 4-fluoroaniline was employed in Procedure G. Purified using silica gel chromatography (0% to 100% EtOAc in hexanes) to afford the desired product as a mixture of cis- and trans-isomers. m/z 385.3 (M+H)$^+$.

Example 300 cis-2-(4-(4-Methoxyphenyl)cyclohexyl)-N-(4-(tetrahydro-2H-pyran-4-yl)phenyl)acetamide

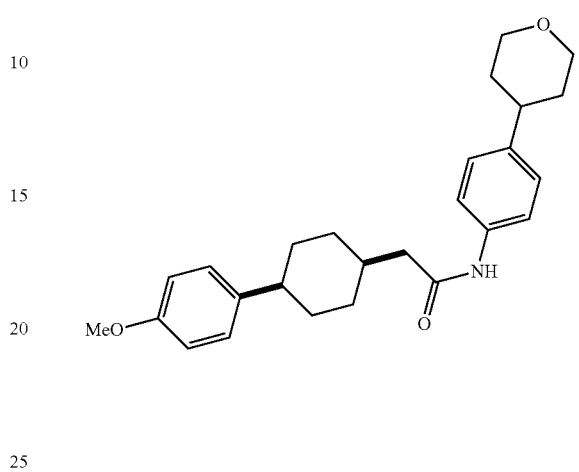

Prepared using General Procedure G employing ethyl 2-(4-(4-methoxyphenyl)cyclohexyl)acetate and 4-(tetrahydro-2H-pyran-4-yl)-benzeneamine. Purified using silica gel chromatography (0% to 80% EtOAc in hexanes) to afford the first eluting isomer as the desired product. $^1$H NMR (400 MHz, CD$_3$OD) δ 7.48 (d, J=8.5 Hz, 2H), 7.33-7.13 (m, 4H), 6.83 (d, J=8.7 Hz, 2H), 4.03 (dd, J=8.5, 5.3 Hz, 2H), 3.75 (s, 3H), 3.63-3.48 (m, 2H), 2.84-2.69 (m, 1H), 2.62-2.42 (m, 3H), 2.34 (s, 1H), 1.82-1.51 (m, 12H). m/z 408.3 (M+H)$^+$.

Example 301

N-(4-Chlorophenyl)-2-(4-(4-hydroxyphenyl)cyclohexyl)acetamide

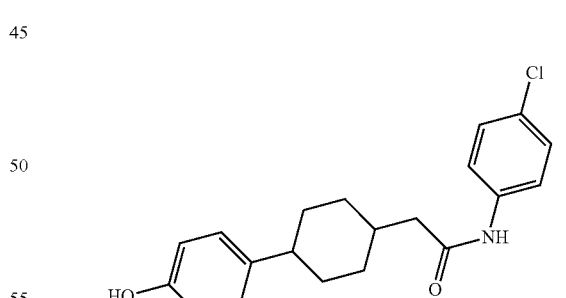

Prepared using General Procedures E and F. Ethyl 2-(4-(4-hydroxyphenyl)cyclohexyl)acetate was employed in Procedure E, and 4-chloroaniline was employed in Procedure F. Purified using silica gel chromatography (0% to 60% EtOAc in hexanes) to afford the desired product as a mixture of cis- and trans-isomers. m/z 344.2 (M+H)$^+$.

Example 302

(S)—N-(4-Cyanophenyl)-2-((1s,4r)-4-phenylcyclohexyl)propanamide

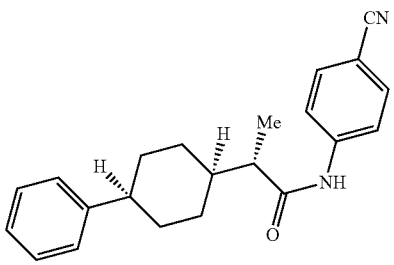 [SMILES: C[C@H](C(=O)Nc1ccc(C#N)cc1)[C@H]1CC[C@@H](c2ccccc2)CC1]

Prepared from 2-((1s,4s)-4-phenylcyclohexyl)acetic acid. This material was converted to the (S)-benzyl imide employing General Procedure N. The imide product was methylated with iodomethane employing General Procedure O. The methylated imide was hydrolyzed to the carboxylic acid employing General Procedure P. (S)-2-((1s,4r)-4-Phenylcyclohexyl)propanoic acid was converted to (S)—N-(4-cyanophenyl)-2-((1s,4r)-4-phenylcyclohexyl)propanamide employing General Procedure Q using 4-cyanoaniline. The product was obtained as a white solid after silica gel chromatography (10% to 30% EtOAc in hexanes). $^1$H NMR (400 MHz; CDCl$_3$): δ 7.70-7.66 (m, 2H), 7.59 (dt, J=6.6, 3.3 Hz, 2H), 7.36 (s, 1H), 7.33-7.25 (m, 4H), 7.22-7.17 (m, 1H), 2.75-2.68 (m, 1H), 2.56-2.48 (m, 1H), 2.02-1.95 (m, 1H), 1.80-1.59 (m, 8H), 1.25 (d, J=6.8 Hz, 3H).

Example 303

(R)—N-(4-Cyanophenyl)-2-((1s,4r)-4-phenylcyclohexyl)propanamide

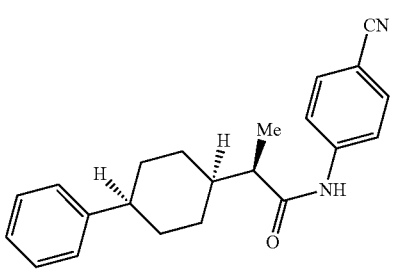 [SMILES: C[C@@H](C(=O)Nc1ccc(C#N)cc1)[C@H]1CC[C@@H](c2ccccc2)CC1]

Prepared from 2-((1s,4s)-4-phenylcyclohexyl)acetic acid. This material was converted to the (R)-benzyl imide employing General Procedure N. The imide product was methylated with iodomethane employing General Procedure O. The methylated imide was hydrolyzed to the carboxylic acid employing General Procedure P. (R)-2-((1s,4r)-4-Phenylcyclohexyl)propanoic acid was converted to (R)—N-(4-cyanophenyl)-2-((1s,4r)-4-phenylcyclohexyl)propanamide employing General Procedure Q using 4-cyanoaniline. The product was obtained as a white solid after silica gel chromatography (10% to 30% EtOAc in hexanes). $^1$H NMR (400 MHz; CDCl$_3$): δ 7.69-7.66 (m, 2H), 7.62-7.60 (m, 2H), 7.33-7.27 (m, 4H), 7.22-7.18 (m, 1H), 2.75-2.69 (m, 1H), 2.55-2.47 (m, 1H), 2.01-1.96 (m, 1H), 1.79-1.58 (m, 8H), 1.25 (d, J=6.8 Hz, 3H).

Example 304

(R)—N-(4-Cyanophenyl)-2-((1s,4s)-4-(4-methoxyphenyl)cyclohexyl)propanamide

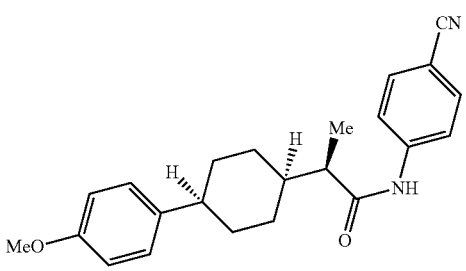 [SMILES: COc1ccc([C@H]2CC[C@@H]([C@@H](C)C(=O)Nc3ccc(C#N)cc3)CC2)cc1]

Prepared from 2-((1s,4s)-4-(4-methoxyphenyl)cyclohexyl)acetic acid. This material was converted to the (R)-benzyl imide employing General Procedure N. The imide product was methylated with iodomethane employing General Procedure O. The methylated imide was hydrolyzed to the carboxylic acid employing General Procedure P. The carboxylic acid was converted to (R)—N-(4-cyanophenyl)-2-((1s,4s)-4-(4-methoxyphenyl)cyclohexyl)propanamide employing General Procedure Q using 4-cyanoaniline. The product was obtained as a white foam after column chromatography (10% to 30% EtOAc in hexanes). $^1$H NMR (400 MHz; CDCl$_3$): δ 7.69-7.66 (m, 2H), 7.62-7.59 (m, 2H), 7.28 (s, 1H), 7.19-7.16 (m, 2H), 6.87-6.84 (m, 2H), 3.80 (s, 3H), 2.69-2.65 (m, 1H), 2.54-2.46 (m, 1H), 1.99-1.94 (m, 1H), 1.78-1.58 (m, 8H), 1.25 (d, J=6.8 Hz, 3H).

Example 305

N-(4-Chlorophenyl)-2-(trans-4-((3-(trifluoromethyl)pyridin-4-yl)oxy) cyclohexyl)butanamide

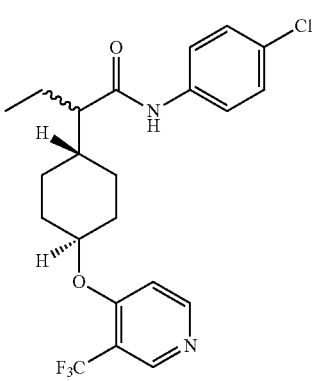 [SMILES: CCC(C(=O)Nc1ccc(Cl)cc1)[C@H]1CC[C@H](Oc2ccncc2C(F)(F)F)CC1]

Intermediate 305A: Ethyl 2-(1,4-dioxaspiro[4.5]decan-8-ylidene)acetate

Triethyl phosphonoacetate (21.79 ml, 109 mmol) was added to a suspension of sodium hydride (3.84 g, 96 mmol) in THF (64.0 ml) and 0° C. Reaction was stirred at room temperature for 30 minutes. After 30 minutes, the reaction was recooled to 0° C. and a solution of 1,4-dioxaspiro[4.5]decan-8-one (10 g, 64.0 mmol) in 5 mL THF was added. The reaction was then stirred at room temperature for 30 minutes prior to quenching with water. The mixture was extracted with DCM three times. Combined organic extracts were dried with sodium sulfate, filtered, and concentrated in vacuo. Crude residue was purified via silica gel chromatography to give Intermediate 305A (13.88 g, 61.3 mmol, 96% yield). TLC: product stains as purple spot in anisaldehyde (Rf=0.75 in 1:1 Hex/EtOAc). $^1$H NMR (400 MHz, chloroform-d) δ: 5.65 (s, 1H), 4.13 (q, J=7.2 Hz, 2H), 3.92-3.99 (m, 4H), 2.94-3.02 (m, 2H), 2.31-2.40 (m, 2H), 1.71-1.79 (m, 4H), 1.26 (t, J=7.2 Hz, 3H).

Intermediate 305B: Ethyl 2-(1,4-dioxaspiro[4.5]decan-8-yl)acetate

Intermediate 305B (13.88 g, 61.3 mmol) was taken up in EtOAc (61.3 ml) and was added to a Parr hydrogenation bottle containing wet 10% palladium on carbon (1.306 g, 12.27 mmol)(54% w/w water) under an atmosphere of nitrogen. The reaction bottle was purged and back-filled with nitrogen three times, and then with hydrogen (3×). After filling the bottle with hydrogen to 50 psi, the bottle was placed in a Parr shaker and shaken. After 4 hours, the reaction was filtered over CELITE® and concentrated in vacuo to give Intermediate 305B (13.78 g, 60.4 mmol, 98% yield). LC-MS Anal. Calc'd for $C_{12}H_{20}O_4$ 228.14, found [M+H] 299.1 $T_r$=0.83 min (Method A). $^1$H NMR (400 MHz, chloroform-d) δ: 4.11 (q, J=7.2 Hz, 2H), 3.88-3.95 (m, 4H), 2.21 (d, J=7.0 Hz, 2H), 1.83 (dqd, J=11.0, 7.5, 3.5 Hz, 1H), 1.68-1.78 (m, 4H), 1.50-1.61 (m, 2H), 1.27-1.35 (m, 2H), 1.24 (t, J=7.2 Hz, 3H).

Intermediate 305C: Ethyl 2-(1,4-dioxaspiro[4.5]decan-8-yl)butanoate

Diisopropylamine (2.347 ml, 16.63 mmol) was taken up in dry THF (15.99 ml) (under $N_2$ atmosphere) and cooled to −78° C. n-BuLi (6.14 ml, 15.35 mmol) (2.5 Min hexanes) was added over ~5 minutes at −78° C. After stirring for 45 minutes, the reaction was warmed to room temperature for 10 minutes and then cooled back to −78° C. 1,3-dimethyltetrahydropyrimidin-2(1H)-one (1.541 ml, 12.79 mmol) was added, followed by a solution of Intermediate 305B (2.92 g, 12.79 mmol) in THF (15.99 ml) dropwise over ~5 minutes. After 1 hour, iodoethane (1.125 ml, 14.07 mmol) (neat) was added dropwise over ~5 minutes. Reaction stirred another 2 hours at −78° C. before slowly warming to room temperature. The reaction was then stirred overnight at room temperature. The reaction was quenched by pouring into 1:1 water/brine and extracted with EtOAc. Combined organics washed with brine, dried with sodium sulfate, filtered and concentrated in vacuo. Crude residue was purified via silica gel column chromatography to give Intermediate 305C (2.27 g, 8.86 mmol, 69% yield). TLC: product stains as purple spot in anisaldehyde (Rf=0.80 in 1:1 Hex/EtOAc). $^1$H NMR (400 MHz, chloroform-d) δ: 4.14 (q, J=7.5 Hz, 2H), 3.88-3.95 (m, 4H), 2.09 (td, J=8.4, 5.6 Hz, 1H), 1.69-1.83 (m, 4H), 1.45-1.64 (m, 6H), 1.33-1.42 (m, 1H), 1.25 (t, J=7.1 Hz, 3H), 0.86 (t, J=7.5 Hz, 3H).

Intermediate 305D: Ethyl 2-(4-oxocyclohexyl)butanoate

Intermediate 305C (2.00 g, 7.80 mmol) was taken up in THF (39.0 ml) and hydrochloric acid, 1M (39.0 ml) was added. Reaction stirred at room temperature for 2 hours. The reaction was concentrated in vacuo, diluted with water and extracted with EtOAc. The combined organic extracts were dried with sodium sulfate, filtered and concentrated in vacuo. The crude material was purified on silica gel column chromatography to give Intermediate 305D (1.47 g, 6.92 mmol, 89% yield). TLC: product stains faintly pink in anisaldehyde (Rf=0.65 in 1:1 Hex/EtOAc). $^1$H NMR (400 MHz, chloroform-d) δ: 4.15 (q, J=7.1 Hz, 2H), 2.25-2.42 (m, 4H), 2.18 (ddd, J=9.3, 7.8, 5.2 Hz, 1H), 2.10 (ddt, J=13.1, 6.2, 3.3 Hz, 1H), 1.90-2.03 (m, 2H), 1.56-1.70 (m, 2H), 1.38-1.56 (m, 2H), 1.25 (t, J=7.2 Hz, 3H), 0.89 (t, J=7.4 Hz, 3H).

Intermediate 305E: Ethyl (R)-2-(trans-4-hydroxycyclohexyl)butanoate

Intermediate 305D (1.47 g, 6.92 mmol) was dissolved in EtOH (13.85 ml) and cooled to 0° C. $NaBH_4$ (0.314 g, 8.31 mmol) was added and the reaction was then allowed to stir at 0° C. for 1 hour. The reaction was quenched with saturated aqueous $NH_4Cl$ and extracted with EtOAc. The combined organic extracts were dried with sodium sulfate, filtered, and concentrated in vacuo. The crude material was purified via silica gel column chromatography to give Intermediate 305E (1.22 g, 5.69 mmol, 82% yield) along with (138 mg, 0.644 mmol, 9.30% yield) of the cis-isomer. $^1$H NMR (400 MHz, chloroform-d) δ: 4.14 (q, J=7.1 Hz, 2H), 3.53 (t, J=10.5 Hz, 1H), 1.92-2.08 (m, 2H), 1.80-1.89 (m, 1H), 1.63-1.70 (m, 1H), 1.52-1.62 (m, 4H), 1.37-1.52 (m, 2H), 1.26 (t, J=7.2 Hz, 3H), 0.95-1.17 (m, 2H), 0.87 (t, J=7.4 Hz, 3H).

Intermediate 305F: Ethyl-2-(trans-4-((3-(trifluoromethyl)pyridin-4-yl)oxy) cyclohexyl)butanoate Intermediate 305E (50 mg, 0.233 mmol) was taken up in DMSO (467 µl) and NaH (11.20 mg, 0.467 mmol) as added slowly, portionwise at room temperature. After 1 hour, 4-chloro-3-(trifluoromethyl)pyridine (50.8 mg, 0.280 mmol) was added and the reaction was heated to 80° C. After 1 hour the reaction was quenched with ammonium chloride and extracted with EtOAc. The combined organic extracts were dried with sodium sulfate, filtered, concentrated in vacuo. The crude material was purified via silica gel column chromatography to give Intermediate 305F (29 mg, 0.081 mmol, 34.6% yield). LC-MS Anal. Calc'd for $C_{18}H_{24}F_3NO_3$ 359.17, found [M+H] 360.1 $T_r$=0.88 min (Method A).

Intermediate 305G: (R)-2-(trans-4-((3-(Trifluoromethyl)pyridin-4-yl)oxy)cyclohexyl) butanoic Acid Intermediate 305F (29 mg, 0.081 mmol) was taken up in THF (323 µl), water (323 µl), and MeOH (161 µl). Lithium hydroxide (19.32 mg, 0.807 mmol) added and reaction stirred at rt for two hours. The reaction was heated to 50° C. for 16 hours. The reaction was then heated to 60° C. for 48 hours. The reaction was concentrated in vacuo, diluted with water, and acidified with glacial acetic acid and extracted with EtOAc. Combined organic extracts were dried with sodium sulfate, filtered, and concentrated in vacuo to give Intermediate 305G (26 mg, 0.079 mmol, 99% yield). LC- MS Anal. Calc'd for $C_{16}H_{20}F_3NO_3$ 331.14, found [M+H] 332.1 $T_r$=0.73 min (Method A).

Example 305: N-(4-Chlorophenyl)-2-(trans-4-((3-(trifluoromethyl) pyridin-4-yl)oxy)cyclohexyl)butanamide Intermediate 305G (27 mg, 0.081 mmol) was placed under a nitrogen atmosphere and taken up in $SOCl_2$ (59.5 µl, 0.815 mmol). 1 drop of anhydrous DMF was added and the mixture was stirred for 1 h at room temperature. The mixture was then concentrated in vacuo and co-evaporation with toluene, in vacuo, was used to remove the remaining thionyl chloride. The crude acyl chloride was dissolved in DCM (815 µl) under a nitrogen atmosphere and TEA (56.8 µl, 0.407 mmol) was added followed by 4-chloroaniline (15.59 mg, 0.122 mmol). The mixture was stirred at room temperature. After 30 minutes, the reaction was concentrated in vacuo, taken up in DMF, filtered, and purified via preparative HPLC to give Example 305 (9.3 mg, 0.021 mmol, 26% yield). LC-MS Anal. Calc'd for $C_{22}H_{24}ClF_3N_2O_2$ 440.15, found [M+H] 441.1 $T_r$=0.91 min (Method A). $^1$H NMR (500 MHz, DMSO-$d_6$) δ: 10.05 (s, 1H), 8.64 (s, 1H), 8.62 (d, J=5.9 Hz, 1H), 7.65 (d, J=8.7 Hz, 2H), 7.41 (d, J=5.8 Hz, 1H), 7.34 (d, J=8.7 Hz, 2H), 4.58 (t, J=9.8 Hz, 1H), 2.04-2.19 (m, 3H), 1.91 (d, J=12.8 Hz, 1H), 1.68 (d, J=12.3 Hz, 1H), 1.48-1.60 (m, J=7.2, 7.2 Hz, 3H), 1.21-1.44 (m, 3H), 1.09-1.21 (m, 1H), 0.83 (t, J=7.2 Hz, 3H).

Enantiomer 1 and Enantiomer 2

Enantiomer 1: Example 305a

N-(4-Chlorophenyl)-2-((1r,4r)-4-((3-(trifluoromethyl)pyridin-4-yl)oxy)cyclohexyl)-2λ$^3$-butanamide (Homochiral, Stereochemistry Unknown)

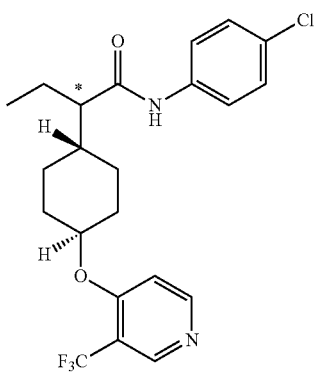 [SMILES: CCC(C(=O)Nc1ccc(Cl)cc1)[C@H]1CC[C@H](Oc2ccncc2C(F)(F)F)CC1]

Enantiomer 2: Example 305b

N-(4-Chlorophenyl)-2-((1r,4r)-4-((3-(trifluoromethyl)pyridin-4-yl)oxy)cyclohexyl)-2λ$^3$-butanamide (Homochiral, Stereochemistry Unknown)

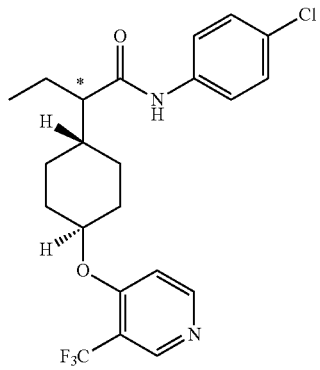 [SMILES: CCC(C(=O)Nc1ccc(Cl)cc1)[C@H]1CC[C@H](Oc2ccncc2C(F)(F)F)CC1]

Example 305a Enantiomer 1 and Example 305b Enantiomer 2 Chiral separation of the racemic sample (Method C) gave Enantiomer 1 $T_r$=2.51 min (Method D) and Enantiomer 2 $T_r$=3.33 min (Method D) Absolute stereochemistry was not determined.

Example 305a: MS(ES): m/z=441.2 [M+H]$^+$. $T_r$=2.247 min (Method B). $^1$H NMR (500 MHz, DMSO-$d_6$) δ: 10.06 (s, 1H), 8.58-8.66 (m, 2H), 7.64 (d, J=8.7 Hz, 2H), 7.39 (d, J=5.8 Hz, 1H), 7.34 (d, J=8.6 Hz, 2H), 4.58 (br. s., 1H), 2.03-2.16 (m, 3H), 1.91 (d, J=13.0 Hz, 1H), 1.67 (d, J=11.5 Hz, 1H), 1.47-1.59 (m, 3H), 1.07-1.42 (m, 4H), 0.82 (t, J=7.2 Hz, 3H).

Example 305b: MS(ES): m/z=441.1 [M+H]$^1$. $T_r$=2.237 min (Method B). $^1$H NMR (500 MHz, DMSO-$d_6$) δ: 10.05 (s, 1H), 8.55-8.70 (m, 2H), 7.64 (d, J=8.7 Hz, 2H), 7.40 (d, J=5.8 Hz, 1H), 7.34 (d, J=8.6 Hz, 2H), 4.58 (br. s., 1H), 2.03-2.16 (m, 3H), 1.91 (d, J=13.1 Hz, 1H), 1.67 (d, J=11.4 Hz, 1H), 1.47-1.59 (m, 3H), 1.08-1.47 (m, 4H), 0.82 (t, J=7.2 Hz, 3H).

Example 306

N-(4-Chlorophenyl)-2-(cis-4-(pyridin-4-yloxy)cyclohexyl)butanamide

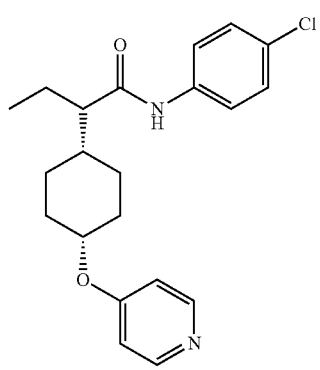 [SMILES: CCC(C(=O)Nc1ccc(Cl)cc1)[C@H]1CC[C@@H](Oc2ccncc2)CC1]

Intermediate 306A: Ethyl 2-(cis-4-(pyridin-4-yloxy)cyclohexyl)but-anoate

Intermediate 305E (100 mg, 0.467 mmol) was dissolved in THF (1867 µl) and pyridin-4-ol (98 mg, 1.027 mmol) and triphenylphosphine (269 mg, 1.027 mmol) were added. Solution was cooled to 0° C. in an ice bath. Diisopropyl azodicarboxylate (200 µl, 1.027 mmol) was added and the reaction was allowed to stir at room temperature once the addition was complete. Stirred at room temperature for 16 hours. Reaction was concentrated in vacuo and purified via silica gel column chromatography to afford Intermediate 306A (89 mg, 0.205 mmol, 43.9% yield). LC-MS Anal. Calc'd for $C_{17}H_{25}NO_3$ 291.18, found [M+H] 292.3 $T_r$=0.84 min (Method A). $^1$H NMR (400 MHz, chloroform-d) δ: 8.34-8.42 (m, 2H), 6.71-6.79 (m, 2H), 4.57-4.64 (m, 1H), 4.15 (q, J=7.1 Hz, 2H), 2.14 (ddd, J=9.8, 7.9, 4.6 Hz, 1H), 1.97-2.07 (m, 2H), 1.38-1.69 (m, 9H), 1.24-1.29 (m, 3H), 0.88 (t, J=7.4 Hz, 3H).

Intermediate 306B: 2-(cis-4-(Pyridin-4-yloxy)cyclohexyl)butanoic Acid

Intermediate 306A (89 mg, 0.305 mmol) was taken up in THF (244 µl), water (244 µl), and MeOH (122 µl). Lithium hydroxide (73.1 mg, 3.05 mmol) was added and the reaction stirred at 60° C. for 16 hours. Lithium hydroxide (73.1 mg, 3.05 mmol) was added and the reaction stirred another 24 hours at 60° C. The reaction was concentrated in vacuo, diluted with water and extracted with EtOAc. The aqueous layer was then treated with AcOH and extracted with EtOAc. Extracted again with 7:3 chloroform:propanol. Organics were dried with sodium sulfate, filtered, and concentrated in vacuo to give Intermediate 306B (73 mg, 0.277 mmol, 91% yield). LC-MS Anal. Calc'd for $C_{15}H_{21}NO_3$ 263.15, found [M+H] 264.2 T, =0.58 min (Method A).

Example 306: N-(4-Chlorophenyl)-2-(cis-4-(pyridin-4-yloxy)cyclohexyl)butanamide Intermediate 306B (35 mg, 0.133 mmol) was placed under a nitrogen atmosphere and taken up in $SOCl_2$ (97 µl, 1.329 mmol). One drop of anhydrous DMF was added and the mixture was stirred for 1 hour at room temperature. The mixture was then concentrated in vacuo and co-evaporation with toluene, in vacuo, was used to remove the remaining thionyl chloride. The crude acyl chloride was dissolved in DCM (1329 µl) under a nitrogen atmosphere and TEA (93 µl, 0.665 mmol) was added followed by 4-chloroaniline (25.4 mg, 0.199 mmol). The mixture was stirred at room temperature for 30 minutes. The reaction was concentrated in vacuo, taken up in DMF, filtered, and purified via preparative HPLC to give Example 306 (20.7 mg, 0.055 mmol, 41%). LC-MS Anal. Calc'd for $C_{21}H_{25}ClN_2O_2$ 372.16, found [M+H] 373.2 $T_r$=0.77 min (Method A). $^1$H NMR (500 MHz, DMSO-$d_6$) δ: 10.07 (s, 1H), 8.31 (d, J=5.5 Hz, 2H), 7.61 (d, J=8.7 Hz, 2H), 7.32 (d, J=8.6 Hz, 2H), 6.91 (d, J=5.6 Hz, 2H), 4.68 (br. s., 1H), 2.13 (t, J=7.9 Hz, 1H), 1.86 (br. s., 2H), 1.20-1.69 (m, 9H), 0.80 (t, J=7.2 Hz, 3H).

Enantiomer 1 and Enantiomer 2

Enantiomer 1: Example 306a

N-(4-Chlorophenyl)-2-(cis-4-(pyridin-4-yloxy)cyclohexyl)butanamide (Homochiral, Absolute Stereochemistry Unknown)

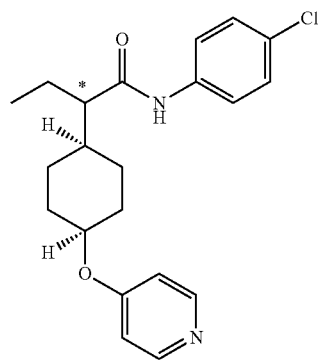 [SMILES: CCC(C(=O)Nc1ccc(Cl)cc1)[C@H]1CC[C@@H](Oc2ccncc2)CC1]

Enantiomer 2: Example 306b

N-(4-Chlorophenyl)-2-(cis-4-(pyridin-4-yloxy)cyclohexyl)butanamide (Homochiral, Stereochemistry Unknown)

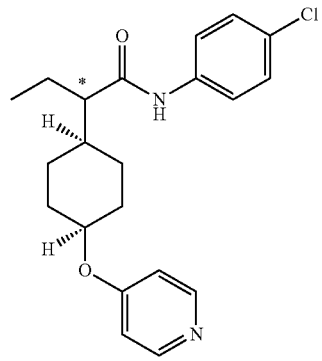 [SMILES: CCC(C(=O)Nc1ccc(Cl)cc1)[C@H]1CC[C@@H](Oc2ccncc2)CC1]

Example 306a Enantiomer 1 and Example 306b Enantiomer 2: Chiral separation of the racemic sample (Method E) gave Enantiomer 1 $T_r$=3.363 min (Method F) and Enantiomer 2 $T_r$=4.011 min (Method F) Absolute stereochemistry was not determined.

Example 306a: MS(ES): m/z=373.3 [M+H]$^+$. $T_r$=1.914 min (Method B). $^1$H NMR (500 MHz, DMSO-$d_6$) δ: 10.03 (s, 1H), 8.34 (d, J=5.7 Hz, 2H), 7.63 (d, J=8.8 Hz, 2H), 7.33 (d, J=8.7 Hz, 2H), 6.92 (d, J=5.9 Hz, 2H), 4.70 (br. s., 1H), 2.15 (t, J=7.9 Hz, 1H), 1.89 (d, J=14.6 Hz, 2H), 1.11-1.72 (m, 9H), 0.82 (t, J=7.2 Hz, 3H).

Example 306b: MS(ES): m/z=372.9 [M+H] $T_r$=1.875 min (Method B). $^1$H NMR (500 MHz, DMSO-$d_6$) δ: 10.04 (s, 1H), 8.35 (d, J=5.4 Hz, 2H), 7.64 (d, J=8.8 Hz, 2H), 7.34 (d, J=8.8 Hz, 2H), 6.93 (d, J=5.7 Hz, 2H), 4.71 (br. s., 1H), 2.15 (t, J=7.8 Hz, 1H), 1.90 (d, J=14.3 Hz, 2H), 1.12-1.73 (m, 9H), 0.83 (t, J=7.2 Hz, 3H).

Example 307

N-(4-Chlorophenyl)-2-(4-(2,6-dimethylpyridin-4-yl)cyclohexyl)propanamide (Homochiral, Absolute and Relative Stereochemistry not Determined)

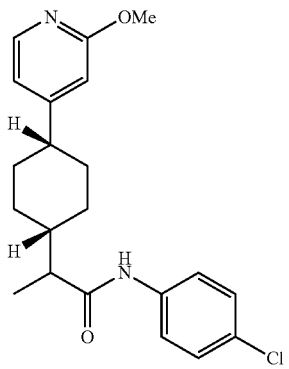

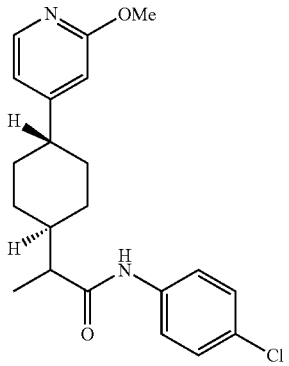

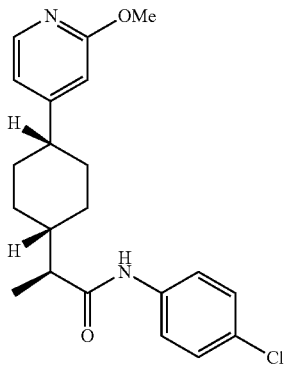

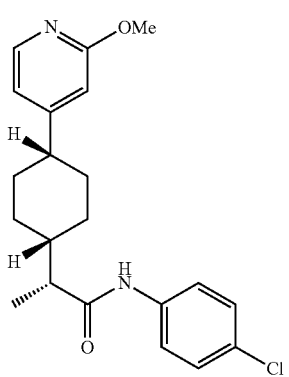

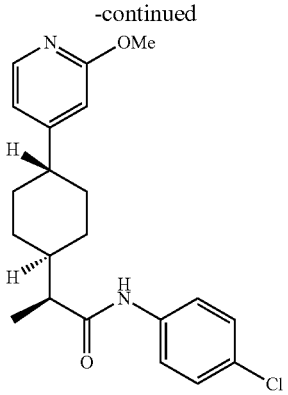

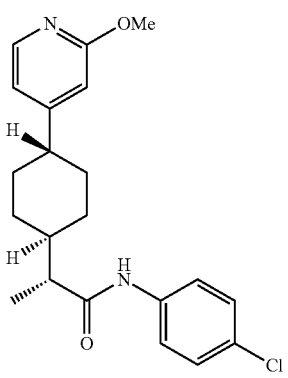

307A. Ethyl 2-(1,4-dioxaspiro[4.5]decan-8-ylidene)propanoate

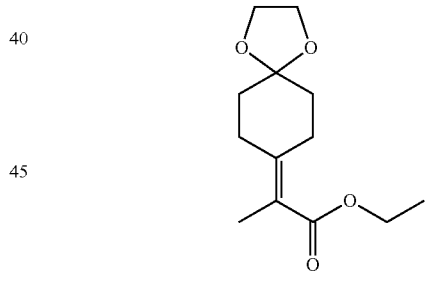

To a suspension of NaH (0.307 g, 7.68 mmol) in THF (8 mL) cooled at 0° C. was added ethyl 2-(diethoxyphosphoryl)propanoate (1.830 g, 7.68 mmol) slowly. After 30 min, 1,4-dioxaspiro[4.5]decan-8-one (1 g, 6.40 mmol) was added. The resulting mixture was stirred at 0° C. for 2 h, then warmed to rt overnight. The mixture was quenched with water, and THF was removed under reduced pressure. The residue was dissolved in EtOAc, washed with water, brine, dried over $Na_2SO_4$, filtered, and concentrated. The crude material was purified by ISCO(EtOAc/Hex 0-30%). Fractions containing the product were concentrated to yield ethyl 2-(1,4-dioxaspiro[4.5]decan-8-ylidene)propanoate (1.2 g, 78% yield) a light yellow oil. $^1$H NMR (400 MHz, chloroform-d) δ 4.19 (q, J=7.1 Hz, 2H), 4.03-3.89 (m, 4H), 2.68-2.53 (m, 2H), 2.46-2.28 (m, 2H), 1.89 (s, 3H), 1.78-1.66 (m, 4H), 1.30 (t, J=7.1 Hz, 3H).

307B. Ethyl 2-(1,4-dioxaspiro[4.5]decan-8-yl)propanoate

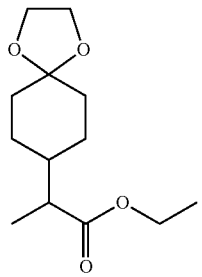 [SMILES: CCOC(=O)C(C)C1CCC2(CC1)OCCO2]

A suspension of ethyl 2-(1,4-dioxaspiro[4.5]decan-8-ylidene)propanoate (500 mg, 2.081 mmol) (307A) and 10% palladium on carbon (25 mg, 0.024 mmol) in EtOAc (5 mL) was hydrogenated in a Parr shaker at 45 psi for 6 h. The catalyst was filtered, the filtrate was concentrated to yield ethyl 2-(4-(3-methylpyridin-4-yl)cyclohexyl)propanoate (450 mg, 89% yield) as a light oil. $^1$H NMR (400 MHz, chloroform-d) δ 4.12 (dtt, J=10.7, 7.1, 3.6 Hz, 2H), 3.98-3.81 (m, 4H), 2.35-2.17 (m, 1H), 1.83-1.68 (m, 3H), 1.66-1.45 (m, 4H), 1.43-1.28 (m, 2H), 1.27-1.22 (m, 3H), 1.14-1.07 (m, 3H).

307C. Ethyl 2-(4-oxocyclohexyl)propanoate

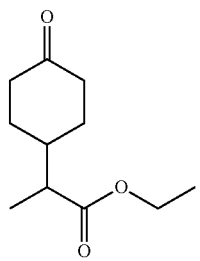

To a solution of ethyl 2-(1,4-dioxaspiro[4.5]decan-8-yl)propanoate (450 mg, 1.857 mmol) (307B) in THF (5 mL) was added 1M hydrogen chloride(aqueous) (0.929 mL, 3.71 mmol). The mixture was heated to 50° C. for 6 h. The reaction mixture was concentrated. The residue was dissolved in EtOAc, washed with water (2×), brine, dried over Na$_2$SO$_4$ and concentrated. The crude material was purified with ISCO(EtOAc/Hex 0-30%). Fractions containing product were concentrated to yield ethyl 2-(4-oxocyclohexyl)propanoate (290 mg, 79% yield) as a clear oil. $^1$H NMR (400 MHz, chloroform-d) δ 4.22-4.06 (m, 2H), 2.46-2.30 (m, 5H), 2.13-1.91 (m, 3H), 1.56-1.42 (m, 2H), 1.31-1.24 (m, 3H), 1.18 (d, J=7.1 Hz, 3H).

307D. Ethyl 2-(4-(((trifluoromethyl)sulfonyl)oxy)cyclohex-3-en-1-yl)propanoate

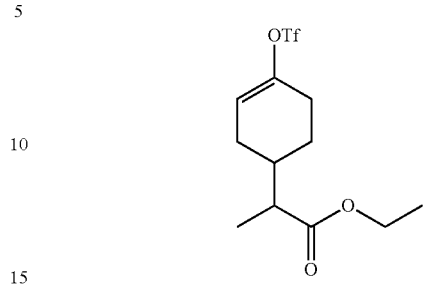

Ethyl 2-(4-oxocyclohexyl)propanoate (200 mg, 1.01 mmol)(307C) and 2,6-di-tert-butyl-4-methylpyridine (238 mg, 1.16 mmol) were dissolved in dry DCM (10 ml). To the reaction mixture trifluoromethanesulfonic anhydride (0.186 mL, 1.11 mmol) was added dropwise and stirred for 2 h. The suspension was filtered. The filtrate was diluted with DCM, washed with 1N HCl (2×), satd. aq. sodium bicarbonate solution, water, brine. The cobined organics were then dried over Na$_2$SO$_4$, filtered, and concentrated to yield ethyl 2-(4-(((trifluoromethyl)sulfonyl)oxy) cyclohex-3-en-1-yl)propanoate (320 mg, 96% yield) as a brown oil. $^1$H NMR (400 MHz, chloroform-d) δ 5.73 (t, J=6.1 Hz, 1H), 4.28-4.05 (m, 2H), 2.52-2.17 (m, 4H), 2.08-1.79 (m, 3H), 1.49 (dt, J=11.1, 6.6 Hz, 1H), 1.31-1.20 (m, 3H), 1.19-1.04 (m, 3H).

307E. Ethyl 2-(4-(4,4,5,5-tetramethyl-1,3,2-dioxaborolan-2-yl)cyclohex-3-en-1-yl)propanoate

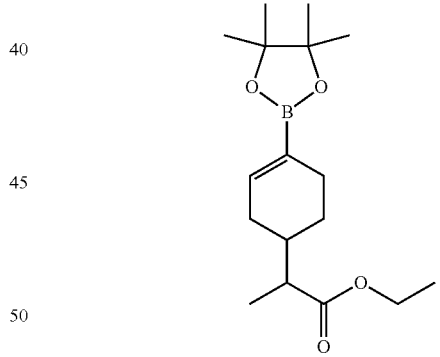

To a solution of ethyl 2-(4-(((trifluoromethyl)sulfonyl)oxy)cyclohex-3-en-1-yl)propanoate (300 mg, 0.908 mmol) (307D) in DMSO (5 mL) was added 4,4,4',4',5,5,5',5'-octamethyl-2,2'-bi(1,3,2-dioxaborolane) (230 mg, 0.908 mmol) and potassium acetate (267 mg, 2.72 mmol). After the mixture was degassed with N$_2$ for 10 min, PdCl$_2$(dppf) (19.9 mg, 0.027 mmol) was added. The mixture was heated at 80° C. overnight. The mixture was partitioned between EtOAc and water. The organic phase was concentrated and purified by ISCO. Fractions containing product were concentrated to yield ethyl 2-(4-(4,4,5,5-tetramethyl-1,3,2-dioxaborolan-2-yl)cyclohex-3-en-1-yl)propanoate(168 mg, 60% yield) as a brown oil. $^1$H NMR (400 MHz, chloroform-d) δ 6.66-6.40 (m, 1H), 4.31-4.00 (m, 2H), 2.34-2.26 (m, 1H), 2.25-2.19 (m, 1H), 2.19-2.04 (m, 2H), 1.95-1.75 (m, 3H), 1.73-1.60 (m, 1H), 1.29-1.24 (m, 15H), 1.13 (dd, J=11.6, 7.0 Hz, 3H).

307F. Ethyl 2-(4-(2-methoxypyridin-4-yl)cyclohex-3-en-1-yl)propanoate

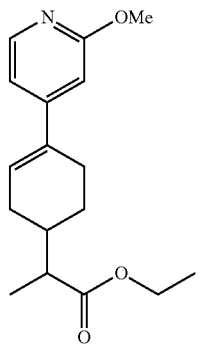 [SMILES: CCOC(=O)C(C)C1CC=C(c2ccnc(OC)c2)CC1]

To a solution of ethyl 2-(4-(4,4,5,5-tetramethyl-1,3,2-dioxaborolan-2-yl)cyclohex-3-en-1-yl)propanoate (100 mg, 0.324 mmol)(307E) in dioxane (3 mL) was added 4-bromo-2-methoxypyridine (61.0 mg, 0.324 mmol), water (1 mL) and $Na_2CO_3$ (138 mg, 1.298 mmol). The mixture was degassed with $N_2$ for 10 min, then $Pd(Ph_3P)_4$ (18.75 mg, 0.016 mmol) was added. The mixture was heated at 100° C. for 16 h. The reaction was allowed to cool to rt, diluted with EtOAc, washed with water, brine, dried over $Na_2SO_4$ and filtered. The filtrate was concentrated. The crude material was purified by ISCO (0-50% EtOAc/hexane). Fractions containing product were concentrated to yield ethyl 2-(4-(2-methoxypyridin-4-yl)cyclohex-3-en-1-yl)propanoate (60 mg, 0.207 mmol, 63.9% yield) as a yellow oil. $^1$H NMR (400 MHz, chloroform-d) δ 8.06 (d, J=5.5 Hz, 1H), 6.88 (dd, J=5.5, 1.1 Hz, 1H), 6.68 (s, 1H), 6.29 (br. s., 1H), 4.33-4.09 (m, 2H), 3.93 (s, 3H), 2.46-2.33 (m, 3H), 2.33-2.23 (m, 1H), 2.09-1.82 (m, 2H), 1.56 (br. s., 1H), 1.48-1.37 (m, 1H), 1.28 (td, J=7.2, 2.3 Hz, 3H), 1.19 (dd, J=10.3, 7.0 Hz, 3H). MS: Anal. Calc'd for $C_{17}H_{23}NO_3$ 289.17, found [M+H] 290.08 LC: tr=0.88 min (Method A.

307G. Ethyl 2-(4-(2-methoxypyridin-4-yl)cyclohexyl)propanoate

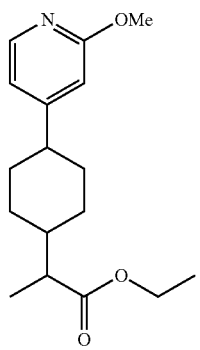 [SMILES: CCOC(=O)C(C)C1CCC(c2ccnc(OC)c2)CC1]

To a solution of ethyl 2-(4-(2-methoxypyridin-4-yl)cyclohex-3-en-1-yl)propanoate (60 mg, 0.207 mmol) (307F) in MeOH (5 mL) was added formic acid, ammonia salt (65.4 mg, 1.037 mmol) and 10% Pd/C (5.96 mg, 0.056 mmol). The mixture was refluxed for 1 h, then the mixture was filtered through CELITE®. The filtrate was concentrated, diluted with EtOAc, washed with satd. aq. sodium bicarbonate solution, water, brine, dried over $Na_2SO_4$, filtered, and concentrated to yield ethyl 2-(4-(2-methoxypyridin-4-yl)cyclohexyl) propanoate (60 mg, 99% yield) as a yellow oil. $^1$H NMR (400 MHz, chloroform-d) δ 8.05 (t, J=5.3 Hz, 1H), 6.86-6.68 (m, 1H), 6.67-6.46 (m, 1H), 4.25-4.08 (m, 2H), 3.92 (d, J=4.0 Hz, 3H), 2.72-2.52 (m, 1H), 2.48-2.20 (m, 1H), 1.98-1.74 (m, 3H), 1.74-1.54 (m, 4H), 1.52-1.38 (m, 2H), 1.26 (dt, J=10.1, 7.2 Hz, 3H), 1.14 (dd, J=6.9, 5.7 Hz, 3H); MS: Anal. Calc'd for $C_{17}H_{25}NO_3$ 291.18, found [M+H] 292.08 LC: tr=0.90 min. (Method R).

Example 307a, 307b: Cis- or trans-N-(4-Chlorophenyl)-2-(4-(2-methoxypyridin-4-yl)cyclohexyl)propanamide (Relative Stereochemistry not Determined)

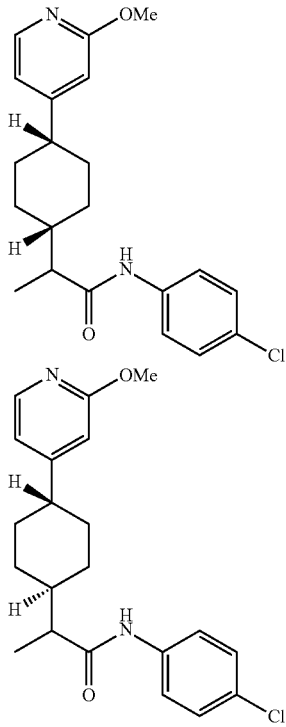

To a solution of ethyl 2-(4-(2-methoxypyridin-4-yl)cyclohexyl)propanoate (60 mg, 0.206 mmol) (307G) in THF (1 mL) was added 4-chloroaniline (52.5 mg, 0.412 mmol) and isopropylmagnesium chloride (0.206 mL, 0.412 mmol). The mixture was heated at 70° C. for 2 h. The reaction was quenched with water and diluted with EtOAc. The organic phase was combined and concentrated to yield a crude residue. The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 25-100% B over 20 minutes, then a 4-minute hold at 100% B; Flow: 20 mL/min. Fractions containing the desired product were combined and dried via centrifugal evaporation.

Racemic mixture cis- or trans-307a: 19.5 mg, 25% yield. $^1$H NMR (500 MHz, DMSO-$d_6$) δ 10.01 (s, 1H), 8.01 (d, J=5.0 Hz, 1H), 7.63 (d, J=8.3 Hz, 2H), 7.33 (d, J=8.5 Hz, 2H), 6.85 (d, J=5.0 Hz, 1H), 6.62 (s, 1H), 3.49 (d, J=5.0 Hz, 1H), 2.43 (t, J=12.1 Hz, 1H), 2.24 (t, J=7.2 Hz, 1H), 1.92 (d, J=12.0 Hz, 1H), 1.87-1.64 (m, 3H), 1.53 (d, J=8.8 Hz, 1H), 1.46-1.31 (m, 2H), 1.25-1.13 (m, 1H), 1.11-0.98 (m, 4H); MS: Anal. Calc'd for $C_{21}H_{25}ClN_2O_2$ 372.2, found [M+H] 373.2 LC: tr=2.158 min (Method A).

Racemic mixture cis- or trans-307b: 21.4 mg, 27.9% yield. $^1$H NMR (500 MHz, DMSO-$d_6$) δ 10.09 (s, 1H), 8.04 (d, J=5.0 Hz, 1H), 7.61 (d, J=8.3 Hz, 2H), 7.33 (d, J=8.4 Hz, 2H), 6.92 (d, J=5.1 Hz, 1H), 6.72 (s, 1H), 3.81 (s, 2H), 3.66-3.51 (m, 3H), 2.65 (d, J=9.8 Hz, 1H), 2.58 (br. s., 1H), 1.93-1.75 (m, 2H), 1.70-1.36 (m, 7H), 1.06 (d, J=6.5 Hz, 3H); MS: Anal. Calc'd for $C_{21}H_{25}ClN_2O_2$ 372.2, found [M+H] 373.2 LC: tr=2.202 min (Method A).

Example 307c, 307d, 307e, 307f: N-(4-Chlorophenyl)-2-(4-(2-methoxypyridin-4-yl)cyclohexyl)propanamide (Homochiral Absolute and Relative Stereochemistry not Determined)

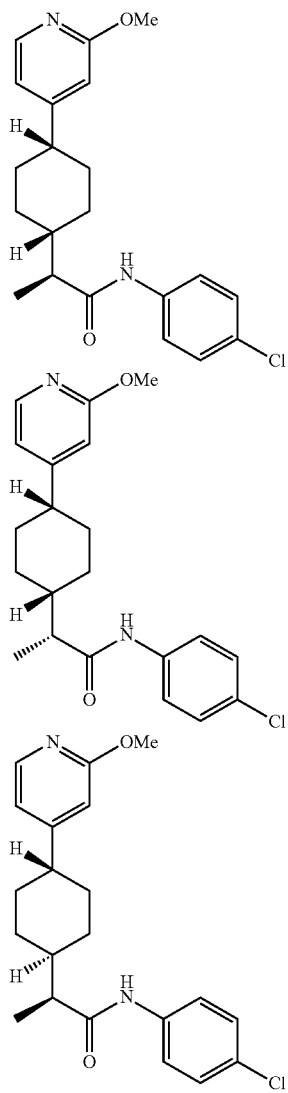

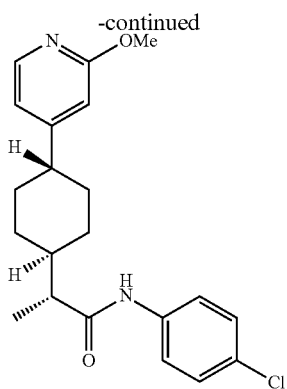

Examples 307A and 307B were further purified through chiral separation. Approximately 10 mg of cis- or trans-racemate 307a was resolved. The material was purified via preparative SFC with the following conditions: Berger SFC MGII; Column: Chiral AD 25×3 cm ID, 5-μm; Mobile Phase:70/30 $CO_2$/MeOH; Detector Wavelength: 220 nm; Flow: 85 mL/min. The fractions ("Peak-1" $t_r$=4.586, "Peak-2" $t_r$=7.553; analytical conditions: Aurora analytical SFC; Column: Chiral AD 250×4.6 mm ID, 5 μm; Mobile Phase: 70/30 $CO_2$/MeOH; Flow: 2.0 mL/min) were collected in MeOH. The stereoisomeric purity of the fractions was estimated to be greater than 99.0% based on the prep-SFC chromatograms conditions.

Example 307c, first eluting isomer: $^1$H NMR (400 MHz, chloroform-d) δ $^1$H NMR (400 MHz, chloroform-d) δ 8.07 (d, J=5.3 Hz, 1H), 7.51-7.45 (m, 2H), 7.30-7.27 (m, 2H), 7.15 (s, 1H), 6.78 (dd, J=5.4, 1.1 Hz, 1H), 6.64 (s, 1H), 3.93 (s, 3H), 2.70 (br. s., 1H), 2.35 (dd, J=10.2, 6.9 Hz, 1H), 1.99-1.88 (m, 1H), 1.83-1.72 (m, 4H), 1.69-1.58 (m, 3H), 1.58-1.48 (m, 1H), 1.22 (d, J=6.7 Hz, 3H) MS: Anal. Calc'd for $C_{21}H_{25}ClN_2O_2$ 372.16, found [M+H] 373.2. LC: $t_r$=0.90 min (Method A).

Example 307b, second eluting isomer: $^1$H NMR (400 MHz, chloroform-d) δ $^1$H NMR (400 MHz, chloroform-d) δ 8.07 (d, J=5.3 Hz, 1H), 7.51-7.45 (m, 2H), 7.30-7.27 (m, 2H), 7.15 (s, 1H), 6.78 (dd, J=5.4, 1.1 Hz, 1H), 6.64 (s, 1H), 3.93 (s, 3H), 2.70 (br. s., 1H), 2.35 (dd, J=10.2, 6.9 Hz, 1H), 1.99-1.88 (m, 1H), 1.83-1.72 (m, 4H), 1.69-1.58 (m, 3H), 1.58-1.48 (m, 1H), 1.22 (d, J=6.7 Hz, 3H) MS: Anal. Calc'd for $C_{21}H_{25}ClN_2O_2$ 372.16, found [M+H] 373.2. LC: $t_r$=0.90 min (Method A).

Approximately 10 mg of cis- or trans-racemate 307b was resolved. The material was purified via preparative SFC with the following conditions: Berger SFC MGII; Column: Chiral AD 25×3 cm ID, 5-μm; Mobile Phase:70/30 $CO_2$/MeOH; Detector Wavelength: 220 nm; Flow: 85 mL/min. The fractions ("Peak-1" $t_r$=9.418, "Peak-2" $t_r$=17.230; analytical conditions: Aurora analytical SFC; Column: Chiral AD 250×4.6 mm ID, 5 μm; Mobile Phase:70/30 $CO_2$/MeOH; Flow: 2.0 mL/min.) were collected in MeOH. The stereoisomeric purity of the fractions was estimated to be greater than 99.0% based on the prep-SFC chromatograms.

Example 307e, first eluting isomer: $^1$H NMR (400 MHz, chloroform-d) δ 8.05 (d, J=5.1 Hz, 1H), 7.50 (d, J=8.9 Hz, 2H), 7.32-7.27 (m, 2H), 7.10 (s, 1H), 6.71 (dd, J=5.3, 1.3 Hz, 1H), 6.55 (s, 1H), 3.91 (s, 3H), 2.42 (br. s., 1H), 2.09 (d, J=7.2 Hz, 1H), 2.05-1.96 (m, 1H), 1.95-1.84 (m, 2H), 1.76-1.61 (m, 1H), 1.52-1.40 (m, 2H), 1.25 (d, J=6.8 Hz, 3H), 1.25-1.01 (m, 3H); MS: Anal. Calc'd for $C_{21}H_{25}ClN_2O_2$ 372.16, found [M+H] 373.2. LC: $t_r$=0.88 min (Method A).

Example 307e, second eluting isomer: $^1$H NMR (400 MHz, chloroform-d) δ 8.05 (d, J=5.1 Hz, 1H), 7.50 (d, J=8.9 Hz, 2H), 7.32-7.27 (m, 2H), 7.10 (s, 1H), 6.71 (dd, J=5.3, 1.3 Hz, 1H), 6.55 (s, 1H), 3.91 (s, 3H), 2.42 (br. s., 1H), 2.09 (d, J=7.2 Hz, 1H), 2.05-1.96 (m, 1H), 1.95-1.84 (m, 2H), 1.76-1.61 (m, 1H), 1.52-1.40 (m, 2H), 1.25 (d, J=6.8 Hz, 3H), 1.25-1.01 (m, 3H); MS: Anal. Calc'd for $C_{21}H_{25}ClN_2O_2$ 372.16, found [M+H] 373.2. LC: $t_r$=0.88 min (Method A).

Examples 308-319

These compounds were obtained from intermediate 307E using procedures for 307F and 307G as well as the procedures for Example 307:

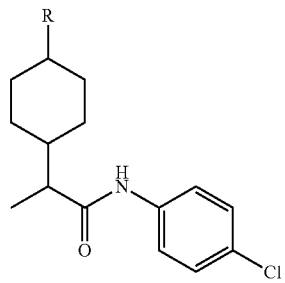

| Example No. | Name | R | Tr (min)$^{Method}$ | [M + H]$^+$ | stereochemistry |
|---|---|---|---|---|---|
| 308a | N-(4-chlorophenyl)-2-(4-(2,6-dimethylpyridin-4-yl)cyclohexyl)propanamide | 2,6-dimethylpyridin-4-yl | 4.837$^G$ | 371.3 | Homochiral with absolute and relative stereochemistry not determined |
| 308b | N-(4-chlorophenyl)-2-(4-(2,6-dimethylpyridin-4-yl)cyclohexyl)propanamide | 2,6-dimethylpyridin-4-yl | 6.082$^G$ | 371.3 | Homochiral with absolute and relative stereochemistry not determined |
| 308c | N-(4-chlorophenyl)-2-(4-(2,6-dimethylpyridin-4-yl)cyclohexyl)propanamide | 2,6-dimethylpyridin-4-yl | 8.542$^G$ | 371.2 | Homochiral with absolute and relative stereochemistry not determined |
| 308d | N-(4-chlorophenyl)-2-(4-(2,6-dimethylpyridin-4-yl)cyclohexyl)propanamide | 2,6-dimethylpyridin-4-yl | 9.256$^G$ | 371.3 | Homochiral with absolute and relative stereochemistry not determined |
| 309a | N-(4-chlorophenyl)-2-(4-(2-methylpyridin-4-yl)cyclohexyl)propanamide | 2-methylpyridin-4-yl | 6.318$^H$ | 357.3 | Homochiral with absolute and relative stereochemistry not determined |

-continued

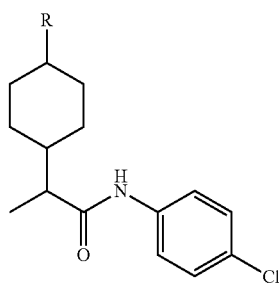

| Example No. | Name | R | Tr (min)$^{Method}$ | [M + H]$^+$ | stereochemistry |
|---|---|---|---|---|---|
| 309b | N-(4-chlorophenyl)-2-(4-(2-methylpyridin-4-yl)cyclohexyl)propanamide | | 8.267$^H$ | 357.0 | Homochiral with absolute and relative stereochemistry not determined |
| 309c | N-(4-chlorophenyl)-2-(4-(2-methylpyridin-4-yl)cyclohexyl)propanamide | | 11.390$^H$ | 357.1 | Homochiral with absolute and relative stereochemistry not determined |
| 309d | N-(4-chlorophenyl)-2-(4-(2-methylpyridin-4-yl)cyclohexyl)propanamide | | 12.356$^H$ | 357.3 | Homochiral with absolute and relative stereochemistry not determined |
| 310a | (+/−)N-(4-chlorophenyl)-2-(4-(2-fluoro-3-methylpyridin-4-yl)cyclohexyl)propanamide | | 2.51$^A$ | 375.2 | Cis- or trans-Racemate relative stereochemistry not determined |
| 310b | (+/−)N-(4-chlorophenyl)-2-(4-(2-fluoro-3-methylpyridin-4-yl)cyclohexyl)propanamide | | 2.51$^A$ | 375.2 | Cis- or trans-Racemate relative stereochemistry not determined |
| 310c | N-(4-chlorophenyl)-2-(4-(2-fluoro-3-methylpyridin-4-yl)cyclohexyl)propanamide | | 7.900$^J$ | 375.1 | Homochiral with absolute and relative stereochemistry not determined |

-continued

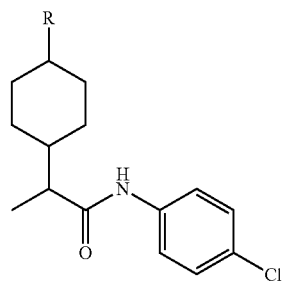

| Example No. | Name | R | Tr (min)$^{Method}$ | [M + H]$^+$ | stereochemistry |
|---|---|---|---|---|---|
| 310d | N-(4-chlorophenyl)-2-(4-(2-fluoro-3-methylpyridin-4-yl)cyclohexyl)propanamide | | 10.924$^I$ | 375.1 | Homochiral with absolute and relative stereochemistry not determined |
| 310e | N-(4-chlorophenyl)-2-(4-(2-fluoro-3-methylpyridin-4-yl)cyclohexyl)propanamide | | 14.488$^I$ | 375.1 | Homochiral with absolute and relative stereochemistry not determined |
| 310f | N-(4-chlorophenyl)-2-(4-(2-fluoro-3-methylpyridin-4-yl)cyclohexyl)propanamide | | 18.052$^J$ | 375.1 | Homochiral with absolute and relative stereochemistry not determined |
| 311a | N-(4-chlorophenyl)-2-(4-(2,3-dimethylpyridin-4-yl)cyclohexyl)propanamide | | 1.951$^A$ | 370.9 | Cis- or trans-Racemate relative stereochemistry not determined |
| 311b | N-(4-chlorophenyl)-2-(4-(2,3-dimethylpyridin-4-yl)cyclohexyl)propanamide | | 2.055$^A$ | 371.2 | Cis- of trans-Racemate relative stereochemistry not determined |
| 311c | N-(4-chlorophenyl)-2-(4-(2,3-dimethylpyridin-4-yl)cyclohexyl)propanamide | | 16.549$^L$ | 371.2 | Homochiral with absolute and relative stereochemistry not determined |

-continued

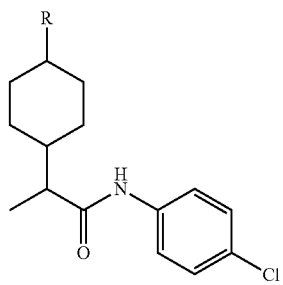

| Example No. | Name | R | Tr (min)$^{Method}$ | [M + H]$^+$ | stereochemistry |
|---|---|---|---|---|---|
| 311d | N-(4-chlorophenyl)-2-(4-(2,3-dimethylpyridin-4-yl)cyclohexyl)propanamide | 2,3-dimethylpyridin-4-yl | 11.907$^K$ | 371.2 | Homochiral with absolute and relative stereochemistry not determined |
| 311e | N-(4-chlorophenyl)-2-(4-(2,3-dimethylpyridin-4-yl)cyclohexyl)propanamide | 2,3-dimethylpyridin-4-yl | 10.090$^K$ | 371.2 | Homochiral with absolute and relative stereochemistry not determined |
| 311f | N-(4-chlorophenyl)-2-(4-(2,3-dimethylpyridin-4-yl)cyclohexyl)propanamide | 2,3-dimethylpyridin-4-yl | 7.396$^L$ | 371.4 | Homochiral with absolute and relative stereochemistry not determined |
| 312a | N-(4-chlorophenyl)-2-(4-(2-(trifluoromethyl)pyridin-4-yl)cyclohexyl)propanamide | 2-(trifluoromethyl)pyridin-4-yl | 5.775$^M$ | 411.3 | Homochiral with absolute and relative stereochemistry not determined |
| 312b | N-(4-chlorophenyl)-2-(4-(2-(trifluoromethyl)pyridin-4-yl)cyclohexyl)propanamide | 2-(trifluoromethyl)pyridin-4-yl | 6.433$^M$ | 411.2 | Homochiral with absolute and relative stereochemistry not determined |
| 312c | N-(4-chlorophenyl)-2-(4-(2-(trifluoromethyl)pyridin-4-yl)cyclohexyl)propanamide | 2-(trifluoromethyl)pyridin-4-yl | 12.376$^M$ | 411.2 | Homochiral with absolute and relative stereochemistry not determined |

-continued

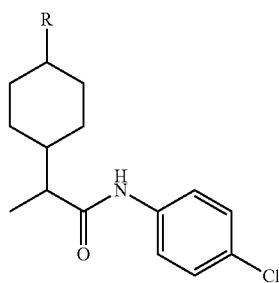

| Example No. | Name | R | Tr (min)$^{Method}$ | [M + H]$^+$ | stereochemistry |
|---|---|---|---|---|---|
| 312d | N-(4-chlorophenyl)-2-(4-(2-(trifluoromethyl)pyridin-4-yl)cyclohexyl)propanamide | 4-(2-(trifluoromethyl)pyridin-4-yl | 14.148$^M$ | 411.2 | Homochiral with absolute and relative stereochemistry not determined |
| 313a | N-(4-chlorophenyl)-2-(4-(3-methylpyridin-4-yl)cyclohexyl)propanamide | 3-methylpyridin-4-yl | 2.055$^A$ | 357.0 | Cis- or trans-Racemate relative stereochemistry not determined |
| 313b | N-(4-chlorophenyl)-2-(4-(3-methylpyridin-4-yl)cyclohexyl)propanamide | 3-methylpyridin-4-yl | 2.093$^A$ | 357.3 | Cis- or trans-Racemate relative stereochemistry not determined |
| 313c | N-(4-chlorophenyl)-2-(4-(3-methylpyridin-4-yl)cyclohexyl)propanamide | 3-methylpyridin-4-yl | 4.118$^N$ | 356.9 | Homochiral with absolute and relative stereochemistry not determined |
| 313d | N-(4-chlorophenyl)-2-(4-(3-methylpyridin-4-yl)cyclohexyl)propanamide | 3-methylpyridin-4-yl | 4.712$^N$ | 357.1 | Homochiral with absolute and relative stereochemistry not determined |
| 313e | N-(4-chlorophenyl)-2-(4-(3-methylpyridin-4-yl)cyclohexyl)propanamide | 3-methylpyridin-4-yl | 5.575$^N$ | 357.0 | Homochiral with absolute and relative stereochemistry not determined |

-continued

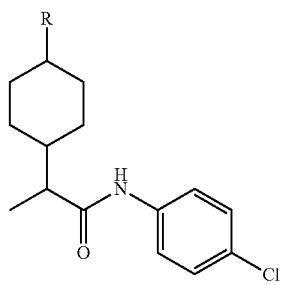

| Example No. | Name | R | Tr (min)$^{Method}$ | [M + H]$^+$ | stereochemistry |
|---|---|---|---|---|---|
| 313f | N-(4-chlorophenyl)-2-(4-(3-methylpyridin-4-yl)cyclohexyl) propanamide | | 6.562$^N$ | 357.1 | Homochiral with absolute and relative stereochemistry not determined |
| 314a | N-(4-chlorophenyl)-2-(4-(6-(4-fluorophenyl) pyrimidin-4-yl)cyclohexyl) propanamide | | 2.391$^A$ | 438.2 | Cis- or trans-Racemate relative stereochemistry not determined |
| 314b | N-(4-chlorophenyl)-2-(4-(6-(4-fluorophenyl) pyrimidin-4-yl)cyclohexyl) propanamide | | 2.433$^A$ | 438.2 | Cis- or trans-Racemate relative stereochemistry not determined |
| 315a | 2-(4-(2-acetamidopyridin-4-yl)cyclohexyl)-N-(4-chlorophenyl) propanamide | | 1.936$^A$ | 400.2 | Cis- or trans-Racemate relative stereochemistry not determined |
| 315b | 2-(4-(2-acetamidopyridin-4-yl)cyclohexyl)-N-(4-chlorophenyl) propanamide | | 1.984$^A$ | 400.18 | Cis- or trans-Racemate relative stereochemistry not determined |

-continued

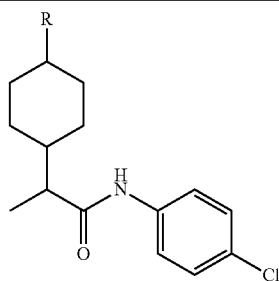

| Example No. | Name | R | Tr (min)$^{Method}$ | [M + H]$^+$ | stereochemistry |
|---|---|---|---|---|---|
| 316a | N-(4-chlorophenyl)-2-(4-(pyridazin-4-yl)cyclohexyl)propanamide | | 15.157$^O$ | 344.2 | Homochiral with absolute and relative stereochemistry not determined |
| 316b | N-(4-chlorophenyl)-2-(4-(pyridazin-4-yl)cyclohexyl)propanamide | | 16.596$^O$ | 344.2 | Homochiral with absolute and relative stereochemistry not determined |
| 316c | N-(4-chlorophenyl)-2-(4-(pyridazin-4-yl)cyclohexyl)propanamide | | 19.948$^O$ | 344.2 | Homochiral with absolute and relative stereochemistry not determined |
| 316d | N-(4-chlorophenyl)-2-(4-(pyridazin-4-yl)cyclohexyl)propanamide | | 22.237$^O$ | 344.2 | Homochiral with absolute and relative stereochemistry not determined |
| 317a | 2-(4-([1,1'-biphenyl]-3-yl)cyclohexyl)-N-(4-chlorophenyl)propanamide | | 7.365$^P$ | 418.2 | Homochiral with absolute and relative stereochemistry not determined |
| 317b | 2-(4-([1,1'-biphenyl]-3-yl)cyclohexyl)-N-(4-chlorophenyl)propanamide | | 8.536$^P$ | 418.2 | Homochiral with absolute and relative stereochemistry not determined |

-continued

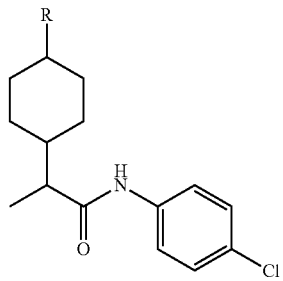

| Example No. | Name | R | Tr (min)^Method | [M + H]+ | stereochemistry |
|---|---|---|---|---|---|
| 317c | 2-(4-([1,1'-biphenyl]-3-yl)cyclohexyl)-N-(4-chlorophenyl)propanamide | 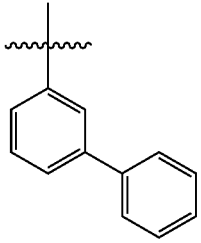 [SMILES: *c1cccc(-c2ccccc2)c1] | 11.309^P | 418.2 | Homochiral with absolute and relative stereochemistry not determined |
| 317d | 2-(4-([1,1'-biphenyl]-3-yl)cyclohexyl)-N-(4-chlorophenyl)propanamide | 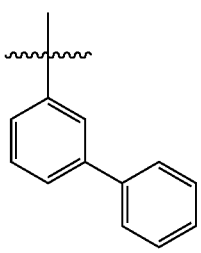 [SMILES: *c1cccc(-c2ccccc2)c1] | 15.497^P | 418.2 | Homochiral with absolute and relative stereochemistry not determined |
| 318a Diastereomer mixture | N-(4-chlorophenyl)-2-(4-(3-fluoropyridin-4-yl)cyclohexyl)propanamide | 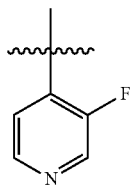 [SMILES: *c1ccncc1F] | 2.102^A | 361.2 | Diastereomeric mixture |
| 318b | N-(4-chlorophenyl)-2-(4-(3-fluoropyridin-4-yl)cyclohexyl)propanamide | 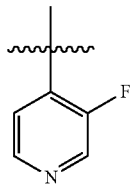 [SMILES: *c1ccncc1F] | 8.602^Q | 361.2 | Homochiral with absolute and relative stereochemistry not determined |
| 318c | N-(4-chlorophenyl)-2-(4-(3-fluoropyridin-4-yl)cyclohexyl)propanamide | 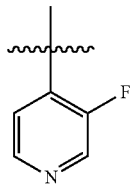 | 9.684^Q | 360.9 | Homochiral with absolute and relative stereochemistry not determined |

-continued

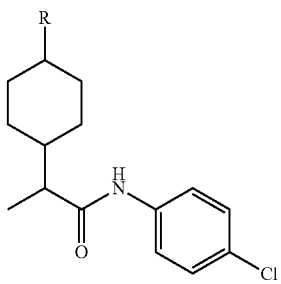

| Example No. | Name | R | Tr (min)^Method | [M + H]+ | stereochemistry |
|---|---|---|---|---|---|
| 318d | N-(4-chlorophenyl)-2-(4-(3-fluoropyridin-4-yl)cyclohexyl)propanamide | 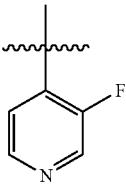 [SMILES: *c1ccncc1F] | 10.803^Q | 361.2 | Homochiral with absolute and relative stereochemistry not determined |
| 318e | N-(4-chlorophenyl)-2-(4-(3-fluoropyridin-4-yl)cyclohexyl)propanamide | 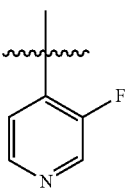 [SMILES: *c1ccncc1F] | 12.223^Q | 361.2 | Homochiral with absolute and relative stereochemistry not determined |
| 319a | N-(4-chlorophenyl)-2-(4-(2-methylpyrimidin-4-yl)cyclohexyl)propanamide | 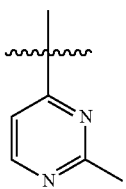 [SMILES: *c1ccnc(C)n1] | 1.827^A | 358.2 | Cis- or trans-Racemate relative stereochemistry not determined |
| 319b | N-(4-chlorophenyl)-2-(4-(2-methylpyrimidin-4-yl)cyclohexyl)propanamide | 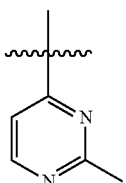 | 1.897^A | 358.2 | Cis- or trans-Racemate relative stereochemistry not determined |

Example 320 rac-2-((trans)-4-((3-chloro-2-methylpyridin-4-yl)oxy)cyclohexyl)-N-(4-chlorophenyl)propanamide (Absolute Stereochemistry not Determined)

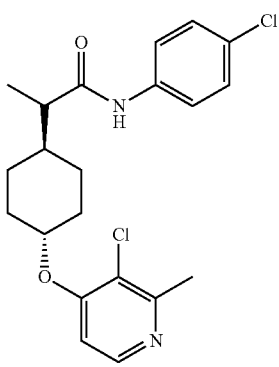 [SMILES: Cc1nccc(O[C@H]2CC[C@H](C(C)C(=O)Nc3ccc(Cl)cc3)CC2)c1Cl]

320A. rac-ethyl 2-((trans)-4-((3-chloro-2-methylpyridin-4-yl)oxy)cyclohexyl)propanoate A solution of ethyl rac-2-((trans)-4-hydroxycyclohexyl)propanoate (Prepared by treating Intermediate 307C with sodium borohydride in methanol) (1.001 g, 5 mmol) in THF (4 mL) was cooled to 0° C. and treated with potassium hexamethyldisilazide (5.50 mL, 5.50 mmol) over 1 min. The reaction was stirred 10 min, then treated with 3,4-dichloro-2-methylpyridine (0.851 g, 5.25 mmol). The reaction was stirred 40 min. at 0° C. then quenched with aq. ammonium chloride. The phases were stirred together 1 h then extracted with 1:1 EtOAc-hexane, and the organic extract was dried and stripped to afford an oil. Prep. HPLC afforded rac-ethyl 2-((trans)-4-((3-chloro-2-methylpyridin-4-yl)oxy)cyclohexyl)propanoate (0.47 g, 29% yield) as a golden oil. MS (ES): m/z=326 [M+H]$^+$. $t_R$=0.78 min (Method A).

320B. rac-2-((trans)-4-((3-chloro-2-methylpyridin-4-yl)oxy)cyclohexyl)propanoic Acid A solution of rac-ethyl 2-((trans)-4-((3-chloro-2-methylpyridin-4-yl)oxy)cyclohexyl)propanoate (0.42 g, 1.289 mmol) in THF (4 mL) was treated with lithium hydroxide (0.154 g, 6.45 mmol) in water (4 mL). Methanol, ~4 mL was added to give a single phase, and the reaction was stirred for 1 h at 50° C. The reaction was then cooled and stirred at rt. Most of the solvent was removed under a stream of nitrogen, and the reaction was diluted to ~6 ml with water. This cloudy suspension was filtered, and the filtrate solution pH was adjusted to ~5.5 with aq. HOAc. The resulting precipitate was filtered, rinsed with water, and air-dried to afford rac-2-((trans)-4-((3-chloro-2-methylpyridin-4-yl)oxy)cyclohexyl)propanoic acid (0.16 g, 42% yield) as a white solid. MS (ES): m/z=298 [M+H]$^+$. $t_R$=0.63 min (Method A).

Example 320: rac-2-((trans)-4-((3-chloro-2-methylpyridin-4-yl)oxy)cyclohexyl)-N-(4-chlorophenyl)propanamide A solution of rac-2-((trans)-4-((3-chloro-2-methylpyridin-4-yl)oxy)cyclohexyl)propanoic acid (0.025 g, 0.084 mmol) and 4-chloroaniline (0.013 g, 0.101 mmol) in DMF (0.4 mL) was treated with triethylamine (0.023 mL, 0.168 mmol) followed by HATU (0.038 g, 0.101 mmol). The resulting solution was stirred 2 h at RT then quenched with 1 drop of water, diluted to 2 mL, and purified by preparative HPLC. Concentration of the appropriate fractions afforded 0.033 g (75%) of the title compound. MS (ES): m/z=407 [M+H]$^+$. $t_R$=2.21 min (Method B).

Example 321

N-(4-Chlorophenyl)-2-(4-methyl-1-(2-(trifluoromethyl)pyridin-4-yl)piperidin-4-yl)acetamide

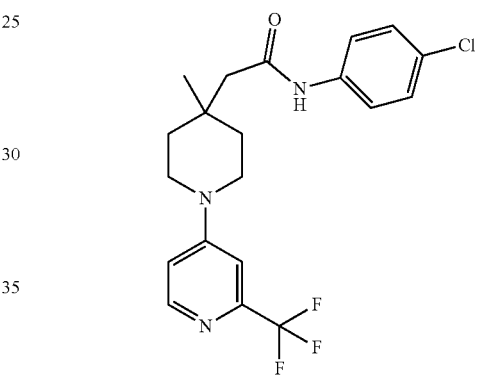

321A. Methyl 2-(4-methylpiperidin-4-yl)acetate

To a flask charged with MeOH (7.5 mL), at 0° C. under nitrogen atmosphere, was slowly added acetyl chloride (1.1 mL, 15.2 mmol). After the addition was complete, the mixture was stirred at 0° C. for 5 minutes before a homogeneous mixture of 2-(4-methylpiperidin-4-yl)acetic acid, HCl (675.0 mg, 3.5 mmol) in MeOH (1.5 mL) was added slowly dropwise. The resultant homogeneous mixture was stirred at 0° C. for 5 minutes then at 60° C. for 8 hours, before being concentrated in vacuo to afford the HCl salt of Preparation 321A as a white solid (718.0 mg; 99% yield) which was used without further purification. MS(ES): m/z=172 [M+H]$^+$. $t_R$=0.46 min (Method A). $^1$H NMR (400 MHz, DMSO-d$_6$) δ 9.41-9.12 (m, 1H), 3.60 (s, 3H), 3.25-3.15 (m, 2H), 2.93-2.82 (m, 2H), 2.39-2.30 (m, 2H), 1.74-1.64 (m, 4H), 1.02 (s, 3H).

321B. Methyl 2-(4-methyl-1-(2-(trifluoromethyl)pyridin-4-yl)piperidin-4-yl)acetate To a homogeneous mixture of 4-chloro-2-(trifluoromethyl)pyridine (300.0 mg, 1.7 mmol) in anhydrous NMP (4 mL), in a sealable vial, was added the HCl salt of methyl 2-(4-methylpiperidin-4-yl)acetate (321A, 412.0 mg, 2.0 mmol) followed by DIPEA (1.3 mL, 7.4 mmol). The vial was sealed and the mixture was stirred at 120° C. After 13 hours, the reaction mixture was cooled to room temperature then partitioned between water and EtOAc. The layers were separated and the aqueous layer was extracted once more with EtOAc. The organic layers were combined, washed with brine, then concentrated in vacuo to afford the crude product. Purification by Isco chromatography afforded methyl 2-(4-methyl-1-(2-(trifluoromethyl)pyridin-4-yl)piperidin-4-yl)acetate as an oil (461.1 mg; 88%). MS(ES): m/z=317 [M+H]$^+$. $t_R$=0.65 min (Method A). $^1$H NMR (400 MHz, CHLOROFORM-d) δ 8.27 (d, J=5.9 Hz, 1H), 6.70 (d, J=2.4 Hz, 1H), 6.43 (dd, J=5.9, 2.4 Hz, 1H), 3.69 (s, 3H), 3.48-3.41 (m, 2H), 3.20-3.08 (m, 2H), 2.44-2.31 (m, 2H), 1.86-1.82 (m, 2H), 1.58 (s, 2H), 1.11 (s, 3H).

321C. 2-(4-Methyl-1-(2-(trifluoromethyl)pyridin-4-yl)piperidin-4-yl)acetic Acid To a homogeneous mixture of methyl 2-(4-methyl-1-(2-(trifluoromethyl)pyridin-4-yl)piperidin-4-yl)acetate (461.1 mg, 1.5 mmol) in MeOH (5 mL), under nitrogen atmosphere, was added dropwise 2M NaOH aqueous solution (1.6 mL, 3.2 mmol). The reaction was then stirred at ambient temperature for 13 hours before being treated with 1N HCl (aq) until pH 4 to pH test strips. The mixture was then partitioned between water and EtOAc, the layers were separated and the aqueous layer was twice extracted with EtOAc. These organic extracts were combined with the original organic layer and were concentrated in vacuo to afford the HCl salt of Preparation 321C as a white solid (362.4 mg, 64% yield) which was used without further purification. MS(ES): m/z=303 [M+H]$^+$. $t_R$=0.56 min (Method A). $^1$H NMR (400 MHz, DMSO-$d_6$) δ 12.03 (br. s, 1H), 8.19 (d, J=5.7 Hz, 1H), 6.80 (d, J=2.3 Hz, 1H), 6.63 (dd, J=5.9, 2.3 Hz, 1H), 3.43-3.37 (m, 2H), 3.18-3.09 (m, 2H), 2.35-2.23 (m, 2H), 1.87-1.72 (m, 2H), 1.71-1.63 (m, 2H), 1.02 (s, 3H).

Example 321: N-(4-Chlorophenyl)-2-(4-methyl-1-(2-(trifluoromethyl)pyridin-4-yl)piperidin-4-yl)acetamide To a mixture of the HCl salt of 2-(4-methyl-1-(2-(trifluoromethyl)pyridin-4-yl)piperidin-4-yl)acetic acid (321C, 25.6 mg, 0.09 mmol) in anhydrous DMF (1 mL), in a sealable vial, was added PyBOP (44.1 mg, 0.09 mmol) followed by DIPEA (0.06 mL, 0.3 mmol). The mixture was stirred for 15 minutes before 4-chloroaniline (13.0 mg, 0.1 mmol) was added, the vial was sealed and the mixture stirred at ambient temperature. After 14.5 hours, the reaction mixture was diluted with DMF, passed through a syringe filter, then purified via preparative HPLC/MS to afford the title compound (21.9 mg; 49% yield). MS(ES): m/z=412 [M+H]$^+$. $t_R$=2.01 min (Method B). $^1$H NMR (500 MHz, DMSO-$d_6$) δ 10.09 (s, 1H), 8.18 (d, J=5.7 Hz, 1H), 7.60 (d, J=8.7 Hz, 2H), 7.33 (d, J=8.7 Hz, 2H), 6.78 (s, 1H), 6.68-6.58 (m, 1H), 3.26-3.06 (m, 2H), 2.54 (s, 2H), 2.42-2.34 (m, 2H), 1.89-1.70 (m, 4H), 1.06 (s, 3H).

Example 322

2-(4-Methyl-1-(2-(trifluoromethyl)pyridin-4-yl)piperidin-4-yl)-N-(1-methylcyclohexyl)acetamide

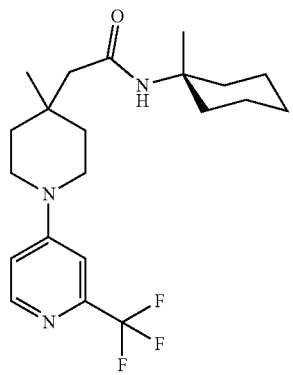

Example 322 (20.3 mg; 46% yield) was prepared following a procedure analogous to that for the synthesis of Example 321 except that 1-methylcyclohexanamine, HCl (16.0 mg, 0.11 mmol) was used instead of 4-chloroaniline). MS(ES): m/z=398 [M+H]$^+$. $t_R$=2.04 min (Method B). $^1$H NMR (500 MHz, DMSO-$d_6$) δ $^1$H NMR (500 MHz, DMSO-$d_6$) δ 8.18 (d, J=5.7 Hz, 1H), 7.19 (s, 1H), 6.77 (s, 1H), 6.68-6.57 (m, 1H), 3.48-3.36 (m, 1H), 3.20-3.04 (m, 2H), 2.13 (t, J=7.9 Hz, 2H), 2.02-1.95 (m, 2H), 1.87-1.69 (m, 2H), 1.68-1.58 (m, 2H), 1.53-1.31 (m, 5H), 1.30-1.13 (m, 7H), 1.02 (s, 3H).

Example 323

(+/−)-N-(4-chlorophenyl)-2-(trans-4-((2-(trifluoromethyl)pyridin-4-yl)oxy)cyclohexyl) propanamide

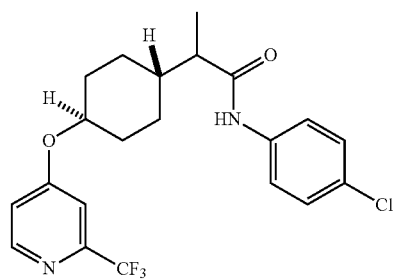 [SMILES: CC(C(=O)Nc1ccc(Cl)cc1)[C@H]1CC[C@H](Oc2ccnc(C(F)(F)F)c2)CC1]

Preparation 323A. (+/−)-ethyl 2-(trans-4-((2-(trifluoromethyl)pyridin-4-yl)oxy)cyclohexyl)propanoate

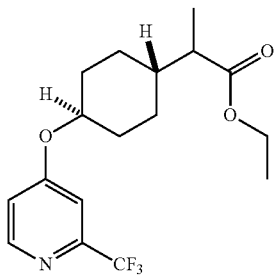 [SMILES: CCOC(=O)C(C)[C@H]1CC[C@H](Oc2ccnc(C(F)(F)F)c2)CC1]

To a solution of ethyl 2-(trans-4-hydroxycyclohexyl)propanoate (0.1294 g, 0.646 mmol) in DMF (1.077 ml) was added NaH (0.043 g, 1.077 mmol). After 30 min, 4-bromo-2-(trifluoromethyl)pyridine (0.071 ml, 0.538 mmol) as added. The reaction was heated at 80° C. overnight. Reaction quenched with a sat. aq. soln of NH₄Cl and diluted with EtOAc. Layers were separated. The aqueous phase was extracted with EtOAc (2×). The combined organic phases were washed with water, dried over Na₂SO₄, filtered, and concentrated to afford a brown residue. Purification of the crude material by silica gel chromatography using an ISCO machine (40 g column, 40 mL/min, 0-30% EtOAc in hexanes over 14 min, $t_r$=9.5 min) gave the title compound (0.0646 g, 0.187 mmol, 34.7% yield) as a colorless residue. ESI MS (M+H)+=346.2. HPLC Peak tr=1.09 minutes. HPLC conditions: A.

Preparation 323B. (+/−)-2-(trans-4-((2-(trifluoromethyl)pyridin-4-yl)oxy)cyclohexyl)propanoic Acid

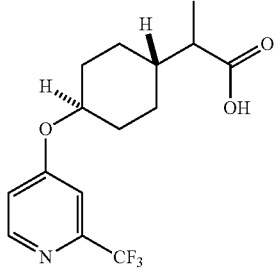 [SMILES: CC(C(=O)O)[C@H]1CC[C@H](Oc2ccnc(C(F)(F)F)c2)CC1]

To a solution of Preparation 323A (0.0437 g, 0.127 mmol) in THF (0.452 ml) and MeOH (0.181 ml) was added lithium hydroxide (1.265 ml, 1.265 mmol). The reaction was heated at 70° C. for 2 h, then allowed to cool to rt. The reaction was adjusted to pH 7 with 1N HCl, then diluted with EtOAc. Layers were separated. The aqueous phase was extracted with EtOAc (3×). The organic phases were combined, dried over Na₂SO₄, filtered, and concentrated to afford the title compound as a colorless residue (18.2 mg, 45% yield). ESI MS (M+H)+=318.1. HPLC Peak $t_r$=0.89 minutes. HPLC conditions: A.

Example 323: (+/−)-N-(4-chlorophenyl)-2-(trans-4-((2-(trifluoromethyl)pyridin-4-yl)oxy)cyclohexyl) Propanamide To a solution of 4-chloroaniline (0.033 g, 0.256 mmol) in THF (0.1 mL) at 0° C. was added a solution of isopropyl-magnesium chloride (0.128 ml, 0.256 mmol). The resulting solution was warmed to rt and stirred for 5 min, then Preparation 323B (0.0221 g, 0.064 mmol) in THF (0.22 mL) was added dropwise. The reaction was heated at 70° C. for 2 h, then allowed to cool to rt. The reaction was quenched with a sat. aq. soln. of NH₄Cl and diluted with EtOAc. Layers were separated. The aqueous phase was extracted with EtOAc (3×). The combined organic phases were dried over Na₂SO₄, filtered, and concentrated to afford a residue. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 45-90% B over 19 minutes, then a 4-minute hold at 100% B; Flow: 20 mL/min. Fractions containing the desired product were combined and dried via centrifugal evaporation to afford Example 323 (18.0 mg, 66%). ESI MS (M+H)+=427.2. HPLC Peak $t_r$=2.218 minutes. Purity=100%. HPLC conditions: B.

Example 324a and b (S)—N-(4-chlorophenyl)-2-(trans-4-((2-(trifluoromethyl)pyridin-4-yl)oxy)cyclohexyl)propanamide and (R)—N-(4-chlorophenyl)-2-(trans-4-((2-(trifluoromethyl)pyridin-4-yl)oxy)cyclohexyl)propanamide (Absolute Stereochemistry Unknown)

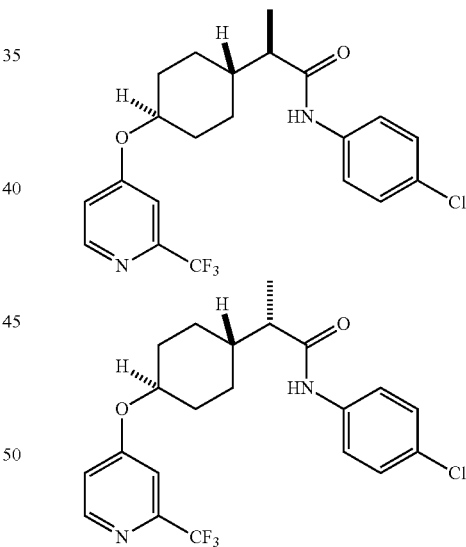

Approximately 17 mg sample of racemic Example 323 was resolved. The isomeric mixture was purified via preparative SFC with the following conditions: Column: Whelk-O R,R, 25×3 cm ID, 5-µm particles; Mobile Phase A: 85/15 CO₂/MeOH with 0.1% DEA; Detector Wavelength: 220 nm; Flow: 100 mL/min. The fractions ("Peak-1" $t_r$=4.300 min, "Peak-2" $t_r$=5.008 min; analytical conditions: Column: Whelk-O R,R, 250×4.6 mm ID, 5-µm particles; Mobile Phase A: 80/20 CO₂/MeOH with 0.1% DEA; Flow: 2.0 mL/min) were collected in MeOH with 0.1% DEA. The stereoisomeric purity of each fraction was estimated to be greater than 99% based on the prep-SFC chromatograms.

Each enantiomer was further purified via preparative LC/MS:

First eluting isomer (Example 324a): The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-90% B over 19 minutes, then a 4-minute hold at 100% B; Flow: 20 mL/min. Fractions containing the desired product were combined and dried via centrifugal evaporation to afford Isomer 1 (6.3 mg, 23%). ESI MS (M+H)+=427.2. HPLC Peak tr=2.296 minutes. Purity=98%. HPLC conditions: B.

Second eluting isomer (Example 324b): The crude material was purified via preparative LC/MS with the following conditions: Column: XBridge Cl 8, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-90% B over 19 minutes, then a 4-minute hold at 100% B; Flow: 20 mL/min. Fractions containing the desired product were combined and dried via centrifugal evaporation to afford Isomer 2 (7.8 mg, 27%). ESI MS (M+H)+=427.0. HPLC Peak tr=2.248 minutes. Purity=95%. HPLC conditions: B.

BIOLOGICAL EXAMPLES

Example 325

Assessment of Inhibitor Activity in HeLa Cell-based Indoleamine 2,3-dioxygenase (IDO) Assay HeLa (ATCC®CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100 U/mL penicillin, 100 μg/mL streptomycin (#SV30010, HyClone) and 10% fetal bovine serum (#SH30071.03 HyClone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 μL of culture medium. After a further 48 hour incubation, 170 μL of supernatant was transferred from each well to a fresh 96-well plate. 12.1 μL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 μL, of the supernatant was transferred from each well to a fresh 96-well plate. 100 μl of 2% (w/v) p-dimethylaminobenzaldehyde (#15647-7, Sigma-Aldrich) in acetic acid (#A6283, Sigma-Aldrich) was added to each well mixed and incubated at room temperature for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Activity for compounds described herein is provided in FIG. 1, wherein potency levels are provided as follows: (Potency: IDO $IC_{50}$: A<0.1 μM; B<1 μM; C<10 μM)

Example 326

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 500 μL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding Trichloroacetic Acid(Sigma-Aldrich) to a final concentration at 0.2%. The cell plate was further incubated at 50° C. for 30 minute. The equal volume supernatant (20 μL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Compounds with an $IC_{50}$ greater than 250 nM are shown with (C), compounds with an $IC_{50}$ less than 250 nM are shown with (B) and those with an $IC_{50}$ less than 50 nM are shown with (A) in Table X below.

TABLE X

Biological activity for Examples tested in the biological assay described in Example 326.
HEK Human IDO-1

| Example # | Biological Activity |
|---|---|
| 305 | C |
| 305a | C |
| 305b | A |
| 306 | A |
| 306a | A |
| 306b | C |
| 307 | A |
| 307a | A |
| 307b | A |
| 307c | A |
| 307d | A |
| 307e | B |
| 307f | A |
| 308a | B |
| 308b | A |
| 308c | C |
| 308d | NT |
| 309a | C |
| 309b | A |
| 309c | C |
| 309d | A |

TABLE X-continued

Biological activity for Examples tested in the biological assay described in Example 326.
HEK Human IDO-1

| Example # | Biological Activity |
|---|---|
| 310a | A |
| 310b | A |
| 310c | A |
| 310d | A |
| 310e | A |
| 310f | B |
| 311a | A |
| 311b | A |
| 311c | C |
| 311d | A |
| 311e | NT |
| 311f | B |
| 312a | B |
| 312b | A |
| 312c | A |
| 312d | B |
| 313a | A |
| 313b | A |
| 313c | C |
| 313d | A |
| 313e | C |
| 313f | A |
| 314a | B |
| 314b | B |
| 315a | B |
| 315b | A |
| 316a | C |
| 316b | C |
| 316c | C |
| 316d | C |
| 317a | A |
| 317b | A |
| 317c | C |
| 317d | C |
| 318a | A |
| 318b | A |
| 318c | C |
| 318d | B |
| 318e | A |
| 319a | B |
| 319b | C |
| 320 | A |
| 321 | B |
| 322 | C |
| 323 | A |
| 324a | B |
| 324b | C |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound having the formula (I):

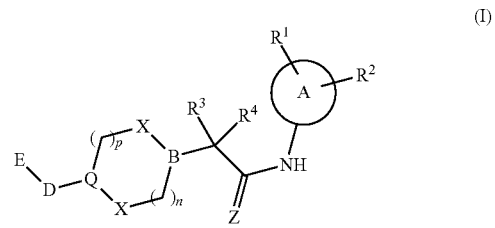

or a pharmaceutically acceptable salt, hydrate or solvate thereof, wherein, the subscript n is 1 or 0; the subscript p is 1 or 0;
the ring designated as A is phenyl, 6-membered heteroaryl, or $C_{5-7}$ cycloalkyl;
Z is O;
B is $C(OR^{5a})$ or $C(R^{3a})$;
each X is independently O, $CHR^5$, $C(O)$, or $CH(OR^{5a})$;
Q is $C(CN)$ or $CR^6$;
D is a bond, O, $C(R^5)_2$, $NR^{5a}$, or $N(R^{5a})_2$;
E is optionally substituted $C_1$-$C_6$ alkyl, optionally substituted phenyl, optionally substituted $C_3$-$C_6$ cycloalkyl, optionally substituted 3- to 6-membered cycloheteroalkyl, or optionally substituted monocyclic heteroaryl;
$R^1$ is halogen, optionally substituted $C_3$-$C_6$ cycloalkyl, optionally substituted 3- to 6-membered cycloheteroalkyl, optionally substituted phenyl, CN, $SO_2NH_2$, $NHSO_2CH_3$, $NHSO_2CF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl; and
$R^2$ is hydrogen, halogen, optionally substituted $C_3$-$C_6$ cycloalkyl, optionally substituted 3- to 6-membered cycloheteroalkyl, optionally substituted phenyl, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl;
$R^3$, and $R^4$ are independently hydrogen, optionally substituted $C_1$-$C_6$ alkyl, optionally substituted $C_1$-$C_6$ haloalkyl, fluorine, OH, CN, $CO_2H$, $C(O)NH_2$, $N(R^5)_2$, optionally substituted —O—$C_1$-$C_6$ alkyl, —$(CR^5R^5)_m$—OH, —$(CR^5R^5)_m$—$CO_2H$, —$(CR^5R^5)_m$—$C(O)NH_2$, —$(CR^5R^5)_m$—$C(O)NHR^5$, —$(CR^5R^5)_mN(R^5)_2$, —NH$(CR^5R^5)_mCO_2H$ or —NH$(CR^5R^5)_m$—$C(O)NH_2$;
$R^{3a}$ is hydrogen, $C_1$-$C_6$ alkyl, fluorine, OH;
each $R^5$ is independently H, F, OH, or optionally substituted $C_1$-$C_6$ alkyl;
each $R^{5a}$ is independently H, or optionally substituted $C_1$-$C_6$ alkyl;
$R^6$ is H, OH, F, optionally substituted $C_1$-$C_6$ alkyl, or optionally substituted —O—$C_1$-$C_6$ alkyl;
and each m is independently 1, 2, or 3.

2. The compound of claim 1, having the formula:

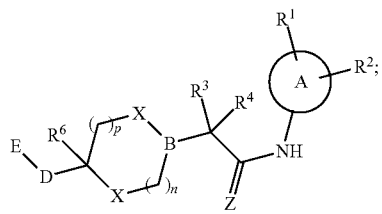

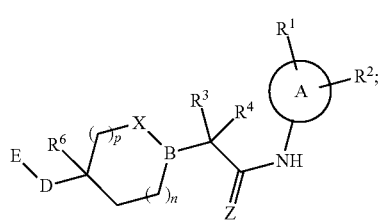

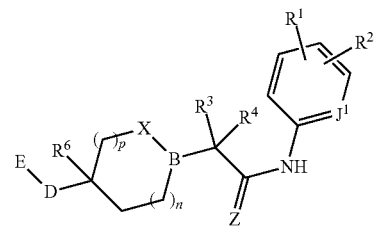

wherein J¹ is CH, N or optionally C(R²) when R² is attached to the ring vertex identified as J¹;

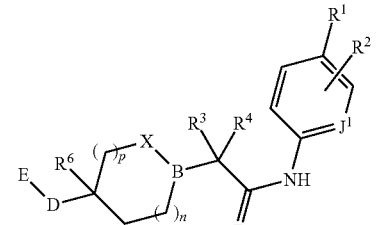

wherein J¹ is CH, N or optionally C(R²) when R² is attached to the ring vertex identified as J¹;

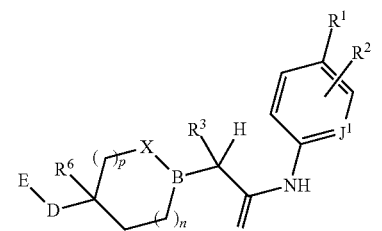

wherein J¹ is CH, N or optionally C(R²) when R² is attached to the ring vertex identified as J¹;

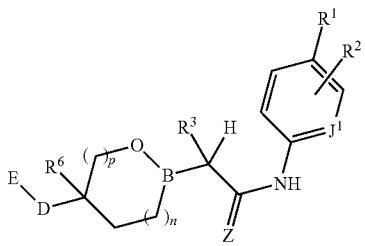

wherein J¹ is CH, N or optionally C(R²) when R² is attached to the ring vertex identified as J¹;

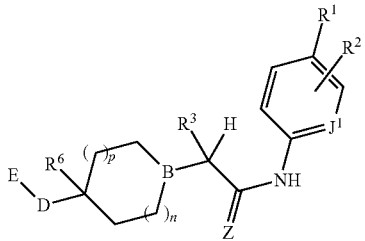

wherein J¹ is CH, N or optionally C(R²) when R² is attached to the ring vertex identified as J¹;

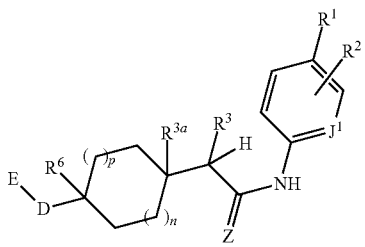

wherein J¹ is CH, N or optionally C(R²) when R² is attached to the ring vertex identified as J¹;

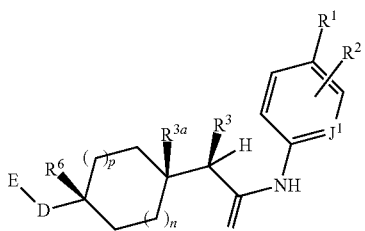

263 wherein J¹ is CH, N or optionally C(R²) when R² is attached to the ring vertex identified as J¹;

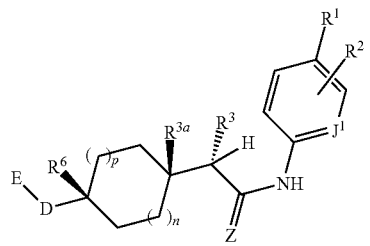

wherein J¹ is CH, N or optionally C(R²) when R² is attached to the ring vertex identified as J¹;

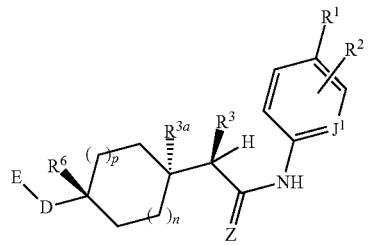

wherein J¹ is CH, N or optionally C(R²) when R² is attached to the ring vertex identified as J¹;

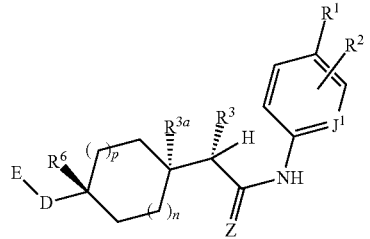

wherein J¹ is CH, N or optionally C(R²) when R² is attached to the ring vertex identified as J¹;

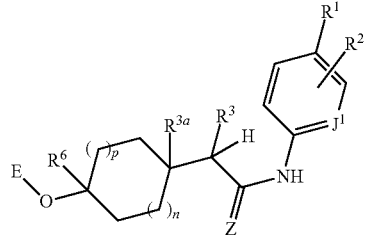

264 wherein J¹ is CH, N or optionally C(R²) when R² is attached to the ring vertex identified as J¹;

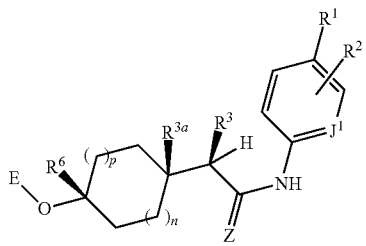

wherein J¹ is CH, N or optionally C(R²) when R² is attached to the ring vertex identified as J¹;

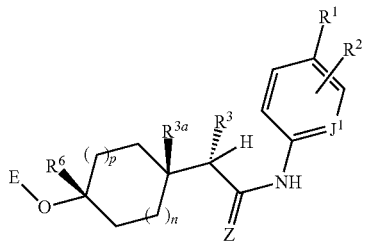

wherein J¹ is CH, N or optionally C(R²) when R² is attached to the ring vertex identified as J¹;

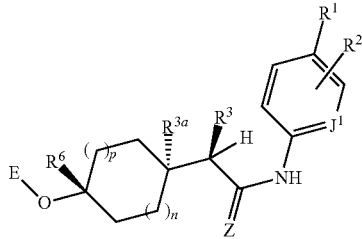

wherein J¹ is CH, N or optionally C(R²) when R² is attached to the ring vertex identified as J¹;

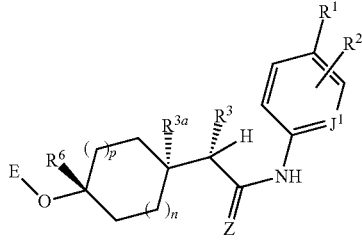

wherein J¹ is CH, N or optionally C(R²) when R² is attached to the ring vertex identified as J¹;

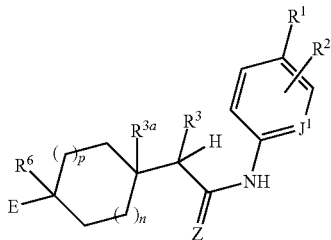

wherein J¹ is CH, N or optionally C(R²) when R² is attached to the ring vertex identified as J¹;

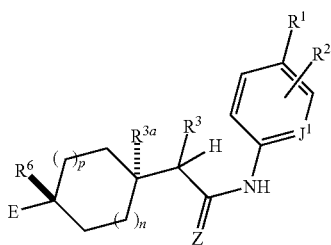

wherein J¹ is CH, N or optionally C(R²) when R² is attached to the ring vertex identified as J¹, and which is substantially free of other isomers at the carbon atoms to which each of R³ᵃ and
R⁶ are attached; or

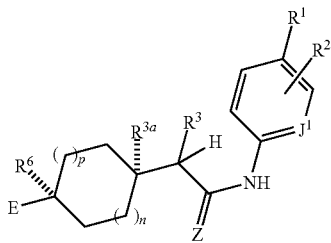

wherein J¹ is CH, N or optionally C(R²) when R² is attached to the ring vertex identified as J¹, and which is substantially free of other isomers at the carbon atoms to which each of R³ᵃ and
R⁶ are attached.

3. The compound of claim 1, having the formula:

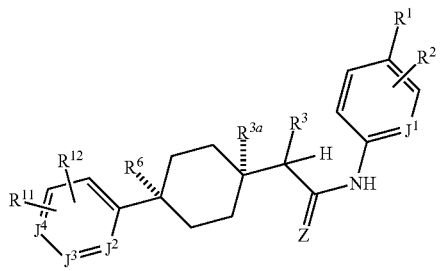

wherein

J¹ is CH, N or optionally C(R²) when R² is attached to the ring vertex identified as J¹;

J² is N or CH, or optionally is C(R¹¹), when R¹¹ is attached to the ring vertex identified as J²;

J³ is N or CH, or optionally is C(R¹¹), when R¹¹ is attached to the ring vertex identified as J³;

J⁴ is N or CH, or optionally is C(R¹²), when R¹² is attached to the ring vertex identified as J⁴;

wherein R¹¹ and R¹² are independently hydrogen halogen, optionally substituted $C_1$-$C_4$ haloalkyl, optionally substituted $C_3$-$C_6$ cycloalkyl, optionally substituted 3- to 6-membered cycloheteroalkyl, optionally substituted phenyl, optionally substituted heteroaryl, optionally substituted $C_1$-$C_4$ alkyl, optionally substituted $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when R¹ and R² are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl;

and which is substantially free of other isomers at the carbon atoms to which each of R³ᵃ and R⁶ are attached.

4. The compound of claim 3, having the formula:

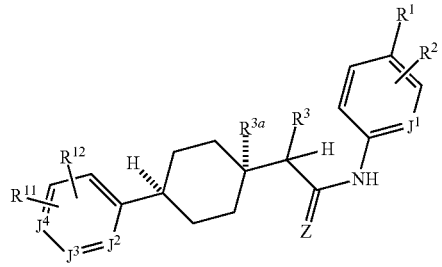

which is substantially free of other isomers at the stereocenters of the cyclohexane ring;

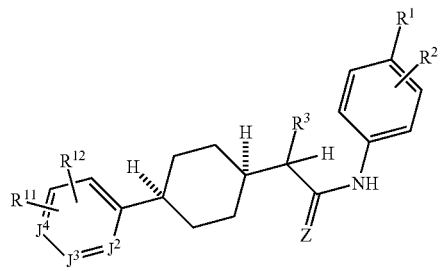

which is substantially free of other isomers at the stereo-
centers of the cyclohexane ring;

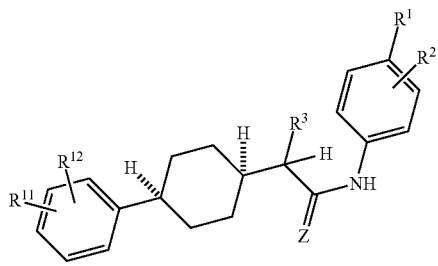

which is substantially free of other isomers at the stereo-
centers of the cyclohexane ring;

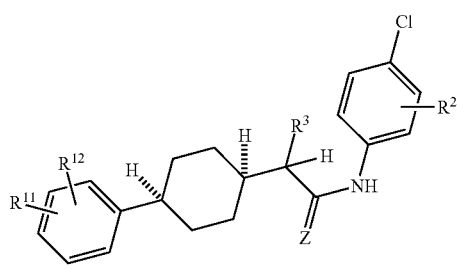

which is substantially free of other isomers at the stereo-
centers of the cyclohexane ring;

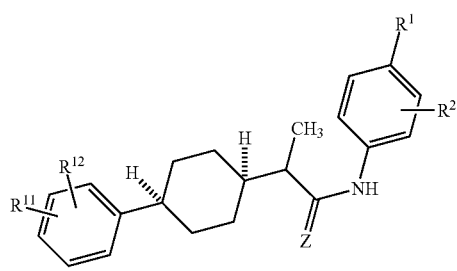

which is substantially free of other isomers at the stereo-
centers of the cyclohexane ring;

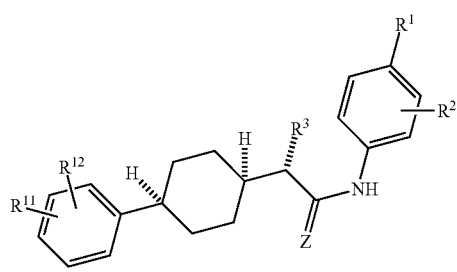

which is substantially free of other isomers at each of the
three stereocenters shown;

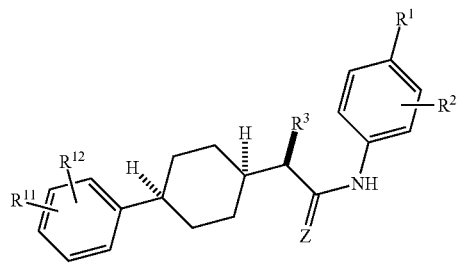

which is substantially free of other isomers at each of the
three stereocenters shown;

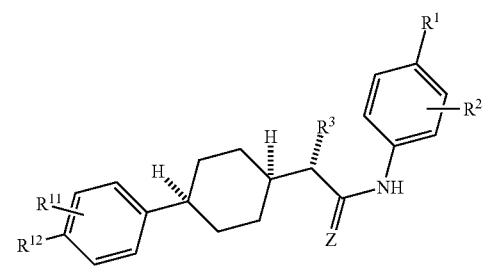

wherein $R^1$ is Cl, F, optionally substituted phenyl, or CN;
and which is substantially free of other isomers at each
of the three stereocenters shown;

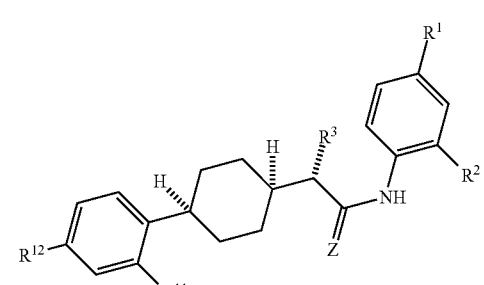

wherein $R^{11}$ is H or F; and $R^{12}$ is H or —O—$C_1$-$C_3$ alkyl;
and which is substantially free of other isomers at each
of the three stereocenters shown;

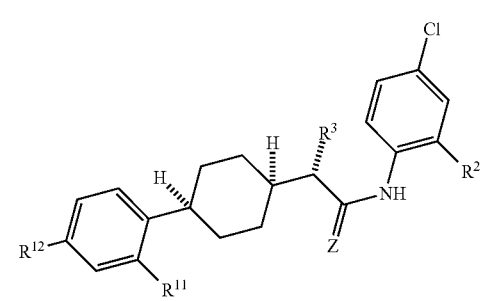

which is substantially free of other isomers at each of the three stereocenters shown;

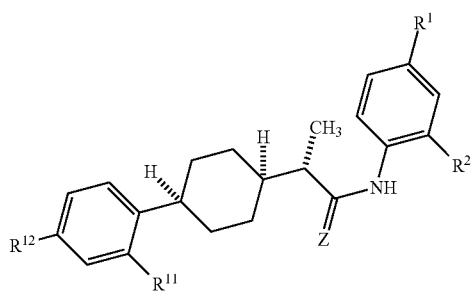

which is substantially free of other isomers at each of the three stereocenters shown;

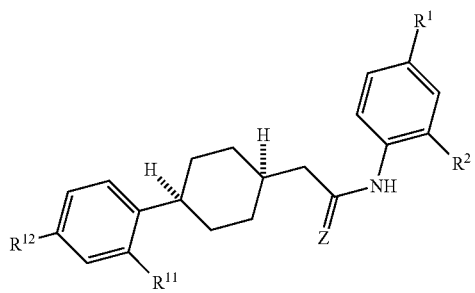

which is substantially free of other isomers at each of the two stereocenters shown;

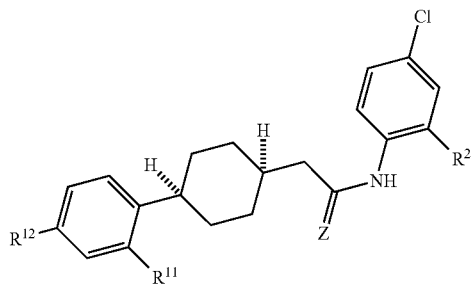

which is substantially free of other isomers at each of the two stereocenters shown;

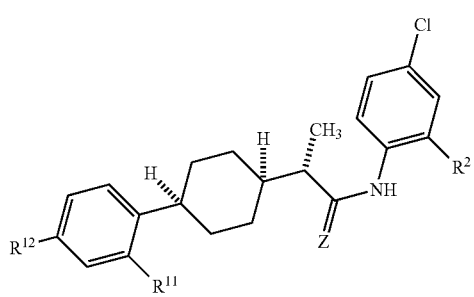

which is substantially free of other isomers at each of the three stereocenters shown; or

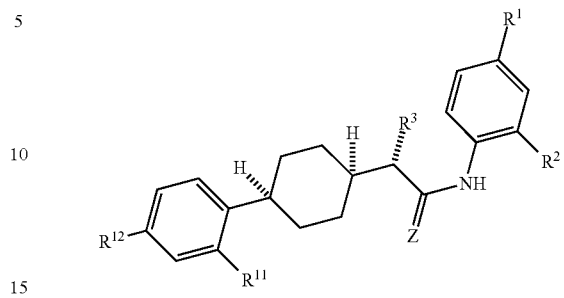

wherein $R^{11}$ is H or F; and $R^{12}$ is $CO_2H$, $C(O)NH_2$, $-(CR^5R^5)_mCO_2H$ or $-(CR^5R^5)_mC(O)NH_2$; and which is substantially free of other isomers at each of the three stereocenters shown.

5. A pharmaceutical composition comprising a compound of claim 1 and a pharmaceutically acceptable excipient.

6. A combination comprising a compound of claim 1 and at least one additional therapeutic agent.

7. The combination of claim 6, wherein the at least one additional therapeutic agent is a chemotherapeutic agent, an immune- and/or inflammation-modulating agent, an anti-hypercholesterolemia agent, or an anti-infective agent.

8. The combination of claim 6, wherein the at least one additional therapeutic agent is an immune checkpoint inhibitor.

9. A kit comprising a compound of claim 1 and at least one additional therapeutic agent.

10. The kit of claim 9, wherein the at least one additional therapeutic agent is a chemotherapeutic agent, an immune- and/or inflammation-modulating agent, an anti-hypercholesterolemia agent, or an anti-infective agent.

11. The kit of claim 9, wherein the at least one additional therapeutic agent is an immune checkpoint inhibitor.

12. A method of treating cancer in a subject, comprising administering to said subject an effective amount of a compound of claim 1 and an immune checkpoint inhibitor.

13. The method of claim 12, wherein said compound and said immune checkpoint inhibitor are administered in combination or sequentially.

14. The method of claim 12, wherein said compound is administered after said immune checkpoint inhibitor.

15. The method of claim 12, wherein said compound is administered prior to said immune checkpoint inhibitor.

16. A method of treating cancer in a subject, said method comprising administering to said subject an effective amount of a compound of claim 1 and an immune checkpoint inhibitor, wherein said administration is prior to, concurrent with, or subsequent to, radiation treatment.

17. The method of claim 16, wherein said compound and said immune checkpoint inhibitor are administered in combination or sequentially.

18. The A method of claim 16, wherein said compound is administered after said immune checkpoint inhibitor.

19. The method of claim 16, wherein said compound is administered prior to said immune checkpoint inhibitor.

20. The combination of claim 8, wherein said immune checkpoint inhibitor is selected from the group consisting of ipilimumab, nivolumab, and lambrolizumab.

21. The kit of claim 11, wherein said immune checkpoint inhibitor is selected from the group consisting of ipilimumab, nivolumab, and lambrolizumab.

22. The method of claim 12, wherein said immune checkpoint inhibitor is selected from the group consisting of ipilimumab, nivolumab, and lambrolizumab.

23. The method of claim 16, wherein said immune checkpoint inhibitor is selected from the group consisting of ipilimumab, nivolumab, and lambrolizumab.

* * * * *

UNITED STATES PATENT AND TRADEMARK OFFICE
CERTIFICATE OF CORRECTION

PATENT NO. : 11,242,319 B2
APPLICATION NO. : 15/524113
DATED : February 8, 2022
INVENTOR(S) : Beck et al.

Page 1 of 1

It is certified that error appears in the above-identified patent and that said Letters Patent is hereby corrected as shown below:

In the Claims

At Column 270, Line 58 (Claim 18), delete "The A method" and substitute therefor – The method –

Signed and Sealed this
Thirtieth Day of August, 2022

Katherine Kelly Vidal
Director of the United States Patent and Trademark Office